(12) United States Patent
Guest et al.

(10) Patent No.: US 11,767,510 B2
(45) Date of Patent: Sep. 26, 2023

(54) DEVICES AND METHODS FOR ISOLATING TUMOR INFILTRATING LYMPHOCYTES AND USES THEREOF

(71) Applicant: INSTIL BIO (UK) LIMITED, Manchester (GB)

(72) Inventors: Ryan Guest, Manchester (GB); Joanne McCaffrey, Manchester (GB)

(73) Assignee: INSTIL BIO (UK) LIMITED, Manchester (GB)

( * ) Notice: Subject to any disclaimer, the term of this patent is extended or adjusted under 35 U.S.C. 154(b) by 0 days.

(21) Appl. No.: 17/733,875

(22) Filed: Apr. 29, 2022

(65) Prior Publication Data

US 2022/0348874 A1 Nov. 3, 2022

Related U.S. Application Data

(63) Continuation of application No. PCT/GB2020/053315, filed on Dec. 18, 2020.

(60) Provisional application No. 62/951,559, filed on Dec. 20, 2019, provisional application No. 62/982,470, filed on Feb. 27, 2020, provisional application No. 63/047,431, filed on Jul. 2, 2020.

(51) Int. Cl.
| | | |
|---|---|---|
| *C12N 5/0783* | (2010.01) | |
| *A61P 35/00* | (2006.01) | |
| *A01N 1/02* | (2006.01) | |
| *A61K 35/17* | (2015.01) | |

(52) U.S. Cl.
CPC ......... *C12N 5/0638* (2013.01); *A01N 1/0221* (2013.01); *A01N 1/0284* (2013.01); *A61K 35/17* (2013.01); *A61P 35/00* (2018.01); *C12N 5/0636* (2013.01); *C12N 2501/2302* (2013.01); *C12N 2501/60* (2013.01); *C12N 2501/998* (2013.01); *C12N 2502/30* (2013.01); *C12N 2509/00* (2013.01)

(58) Field of Classification Search
CPC .................................................. C12N 5/0638
See application file for complete search history.

(56) References Cited

U.S. PATENT DOCUMENTS

| | | | |
|---|---|---|---|
| 5,498,599 A | 3/1996 | Choi et al. | |
| 7,847,067 B2 | 12/2010 | Abo et al. | |
| 8,034,334 B2 | 10/2011 | Dudley et al. | |
| 8,287,857 B2 | 10/2012 | Dudley et al. | |
| 8,383,099 B2 | 2/2013 | Dudley et al. | |
| 8,809,050 B2 | 8/2014 | Vera et al. | |
| 8,956,860 B2 | 2/2015 | Vera et al. | |
| 9,074,185 B2 | 7/2015 | Dudley et al. | |
| 9,567,565 B2 | 2/2017 | Vera et al. | |
| 9,844,569 B2 | 12/2017 | Gros et al. | |
| 10,130,659 B2 | 11/2018 | Wardell et al. | |
| 10,166,257 B2 | 1/2019 | Wardell et al. | |
| 10,202,454 B2 | 2/2019 | Freeman et al. | |
| 10,272,113 B2 | 4/2019 | Wardell et al. | |
| 10,363,273 B2 | 7/2019 | Wardell et al. | |
| 10,398,734 B2 | 9/2019 | Wardell et al. | |
| 10,415,015 B2 | 9/2019 | Veerapathran et al. | |
| 10,420,799 B2 | 9/2019 | Wardell et al. | |
| 10,435,455 B1 | 10/2019 | Sonntag et al. | |
| 10,463,697 B2 | 11/2019 | Wardell et al. | |
| 10,517,894 B2 | 12/2019 | Frank et al. | |
| 10,533,156 B2 | 1/2020 | Vera et al. | |
| 10,537,595 B2 | 1/2020 | Wardell et al. | |
| 10,570,201 B2 | 2/2020 | Grosveld et al. | |
| 10,639,330 B2 | 5/2020 | Wardell et al. | |
| 10,646,517 B2 | 5/2020 | Wardell et al. | |
| 10,653,723 B1 | 5/2020 | Wardell et al. | |
| 10,695,372 B2 | 6/2020 | Wardell et al. | |
| 10,894,063 B2 | 1/2021 | Wardell et al. | |
| 10,905,718 B2 | 2/2021 | Wardell et al. | |
| 10,918,666 B2 | 2/2021 | Wardell et al. | |
| 10,925,900 B2 | 2/2021 | Wardell et al. | |
| 10,933,094 B2 | 3/2021 | Wardell et al. | |
| 10,946,044 B2 | 3/2021 | Wardell et al. | |
| 10,946,045 B2 | 3/2021 | Wardell et al. | |
| 10,953,046 B2 | 3/2021 | Wardell et al. | |
| 10,953,047 B2 | 3/2021 | Wardell et al. | |
| 11,007,225 B1 | 5/2021 | Wardell et al. | |
| 11,007,226 B2 | 5/2021 | Wardell et al. | |
| 11,013,770 B1 | 5/2021 | Wardell et al. | |

(Continued)

FOREIGN PATENT DOCUMENTS

| | | |
|---|---|---|
| CL | 2019002769 | 9/2019 |
| EP | 0446450 A1 | 9/1991 |

(Continued)

OTHER PUBLICATIONS

Klapper et al. (J Immunol Methods. Jun. 30, 2009; 345(1-2): 90-99. doi:10.1016/j.jim.2009.04.009.) (Year: 2009).*
Kverneland et al. (Journal for ImmunoTherapy of Cancer 2021;9:e003499. doi:10.1136/jitc-2021-003499) (Year: 2021).*
Ellebaek et al. (Journal of Translational Medicine 2012, 10:169 doi:10.1186/1479-5876-10-169). (Year: 2012).*
Demetriou et al. ("CD2 expression acts as a quantitative checkpoint for immunological synapse structure and T-cell activation." bioRxiv preprint doi: https://doi.org/10.1101/589440; this version posted Mar. 29, 2019). (Year: 2019).*
Abbas, Abul K, et al., "Revisiting IL-2: Biology and therapeutic prospects," Science Immunology, 3(25): eaat1482, (2018).

(Continued)

*Primary Examiner* — Scott Long
(74) *Attorney, Agent, or Firm* — Alston & Bird LLP

(57) ABSTRACT

The present invention provides methods for isolating and cryopreserving tumor infiltrating lymphocytes (TILs) and producing therapeutic populations of TILs, including methods via use of a kit and a semi-automatic device for aseptic disaggregation, enrichment, and cryopreservation of a resected tumor prior to expansion of the TIL population. The present invention also provides methods for expansion, and/or stabilization of TILs, for instance UTILs, compositions involving the same and methods of treatment involving the same.

14 Claims, 69 Drawing Sheets

(56) References Cited

U.S. PATENT DOCUMENTS

| | | |
|---|---|---|
| 11,026,974 B2 | 6/2021 | Frank et al. |
| 11,040,070 B2 | 6/2021 | Wardell et al. |
| 11,052,115 B2 | 7/2021 | Wardell et al. |
| 11,052,116 B2 | 7/2021 | Wardell et al. |
| 11,058,728 B1 | 7/2021 | Frank et al. |
| 11,077,182 B2 | 8/2021 | Hinrichs et al. |
| 11,083,752 B2 | 8/2021 | Wardell et al. |
| 11,123,371 B2 | 9/2021 | Frank et al. |
| 11,141,434 B2 | 10/2021 | Rabinovich et al. |
| 11,141,438 B2 | 10/2021 | Frank et al. |
| 11,168,303 B2 | 11/2021 | Wardell et al. |
| 11,168,304 B2 | 11/2021 | Wardell et al. |
| 11,179,419 B2 | 11/2021 | Frank et al. |
| 11,202,803 B1 | 12/2021 | Wardell et al. |
| 11,202,804 B2 | 12/2021 | Wardell et al. |
| 11,220,670 B2 | 1/2022 | Simpson-Abelson et al. |
| 11,241,456 B2 | 2/2022 | Wardell et al. |
| 11,254,913 B1 | 2/2022 | Wardell et al. |
| 11,266,694 B2 | 3/2022 | Frank et al. |
| 11,273,180 B2 | 3/2022 | Wardell et al. |
| 11,273,181 B2 | 3/2022 | Wardell et al. |
| 11,291,687 B2 | 4/2022 | Wardell et al. |
| 11,293,009 B2 | 4/2022 | Simpson-Abelson et al. |
| 11,304,979 B2 | 4/2022 | Wardell et al. |
| 11,304,980 B2 | 4/2022 | Frank et al. |
| 11,311,578 B2 | 4/2022 | Frank et al. |
| 11,337,998 B2 | 5/2022 | Wardell et al. |
| 11,344,579 B2 | 5/2022 | Wardell et al. |
| 11,344,580 B2 | 5/2022 | Frank et al. |
| 11,344,581 B2 | 5/2022 | Frank et al. |
| 11,351,197 B2 | 6/2022 | Frank et al. |
| 11,351,198 B2 | 6/2022 | Frank et al. |
| 11,351,199 B2 | 6/2022 | Frank et al. |
| 11,357,841 B2 | 6/2022 | Ritthipichai et al. |
| 11,364,266 B2 | 6/2022 | Frank et al. |
| 11,369,637 B2 | 6/2022 | Frank et al. |
| 11,384,337 B2 | 7/2022 | Chartier-Courtaud et al. |
| 11,401,507 B2 | 8/2022 | Simpson-Abelson et al. |
| 2010/0279405 A1 | 11/2010 | Peterson et al. |
| 2012/0244133 A1 | 9/2012 | Rosenberg et al. |
| 2013/0102075 A1 | 4/2013 | Vera et al. |
| 2013/0115617 A1 | 5/2013 | Wilson et al. |
| 2014/0047572 A1 | 2/2014 | Chen et al. |
| 2014/0050708 A1 | 2/2014 | Powell et al. |
| 2014/0099309 A1 | 4/2014 | Powell et al. |
| 2015/0119351 A1 | 4/2015 | Lubin et al. |
| 2016/0208216 A1 | 7/2016 | Vera et al. |
| 2018/0057592 A1 | 3/2018 | Frazier et al. |
| 2018/0127715 A1 | 5/2018 | Veerapathran et al. |
| 2018/0133253 A1 | 5/2018 | Gros et al. |
| 2018/0200367 A1 | 7/2018 | Borrello et al. |
| 2018/0207201 A1 | 7/2018 | Wardell et al. |
| 2018/0228841 A1 | 8/2018 | Frank et al. |
| 2018/0280436 A1 | 10/2018 | Wardell et al. |
| 2018/0282694 A1 | 10/2018 | Wardell et al. |
| 2018/0325954 A1 | 11/2018 | Wardell et al. |
| 2019/0000882 A1 | 1/2019 | Wardell et al. |
| 2019/0000883 A1 | 1/2019 | Wardell et al. |
| 2019/0032011 A1 | 1/2019 | Better et al. |
| 2019/0040111 A1 | 2/2019 | Tran et al. |
| 2019/0070222 A1 | 3/2019 | Wardell et al. |
| 2019/0083536 A1 | 3/2019 | Wardell et al. |
| 2019/0083538 A1 | 3/2019 | Wardell et al. |
| 2019/0083539 A1 | 3/2019 | Wardell et al. |
| 2019/0085046 A1 | 3/2019 | Yoseph et al. |
| 2019/0085047 A1 | 3/2019 | Hinrichs et al. |
| 2019/0085063 A1 | 3/2019 | Frigault et al. |
| 2019/0136230 A1 | 5/2019 | Sather et al. |
| 2019/0177395 A1 | 6/2019 | Tran et al. |
| 2019/0177692 A1 | 6/2019 | June et al. |
| 2019/0231820 A1 | 8/2019 | Fardis et al. |
| 2019/0247433 A1 | 8/2019 | Kalra et al. |
| 2019/0262400 A1 | 8/2019 | Davila et al. |
| 2019/0276802 A1 | 9/2019 | Simpson-Abelson et al. |
| 2019/0298770 A1 | 10/2019 | Rabinovich et al. |
| 2019/0322722 A1 | 10/2019 | Sonntag et al. |
| 2019/0345445 A1 | 11/2019 | Veerapathran et al. |
| 2019/0358259 A1 | 11/2019 | Wardell et al. |
| 2019/0358260 A1 | 11/2019 | Wardell et al. |
| 2019/0358261 A1 | 11/2019 | Wardell et al. |
| 2019/0374577 A1 | 12/2019 | Ritthipichai et al. |
| 2020/0000904 A1 | 1/2020 | McGranahan et al. |
| 2020/0032197 A1 | 1/2020 | Guest et al. |
| 2020/0056237 A1 | 2/2020 | Lu et al. |
| 2020/0095548 A1 | 3/2020 | Gros et al. |
| 2020/0095550 A1 | 3/2020 | Vera et al. |
| 2020/0121719 A1 | 4/2020 | Lotze et al. |
| 2020/0155601 A1 | 5/2020 | Wardell et al. |
| 2020/0157241 A1 | 5/2020 | Morgan et al. |
| 2020/0206265 A1 | 7/2020 | Perez et al. |
| 2020/0224161 A1 | 7/2020 | Karyampudi et al. |
| 2020/0246384 A1 | 8/2020 | Wardell et al. |
| 2020/0247869 A1 | 8/2020 | Tran et al. |
| 2020/0263130 A1 | 8/2020 | Bridgeman et al. |
| 2020/0276241 A1 | 9/2020 | Wardell et al. |
| 2020/0276242 A1 | 9/2020 | Wardell et al. |
| 2020/0277573 A1 | 9/2020 | Simpson-Abelson et al. |
| 2020/0281978 A1 | 9/2020 | Wardell et al. |
| 2020/0289569 A1 | 9/2020 | Wardell et al. |
| 2020/0289570 A1 | 9/2020 | Moriarity et al. |
| 2020/0299644 A1 | 9/2020 | Frank et al. |
| 2020/0306306 A1 | 10/2020 | Wardell et al. |
| 2020/0306307 A1 | 10/2020 | Wardell et al. |
| 2020/0306310 A1 | 10/2020 | Moriarity et al. |
| 2020/0316121 A1 | 10/2020 | Deniger et al. |
| 2020/0347350 A1 | 11/2020 | Karyampudi et al. |
| 2021/0000872 A1 | 1/2021 | Price et al. |
| 2021/0079348 A1 | 3/2021 | Wardell et al. |
| 2021/0100842 A1 | 4/2021 | Wardell et al. |
| 2021/0100843 A1 | 4/2021 | Wardell et al. |
| 2021/0106625 A1 | 4/2021 | Wardell et al. |
| 2021/0123020 A1 | 4/2021 | Simpson-Abelson et al. |
| 2021/0128620 A1 | 5/2021 | Wardell et al. |
| 2021/0128621 A1 | 5/2021 | Wardell et al. |
| 2021/0128622 A1 | 5/2021 | Wardell et al. |
| 2021/0128623 A1 | 5/2021 | Wardell et al. |
| 2021/0128624 A1 | 5/2021 | Wardell et al. |
| 2021/0128625 A1 | 5/2021 | Wardell et al. |
| 2021/0130779 A1 | 5/2021 | Chartier-Courtaud et al. |
| 2021/0137930 A1 | 5/2021 | Fardis et al. |
| 2021/0137984 A1 | 5/2021 | Wardell et al. |
| 2021/0145877 A1 | 5/2021 | Fardis et al. |
| 2021/0187029 A1 | 6/2021 | Lotze et al. |
| 2021/0189339 A1 | 6/2021 | Simpson-Abelson et al. |
| 2021/0205365 A1 | 7/2021 | Price et al. |
| 2021/0207091 A1 | 7/2021 | Wardell et al. |
| 2021/0207092 A1 | 7/2021 | Wardell et al. |
| 2021/0214685 A1 | 7/2021 | Wardell et al. |
| 2021/0252062 A1 | 8/2021 | Frank et al. |
| 2021/0252063 A1 | 8/2021 | Frank et al. |
| 2021/0260121 A1 | 8/2021 | Frank et al. |
| 2021/0274776 A1 | 9/2021 | Veerapathran et al. |
| 2021/0309968 A1 | 10/2021 | Simpson-Abelson et al. |
| 2021/0335467 A1 | 10/2021 | Brooks et al. |
| 2021/0353677 A1 | 11/2021 | Wardell et al. |
| 2021/0361712 A1 | 11/2021 | Wardell et al. |
| 2021/0361713 A1 | 11/2021 | Wardell et al. |
| 2021/0369775 A1 | 12/2021 | Fardis et al. |
| 2021/0379111 A1 | 12/2021 | Wardell et al. |
| 2021/0401889 A1 | 12/2021 | Frank et al. |
| 2021/0407639 A1 | 12/2021 | Brooks et al. |
| 2021/0407640 A1 | 12/2021 | Brooks et al. |
| 2022/0000923 A1 | 1/2022 | Wardell et al. |
| 2022/0000924 A1 | 1/2022 | Wardell et al. |
| 2022/0000925 A1 | 1/2022 | Wardell et al. |
| 2022/0000926 A1 | 1/2022 | Frank et al. |
| 2022/0000927 A1 | 1/2022 | Frank et al. |
| 2022/0000928 A1 | 1/2022 | Frank et al. |
| 2022/0000929 A1 | 1/2022 | Frank et al. |
| 2022/0008469 A1 | 1/2022 | Wardell et al. |
| 2022/0008470 A1 | 1/2022 | Frank et al. |
| 2022/0010278 A1 | 1/2022 | Chartier-Courtaud et al. |
| 2022/0025052 A1 | 1/2022 | Rabinovich et al. |
| 2022/0033775 A1 | 2/2022 | Chartier-Courtaud et al. |

(56) References Cited

U.S. PATENT DOCUMENTS

| | | |
|---|---|---|
| 2022/0059202 A1 | 2/2022 | Brooks et al. |
| 2022/0072039 A1 | 3/2022 | Fardis et al. |
| 2022/0088069 A1 | 3/2022 | Fardis et al. |
| 2022/0088080 A1 | 3/2022 | Frank et al. |
| 2022/0088081 A1 | 3/2022 | Frank et al. |
| 2022/0090018 A1 | 3/2022 | Wardell et al. |
| 2022/0096555 A1 | 3/2022 | Frank et al. |
| 2022/0112557 A1 | 4/2022 | Chartier-Courtaud et al. |
| 2022/0118011 A1 | 4/2022 | Wardell et al. |
| 2022/0118012 A1 | 4/2022 | Fardis et al. |
| 2022/0122707 A1 | 4/2022 | Brooks et al. |
| 2022/0133795 A1 | 5/2022 | Karyampudi et al. |
| 2022/0133798 A1 | 5/2022 | Frank et al. |
| 2022/0160760 A1 | 5/2022 | Bridgeman et al. |
| 2022/0193131 A1 | 6/2022 | Chartier-Courtaud et al. |
| 2022/0204932 A1 | 6/2022 | Chartier-Courtaud et al. |

FOREIGN PATENT DOCUMENTS

| | | |
|---|---|---|
| EP | 3674396 A1 | 7/2020 |
| WO | WO 1995/018858 A1 | 7/1995 |
| WO | WO 1996/017060 A1 | 6/1996 |
| WO | WO 1999/023199 A1 | 5/1999 |
| WO | WO 2004/021995 A2 | 3/2004 |
| WO | WO 2008/136843 A1 | 11/2008 |
| WO | WO 2011/072088 A2 | 6/2011 |
| WO | WO 2012/129201 A1 | 9/2012 |
| WO | WO 2013/070899 A1 | 5/2013 |
| WO | WO 2013/173835 A1 | 11/2013 |
| WO | WO 2013/188427 A1 | 12/2013 |
| WO | WO 2014/133568 A1 | 9/2014 |
| WO | WO 2015/009604 A1 | 1/2015 |
| WO | WO 2015/123527 A1 | 8/2015 |
| WO | WO 2015/131087 A1 | 9/2015 |
| WO | WO 2015/188839 A2 | 12/2015 |
| WO | WO 2017/103596 A1 | 6/2017 |
| WO | WO 2017/179015 A1 | 10/2017 |
| WO | WO 2018/009894 A1 | 1/2018 |
| WO | WO 2018/014039 A1 | 1/2018 |
| WO | WO 2018/081473 A1 | 5/2018 |
| WO | WO 2018/081789 A1 | 5/2018 |
| WO | WO 2018/094167 A1 | 5/2018 |
| WO | WO 2018/129332 A1 | 7/2018 |
| WO | WO 2018/129336 A1 | 7/2018 |
| WO | WO 2018/130845 A1 | 7/2018 |
| WO | WO 2018/182817 A1 | 10/2018 |
| WO | WO 2018/209115 A1 | 11/2018 |
| WO | WO 2018/226714 A1 | 12/2018 |
| WO | WO 2019/100023 A1 | 5/2019 |
| WO | WO 2019/103857 A1 | 5/2019 |
| WO | WO 2019/118873 A2 | 6/2019 |
| WO | WO 2019/136456 A1 | 7/2019 |
| WO | WO 2019/136459 A1 | 7/2019 |
| WO | WO 2019/145711 A1 | 8/2019 |
| WO | WO 2019/157130 A1 | 8/2019 |
| WO | WO 2019/160829 A1 | 8/2019 |
| WO | WO 2019/190579 A1 | 10/2019 |
| WO | WO 2019/210131 A1 | 10/2019 |
| WO | WO 2019/217753 A1 | 11/2019 |
| WO | WO 2019/243835 A1 | 12/2019 |
| WO | WO 2020/061429 A1 | 3/2020 |
| WO | WO 2020/096682 A2 | 5/2020 |
| WO | WO 2020/096927 A1 | 5/2020 |
| WO | WO 2020/096986 A2 | 5/2020 |
| WO | WO 2020/096988 A2 | 5/2020 |
| WO | WO 2020/096989 A1 | 5/2020 |
| WO | WO 2020/114491 A1 | 6/2020 |
| WO | WO 2020/117233 A1 | 6/2020 |
| WO | WO 2020/131547 A1 | 6/2020 |
| WO | WO 2020/146740 A1 | 7/2020 |
| WO | WO 2020/152451 A1 | 7/2020 |
| WO | WO 2020/177920 A2 | 9/2020 |
| WO | WO 2020/180733 A1 | 9/2020 |
| WO | WO 2020/232029 A1 | 11/2020 |
| WO | WO 2021/014174 A1 | 1/2021 |
| WO | WO 2021/081378 A1 | 4/2021 |
| WO | WO 2021/118990 A1 | 6/2021 |
| WO | WO 2021/123555 A1 | 6/2021 |
| WO | WO 2021/123832 A1 | 6/2021 |
| WO | WO 2021/216920 A1 | 10/2021 |
| WO | WO 2021/226061 A1 | 11/2021 |
| WO | WO 2021/226085 A1 | 11/2021 |
| WO | WO 2022/016112 A1 | 1/2022 |
| WO | WO 2022/016114 A1 | 1/2022 |
| WO | WO 2022/076606 A1 | 4/2022 |
| WO | WO 2022/076952 A1 | 4/2022 |
| WO | WO 2022/087324 A1 | 4/2022 |
| WO | WO 2022/125941 A1 | 6/2022 |
| WO | WO 2022/130015 A2 | 6/2022 |
| WO | WO 2022/130016 A1 | 6/2022 |
| WO | WO 2022/130017 A2 | 6/2022 |
| WO | WO 2022/133140 A1 | 6/2022 |
| WO | WO 2022/133149 A1 | 6/2022 |
| WO | WO 2022/147196 A2 | 7/2022 |
| WO | WO 2022/165260 A1 | 8/2022 |

OTHER PUBLICATIONS

Ahmadzadeh, Mojgan et al., "Tumor-infiltrating human CD4+ regulatory T cells display a distinct TCR repertoire and exhibit tumor and neoantigen reactivity," Science Immunology, 4(31): eaao4310, (2019).

Albu, Roxana I. et al., "Extracellular domain N-glycosylation controls human thrombopoietin receptor cell surface levels," Frontiers in Endocrinology, 2:71, (Nov. 2011).

Aldhamen, Ya et al., "Improved cytotoxic T-lymphocyte immune responses to a tumor antigen by vaccines co-expressing the SLAM-associated adaptor EAT-2," Cancer Gene Therapy, 20:564-575, (2013).

Alfaguter, Inbar Azoulay et al., "Silencing PD-1 using PH-762 (PD-1 targeting INTASYL compound) to improve Iovance TIL effector function using Gen 2 manufacturing method," P149 SITC Annual Meeting, National Harbor, MD, (Nov. 6-10, 2019).

Almeida, Afonso R.M. et al., "Homeostasis of Peripheral CD4+ T Cells: IL-2R α and IL-2 Shape a Population of Regulatory Cells That Controls CD4+ T Cells," J Immunol, 169:4850-4860, (2002).

Alva, Ajjai et al., "Contemporary experience with high-dose interleukin-2 therapy and impact on survival in patients with metastatic melanoma and metastatic renal cell carcinoma," Cancer Immunol Immunother., 65:1533-1544, (2016).

Alvarez-Vallina, Luis et al., "Antigen-specific targeting of CD28-mediated T cell co-stimulation using chimeric single-chain antibody variable fragment-CD28 receptors," Eur. J. Immunol., 26:2304-2309, (1996).

Amaria, Rodabe Navroze et al., "Adoptive transfer of tumor-infiltrating lymphocytes in patients with sarcomas, ovarian and pancreatic cancers," J Clin Oncol., 37:Suppl., Abstract TPS2650, (2019).

Andersen et al., "T cells isolated from patients with checkpoint inhibitor-resistant melanoma are functional and can mediate tumor regression," Ann. Oncol. 29(7):1575-1581, (Jul. 1, 2018).

Andrews, Sarah F. et al., "T-bet+ memory B cells stay in place," Immunity, 52:724-726, (2020).

Antohe, Mihaela et al., "Tumor infiltrating lymphocytes: The regulator of melanoma evolution (Review)," Oncol Lett., 17:4155-4161, (2019).

Armstrong, M., "Iovance delayed again," BioInformant, (May 19, 2021). [Retrieved from the internet May 19, 2021; URL: <https://www.evaluate.com/node/16891/pdf>].

Atkins, Michael B. et al., "High-Dose Recombinant Interleukin 2 Therapy for Patients with Metastatic Melanoma: Analysis of 270 Patients Treated Between 1985 and 1993," Journal of Clinical Oncology, 17:(7):2105-2116, (Jul. 7, 1999).

Aversa, G. et al., "Engagement of the signaling lymphocytic activation molecule (SLAM) on activated T cells results in IL-2-independent, cyclosporin A-sensitive T cell proliferation and IFN-gamma production," J Immunol., 158-4036-4044, (1997).

(56) References Cited

OTHER PUBLICATIONS

Bajgain, P., et al., "Optimizing the production of suspension cells using the G-Rex "M" series," Mol. Ther. Methods Clin. Dev., 1:14015, (2014).

Baldan, V. et al., "Efficient and reproducible generation of tumour-infiltrating lymphocytes for renal cell carcinoma," BJC, 112:1510-1518, (2015).

Bast, Robert C., Jr. et al., "Critical questions in ovarian cancer research and treatment: Report of an American Association for Cancer Research Special Research," Cancer, 125:1963-1972, (2019).

Bedognetti, D. et al., "CXCR3/CCR5 Pathways in Metastatic Melanoma Pateients Treated with Adoptive Therapy and Interleukin-2," BJC, 109: 2412-2423, (2013).

Beltra, Jean-Christophe et al., "Developmental Relationships of Four Exhausted CD8+ T Cell Subsets Reveals Underlying Transcriptional and Epigenetic Landscape Control Mechanisms," Immunity, 52:825-841, (May 2020).

Besser, M.J., et al., "Adoptive transfer of tumor-infiltrating lymphocytes in patients with metastatic melanoma: intent-to-treat analysis and efficacy after failure to prior immunotherapies," Clin. Cancer Res., 19(17):4792-4800, (2013).

Besser, M.J., et al., "Clinical responses in a phase II study using adoptive transfer of short-term cultured tumor infiltration lymphocytes in metastatic melanoma patients," Clin. Cancer Res., 16(9):2646-2655, (2010).

Bhatia, Alka et al., "Tumour Infiltrating Lymphocytes: Changing Trends," Clinics in Oncology, 3:1409, (2018).

Blank, Christian U. et al., "Defining 'T cell exhaustion'," Nature Reviews Immunology, 19:665-674, (2019).

Boldajipour, Bjan et al., "Tumor-infiltrating lymphocytes are dynamically desensitized to antigen but are maintained by homeostatic cytokine," JCI Insight., 1(20):e89289, (2016).

Bologna et al., "Disclosures: Slamf-1/CD150 Is a Signaling Receptor Expressed by a Subset of Chronic Lymphocytic Leukemia Patients Characterized by a Favorable Prognosis," Blood 120(21):1770, (Nov. 16, 2012).

Bonanno, L. et al., The role of immune microenvironment in small-cell lung cancer: Distribution of PD-L1 expression and prognostic role of FOXP3-positive tumour infiltrating lymphocytes,: European Journal of Cancer, 101:191-200, (2018).

Borsa, Mariana et al., "Modulation of asymmetric cell division as a mechanism to boost CD8+ T cell memory," Sci. Immunol., 4(34):1-15, (Apr. 12, 2019).

Boussiotis, Vassiliki A. et al., "Prevention of T Cell Anergy by Signaling Through the γc Chain of the IL-2 Receptor," Science, 266:1039-1042, (Nov. 11, 1994).

Bowtell, David D. et al., "Rethinking ovarian cancer II: reducing mortality from high-grade serous ovarian cancer," Nat. Rev. Cancer, 15:668-679, (2015).

Brauner et al., "Workflow automation and parallelization improves the isolation and analysis of tumor-infiltrating immune cell subpopulations," Cancer Res. 77 (13_Supplement):1672, (Jul. 1, 2017).

Bridgeman et al., "Building better chimeric antigen receptors for adoptive T cell therapy," Curr. Gene Ther., 10(2):77-90, (2010).

Bridgeman et al., "CD3ζ-based chimeric antigen receptors mediate T cell activation via cis-and trans-signaling mechanisms: implications for optimization of receptor structure for adoptive cell therapy," Clin. Exp. Immunol., 175(2):258-267, (2014).

Bridgeman et al., Instil Bio Website, "In vitro analysis of tumor infiltrating lymphocytes," (Nov. 1, 2018). [Retrieved from Internet May 3, 2022; <URL: https://instilbio.com/wp-content/uploads/2021/01/2018-SITC-Poster-In-vitro-analysis-of-Tumour-Infiltrating-Lymphocytes-engineered-with-costimulatory.pdf>].

Bridgeman, John S. et al., "Genetic Engineering of Tumour Infiltrating Lymphocytes (TIL) with a Novel Recombinant Growth Factor Receptor for Treatment of Solid Tumours," Immetacyte, Ltd., 1 pg., (2018).

Bridgeman, John S. et al., "In vitro analysis of Tumour Infiltrating Lymphocytes engineered with costimulatory antigen receptors delivering targeted costimulation," Immetacyte, Ltd., 1 pg., (2018).

Bright, Richard et al. "Clinical Response Rates from Interleukin-2 Therapy for Metastatic Melanoma Over 30 Years' Experience: A Meta-Analysis of 3312 Patients," J Immunother, 40(1): 21-30, (Jan. 2017).

Browning et al., "The T cell activation marker CD150 can be used to identify alloantigen-activated CD4(+)25+ regulatory T cells," Cell. Immunol., 227(2):129-139, (2004).

Buchbinder, Elizabeth I. et al., "A retrospective analysis of High-Dose Interleukin (HD IL-2) following IL-2 Ipilimumab in metastatic melanoma," Journal for ImmunoTherapy of Cancer, 7:52, (2016).

Buchbinder, Elizabeth I. et al., "Therapy with high-dose Interleukin-2 (HD IL-2) in metastatic melanoma and renal cell carcinoma following PD1 and PDL1 inhibition," Journal for ImmunoTherapy of Cancer, 7:49, (2019).

Byrne, Ann et al., "Tissue-resident memory T cells in breast cancer control and immunotherapy responses," Nature Reviews Clinical Oncology, 17:341-348, (2020).

Cafri, Gal et al., "Memory T cells targeting oncogenic mutations detected in peripheral blood of epithelial cancer patients," Nature Communications, 10:449, (2019).

Camp, F.A., et al., "Implications of Antigen Selection on T Cell-Based Immunotherapy," Pharmaceuticals (Basel), 14(10):993, (2021).

Canale, Fernando P. et al., "CD39 Expression Defines Cell Exhaustion in Tumor-Infiltrating CD8+ T cells," Cancer Research, 78(1):115-128, (2018).

Caushi, Justina X. et al., "Transcriptional programs of neoantigen-specific TIL in anti-PD-1-treated lung cancers," Nature, 596:126-132, (2021).

Cervera-Carrascon, V. et al., "TNFa and IL-2 armed adenoviruses enable complete responses by anti-PD-1 checkpoint blockade," OncoImmunology, 7(5):1-11, (2018).

Chacon, Jessica Ann et al., "Manipulating the Tumor Microenvironment Ex Vivo for Enhanced Expansion of Tumor-Infiltrating Lymphocytes for Adoptive Cell Therapy," Clin Cancer Research, 21(3):611-621, (Feb. 2015).

Challier, Cécile et al., "The cytoplasmic domain of Mpl receptor transduces exclusive signals in embryonic and fetal hematopoietic cells," Blood, 100:2063-2070, (2002).

Charych, Deborah et al., "NKTR-214, an Engineered Cytokine with Biased IL2 Receptor Binding, Increased Tumor Exposure, and Marked Efficacy in Mouse Tumor Models," Clin. Cancer Res., 22(3):680-290, (Feb. 1, 2016).

Charych, Deborah et al., "Tipping the balance in the tumor microenvironment: An engineered cytokine (NKTR-214) with altered IL2 receptor binding selectivity and improved efficacy," Cancer Research, 73(8), Abstract, (Apr. 2013).

Chen, Zeyu et al., "TCF-1-Centered Transcriptional Network Drives an Effector versus Exhausted CD8 T Cell-Fate Decision," Immunity, 51:1-16, (2019).

Chesney, Ja et al., "Trial in Progress: A Phase 2 Multicenter Study (IOV-LUN-202) of Autologous Tumor-Infiltrating Lymphocyte (TIL) Cell Therapy (LN-145) in Patients with Metastatic Non-Small Cell Lung Cancer (mNSCLC)," 7948 AACR Annual Meeting, New Orleans, LA, (Apr. 8-13, 2022).

Chesney, Jason Alan et al., "A phase II study of autologous tumor infiltrating lymphocytes (TIL, LN-144/LN-145) in patients with solid tumors," 290a ASCO Annual Meeting, Chicago, IL, (May 31-Jun. 4, 2019).

Chesney, Jason Alan et al., "A phase II study of autologous tumor infiltrating lymphocytes (TIL, LN-144/LN-145) in patients with solid tumors," J Clin Oncol., 37:Suppl., Abstract TPS2648, (2019).

Chu, Talyn et al., "Charting the Roadmap of T Cell Exhaustion," Immunity, 52:724-26, (2020).

Chuang, Huai-Chia et al., "Epstien-Barr virus LMP1 inhibits the expression of SAP gene and upregulates Th1 cytokines in the pathogenesis of hemophagocytic syndrome," Blood, 106:3090-3096, (2005).

CipherBio Data Team, "$18 Billion Invested in 135 Cell Therapy Companies," CipherBio News, (Aug. 18, 2021). [Retrieved from the internet Aug. 18, 2021; URL: <https://cipherbio.com>].

clinicaltrials.gov, "Study of Autologous Tumor Infiltrating Lymphocytes in Patients with Solid Tumors, Trial Record 1 of 1 for:

(56) References Cited

OTHER PUBLICATIONS

IOV-COM-202," (Apr. 14, 2020). [Retrieved from the Internet Apr. 14, 2020: <URL: https://www.clinicaltrials.gov/ct2/show/NCT03645928?term=IOV-COM-202&draw=2&rank=1>].
clinicaltrials.gov, "Study of Lifileucel (LN-144), Autologous Tumor Infiltrating Lymphocytes, in the Treatment of Patients With Metastatic Melanoma (LN-144), Trial record 5 of 14 for: iovance," (Dec. 23, 2019) [Retrieved from the Internet Dec. 23, 2019): <URL: https://https://www.clinicaltrials.gov/ct2/show/study/NCT02360579?term=iovance&draw=2&show_locs=Y#locn>].
Clover Biotech Research, "Iovance Biotherapeutics: Compelling Bet in Metastatic Melanoma," 6 pgs., Press Release, Aug. 14, 2018.
Cohen, Paul A. et al., "Pathological chemotherapy response score is prognostic in tubo-ovarian high-grade serous carcinoma: A systematic review and meta-analysis of individual patient data," Gynecologic Oncology, 154:441-448, (2019).
Costantini, A. et al., "Effects of cryopreservation on lymphocyte immunophenotype and function," JIM, 278:145-155, (2003).
Creelan, Ben et al., "Durable complete responses to adoptive cell transfer using tumor infiltrating lymphocytes (TIL) in non-small cell lung cancer (NSCLC): A phase I trial," AACR Annual Meeting, CT056, Abstract, (2020).
Creelan, Benjamin C. et al., "Tumor-infiltrating lymphocyte treatment for anti-PD-1-resistant metastatic lung cancer: a phase 1 trial," Nature Medicine, 27:1410-1418, (2021).
Crookes, H. et al., "Stability consideration for cryopreserved starting material to facilitate large-scale production of ATMPs," Cytotherapy, 22:S26-S186, Abstracts, (2020).
Crowther, Michael D. et al., "T-Cell Gene Therapy in Cancer Immunotherapy: Why It is No Longer Just CARs on the Road," 9(7):1588, (2020).
Crunkhorn, Sarah, "Designing cytokine mimics can optimize cancer therapy potential," Nature Reviews Drug Discovery, 18(3):173, (Mar. 2019).
Cubas, Rafael et al., "AKT inhibition during ex vivo TIL expansion enhances cytokine production and function while increasing the population of less differentiated (CD39-CD69-) CD8+ T-Cells," 54P ESMO Immuno-Oncology, Geneva, Switzerland, (Dec. 8-11, 2021).
Cytiva, "Improve outcomes for TIL therapies by tackling process challenges," Fierce Biotech, [Retrieved from the Internet Nov. 24, 2020: https://www.fiercebiotech.com/sponsored/improve-outcomes-for-til-therapies-by-tackling-process-challenges].
Dafni, U., et al., "Efficacy of adoptive therapy with tumor-infiltrating lymphocytes and recombinant interleukin-2 in advanced cutaneous melanoma: a systematic review and meta-analysis," Ann. Oncol., 30(12):1902-1913, (2019).
Danaher, Patrick et al., "Gene expression markers of tumor-infiltrating leukocytes," NanoString Technologies, 1 pg., (Nov. 2016).
Dangaj, Denarda et al., "Cooperation between Constitutive and Inducible Chemokines Enables T Cell Engraftment and Immune Attack in Solid Tumors," Cancer Cell, 35:885-900, (2019).
Davar, Diwakar et al., "High-dose interleukin-2 (HD IL-2) for advanced melanoma: a single center experience from the University of Pittsburgh Cancer Institute," Journal for ImmunoTherapy of Cancer, 5:1-10, (2017).
Deleeuw, Ronald J. et al., "The Prognostic Value of FoxP3+ Tumor-Infiltrating Lymphocytes in Cancer: A Critical Review of the Literature," Clin Cancer Res, 18(11):3022-3029, (2012).
Deniger, D.C., et al., "A Pilot Trial of the Combination of Vemurafenib with Adoptive Cell Therapy in Patients with Metastatic Melanoma," Clin. Cancer Res., 23(2):351-362 (2017).
Dillman, R.O., et al., "Continuous interleukin-2 and tumor-infiltrating lymphocytes as treatment of advanced melanoma. A national biotherapy study group trial," Cancer, 68(1):1-8, (1991).
Ding, Wei et al., "Prognostic value of tumor-infiltrating lymphocytes in hepatocellular carcinoma," Medicine, 97:e13301, (2018).
Donia et al., "Simplified protocol for clinical-grade tumor-infiltrating lymphocyte manufacturing with use of the Wave bioreactor," Cytotherapy 16(8):1117-1120, (Aug. 1, 2014).
Donia, M., et al., "Characterization and comparison of 'standard' and 'young' tumour-infiltrating lymphocytes for adoptive cell therapy at a Danish translational research institution," Scand. J. Immunol. 75(2):157-167, (2012).
Drachman et al., "Studies with chimeric Mpl/JAK2 receptors indicate that both JAK2 and the membrane-proximal domain of Mpl are required for cellular proliferation," J. Biol. Chem., 277(26):23544-23553, (2002).
Dudley, M.E., "Adoptive Cell Therapy for Patients with Melanoma," J. Cancer, 2:360-362, (2011).
Dudley, M.E., et al., "A phase I study of nonmyeloablative chemotherapy and adoptive transfer of autologous tumor antigen-specific T lymphocytes in patients with metastatic melanoma," J. Immunother., 25(3):243-251, (2002).
Dudley, M.E., et al., "Adoptive cell therapy for patients with metastatic melanoma: evaluation of intensive myeloablative chemoradiation preparative regimens," J. Clin. Oncol., 26(32):5233-5239, (2008).
Dudley, M.E., et al., "Adoptive cell transfer therapy following non-myeloablative but lymphodepleting chemotherapy for the treatment of patients with refractory metastatic melanoma," J. Clin. Oncol., 23(10):2346-2357, (2005).
Dudley, M.E., et al., "Adoptive cell transfer therapy." Semin. Oncol., 34(6):524-531, (2007).
Dudley, M.E., et al., "Adoptive-cell-transfer therapy for the treatment of patients with cancer," Nat. Rev. Cancer, 3(9):666-675, (2003).
Dudley, M.E., et al., "Cancer regression and autoimmunity in patients after clonal repopulation with antitumor lymphocytes," Science, 298(5594):850-854, (2002).
Dudley, M.E., et al., "CD8+ enriched "young" tumor infiltrating lymphocytes can mediate regression of metastatic melanoma," Clin. Cancer. Res., 16(24):6122-6131, (2010).
Dudley, M.E., et al., "Generation of tumor-infiltrating lymphocyte cultures for use in adoptive transfer therapy for melanoma patients," J. Immunother., 26(4):332-342, (2003).
Dudley, M.E., et al., "Randomized selection design trial evaluating CD8+-enriched versus unselected tumor-infiltrating lymphocytes for adoptive cell therapy for patients with melanoma," J. Clin. Oncol., 31(17):2152-2159, (2013).
Dudley, Mark E. et al., "Adoptive Cell Transfer Therapy Following Non-Myeloablative but Lymphodepleting Chemotherapy for the Treatment of Patients with Refractory Metastatic Melanoma," J Clin Oncol., 23:2346-2357, (2018).
Dudley, Mark E. et al., "Cancer Regression and Autoimmunity in Patients after Clonal Repopulation with Antitumor Lymphocytes," Science, 298:850-854, (2002).
Dunbar, P. Rod et al., "Cutting Edge: Rapid Cloning of Tumor-Specific CTL Suitable for Adoptive Immunotherapy of Melanoma," JIM, 162:6959-6962, (1999).
Duraiswamy, Jaikumar et al., "Myeloid antigen-presenting cell niches sustain antitumor T cells and license PD-1 blockade via CD28 costimulation," Cancer Cell, 39:1-20, (2021).
Eisenberg, Galit et al., "Soluble SLAMF6 Receptor Induces Strong CD8+ T-cell Effector Function and Improves Anti-melanoma Activity In Vivo," Cancer Immunology Research 6(2):127-138, (2018).
Elkord, Eyad, "Frequency of human T regulatory cells in peripheral blood in significantly reduced by cryopreservation," JIM, 347:87-90, (2009).
Ellebaek, Eva et al., "Adoptive cell therapy with autologous tumor infiltrating lymphocytes and low-dose Interleukin-2 in metastatic melanoma patients," Journal of Translational Medicine, 10:169, (2012).
Fan, Xiaozhou et al., "Engagement of the ICOS pathway markedly enhances efficacy of CTLA-4 blockade in cancer immunotherapy," J. Exp. Med., 211:715-725, (2014).
Fan, Xin-Juan et al., "Impact of Cold Ischemic Time and Freeze-Thaw Cycles on RNA, DNA and Protein Quality in Colorectal Cancer Tissues Biobanking," Journal of Cancer, 10(20):4978-4988, (2019).

(56) References Cited

OTHER PUBLICATIONS

Forget, M.A., et al., "Activation and propagation of tumor-infiltrating lymphocytes on clinical-grade designer artificial antigen-presenting cells for adoptive immunotherapy of melanoma," J. Immunother., 37(9):448-460, (2014).

Forget, M.A., et al., "The beneficial effects of a gas-permeable flask for expansion of Tumor-Infiltrating lymphocytes as reflected in their mitochondrial function and respiration capacity," Oncoimmunology, 5(2):e1057386, (2015).

Forget, Marie-Andrée et al., A Novel Method to Generate and Expand Clinical-Grade, Genetically Modified, Tumor-Infiltrating Lymphocytes, Frontiers in Immunology, 8(908):1-8, (2017).

Forget, Marie-Andrée et al., "Prospective Analysis of Adoptive TIL Therapy in Patients with Metastatic Melanoma: Response, Impact of Anti-CTLA4, and Biomarkers to Predict Clinical Outcome," Clin Cancer Res, 24:4416-4428, (2018).

Forget, Marie-Andrée et al., "TIL therapy and anti-CTLA4: can they co-exist?," Oncotarget, 10:1-2, (2019).

Fox, Norma E. et al., "F104S c-Mpl responds to a transmembrane domain-binding thrombopoietin receptor agonist: Proof of concept that selected receptor mutations in congenital amegakaryocytic thrombocytopenia can be stimulated with alternative thrombopoietic agents," Exp Hematol., 38(5):384-391, (2010).

Frank, Ian et al., "Remarkably stable tumor-infiltrating lymphocytes (TIL) for infusion phenotype following cryopreservation," Poster #11, Lion Biotechnologies, Society for Immunotherapy of Cancer, National Harbor, Maryland, MD, 1 pg., (Nov. 9-13, 2016).

Friedman, K.M., et al., "Augmented lymphocyte expansion from solid tumors with engineered cells for costimulatory enhancement," J. Immunother., 34(9):651-661, (2011).

Friedman, K.M., et al., "Tumor-specific CD4+ melanoma tumor-infiltrating lymphocytes," J. Immunother., 35(5):400-408, (2012).

Fujii, Hodaka et al., "Functional dissection of the cytoplasmic subregions of the IL-2 receptor βc chain in primary lymphocyte populations," The EMBO Journal, 17:6551-6557, (1998).

Ganesan, Anusha-Preethi et al., "Tissue-resident memory features are linked to the magnitude of cytotoxic T cell responses in human lung cancer," Nature Immunology, 18:940-950, (2017).

Garber, Ken, "Pursuit of tumor-infiltrating lymphocyte immunotherapy speeds up," Nat Biotechnol., 37(9):969-971, (Sep. 2019).

Gastman et al., "544: DELTA-1: A global, multicenter phase 2 study of ITIL-168, an unrestricted autologous tumor-infiltrating lymphocyte (TIL) cell therapy, in adult patients with advanced cutaneous melanoma," J. Immunother. Canc. 9(Supplement 2):A573, (Nov. 1, 2021). [Retrieved from the Internet Nov. 1, 2021 <URL: https://jitc.bmj.com/content/jitc/9/Suppl_2/A573.full.pdf>].

Gattinoni, Luca et al., "Adoptive immunotherapy for cancer: building on success," Nature Reviews Immunology, 6:383-393, (2006).

Gee, Marvin H. et al., "Antigen Identification for Orphan T Cell Receptors Expressed on Tumor-Infiltrating Lymphocytes," Cell, 172:1-15, (2018).

Gettinger, S. et al., "Phase II, multicenter study of autologous tumor infiltrating lymphocytes (TIL, LN 144/LN-145/LN-145-S1) in patients with solid tumours," Journal of Thoracic Oncology, 16(4S):S799-800, (2021).

Gettinger, S.N. et al., "A dormant TIL phenotype defines non-small cell lung carcinomas sensitive to immune checkpoint blockers," Nature Communications, 9(3196):1-15, (2018).

Ghasemi, Reza et al., "Selective targeting of IL-2 to NKG2D bearing cells for improved immunotherapy," Nature Communications, 7(1):1-15, (2016).

Giraldo et al., "Tumor-Infiltrating and Peripheral Blood T-cell Immunophenotypes Predict Early Relapse in Localized Clear Cell Renal Cell Carcinoma," Clin. Cancer Res., 23(15):4416-4428, (Feb. 17, 2017).

Goedegebuure, P.S., et al., "Adoptive immunotherapy with tumor-infiltrating lymphocytes and interleukin-2 in patients with metastatic malignant melanoma and renal cell carcinoma: a pilot study," J. Clin. Oncol., 13(8):1939-1949, Abstract (1995).

Goff, S.L., et al., "Randomized, Prospective Evaluation Comparing Intensity of Lymphodepletion Before Adoptive Transfer of Tumor-Infiltrating Lymphocytes for Patients With Metastatic Melanoma," J. Clin. Oncol., 34(20):2389-2397, (2016).

Goff, S.L., et al., "Tumor infiltrating lymphocyte therapy for metastatic melanoma: analysis of tumors resected for TIL," J. Immunother., 33(8):840-847, (2010).

Gokuldass, Aishwarya et al., "Redirected lysis assay as an efficient potency assay to assess TILs for immunotherapy," Poster #14, Lion Biotechnologies, Society for Immunotherapy of Cancer, National Harbor, Maryland, MD, 1 pg., (Nov. 9-13, 2016).

Gontcharova, V. et al., "Persistence of cryopreserved tumor-infiltrating lymphocyte product lifileucel (LN-144) in C-144-01 study of advanced metastatic melanoma," AACR Annual Meeting, LB-069 /14, Abstract, (Mar. 29-Apr. 3, 2019).

Gordiienko, I.M. et al., "Differential expression of CD150/SLAMF1 in normal and malignant B cells on the different stages of maturation," Exp.Oncol., 38(2):101-107, (2016).

Granhøj, J.S., et al., "Tumor-infiltrating lymphocytes for adoptive cell therapy: recent advances, challenges, and future directions," Expert Opin. Biol. Ther., 22(5):627-641, (2022).

Grimm, E.A., et al., "Characterization of interleukin-2-initiated versus OKT3-initiated human tumor-infiltrating lymphocytes from glioblastoma multiforme: growth characteristics, cytolytic activity, and cell phenotype," Cancer Immunol. Immunother., 32(6):391-399, Abstract (1991).

Grimm, Elizabeth A. et al., "Lymphokine-Activated Killer (LAK) Cell Phenomenon," J Exp. Med., 155:1823-1841, (Jun. 1982).

Gros, Alena et al., "PD-1 identifies the patient-specific CD8+ tumor-reactive repertoire infiltrating human tumors," J Clin. Invest., 124(5):2246-2259, (2014).

Gros, Alena et al., "Recognition of Human Gastrointestinal Cancer Neoantigens by Circulating PD-1 Lymphocytes," J Clin. Invest., 129(11):4992-5004, (2019).

Guo, Xinyi et al., "Global characterization of T cells in non-small-cell lung cancer by single-cell sequencing," Nature Medicine, 24:978-985, (2018).

Gurney, Austin L. et al., "Distinct regions of c-Mpl cytoplasmic domain are coupled to the JAK-STAT signal transduction pathway and Shc phosphorylation," PNAS, 92:5292-5296, (1995).

Halbert, Brian et al., "Successful Generation of Tumor-Infiltrating Lymphocyte (TIL) Product From Renal Cell Carcinoma Tumors for Adoptive Cell Therapy," 176 SITC, Washington DC & Virtual, (Nov. 10-14, 2021).

Hall, M., et al., "Expansion of tumor-infiltrating lymphocytes (TIL) from human pancreatic tumors," J. Immunother. Cancer, 4:61, (2016).

Hamalainen, Heli et al., "Signaling lymphocytic activation molecule (SLAM) is differentially expressed in human Th1 and Th2 cells," Journal of Immunological Methods, 242:9-19, (2000).

Hamanishi, Junzo et al., "Programmed cell death 1 ligand 1 and tumor-infiltrating CD8+ T lymphocytes are prognostic factors of human ovarian cancer," PNAS, 104:3360-3365, (Feb. 27, 2007).

Harjes, Ulrike, "States of exhaustion," Nature Reviews Cancer, 19;185, (2019).

Hatzis, Christos et al., "Effects of Tissue Handling on RNA Integrity and Microarray Measurements from Resected Breast Cancers," J Natl. Cancer Inst., 103:1871-1883, (Dec. 21, 2011).

Hawkins, Robert et al., "Treatment patterns and health outcomes in metastatic renal cell carcinoma patients treated with targeted systemic therapies in the UK," BMC Cancer, 20:670, (2020).

Hayakawa, M., et al., "[Study on adoptive immunotherapy with tumor-infiltrating lymphocytes (TIL) for renal cell carcinoma] Japanese," Nihon Hinyokika Gakkai Zasshi, 81(1):103-109, (1990).

He, J., et al., "Ex vivo expansion of tumor-infiltrating lymphocytes from nasopharyngeal carcinoma patients for adoptive immunotherapy," Chin. J. Cancer, 31(6):287-294, (2012).

Heemskerk, Bianca et al., "Adoptive Cell Therapy for Patients with Melanoma, Using Tumor-Infiltrating Lymphocytes Genetically Engineered to Secrete Interleukin-2," Human Gene Therapy, 19:496-510, (May 2008).

(56) References Cited

OTHER PUBLICATIONS

Henning, Golo et al., "Signaling lymphocytic activation molecule (SLAM) regulates T cellular cytotoxicity," Eur. J. Immunol.31:2741-2750, (2001).
Hildreth, C., "CAR-T Companies Proliferate: List of CAR-T Companies Worldwide," BioInformant, (Aug. 30, 2021). [Retrieved from the internet Nov. 19, 2021; URL: <https://bioinformant.com/car-t-companies-the-meteoric-rise-of-cellular-immunotherapies/>].
Hinrichs, Christian S. et al., "Exploiting the curative potential of adoptive T-cell therapy for cancer," Imuunol. Reviews, 257:56-71, (2014).
Hoch, Ute et al., "NKTR-214: An immunotherapy with altered selectivity at the IL2 receptor; pharmacokinetics (PK) and pharmacodynamics (PD) in animal models," Molecular Cancer Therapeutics, 12(11), Abstract, (Nov. 2013).
Hong, J.J., et al., "Successful treatment of melanoma brain metastases with adoptive cell therapy," Clin. Cancer Res., 16(19):4892-4898, (2010).
Hopewell, E.L., et al., "Tumor-infiltrating lymphocytes: Streamlining a complex manufacturing process," Cytotherapy, 21(3):307-314, (2019).
Howie, Duncan et al., "The role of SAP in murine CD150 (SLAM)-mediated T-cell proliferation and interferon γ production," Blood, 100:2899-2907, (2002).
Huang, Chih-Yang et al., "Cytosolic high-mobility group box protein 1 (HMGB1) and/or PD-1+ TILs in the tumor microenvironment may be contributing prognostic biomarkers for patients with locally advanced rectal cancer who have undergone neoadjuvant chemoradiotherapy," Cancer Immunology, Immunotherapy, 67:551-562, (2018).
Huang, J., et al., "Survival, persistence, and progressive differentiation of adoptively transferred tumor-reactive T cells associated with tumor regression," J. Immunother., 28(3):258-267, (2005).
Hulen, Thomas Morgan et al., "ACT Up TIL Now: The Evolution of Tumor-Infiltrating Lymphocytes in Adoptive Cell Therapy for the Treatment of Solid tumors," Immuno, 1:194-211, (2021).
Ikarashi, H., et al., "Solid-phase anti-CD3 antibody activation and cryopreservation of human tumor-infiltrating lymphocytes derived from epithelial ovarian cancer," Jpn. J. Cancer Res., 83(12):1359-1365, (1992).
Imai et al., "Expression of multiple immune checkpoint molecules on T cells in malignant ascites from epithelial ovarian carcinoma," Oncol. Lett., 15(5):6457-6468, (Feb. 21, 2018).
Inozume, T., et al., "Selection of CD8+PD-1+ lymphocytes in fresh human melanomas enriches for tumor-reactive T cells," J. Immunother., 33(9):956-964, (2010).
Iovance Biotherapeutics, "Iovance Biotherapeutics Announces 33-Month Follow Up Data for Lifileucel in Advanced Melanoma at ASCO 2021 Annual Meeting," Press Release, 2 pgs., Jun. 6, 2021.
Iovance Biotherapeutics, "Iovance Biotherapeutics Announces Clinical Data for LN-145 in Non-Small Cell Lung Cancer," Press Release, 2 pgs., Jun. 29, 2021.
Iovance Biotherapeutics, "Iovance Biotherapeutics Announces Clinical Data Updates for Lifileucel in Advanced Melanoma at Upcoming ASCO 2021 Annual Meeting," Press Release, 2 pgs., May 19, 2021.
Iovance Biotherapeutics, "Iovance Biotherapeutics Announces Clinical Data Updates for Lifileucel in Advanced Melanoma During American Association for Cancer Research (AACR) 2021 Annual Meeting," Press Release, 3 pgs., Apr. 9, 2021.
Iovance Biotherapeutics, "Iovance Biotherapeutics Announces New LN-144 Phase 2 Clinical Data from Metastatic Melanoma Trial to be Presented at SITC Meeting," Press Release, 5 pgs, Nov. 9, 2017.
Iovance Biotherapeutics, "Iovance Biotherapeutics announces Preliminary Phase 2 Dada for TIL Treatment in Head and Neck and Cervical Cancers," Press Release, 3 pgs., Jan. 24, 2018.
Iovance Biotherapeutics, "Iovance Biotherapeutics Announces Updated Phase 2 Clinical Data from the Lifileucel Metastatic Melanoma Trial at the Society for Immunotherapy of Cancer 34th Annual Meeting," Press Release, 2 pgs., Nov. 8, 2019.
Iovance Biotherapeutics, "Iovance Biotherapeutics announces updates to tumor infiltrating lymphocyte (TIL) therapy clinical programs," Press Release, 2 pgs., May 15, 2019.
Iovance Biotherapeutics, "Iovance Biotherapeutics reports results from FDA end of Phase 2 meeting and provides updates about the company's clinical program," Press Release, 3 pgs., Oct. 11, 2018.
Iovance Biotherapeutics, "Journal of Clinical Oncology Publishes Clinical Data for Cohort 2 in Iovance C-144-01 Study of Lifileucel TIL-Therapy in Metastatic Melanoma," Press Release, 2 pgs., May 12, 2021.
Iovance Biotherapeutics, "Lion Biotechnologies Announces First Patient Dosed in Second Cohort of LN-144 Phase 2 Trial for Metastatic Melanoma," Press Release, 2 pgs., May 19, 2017.
Iovance Biotherapeutics, "Updated Results of Studies in Advanced Cervical Cancer and Melanoma Support Long-Term Efficacy of Iovance Tumor Infiltrating Lymphocyte (TIL) Therapy," Press Release, 3 pgs., May 31, 2019.
Iovance Biotherapeutics, Cohort 2 by Investigator, Responders Previously Progressed on Checkpoint Inhibitors, Chart, 1 pg., (2020).
Itzhaki, O., et al., "Establishment and large-scale expansion of minimally cultured "young" tumor infiltrating lymphocytes for adoptive transfer therapy," J. Immunother., 34(2):212-220, (2011).
Janakiram, M. et al., "Tumor infiltrating lymphocytes as a prognostic and predictive biomarker in breast cancer," Molecular Pathology of Breast Cancer, 12:1-20, (2016).
Jang et al., "Characterization of T cell repertoire of blood, tumor, and ascites in ovarian cancer patients using next generation sequencing," Oncoimmunology, 4(11):e1030561, (2015).
Jansen, Caroline S. et al., "An intra-tumoral niche maintains and differentiates stem-like CD8 T cells," Nature, 576:465-470, (2019).
Jazaeri, Amir A. et al., "Safety and efficacy of adoptive cell transfer using autologous tumor infiltrating lymphocytes (LN-145) for treatment of recurrent, metastatic, or persistent cervical carcinoma," 182 ASCO Annual Meeting, Chicago, IL, (May 31-Jun. 4, 2019).
Jazaeri, Amir A. et al., "Safety and efficacy of adoptive cell transfer using autologous tumor infiltrating lymphocytes (LN-145) for treatment of recurrent, metastatic, or persistent cervical carcinoma," J. Clin. Oncol., 37:Suppl., Abstract 2538, (2019).
Jazaeri, Amir, "A phase 2, multicenter study to evaluate the efficacy and safety of using autologous tumor infiltrating lymphocytes (LN-145) in patients with recurrent, metastatic, or persistent cervical carcinoma," P220 SITC Annual Meeting, National Harbor, MD, (Nov. 8-12, 2017).
Jazaeri, Amir, "In vivo persistence of Iovance tumour-infiltrating lymphocytes LN-145 in cervical cancer patients," 3688 ESMO Virtual Congress, (Sep. 19-21, 2020).
Jazaeri, Amir, "In vivo persistence of Iovance tumour-infiltrating lymphocytes LN-145 in cervical cancer patients," Iovance Biotherapeutics, Inc., 873P, Abstract, (2020).
Jazaeri, Amir, "Trial in Progress: A Phase 2, Multicenter Study to Evaluate the Efficacy and Safety Using Autologous Tumor Infiltrating Lymphocytes (LN-145) in Patients with Recurrent, Metastatic, or Persistent Cervical Carcinoma," 329a ASCO Annual Meeting, McCormick Place, Chicago, IL, (Jun. 1-5, 2018).
Jespersen, Henrik et al., "Clinical responses to adoptive T-cell transfer can be modeled in an autologous immune-humanized mouse model," Nature Communications, 8:707, (2017).
Jiang, Li et al., "Ovarian Cancer-Intrinsic Fatty Acid Synthase Prevents Anti-tumor Immunity By Disrupting Tumor-Infiltrating Dendritic Cells," Frontiers in immunology, 9:2927, (2018).
Jiang, Peng et al., "Signatures of T cell dysfunction and exclusion predict cancer immunotherapy response," Nature Medicine, 24:1550-1558, (2018).
Jimenez-Reinoso, A., et al., "Synthetic TILs: Engineered Tumor-Infiltrating Lymphocytes With Improved Therapeutic Potential," Front. Oncol., 10:593848, (2021).
Jin, Jianjian et al., "Simplified Method of the Growth of Human Tumor Infiltrating Lymphocytes in Gas-permeable Flasks to Numbers Needed for Patient Treatment," J Immunother. 35(3):283-292, (2012).

(56) References Cited

OTHER PUBLICATIONS

Jinghua, Lu et al., "Molecular Constraints on CDR3 For Thymic Selection of MHC-restricted TCRs From a Random Pre-selection Repertoire," Nature Communications, 10:1-14, (2019).
Jones, E. Yvonne, "Designer protein delivers signal of choice," Nature, 565:165-166, (Jan. 10, 2019).
Kalaora, Shelly et al., "Combined analysis of Antigen Presentation and T-cell Recognition Reveals Restricted Immune Responses in Melanoma," Cancer Discov 8(11): 1366-1375, (2018).
Kallies, Axel et al., "Precursor exhausted T cells: key to successful immunotherapy?" Nature Reviews Immunology, 20:128-136, (2020).
Kao, Yun-Ruei et al., "Thrombopoietin receptor-independent stimulation of hematopoietic stem cells by eltrombopag," Sci. Transl. med., 10:eaas9563, (2018).
Kappler, John et al., "Pillars Article: The Major Histocompatibility Complex-restricted Antigen Receptor on T Cells in Mouse and Man: Identification of Constant and Variable Peptides," Cell, 35:295-302, (1983).
Karyampudi, Lavakumar et al., "Iovance Peripheral Blood Lymphocytes (PBL): A Potential Cell Therapy Strategy for the Treatment of Chronic Lymphocytic Leukemia," PF447 EHA Annual Meeting, RAI Amsterdam, Amsterdam, Netherlands, (Jun. 13-16, 2019).
Karyampudi, Lavakumar et al., "Phenotypic and functional characterization of tumor infiltrating lymphocytes (TIL) grown from non-hodgkin lymphoma tumors—implications for the development of novel therapies for lymphoma," ESMO Annual Meeting, Madrid, Spain, (Sep. 7-12, 2017).
Kawahara et al., "Engineering of mammalian cell membrane proteins," Curr. Opin. Chem. Eng., 1:411-417, (2012).
Kawahara et al., "Growth promotion of genetically modified hematopoietic progenitors using an antibody/c-Mpl chimera," Cytokine, 55(3):402-408, (2011).
Kawahara, Masahiro et al., "Engineering cytokine receptors to control cellular functions," Biochemical Engineering Journal, 48:283-294, (2010).
Kershaw, Michael H. et al., "A Phase I Study on Adoptive Immunotherapy Using Gene-Modified T Cells for Ovarian Cancer," Clin Cancer Res, 12:6106-6115, (2006).
Khalil, Danny N. et al., "In situ vaccination with defined factors overcomes T cell exhaustion in distant tumors," J Clin. Invest., 129:3435-3447, (2019).
Khan, Omar et al., "TOX transcriptionally and epigenetically programs CD8+ T cell exhaustion," Nature, 571:211-218, (2019).
Kim, Peter et al., "Adoptive T Cell Therapy Targeting Somatic P53 Mutations," J Immunother Cancer, 8: A165, (2020).
Kirken, Robert A. et al., "Activation of JAK3, but not JAK1, is Critical for IL-2-Induced Proliferation and STAT5 Recruitment by a COOH-Terminal Region of the IL-2 Receptor β-Chain," Cytokine, 7:689-700, (1995).
Kivimäe, Saul et al., "Harnessing the innate and adaptive immune system to eradicate treated and distant untreated solid tumors," Society for Immunotherapy of Cancer 2017 Annual Meeting, Poster #P275, (2017).
Klapper, J.A., et al., "Single-pass, closed-system rapid expansion of lymphocyte cultures for adoptive cell therapy," J. Immunol. Methods, 345(1-2):90-99, (2009).
Klapper, J.A., et al., "Thoracic mastectomy for adoptive immunotherapy of melanoma: a single-institution experience," J. Thorac. Cardiovasc. Surg., 140(6):1276-1282, (2010).
Kotsakis, Athanasios et al., "Myeloid-derived suppressor cell measurements in fresh and cryopreserved blood samples," JIM, 381(102):14-22, (2012).
Kovacsovics-Bankowski et al., "Detailed characterization of tumor infiltrating lymphocytes in two distinct human solid malignancies show phenotypic similarities," J. Immunother. Cancer, 2(1):38, (2014).
Krause, Anja et al., "Antigen-dependent CD28 Signaling Selectively Enhances Survival and Proliferation in Genetically Modified Activated Human Primary T Lymphocytes," J. Exp. Med., 188:619-626, (1998).
Kreher, Christian R. et al., "CD4+ and CD8+ cells in cryopreserved human PBMC maintain full functionality in cytokine ELISPOT assays," JIM, 278:79-93, (2003).
Krishna, Sri et al., "Stem-like CD8 T cells Mediate Response of Adoptive Cell Immunotherapy Against Human Cancer," Science, 370: 1328-1334, (2020).
Kurtulus, Sema et al., "Checkpoint Blockade Immunotherapy Induces Dynamic Changes in PD-1-CD8+Tumor-Infiltrating T Cells," Immunity, 50:1-14, (2019).
Kverneland, Anders Handrup et al., "Adoptive cell therapy with tumor-infiltrating lymphocytes supported by checkpoint inhibition across multiple solid cancer types," Journal for ImmunoTherapy of Cancer, 9:e003499, (2021).
Kvistborg, Pia et al., "TIL therapy broadens the tumor-reactive CD8+ T cell compartment in melanoma patients," OncoImmunology, 1:409-418, (2012).
Lanitis, Evripidis et al., "Chimeric antigen receptor T Cells with dissociated signaling domains exhibit focused antitumor activity with reduced potential for toxicity in vivo," Cancer Immunol. Res., 1(1):43-53, (2013).
Lauss, Martin et al., "Mutational and putative neoantigen load predict clinical benefit of adoptive T cell therapy in melanoma," Nature Communications, 8:1738, (2017).
Lazear, Eric et al., "Targeting of IL-2 to cytotoxic lymphocytes as an improved method of cytokine-driven immunotherapy," Oncoimmunology, 1265721:1-3, (2017).
Lazier, Eric et al., "Novel Immuno-oncology Strategy for Targeted Cytotoxic Lymphocyte Activation," Courier Therapeutics, University of Virginia, 1 pg., (2017).
Lee, S., et al., "Tumor-infiltrating lymphocytes in melanoma," Curr. Oncol. Rep., 14(5):468-474, (2012).
Lee, Sylvia et al. "Phase 2 Study to Assess the Efficacy and Safety of Autologous Tumor Infiltrating Lymphocytes (LN-145) Alone and In Combination with Anti-PD-L1 Inhibitor Durvalumab (MEDI4736) in Patients with Locally Advanced or Metastatic Non-Small Cell Lung Cancer (NSCLC)," 318a ASCO Annual Meeting, McCormick Place, Chicago, IL, (Jun. 1-15, 2018).
Leidner, R. "A phase 2 study to evaluate the safety and efficacy of using autologous tumor infiltrating lympho cytes (LN-145) in patients with recurrent and/or metastatic squamous cell carcinoma of the head and neck," P221 SITC Annual meeting, National Harbor, MD, (Nov. 8-12, 2017).
Létourneau, Sven et al., "IL-2/anti-IL-2 antibody complexes show strong biological activity by avoiding interaction with IL-2 receptor alpha subunit CD25," PNAS, 107(5):2171-2176, (Feb. 2, 2010).
Li, Bo et al., "Landscape of tumor-infiltrating T cell repertoire of human cancers," Nature Genetics, 48(7):725-732, (2016).
Li, Jinyang et al., "Tumor Cell-Intrinsic Factors Underlie Heterogeneity of Immune Cell Infiltration and Response to Immunotherapy," Immunity, 49:1-16, (2018).
Li, Kang et al., "Superior expansion of T cells using NKG2D-targeted delivery of IL-2: Implications for adoptive T cell immunotherapy," Courier Therapeutics, University of Virginia, 1 pg., (2017).
Li, Qiang John et al., "Expansion of tumor-infiltrating lymphocytes (TIL) using Iovance's Gen 2 process from bladder cancer for adoptive immunotherapy," A05 AACR Annual Meeting, Denver, CO, (May 18-21, 2019).
Li, Taiwen et al., "TIMER: A Web Server for Comprehensive Analysis of Tumor-Infiltrating Immune Cells," Cancer Research, 77(21):e108-e110, (2017).
Li, Xue et al., "Clonal replacement of novel T cells: a new phenomenon in the tumor microenvironment following PD-1 blockade," Signal Transduction and Targeted Therapy, 4:43, (2019).
Lion Biotherapeutics, Inc., "Lion Biotechnologies Announces 5-Year Extension of National Cancer Institute CRADA for Development of Novel TIL Immuno-Oncology Therapies," Press Release, 2 pgs., Aug. 24, 2016.

(56) References Cited

OTHER PUBLICATIONS

Lion Biotherapeutics, Inc., "Lion Biotechnologies Announces Presentations at Upcoming SITC 31st Annual Meeting," Press Release, 2 pgs., Oct. 26, 2016.

Lion Biotherapeutics, Inc., "Lion Biotechnologies Appoints Maria Fardis, Ph.D., as CEO," Press Release, 2 pgs., Jun. 3, 2016.

Lion Biotherapeutics, Inc., "Lion Biotechnologies manufacturing capabilities and research programs unaffected by review of National Cancer Institute's Manufacturing Facilities," Press Release, 1 pg., Apr. 17, 2016.

Lion Biotherapeutics, Inc., "Lion Biotechnologies submits investigational new drug application to conduct Phase 2 study in metastatic melanoma," Press Release, 1 pg., Jan. 5, 2015.

Lo, Winifred et al., "Immunologic recognition of a shared p53 mutated neoantigen in a patient with metastatic colorectal cancer," Cancer Immunology Research, 7(4):534-543, (2019).

Lowery, F.J., et al., "Molecular signatures of antitumor neoantigen-reactive T cells from metastatic human cancers," Science, 375(6583):877-884, (2022).

Lu, Jinghua et al., "Molecular constraints on CDR3 for thymic selection of MHC-restricted TCRs from a random pre-selection repertoire," Nature Commun., 10:1019, (2019).

Luen, Stephen J. et al., "Tumour-infiltrating lymphocytes and the emerging role of immunotherapy in breast cancer," Pathology, 49(2):141-155, (Feb. 2017).

Maecker, Holden T. et al., "Impact of cryopreservation on tetramer, cytokine flow cytometry and ELISPOT," BMC Immunology, 6(17):1-14, (2005).

Magalhaes et al., "Facing the future: challenges and opportunities in adoptive T cell therapy in cancer," Expert Opin. Biol. Ther. 19(8):811-827, (Apr. 30, 2019).

Malekzadeh, Parisa et al., "Antigen Experienced T Cells from Peripheral Blood Recognize p53 Neoantigens," Clin Cancer Res., 26(6):1267-1276, (2020).

Malekzadeh, Parisa et al., "Neoantigen screening identifies broad TP53 mutant immunogenicity in patients with epithelial cancers," J Clin Invest, 129(3):e123791, (2019).

Malone, C.C., et al., "Characterization of human tumor-infiltrating lymphocytes expanded in hollow-fiber bioreactors for immunotherapy of cancer," Cancer Biother. Radiopharm., 16(5):381-390, Abstract (2001). doi:10.1089/108497801753354285.

Mann, Thomas H. et al., "Tick-TOX, it's time for T cell exhaustion," Nature Immunology, 20:1092-1094, (2019).

Matthys, Gemma et al., "Clinical Pharmacokinetics, Platelet Response, and Safety of Eltrombopag at Supratherapeutic Doses of up to 200 mg Once Daily in Healthy Volunteers," J Clin Pharmacol., 51:301-308, (2011).

Maus, Marcela V., "Tumour tamed by transfer of one T Cell," Nature, 558:193-195, (2018).

Mavaddat, N. et al., "Signaling lymphocytic activation molecule (SLAM, CDw150) is homophilic but self-associates with very low affinity," Journal of Biological Chemistry, 275:28100-28109, (2000).

McCaffrey, J. et al., "Development of a standardised approach to in situ collection of solid tissues as starting materials for the manufacture of ATMP or cell based medicinal products," Cryotherapy, 22:S26-S186, Abstracts, (2020).

McCaffrey, J. et al., "Optimisation of the cryopreservation parameters for hematopoietic and tissue derived immune cell recovery," Immetacyte Ltd., 1 pg., (2018).

McLane, Laura M. et al., "CD8 T Cell Exhaustion During Chronic Viral Infection and Cancer," Annu. Rev. Immunol., 37:457-495, (2019).

Mehrle, Stefan et al., "Enhancement of anti-tumor activity in vitro and in vivo by CD150 and SAP," Molecular Immunology, 45:796-804, (2008).

Met, Özcan et al., "Principles of adoptive T cell therapy in cancer," Seminars in Immunopathology, 41:49-58, (2019).

Miller, Brian C. et al., "Subsets of exhausted CD8+ T cells differentially mediate tumor control and respond to checkpoint blockade," Nature Immunology, 20:326-336, (Mar. 2019).

Minutolo, Nicholas G. et al., "The Emergence of Universal Immune Receptor T Cell Therapy for Cancer," Frontiers in Oncology, 9:176, (2019).

Morgan, R.A., et al., "Adoptive cell therapy: genetic modification to redirect effector cell specificity," Cancer J., 16(4):336-341, (2010).

Morgan, Richard A. et al., "Cancer Regression in Patients After Transfer of Genetically Engineered Lymphocytes," Science, 314:126-129, (2006).

Naito, Yoshitaka et al., "CD8+ T cells infiltrated within cancer cell nests as a prognostic factor in human colorectal cancer," Cancer Research 58:3491-3494, (Aug. 15, 1998).

Natarajan, Arvind et al., "Preclinical Activity and Manufacturing Feasibility of Genetically Modified PDCD-1 Knockout (KO) tumor-Infiltrating Lymphocyte (TIL) cell Therapy," 1015 AACR Annual Meeting, New Orleans, LA, (Apr. 8-13, 2022).

Nektar, "Nektar Therapeutics Announces Publication of Two Manuscripts on lead Immuno-oncology Candidate, Bempegaldesleukin (Bempeg) in Nature Communications," 2 pgs., San Francisco, CA, (Feb. 3, 2020).

Nektar, "Preclinical Data Presented at ASCO 2016 Annual Meeting Demonstrate that Single-Agent NKTR-214 Produces a Large Increase in Tumor-Infiltrating Lymphocytes to Provide Durable Anti-Tumor Activity," 2 pgs., San Francisco, CA, (Jun. 6, 2016).

Nelson, Brad H., "CD20+ B Cells: The Other Tumor-Infiltrating Lymphocytes," JIM, 185(9):4977-82, (Nov. 2010).

Nguyen et al., "Expansion and Characterization of Human Melanoma Tumor-infiltrating Lymphocytes (TILs)," PLoS One 5(11):e13940, (Nov. 10, 2010).

Nishimura, Christopher D. et al., "c-MPL provides tumor-targeted T-cell receptor-transgenic T cells with costimulation and cytokine signals," Blood, 130:2739-2749, (2017).

Oberst, Andrew et al., "Catalytic activity of the caspase-8-FLIPL complex inhibits RIPK3-dependent necrosis," Nature, 471:363-367, (2011).

O'Malley, David et al., "Phase 2 Efficacy and Safety of Autologous Tumor-Infiltrating Lymphocyte (TIL) Cell Therapy in Combination with Pembrolizumab in Immune Checkpoint Inhibitor-Naïve Patients with Advance Cancers," 36th Annual Meeting & Pre-Conference Programs SITC, Washington, DC, (Nov. 10-14, 2021).

Onmimus, Kenneth et al., "Expansion of Tumor-Infiltrating Lymphocytes (TIL) Using Static Bag for the Clinical Manufacturing Rapid Expansion Protocol (REP) Process," 101 SITC, Washington, DC & Virtual, (Nov. 10-14, 2021).

Oppermans, Natasha et al., "Transgenic T-cell receptor immunotherapy for cancer: building on clinical success," Therapeutic Advances in Vaccines and Immunotherapy, 8:1-17, (2020).

Orrego, Enrique et al., "Distribution of tumor-infiltrating immune cell in glioblastoma," CNS Oncol., 7(4): CNS21, (Dec. 2018).

Otto, Grant, "A human antibody selectively targets regulatory T cells," Nature Reviews Drug Discovery, 17;546, (2018).

Owens et al., "Ex vivo expanded tumour-infiltrating lymphocytes from ovarian cancer patients release anti-tumour cytokines in response to autologous primary ovarian cancer cells," Cancer Immunol. Immunother. 67(10):1519-1531, (Jul. 23, 2018).

Paijens, Sterre T. et al., "Tumor-infiltrating lymphocytes in the immunotherapy era," Cellular & Molecular Immunology, 18:842-859, (2021).

Panchal, Neelam et al., "Transfer of gene-corrected T cells corrects humoral and cytotoxic defects in patients with X-linked lymphoproliferative disease," J Allergy Clin Immunol, 142:P235-245, (2018).

Parisi, Giulia et al., "Persistence of adoptively transferred T cells with a kinetically engineered IL-2 receptor agonist," Nature Communications, 11(660):1-12, (2020).

Parkhurst, M.R., et al., "T cells targeting carcinoembryonic antigen can mediate regression of metastatic colorectal cancer but induce severe transient colitis," Mol. Ther., 19(3):620-626, (2011).

Pathak et al., "Eltrombopag for the treatment of thrombocytopenia in patients with malignant and non-malignant hematologic disorders," Expert Opin. Drug Metab. Toxicol., 9(12):1667-1675, (2013).

Pauken, Kristen E. et al., "Epigenetic stability of exhausted T cells limits durability of reinvigoration by PD-1 blockade," Science, 354:1160-1165, (2016).

(56) References Cited

OTHER PUBLICATIONS

Pillai, M. et al., "Tumour Infiltrating Lymphocyte Therapy: Clinical Outcomes in Pre-treated Metastatic Melanoma Patients and Biomarker Correlations," Immetacyte, Ltd., 1 pg., (2018).
Pilon-Thomas, Shari, "Adoptive Cell Therapy Using Tumor Infiltrating Lymphocytes (TIL) and Application to Bladder Cancer," 30 pgs., (2017).
Pinilla-Ibarz, Javier et al., "Trial in Progress: Phase 1/2 Study Evaluating the Safety and Efficacy of IOV-2001, Autologous, Non-Genetically Modified, Polyclonal T-Cell Product, in Patients with Relapsed or Refractory Chronic Lymphocytic Leukemia (CLL) or Small Lymphocytic Lymphoma (SLL) (IOV-CLL-01)," 2846 ASH 2021, Atlanta, GA & Virtual, (Dec. 11-14, 2021).
Plo et al., "Genetic Alterations of the Thrombopoietin/MPL/JAK2 Axis Impacting Megakaryopoiesis," Front Endocrinol (Lausanne), 8:234, (Sep. 12, 2017).
Poschke et al., "The Outcome of Ex Vivo TIL Expansion Is Highly Influenced by Spatial Heterogeneity of the Tumor T-Cell Repertoire and Differences in Intrinsic In Vitro Growth Capacity between T-Cell Clones," Clin. Cancer Res., 26(16):4289-4301, (Apr. 17, 2020).
Powell, Daniel J., Jr. et al., "Translating fundamental immunobiology into adoptive T-cell therapy for ovarian cancer," Clin Cancer Res, 24:IA24, Suppl. 15, (2018).
Price-Troska, Tammy et al., "Inhibiting IL-2 signaling and the regulatory T-cell pathway using computationally designed peptides," Invest New Drugs, 37:9-16, (2018).
Prieto, P.A., et al., "Enrichment of CD8+ cells from melanoma tumor-infiltrating lymphocyte cultures reveals tumor reactivity for use in adoptive cell therapy," J. Immunother., 33(5):547-556, (2010).
Quiroga, Maria F. et al., "Activation of Signaling Lymphocytic Activation Molecule Triggers a Signaling Cascade that Enhances Th1 Responses in Human Intracellular Infection," The Journal of Immunology, 173:4120-4129, (2004).
Ren, Lili et al., "Similarity and difference in tumor-infiltrating lymphocytes in original tumor tissues and those of in vitro expanded populations in head and neck cancer," Oncotarget, 9:3805-3814, (2018).
Restifo, N.P., et al., "Adoptive immunotherapy for cancer: harnessing the T cell response," Nat. Rev. Immunol., 12(4):269-281, (2012).
Ribba, Benjamin et al., "Prediction of the Optimal Dosing Regimen Using a Mathematical Model of Tumor Uptake for Immunocytokine-Based Cancer Immunotherapy," Clin Cancer Res, 24:3325-3333, (2018).
Ring, Aaron M. et al., "Mechanistic and structural insight into the functional dichotomy between IL-2 and IL-15," Nature Immunol., 13(12):1187-1195, (Dec. 2012).
Ripley, R.T., et al., "Liver resection for metastatic melanoma with postoperative tumor-infiltrating lymphocyte therapy," Ann. Surg. Oncol., 17(1):163-170, (2010).
Ritthipichai, Krit, "Activating OX40 receptor promotes the expansion of CD8+ TIL with enhanced T-cell effector function," LB-110 AACR Annual Meeting, Chicago, IL, (Apr. 14-18, 2018).
Ritthipichai, Krit, "Genetic modification of Iovance's TIL through TALEN-mediated knockout of PD-1 as a strategy to empower TIL therapy for cancer," AACR Annual Meeting, 1052P, Abstract, (2020).
Ritthipichai, Krit, "K+ Channel Activation Promotes Tumor Infiltrating Lymphocyte (TIL) Expansion and Enhances Expression of CCR7," 66 AAI Annual Meeting, Washington, DC, (May 12-16, 2017).
Ritthipichai, Krit, "Studies of Key Quality Attributes for TIL Product, LN-144," P194 SITC Annual Meeting, National Harbor, MD, (Nov. 8-12, 2017).
Robbins, P.F., et al., "Cutting edge: persistence of transferred lymphocyte clonotypes correlates with cancer regression in patients receiving cell transfer therapy," J. Immunol., 173(12):7125-7130, (2004).
Robbins, Paul F. et al., "Mining exomic sequencing data to identify mutated antigens recognized by adoptively transferred tumor-reactive T cells," Nature Medicine, 19(6):747-752, (2013).
Robertson, Jane et al., "Tumour Infiltrating Lymphocyte-Adoptive Cell Therapy: the emerging importance of clonal neoantigen targets for next-generation products in Non-Small Cell Lung Cancer," IOTECH, 3:1-7, (2019).
Rohaan, Maartje W. et al., "Adoptive transfer of tumor-infiltrating lymphocytes in melanoma: a viable treatment option," Journal of ImmunoTherapy of Cancer, 6(1):102, (2018).
Romagnoli, Gloria et al., "Morphological Evaluation of Tumor-Infiltrating Lymphocytes (TILs) to Investigate Invasive Breast Cancer Immunogenicity, Reveal Lymphocytic Networks and Help Relapse Prediction: A Retrospective Study," Int. J. Mol. Sci., 18(9):1936, (2017).
Rosenberg, S.A., et al., "A new approach to the adoptive immunotherapy of cancer with tumor-infiltrating lymphocytes," Science, 233(4770):1318-1321, (1986).
Rosenberg, S.A., et al., "Adoptive cell therapy for the treatment of patients with metastatic melanoma," Curr. Opin. Immunol., 21(2):233-240, (2009).
Rosenberg, S.A., et al., "Cancer immunotherapy," N. Engl. J. Med., 359(10):1072, (2008).
Rosenberg, S.A., et al., "Cancer regression in patients with metastatic melanoma after the transfer of autologous antitumor lymphocytes," Proc. Natl. Acad. Sci. U.S.A., 101 Suppl 2(Suppl 2):14639-14645, (2004).
Rosenberg, S.A., et al., "Cell transfer therapy for cancer: lessons from sequential treatments of a patient with metastatic melanoma," J. Immunother., 26(5):385-393, (2003).
Rosenberg, S.A., et al., "Treatment of patients with metastatic melanoma with autologous tumor-infiltrating lymphocytes and interleukin 2," J. Natl. Cancer Inst., 86(15):1159-1166, (1994).
Rosenberg, Steven A. et al., "Abstract IA14: Cell transfer immunotherapy targeting unique somatic mutations in cancer," Cancer Immunol Res 7(2):IA14, Supplement, (2019).
Rosenberg, Steven A. et al., "Adoptive cell transfer as personalized immunotherapy for human cancer," Science, 348:62-68, (2015).
Rosenberg, Steven A. et al., "Adoptive cell transfer: a clinical path to effective cancer immunotherapy," Cancer, 8:299-308, (Apr. 2008).
Rosenberg, Steven A. et al., "Durable complete responses in heavily pretreated patients with metastatic melanoma using T-cell transfer immunotherapy," Clinl Cancer Res, 17(13):4550-4557, (2011).
Rosenberg, Steven A. et al., "Finding suitable targets is the major obstacle to cancer gene therapy," Cancer Gene Therapy, 21:45-47, (2014).
Rosenberg, Steven A. et al., "Gene transfer into humans-immunotherapy of patients with advanced melanoma, using tumor-infiltrating lymphocytes modified by retroviral gene transduction," NEJM, 323(9):570-578, (Aug. 30, 1990).
Rosenberg, Steven A. et al., "Use of Tumor-Infiltrating Lymphocytes and Interleukin-2 in the Immunotherapy of Patients with Metastatic Melanoma," NEJM, 319:1676-1680, (Dec. 22, 1988).
Royer, Yohan et al., "Janus Kinases Affect Thrombopoietin Receptor Cell Surface Localization and Stability," The Journal of Biological Chemistry, 280:27251-27261, (2005).
Sadelain, Michel et al., "Therapeutic T cell engineering," Nature, 545:423-431, (2017).
Saka, Koichiro et al., "Top-down motif engineering of a cytokine receptor directing ex vivo expansion of hematopoietic stem cells," Journal of Biotechnology, 168:659-665, (2013).
Sakaguchi, Shimon et al., "Immunologic self-tolerance maintained by activated T cells expressing IL-2 receptor alpha-chains (CD25)," J Immunol., 155(3):1151-1164, (1995).
Sakellariou-Thompson, Donastas et al. "4-1BB Agonist Focuses CD8+ Tumor-Infiltrating T-Cell Growth into a Distinct Repertoire Capable of Tumor Recognition in Pancreatic Cancer," Clin Cancer Research, 23:7263-7275, (2017).
Santoiemma, Phillip P. et al., "Systematic evaluation of multiple immune markers reveals prognostic factors in ovarian cancer," Gynecol. Oncol., 143:120-127, (2016).

(56) References Cited

OTHER PUBLICATIONS

Santoiemma, Phillip P. et al., "Tumor infiltrating lymphocytes in ovarian cancer," Cancer Biology & Therapy, 16:807-820, (Jun. 2015).

Sarnaik, Amod A. et al., "Lifileucel, a Tumor-Infiltrating Lymphocyte Therapy, in Metastatic Melanoma," J Clin Oncol., 39:2656-2666, (2021).

Sarnaik, Amod et al., "A Phase 2, Multicenter Study to Assess the Efficacy and Safety of Autologous Tumor Infiltrating Lymphocytes (LN-144) for Treatment of Patients with Metastatic Melanoma," CT169 AACR Annual Meeting, Chicago, IL, (Apr. 14-18, 2018).

Sarnaik, Amod et al., "Efficacy of Single Administration of Tumor Infiltrating Lymphocytes (TIL) in Heavily Pre-Treated Metastatic Melanoma Patients Following Checkpoint Therapy," Lion Biotechnologies,140 ASCO Annual Meeting, Chicago, IL, (Jun. 2-6, 2017).

Sarnaik, Amod et al., "Long-term follow up of lifileucel (LN-144) cryopreserved autologous tumor infiltrating lymphocyte therapy in patients with advanced melanoma progressed on multiple prior therapies," ASCO Annual Meeting, Tampa FL, (2020).

Sarnaik, Amod et al., "Novel Cryopreserved Tumor Infiltrating Lymphocytes (LN-144) Administered to Patients with Metastatic Melanoma Demonstrates Efficacy and Tolerability in a Multicenter Phase 2 Clinical Trial," P515 SITC Annual Meeting, National Harbor, MD, (Nov. 8-12, 2017).

Sarnaik, Amod et al., "Safety and efficacy of cryopreserved autologous tumor infiltrating lymphocyte therapy (LN-144, lifileucel) in advanced metastatic melanoma patients following progression on checkpoint inhibitors," 022 SITC Annual Meeting, Washington, DC, (Nov. 7-11, 2018).

Sarnaik, Amod et al., "Safety and efficacy of cryopreserved autologous tumor infiltrating lymphocyte therapy (LN-144, lifileucel) in advanced metastatic melanoma patients who progressed on multiple prior therapies including anti-PD-1," 162 ASCO Annual Meeting, Chicago, IL, (May 31-Jun. 4, 2019).

Sarnaik, Amod et al., "Safety and efficacy of cryopreserved autologous tumor infiltrating lymphocyte therapy (LN-144, lifileucel) in advanced metastatic melanoma patients who progressed on multiple prior therapies including anti-PD-1," J Clin Oncol., 37:Suppl., Abstract 2518, (2019).

Sarnaik, Amod et al., "Safety and efficacy of lifileucel (LN-144) tumor infiltrating lymphocyte therapy in metastatic melanoma patients after progression on multiple therapies—independent review committee data update," P865 SITC Annual Meeting, National Harbor, MD, (Nov. 6-10, 2019).

Sato, Eiichi et al., "Intraepithelial CD8+ tumor-infiltrating lymphocytes and a high CD8+/regulatory T cell ratio are associated with favorable prognosis in ovarian cancer," PNAS, 102:18538-18543, (Dec. 20, 2005).

Satpathy, Ansuman T. et al., "Massively parallel single-cell chromatin landscapes of human immune cell development and intratumoral T cell exhaustion," Nature Biotechnology, 37:925-936, (Aug. 2019).

Scheper, Wouter et al., "Low and variable tumor reactivity of the intratumoral TCR repertoire in human cancers," Nature Medicine, 25:89-94, (2018).

Schoenfeld, Adam J. et al., "First Phase 2 Results of Autologous Tumor-Infiltrating Lymphocyte (LN-145) Monotherapy in Patients with Advanced, Immune Checkpoint Inhibitor-Treated, Non-Small Cell Lung Cancer (NSCLC)," 458 SITC, Washington, DC & Virtual, (Nov. 10-14, 2021).

Schwartzberg, Pamela L. et al., "SLAM receptors and SAP influence lymphocyte interactions, development and function," Nat Rev Immunol., 9(1):39-46, (2009).

Seitter, Samantha J. et al., "Impact of Prior Treatment on the Efficacy of Adoptive Transfer of Tumor-Infiltrating Lymphocytes in Patients with Metastatic Melanoma," 27(19):5289-5298, (2021).

Sen, Debattama R. et al., "The epigenetic landscape of T cell exhaustion," Science, 354:1165-1169, (2016).

Sethuraman, Jyothi et al., "Successful expansion and characterization of tumor infiltrating lymphocytes (TILs) from non-melanoma tumors," Poster #42, Lion Biotechnologies, Society for Immunotherapy of Cancer, National Harbor, Maryland, MD, 1 pg., (Nov. 9-13, 2016).

Sharifi, Reza et al., "SAP mediates specific cytotoxic T-cell functions in X-linked lymphoproliferative disease," Blood, 103(10):3821-3827, (2004).

Shen, Xinglei et al., "Persistence of Tumor Infiltrating Lymphocytes in Adoptive Immunotherapy Correlates with Telomere Length," J Immunother., 30:123-129, (2007).

Sidaway, Peter, "TIL infusions effective in HPV-associated cancers," Nature Reviews Clinical Oncology, 16:144, (2019).

Silva, Daniel-Adriano et al., "De novo design of potent and selective mimics of IL-2 and IL-15," Nature, 565:186-191, (2019).

Simpson-Abelson, Michelle R. et al., "Emigrant Tumor Infiltrating Lymphocytes (TIL) Profoundly Differ from Remnant T-Cells," 649 AACR Annual Meeting, Washington, DC, (Apr. 1-5, 2017).

Simpson-Abelson, Michelle R. et al., "Expanding Iovance's tumor infiltrating lymphocytes (TIL) from core biopsies for adoptive T cell therapy using a 22-day manufacturing process," P145 SITC Annual Meeting, National Harbor, MD, (Nov. 6-10, 2019).

Simpsdn-Abelson, Michelle R. et al., "Iovance generation-2 tumour-infiltrating lymphocyte (TIL) product is reinvigorated during the manufacturing process," 1053P ESMO Virtual Congress, (Sep. 19-21, 2020).

Simpson-Abelson, Michelle R. et al., "PD1-positive tumor-infiltrating lymphocytes (TIL) for the next generation of adoptive T cell therapy," P210 SITC Annual Meeting, Washington, DC, (Nov. 7-11, 2018).

Simpson-Abelson, Michelle R. et al., "The T-cell Growth Factor Cocktail IL-2/IL-15/IL-21 Enhances Expansion and Effector Function of Tumor-Infiltrating T Cells in a Novel Process Developed by Iovance," P357 SITC Annual Meeting, National Harbor, MD, (Nov. 8-12, 2017).

Sims et al., "Diversity and divergence of the glioma-infiltrating T-cell receptor repertoire," Proc. Natl. Acad. Sci. U.S.A., 113(25):E3529-E3537, (2016).

Singer, Meromit et al., "A Distinct Gene Module for Dysfunction Uncoupled from Activation in Tumor-Infiltrating T Cells," Cell, 166:1500-1511, (2016).

Smith, Jenessa B. et al., "Tumor regression and delayed onset toxicity following B7-HR CAR T cell Therapy," Mol. Ther., 24:1987-1999, (2016).

Smyrk, Thomas C. et al., "Tumor-Infiltrating Lymphocytes Are a Marker for Microsatellite Instability in Colorectal Carcinoma," 91(12):2417-2422, (Jun. 15, 2001).

Sockolosky, Jonathan T. et al., "Selective targeting of engineered T cells using orthogonal IL-2 cytokine-receptor complexes," Science, 359:1037-1042, (2018).

Sogo et al., "T cell growth control using hapten-specific antibody/interleukin-2 receptor chimera," Cytokine, 46(1):127-136, (2009).

Somerville, R.P., et al., "Clinical scale rapid expansion of lymphocytes for adoptive cell transfer therapy in the WAVE® bioreactor," J. Transl. Med., 10:69, (2012).

Song, De-Gang et al., "In Vivo Persistence, Tumor Localization, and Antitumor Activity of CAR-Engineered T Cells is Enhanced by Costimulatory Signaling through CD137 (4-1BB)," Cancer Res., 71:4617-4627, (2011).

Spindler, Matthew J. et al., "Massively parallel interrogation and mining of natively paired human TCRαβ repertoires," Nature Biotechnology, 38:609-619, (2020).

Spruessel, Annika et al., "Tissue ischemia time affects gene and protein expression patterns within minutes following surgical tumor excision," BioTechniques, 36(6):1030-1037, (2004).

Stevanovic, S., et al., "Complete regression of metastatic cervical cancer after treatment with human papillomavirus-targeted tumor-infiltrating T cells," J. Clin. Oncol., 33(14):1543-1550, (2015).

Subramanian, Krithika, "TILs Show Growing Potential as Novel Immunotherapy," OncologyLive, 19(19):1-12, (2018).

Sun, Hongliang et al., "Eltrombopag, a thrombopoietin receptor agonist, enhances human umbilical cord blood hematopoietic stem/primitive progenitor cell expansion and promotes multi-lineage hematopoiesis," Stem Cell Research, 9:77-86, (2012).

(56) References Cited

OTHER PUBLICATIONS

Sykorova, M. et al., "CoStAR (Costimulatory Antigen Receptor) Enhancement of Tumour Infiltrating Lymphocyte Therapy," InstilBio, 1 pg., (2019).
Synthorx, "Synthorx to Present Preclinical Data for THOR-707, a "Not-Alpha" IL-2 Synthorin, for the Treatment of Solid Tumors at SITC 2018," NEJM, 375:2255-2262, (2016).
Tang, Haidong et al., "Facilitating T Cell Infiltration in Tumor Microenvironment Overcomes Resistance to PD-L1 Blockade," Cancer Cell, 29:285-296, (2016).
Tang, Li et al., "Enhancing T Cell therapy through TCR-signaling-responsive nanoparticle drug delivery," Nature Biotechnology, 36:707-716, (2018).
Tanyi, Janos L. et al., "Personalized cancer vaccine effectively mobilizes antitumor T cell immunity in ovarian cancer," Sci. Transl. Med., 10:eaao5931, (2018).
Tong, Wei et al., "The Membrane-proximal Region of the Thrombopoietin Receptor Confers Its high Surface Expression by JAK2-dependent and -independent Mechanisms," Journal of Biological Chemistry, 281:38930-38940, (2006).
Topalian, S.L., et al., "Expansion of human tumor infiltrating lymphocytes for use in immunotherapy trials," J. Immunol. Methods, 102(1):127-141, (1987).
Tran, Eric et al., "Cancer Immunotherapy Based on Mutation-Specific CD4+ T Cells in a Patient with Epithelial Cancer," Science, 344:641-645, (May 2014.).
Tran, Eric et al., "'Final common pathway' of human cancer immunotherapy: targeting random somatic mutations," Nature Immunology, 18:255-262, (2017).
Tran, Eric et al., "T-Cell Transfer Therapy Targeting Mutant KRAS in Cancer," Science, 344:641-645, (May 2014.).
Tran, K.Q., et al., "Minimally cultured tumor-infiltrating lymphocytes display optimal characteristics for adoptive cell therapy," J. Immunother., 31(8):742-751, (2008).
Turcotte, S., et al., "Phenotype and function of T cells infiltrating visceral metastases from gastrointestinal cancers and melanoma: implications for adoptive cell transfer therapy," J. Immunol., 191(5):2217-2225, (2013).
U.S. Securities and Exchange Commission, Form 8-K for Iovance Biotherapeutics, Inc., First Quarter Financial Results and Corporate Updates, dated May 6, 2021.
Usacheva, Anna et al., "Contribution of the Box 1 and Box 2 Motifs of Cytokine Receptors to Jak1 Association and Activation," The Journal of Biological Chemistry, 277:48220-48226, (2002).
Veatch, Joshua R. et al., "Tumor-infiltrating BRAFV600E-specific CD4+ T cells correlated with complete clinical response in melanoma," J Clin Invest., 128(4):1563-1568, (2018).
Veatch, Joshua R. et al., "Tumor-infiltrating lymphocytes make inroads in non-small-cell lung cancer," Nature Medicine, 27:1338-1344, (Aug. 2021).
Veerapathran, Anand et al., "Artificial antigen presenting cells promote expansion of tumor-infiltrating lymphocytes (TILs)," Poster #47, Lion Biotechnologies, Society for Immunotherapy of Cancer, National Harbor, Maryland, MD, 1 pg., (Nov. 9-13, 2016).
Venkataraman, M., "Cryopreservation-Induced Enhancement of Interleukin-2 Production in Human Peripheral Blood Mononuclear Cells," Cryobiology 29:165-174, (1992).
Venkataraman, M., "Effects of Cryopreservation on Immune Responses: VII. Freezing Induced Enhancement of IL-6 Production in Human Peripheral Blood Mononuclear Cells," Cryobiology 31:468-477, (1994).
Vodnala, Suman Kumar et al., "Identifying the source of tumour-infiltrating T cells," Nature, 576:385-386, (2019).
Vodnala, Suman Kumar et al., "T cell stemness and dysfunction in tumors are triggered by a common mechanism," Science, 363(6434):eaau0135, (Mar. 2019).
Wang, L.L., et al., "Cell therapies in the clinic," Bioeng. Transl. Med., 6(2):e10214, (2021).
Wang, S., et al., "Perspectives of tumor-infiltrating lymphocyte treatment in solid tumors," BMC Med., 19(1):140, (2021).
Wang, Sheng-Yuan et al., "The Influence of Cryopreservation on Cytokine Production by Human T Lymphocytes," Cryobiology, 37:22-29, (1998).
Wardell, Seth et al., "A Cryopreserved Tumor Infiltrating Lymphocyte (TIL) Product for LN-144, Generated with an Abbreviated Method Suitable for High Throughput Commercial Manufacturing Exhibits Favorable Quality Attributes for Adoptive Cell Transfer," P203 SITC 32nd Annual Meeting, National Harbor, MD, 1 pg., (Nov. 8-12, 2017).
Wardell, Seth et al., "Iovance Gen 2 TIL Manufacturing Process Produces Drug Products that Exhibit Favorable Quality Attributes for Adoptive Cell Transfer Across 5 Solid Tumor Indications," P226 SITC Annual Meeting, National Harbor, MD, (Nov. 6-10, 2019).
Weber, Amy Mackay et al., "Targeting 4-1BB in tumors enhances anti-tumor immune responses," AACR Meeting, 2403/207, Abstract, (2019).
Weber, Evan W. et al., "The Emerging Landscape of Immune Cell Therapies" Cell, 181:46-62, (2020).
Weber, Evan W. et al., "Transient "rest" induces functional reinvigoration and epigenetic remodeling in exhausted CAR-T cells," BioRxIV, 1-37, (2020).
Weber, J., et al., "White paper on adoptive cell therapy for cancer with tumor-infiltrating lymphocytes: a report of the CTEP subcommittee on adoptive cell therapy," Clin. Cancer Res., 17(7):1664-1673, (2011).
Weinstein-Marom, H., et al., "Genetic Modification of Tumor-Infiltrating Lymphocytes via Retroviral Transduction," Front. Immunol., 11:584148, (2021).
Wherry, E. John, "T cell exhaustion," Nature Immunology, 12:492-499, (Jun. 2011).
Wilson Wolf, "G-Rex Product Brochure" Wilson Wolf Company Website, (2016). [Retrieved from the internet Aug. 18, 2022; URL: <https://www.wilsonwolf.com/wp-content/uploads/2016/11/G-Rex-Brochure.pdf>].
Winifred, Lo et al., "Immunologic Recognition of a Shared p53 Mutated Neoantigen In A Patient With Metastatic Colorectal Cancer," Cancer Immunol Res 7 (4): 534-543, (2019).
Wong, Sandi, "Iovance shows autologous tumor-infiltrating lymphocytes effective after anti-PD-1," BioCentury, [Retrieved from the Internet Nov. 23, 2019: <URL: https://www.biocentury.com/article/303797/iovance-shows-autologous-tumor-infiltrating-lymphocytes-effective-after-anti-pd-1x>].
Wu, Ning et al., "SLAM family receptors in normal immunity and immune pathologies," Current Opinion in Immunology, 38:45-51, (2016).
Wu, R., et al., "Adoptive T-cell therapy using autologous tumor-infiltrating lymphocytes for metastatic melanoma: current status and future outlook," Cancer J., 18(2):160-175, (2012).
Xia et al., "T Cell Dysfunction in Cancer Immunity and Immunotherapy," Front. Immunol., 10:1719, (Jul. 19, 2019).
Yamane, Noriko et al., "Characterization of novel non-peptide thrombopoietin mimetics, their species specificity and the activation mechanism of the thrombopoietin receptor," European Journal of Pharmacology, 586:44-51, (2008).
Yang, S., et al., "A simplified method for the clinical-scale generation of central memory-like CD8+ T cells after transduction with lentiviral vectors encoding antitumor antigen T-cell receptors," J. Immunother., 33(6):648-658, (2010).
Yannelli, J.R., et al., "Growth of tumor-infiltrating lymphocytes from human solid cancers: summary of a 5-year experience," Int. J. Cancer, 65(4):413-421, (1996).
Ye, Q., et al., "Engineered artificial antigen presenting cells facilitate direct and efficient expansion of tumor infiltrating lymphocytes," J. Transl. Med., 9:131, (2011).
Ye, Qunrui et al., "Activation-induced CD137 expression accurately identifies naturally occurring tumor-reactive T cells in cancer patients," OncoImmunology, 2:12, e27184, (Dec. 2013).
Ye, Qunrui et al., "CD137 Accurately Identifies and Enriches for Naturally Occurring Tumor-Reactive T Cells in Tumor," Clin Cancer Res, 20:44-55, (2014).
Yee, C. et al., "Adoptive T cell therapy using antigen-specific CD8+ T cell clones for the treatment of patients with metastatic melanoma:

(56) References Cited

OTHER PUBLICATIONS

In vivo persistence, migration, and antitumor effect of transferred T cells," PNAS, 99:16168-16173, (Dec. 10, 2002).
Yigit, Burcu et al., "SLAMF6 as a Regulator of Exhausted CD8+ T Cells in Cancer," Cancer Immunology Research, 7(9):1485-1496, (2019).
Yong-Chen, Lu et al., "An Efficient Single-Cell RNA-Seq Approach to Identify Neoantigen-Specific T Cell Receptors," Molecular Therapy 26(2): 379-389, (Feb. 2018).
Yossef, Rami et al. "Abstract B055: Enhanced detection of T-cells targeting unique neoantigens and shared mutated oncogenes for personalized cancer immunotherapy," Cancer Immunol. Res., 7(2):B055, Supplement, (2019).
Yost, Kathryn E. et al., "Clonal replacement of tumor-specific T cells following PD-1 blockade," 25:1251-1259, (2019).
Yron, I., et al., "In vitro growth of murine T cells. V. The isolation and growth of lymphoid cells infiltrating syngeneic solid tumors," J. Immunol., 125(1):238-245, (1980).
Yu, Peng-Cheng et al., "Association between density of tumor-infiltrating lymphocytes and prognoses of patients with gastric cancer," Medicine, 97(27):1-8, (2018).
Zacharakis, Nikolaos et al., "Breast Cancers Are Immunogenic: Immunologic Analyses and a Phase II Pilot Clinical Trial Using Mutation-Reactive Autologous Lymphocytes," J Clin. Oncol., 40:1741-1754, (Feb. 2, 2022).
Zacharakis, Nikolaos et al., "Immune recognition of somatic mutations leading to complete durable regression in metastatic breast cancer," Nature Medicine, 24:724-730, (2018).
Zgura, Anca et al., Relationship between Tumor Infiltrating Lymphocytes and Progression in Breast Cancer, Maedica (Bucur). Dec. 2018; 13(4): 317-320.
Zhang, Shu-Qi et al., "High-throughput determination of the antigen specificities of T cell receptors in single cells," Nature Biotechnology, 36:1156-1159, (2018).
Zhao, L., et al., "Engineered T Cell Therapy for Cancer in the Clinic," Front. Immunol., 10:2250, (2019).
Zhao, Yan-Jie et al., "Expression of PD-1 on CD4+ Tumor-Infiltrating Lymphocytes in Tumor Microenvironment Associated with Pathological Characteristics of Breast Cancer," J Immunol. Res., 2018:1-18, (2018).
Zheng, Chunhong et al., "Landscape of Infiltrating T Cells in Liver Cancer Revealed by Single-Cell Sequencing," Cell, 169:1342-1356, (2017).
Zhou et al., "Characterization of T-Cell Memory Phenotype after In Vitro Expansion of Tumor-infiltrating Lymphocytes from Melanoma Patients," Anticancer Res., 31(12):4099-4109, (Dec. 2011).
Zhou, J., et al., "Persistence of multiple tumor-specific T-cell clones is associated with complete tumor regression in a melanoma patient receiving adoptive cell transfer therapy," J. Immunother., 28(1):53-62, (2005).
Zhou, J., et al., "Selective growth, in vitro and in vivo, of individual T cell clones from tumor-infiltrating lymphocytes obtained from patients with melanoma," J. Immunol., 173(12):7622-7629, (2004).
Zidlik, Vladimir et al., "Tumor Infiltrating Lymphocytes in Malignant Melanoma—Allies or Foes?" Biomed Pap Med Fac Univ Palacky Olomouc Czech Repub., 164(1):43-48, (2020).
Zhang, Ling et al., "Tumor-Infiltrating Lymphocytes Genetically Engineered with an Inducible gene Encoding Interleukin-12 for the Immunotherapy of Metastic Melanoma," Clin Cancer Res, 21(10): 2278-2288, (May 2015).
WIPO Application No. PCT/GB2016/053949, PCT International Preliminary Report on Patentability dated Jun. 19, 2018.
WIPO Application No. PCT/GB2016/053949, PCT International Search Report and Written Opinion of the International Searching Authority dated Feb. 24, 2017.
WIPO Application No. PCT/GB2018/050088, PCT International Preliminary Report on Patentability dated Jul. 16, 2019.
WIPO Application No. PCT/GB2018/050088, PCT International Search Report and Written Opinion of the International Searching Authority dated Apr. 19, 2018.
WIPO Application No. PCT/GB2019/050188, PCT International Preliminary Report on Patentability dated Jul. 28, 2020.
WIPO Application No. PCT/GB2019/050188, PCT International Search Report and Written Opinion of the International Searching Authority dated Apr. 11, 2019.
WIPO Application No. PCT/GB2019/051745, PCT International Preliminary Report on Patentability dated Dec. 22, 2020.
WIPO Application No. PCT/GB2019/051745, PCT International Search Report and Written Opinion of the International Searching Authority dated Oct. 18, 2019.
WIPO Application No. PCT/GB2020/051790, PCT International Preliminary Report on Patentability dated Jan. 25, 2022.
WIPO Application No. PCT/GB2020/051790, PCT International Search Report and Written Opinion of the International Searching Authority dated Oct. 2, 2020.
WIPO Application No. PCT/GB2020/053315, PCT International Search Report and Written Opinion of the International Searching Authority dated May 3, 2021.
WIPO Application No. PCT/IB2021/000882, PCT International Search Report and Written Opinion of the International Searching Authority dated May 13, 2022.
WIPO Application No. PCT/GB2020/053315, PCT International Preliminary Report on Patentability dated May 17, 2022.
WIPO Application No. PCT/IB2021/000883, PCT International Search Report and Written Opinion of the International Searching Authority dated Jun. 15, 2022.
WIPO Application No. PCT/IB2021/000878, PCT International Search Report and Written Opinion of the International Searching Authority dated Aug. 5, 2022.
Bierer et al ("The Biologic Roles of CD2, CD4, and CDS Int-Cell Activation," Ann. Rev. Immunol. 1989. 7:579-99) (Year: 1989).

\* cited by examiner

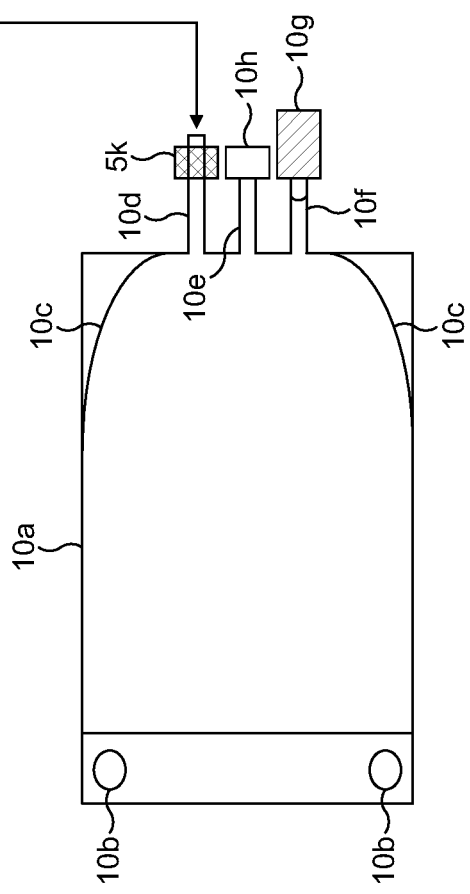

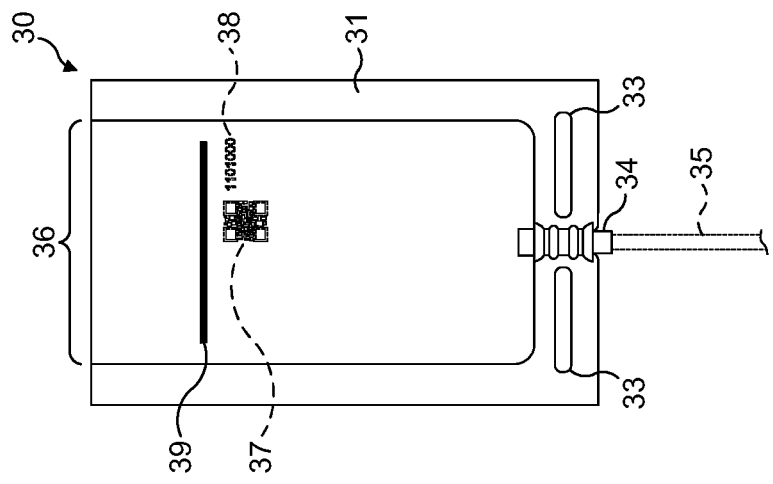
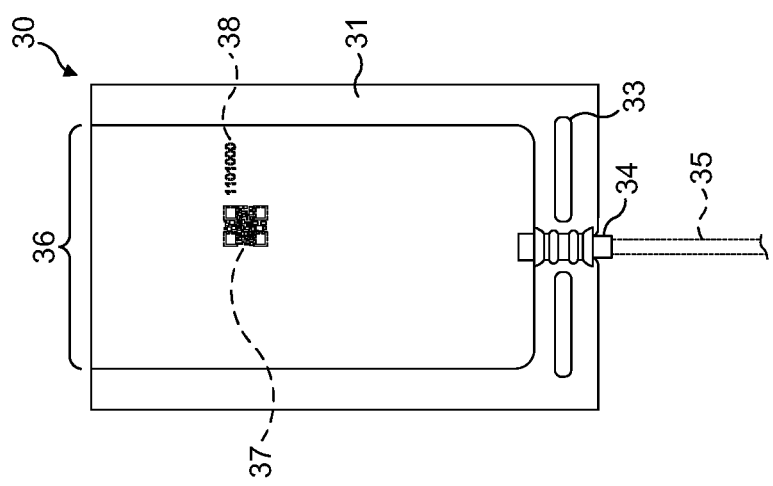
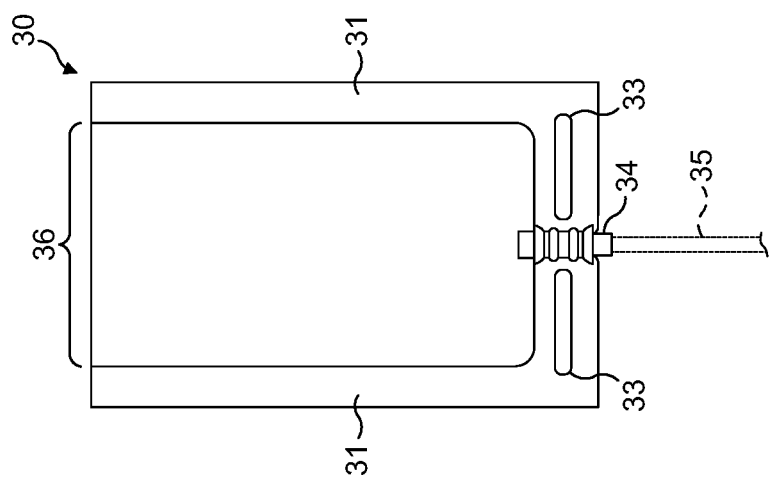

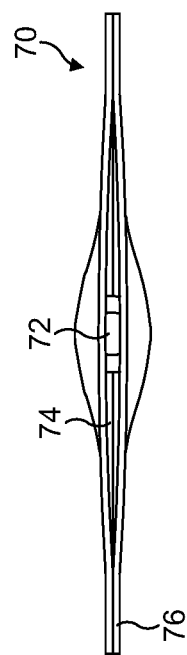
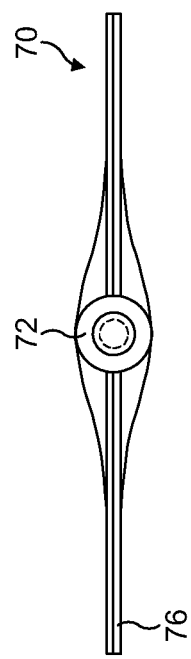
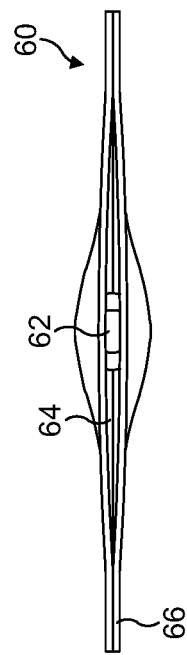
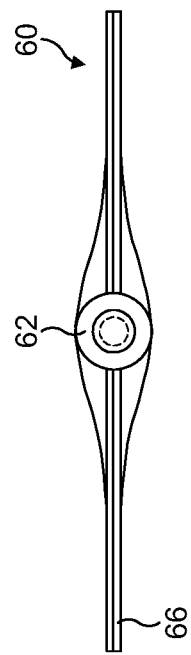

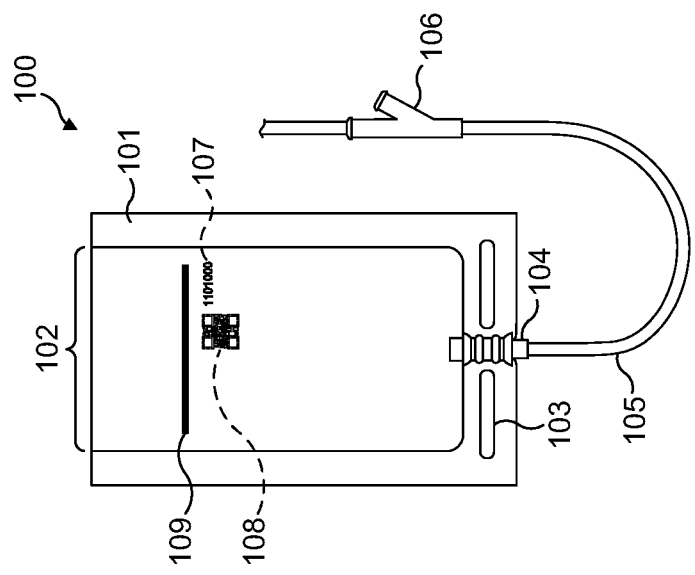
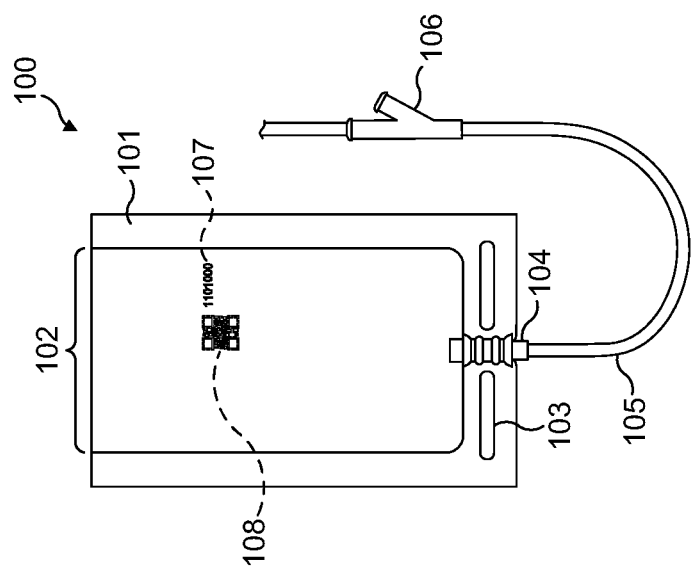
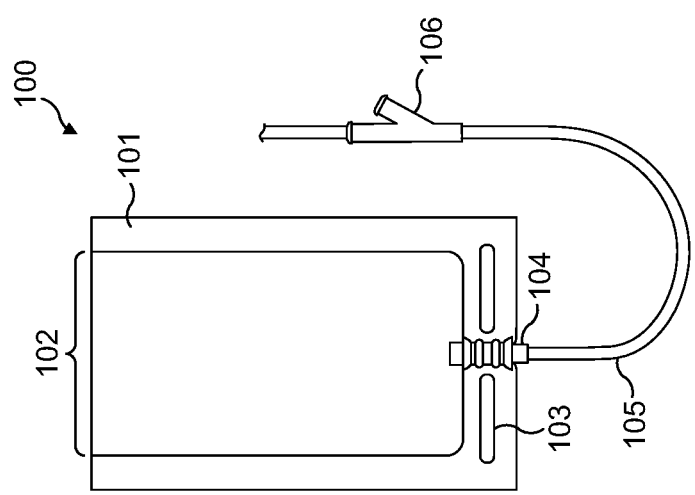

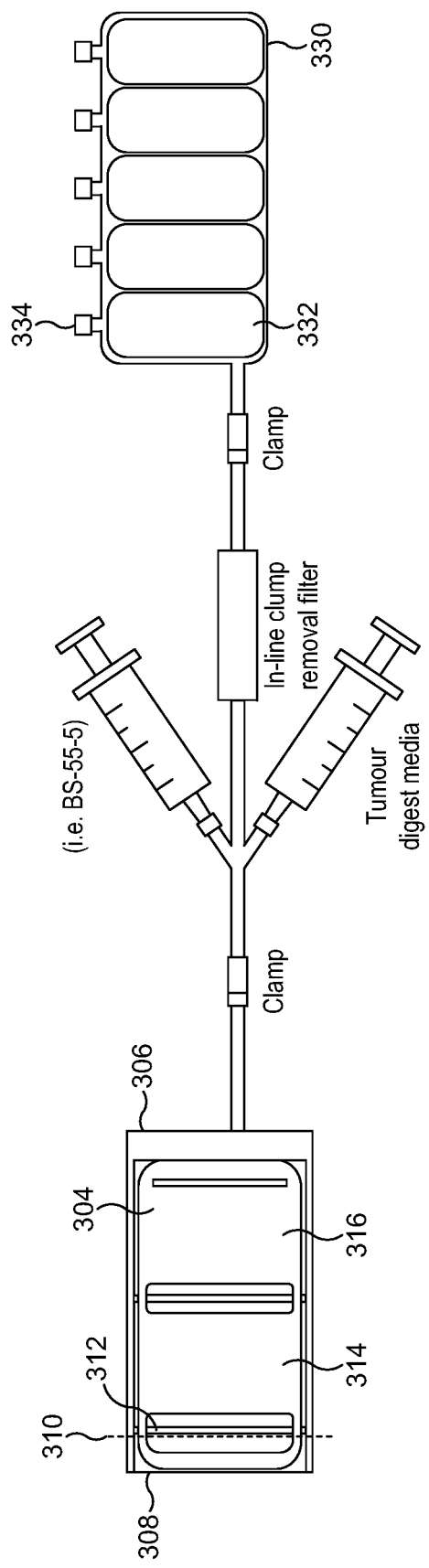
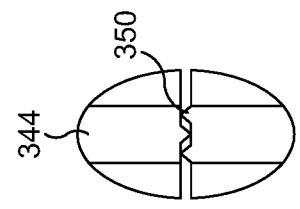
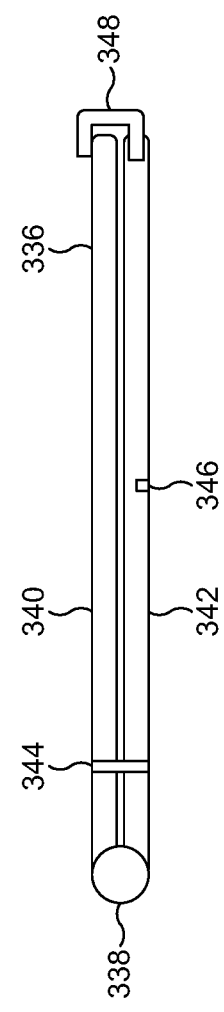
FIG. 36A
FIG. 36B
FIG. 36C

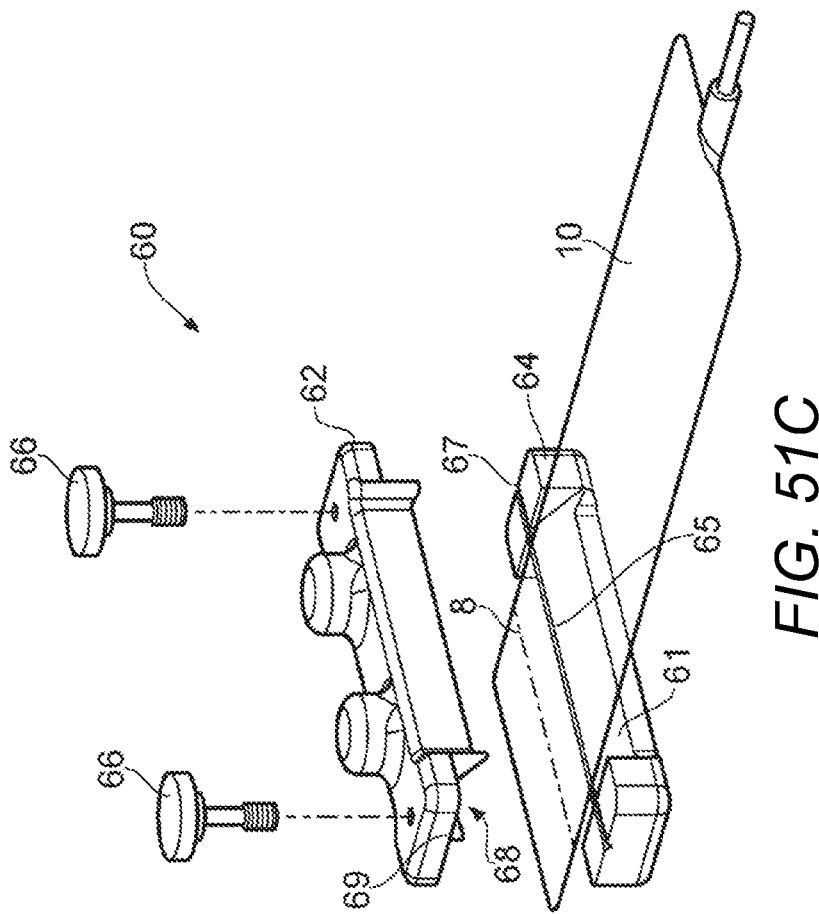
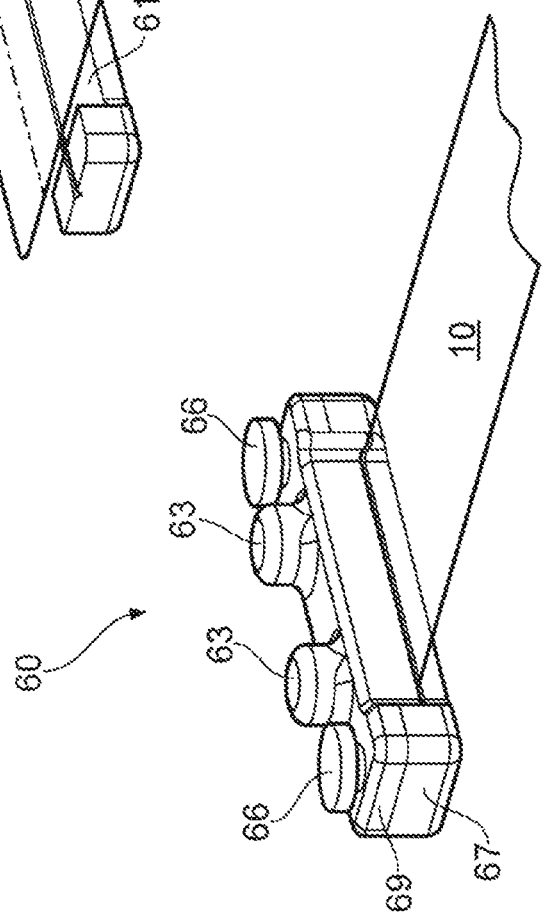
FIG. 51C
FIG. 51B

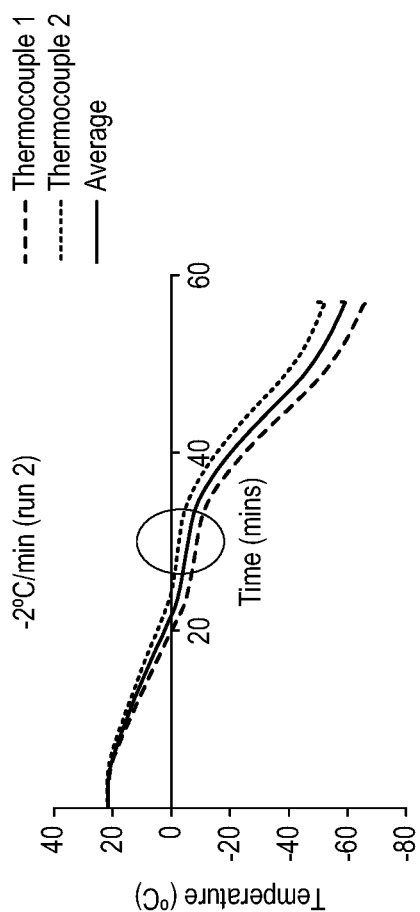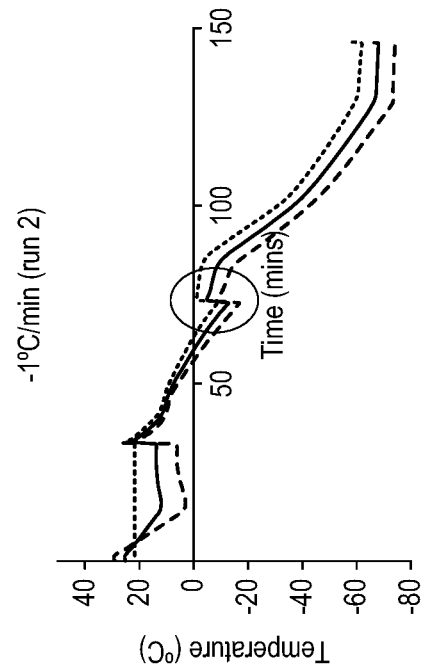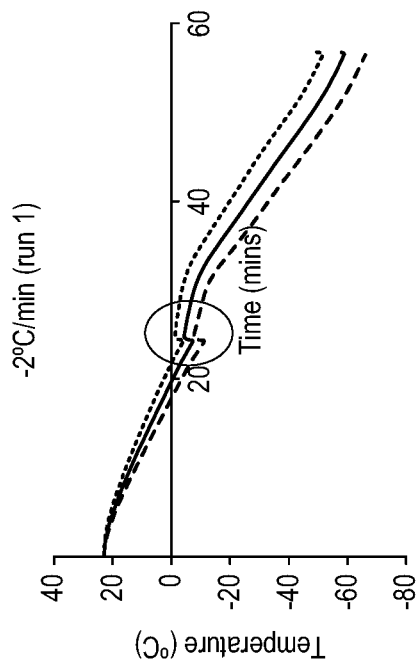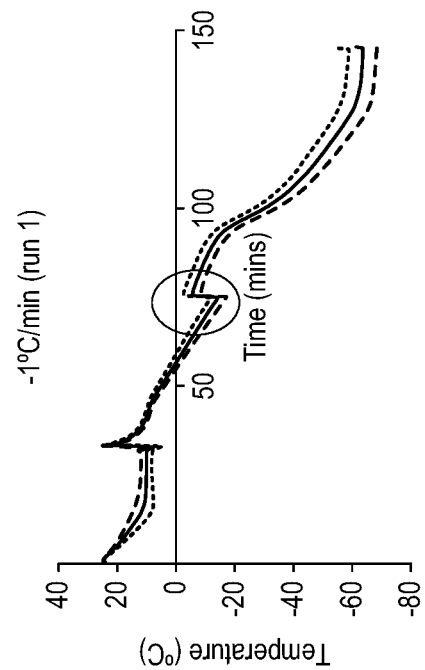
FIG. 70

A.

B.

C.

D.

E.

F.

G.

H.

A.

B.

C.

D.

D.

E.

F.

| Process Step | Unit Operation /Change | MS v1.0 | MS v1.1 | UTIL-01 | ITIL-168 Process |
|---|---|---|---|---|---|
| Tumour Digest Preparation | Tumour Disaggregation | Manual disaggregation in bottles | Manual disaggregation in bottles | Automated disaggregation in bags using the Tiss-u-stor device) | Automated disaggregation in bags using the Tiss-u-stor device) |
| | Tumour Digest Formulation | Non-cryopreserved | Non-cryopreserved | Cryopreserved | Cryopreserved |
| TIL Outgrowth | Culture Vessels for Tumour Digest | Open process in plates | Open process in plates | Open process in plates | Closed process in plates |
| | Seeding Density | Target of 1 x $10^6$ viable cells/mL | Target of 1 x $10^6$ viable cells/mL | Target of 0.5 x $10^6$ viable cells/mL | Target of 0.25 x $10^6$ viable cells/mL |
| | Cell Count Test Method | Hemocytometer | Flow cytometry | Flow cytometry | Flow cytometry |
| | Material | Gentamycin & Amtphotericin B | Gentamycin & Amtphotericin B | Gentamycin & Amtphotericin B | Gentamycin & Amtphotericin B, & Vancomycin |
| | Material | Heat inactivated and 0.1 μm filtered Human AB donors | Heat inactivated and 0.1 μm filtered FBS | Heat inactivated and 0.1 μm filtered FBS | Heat inactivated and 0.1 μm filtered FBS |
| TIL REP | Material | Heat inactivated and 0.1 μm filtered FBS | Heat inactivated and 0.1 μm filtered FBS | Heat inactivated and 0.1 μm filtered FBS | Heat inactivated and 0.1 μm filtered FBS |
| TIL Outgrowth to REP | Post TIL Outgrowth, Cryopreservation, Thaw/wash and Recovery | Hold step with Cryopreservation and 1-3 days post thaw recovery | Hold step with Cryopreservation and 1-3 days post thaw recovery | Continuous processing without cryopreservation | Continuous processing without cryopreservation |
| Harvest to Drug Product Formulation | Drug Product | Haemonetics Cell Saver 5 (Manual formulation to 270 mL) | Haemonetics Cell Saver 5 (Manual formulation to 270 mL) | Haemonetics Cell Saver 5 (Manual formulation to 270 mL) | Cytiva Sella S-2000 (Automated formulation to 110 mL) |
| Drug Product Formulation | Drug Product | Non-cryopreserved | Non-cryopreserved | Cryopreserved | Cryopreserved |

FIG. 77

| Process Step | Day | Unit Operation | Process Control | Description |
|---|---|---|---|---|
| Receipt and Release | | Cryopreserved Tumour Digest Receipt, Inspection and Release | | Receipt, Inspection, and Release of cryopreserved tumour digest |
| TIL Outgrowth | 1 | Cryopreserved Tumour Digest Thaw and Wash | | Thaw, wash, and dilution of tumour digest in media supplemented with FBS, IL-2, and antimicrobial reagents |
| | 1 | TIL Outgrowth Seeding | Cell Counts | Seeding of washed cells in culture bag(s) in media supplemented with FBS, IL-2, and antimicrobial reagents |
| | 1 | TIL Outgrowth Incubation | | Incubation of washed cells in culture bag(s) in media supplemented with FBS, IL-2, and antimicrobial reagents for up to 12 days |
| | 8 | TIL Outgrowth Media Addition | Cell Counts | Continued expansion of TILs in media supplemented with FBS, IL-2, and antimicrobial reagents |
| | 11 | TIL Outgrowth Media Addition | Cell Counts | Continued expansion of TILs in media supplemented with FBS, IL-2, and antimicrobial reagents |
| | 13 | TIL Outgrowth Concentration | Cell Counts | TIL concentration by centrifugation in bag(s) |
| TIL Rapid Expansion Phase | 13 | TIL Activation | Cell Counts | TIL activation with anti-CD3 and irradiated feeder cells in media containing Human AB serum and IL-2 for up to 6 days in culture bag(s) Cryopreserve excess TILs, if available |
| | 19 | TIL Seeding in Bioreactor | Cell Counts | TIL seed in bioreactor in media supplemented with Human AB serum and IL-2 for up to 8 days |
| | 20-27 | TIL Expansion in Bioreactor (Perfusion) | Cell Counts | TIL expansion in bioreactor bag with continuous feed of media supplemented with IL-2 |
| Harvest | $X^1$ | Harvest Wash and Concentration | Cell Counts | Washed to reduce impurities and concentrate TIL |
| Drug Product Formulation | $X^1$ | Formulated Drug Product | Cell Counts, Dose, Viability, Identity/Purity, Potency | TIL formulation with cryoprotectant |
| Cryopreservation | $X^1$ | Drug Product Cryopreservation | Temperature | Controlled rate freezing of Drug Product |
| Release and Shipment | | Drug Product Storage, Packaging, and Transportation | Temperature | Product storage in $\leq -130°C$ and release Shipment to clinic/infusion center |

FIG. 78

DEVICES AND METHODS FOR ISOLATING TUMOR INFILTRATING LYMPHOCYTES AND USES THEREOF

RELATED APPLICATIONS AND INCORPORATION BY REFERENCE

This application is a continuation of PCT/GB2020/053315 filed Dec. 18, 2020, which claims the benefit of priority from U.S. Patent Application Ser. No. 62/951,559 filed Dec. 20, 2019, U.S. Patent Application Ser. No. 62/982,470 filed Feb. 27, 2020, and U.S. Patent Application Ser. No. 63/047,431 filed Jul. 2, 2020, the contents of which are incorporated herein by reference in their entireties.

Reference is made to United Kingdom patent application Serial No. GB1700621.4, filed Jan. 13, 2017, European patent application EP18701791.8, filed Jan. 12, 2018, international patent application Serial No. PCT/GB2018/050088, filed Jan. 12, 2018, published as PCT Publication No. WO 2018/130845 on Jul. 19, 2018, European patent publication: EP3568459, and U.S. Patent Application Ser. No. 62/951,559, filed Dec. 20, 2019, which are hereby incorporated reference.

Reference is made to United Kingdom patent application Serial No. GB1902763.0, filed Mar. 1, 2019, United Kingdom patent application Serial No. GB1904249.8, filed Mar. 27, 2019, and international patent application Serial No. PCT/EP2020/000053, filed Feb. 28, 2020, published as WO 2020/177920 on Sep. 10, 2020.

The foregoing applications, Biomarker Predictive of Tumour Infiltrating Lymphocyte Therapy and the Uses Thereof, WO2019145711A1 PCT/GB2019/050188, Tumor Infiltrating Lymphocyte Therapy and Uses Thereof USA, PCT/GB2020/051790 and U.S. application Ser. No. 62/878,001, Receptors Providing Targeted Costimulation for Adoptive Cell Therapy WO 2020/152451, U.S. application Ser. No. 62/951,770 and GB1900858.0, Cells Expressing Recombinant Growth Factor Receptors WO 2017/103596A1, U.S. application Ser. No. 16/061,435, and European patent publication EP3390436, and Chimeric Growth Factor Receptors WO2019243835A1 PCT/GB2019/051745, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention provides methods and devices for isolating and freezing tumor infiltrating lymphocytes (TILs) from a resected tumor via semi-automatic aseptic tissue processing of the tumor and thereby producing therapeutic populations of TILs.

BACKGROUND OF THE INVENTION

T cells are derived from hemopoietic stem cells resident in bone marrow but subsequently migrate to and mature in the thymus. During the process of maturation, T cells undergo a series of selection events, thereby generating a diverse repertoire of T cells. These cells are then released into the peripheral circulation to carry out their specific functions as a part of the adaptive immune system.

T cells are not a homogeneous group of cells but consist of many lineages, of which the predominant types are defined by the expression of two further cell markers. CD4 expressing T cells are generally termed helper (Th) and are thought to orchestrate many functions of the immune system by cell-cell contact and through the production of mediator molecules called cytokines. CD8 T cells are considered to be cytotoxic (Tc) and are thought to be the cells which perform direct killing of target cells. These activities are all controlled through the T cell receptor/antigen/MHC interaction—consequently, upon successful recognition of a peptide/MHC on a target cell, CD4 and CD8 cells act in concert through cytokine production and cytotoxic activity to eliminate target cells, including virus infected and tumor cells.

T cells do not recognize intact proteins (antigens) but respond to short, protein fragments presented on the surface of target cells by specific proteins called the Major Histocompatibility Complex (MHC). During the maturation process, T cells express on their cell surface an antigen-specific T cell receptor (TCR), which recognizes these short protein (peptide) antigens presented by MHC molecules. Consequently, only when the correct peptide is presented on the surface of a target cell associated with the correct MHC molecule will the T cell activate its immune functions. Therefore, the frequency of tumor specific T cells are enriched in the tumor making it an ideal source for tumor specific T cells i.e. tumor-infiltrating lymphocytes (TEL) (Andersen et al., Cancer Res. 2012 Apr. 1; 72(7):1642-50. doi: 10.1158/0008-5472.CAN-11-2614. Epub 2012 Feb. 6).

Of course, this is a highly simplified view and represents a short general overview of T cell function. The adaptive immune response does not act in isolation but requires extensive interaction with a range of immune and non-immune cells to facilitate the efficient trafficking of T cells to the required site of activity, to ensure that the correct immune response is initiated and that the immune response is controlled and turned off after it is needed. Therefore, even in patients where the manufactured TIL initiate an immune response to the tumor it may then be supported or dampened by the patient's own immune system and the tumor environment.

Tumor specific TIL are T cells isolated from a tumor of a patient with metastatic cancer. In most cancer patients circulating tumor-specific T cells can hardly be detected in blood. However, certain cancers such as cutaneous melanoma appear to be immunogenic as it has the ability to induce significant numbers of T cells with anti-tumor activity during the natural course of the tumor growth, especially within the tumor areas (Muul et al., J Immunol. 1987 Feb. 1:138(3):989-95). Tumor-reactive T cells "selected as T cell specific for the tumor" can be isolated from tumor material and expanded ex vivo into high numbers. Reports have shown that these cells contain anti-tumor reactivity, which can result in tumor destruction and clinical responses upon reinfusion into the patient (Dudley et al., Science. 2002 Oct. 25; 298(5594):850-4. Epub 2002 Sep. 19). In subsequent trials the importance of T cell characteristics was confirmed and the benefit of "young" rapidly growing cells "Young TILs" was confirmed whereby cells are "not selected for specificity" at all. Remarkably this produces excellent response rates in TIL or CD8 selected TIL of around 50% (Besser et al., Anticancer Res. 2009 January:29(1):145-54;

Dudley et al., Clin Cancer Res. 2010 Dec. 15; 16(24):6122-31. doi: 10.1158/1078-0432.CCR-10-1297. Epub 2010 Jul. 28).

Studies by Andersen et al. (Cancer Res. 2012 Apr. 1; 72(7):1642-50. doi: 10.1158/0008-5472.CAN-11-2614. Epub 2012 Feb. 6) identified that melanoma specific T cells (for known cancer antigens) are enriched within the tumor compared with T cells in the peripheral blood. This supports the dogma that the isolated TIL population are enriched tumor specific T cells resulting in an enhanced anti-tumor activity when compared with early trials in melanoma patients using T cells isolated from peripheral blood and expanded in similar levels of IL2 or intravenous IL-2 alone (LAK cells—Bordignon et al., Haematologica. 1999 December; 84(12):1110-49).

U.S. Pat. No. 10,398,734 relates to methods for expanding TILs and producing therapeutic populations of TILs. The tumor of the '734 patent is shipped as a bulk tumor, and the TILs inside the bulk tumor rapidly become oxygen deficient and deteriorate progressively over time. The tumor of the '734 patent is also processed to fragments which have deteriorated internal cell populations. Furthermore, the TILs used for manufacturing will only be TILs expanded from tissue fragments and not any TILs retained in the interior. Therefore, the resulting cell population may not reflect the full diversity of the tumor environment.

Harvesting TILs requires the aseptic disaggregation of solid tissue as a bulk tumor prior to the culture and expansion of the TIL population. The conditions during solid tissue disaggregation and time taken to harvest the cells have a substantial impact on the viability and recovery of the fin al cellularized material. A solid tissue derived cell suspension that is obtained using conventional methods often includes a wide variety of different cell types, disaggregation media, tissue debris and/or fluids. This may necessitate the use of selective targeting and/or isolation of cell types, for example, prior to manufacture of regenerative medicines, adoptive cell therapies, ATMPs, diagnostic in vitro studies and/or scientific research.

Currently, selection or enrichment techniques generally utilize one of: size, shape, density, adherence, strong protein-protein interactions (i.e. antibody-antigen interactions). For example, in some instances selection may be conducted by providing a growth supporting environment and by controlling the culture conditions or more complex cell marker interactions associated with semi-permanent or permanent coupling to magnetic or non-magnetic solid or semisolid phase substrates.

For enrichment, isolation, or selection, any sorting technology can be used, for example, affinity chromatography or any other antibody-dependent separation technique known in the art. Any ligand-dependent separation technique known in the art may be used in conjunction with both positive and negative separation techniques that rely on the physical properties of the cells. An especially potent sorting technology is magnetic cell sorting. Methods to separate cells magnetically are commercially available e.g. from Thermo Fisher, Miltenyi Biotech, Stemcell Technologies, Cellpro Seattle, Advanced Magnetics, Boston Scientific, or Quad Technologies. For example, monoclonal antibodies can be directly coupled to magnetic polystyrene particles like Dynal M 450 or similar magnetic particles and used, for example for cell separation. The Dynabeads technology is not column based, instead these magnetic beads with attached cells enjoy liquid phase kinetics in a sample tube, and the cells are isolated by placing the tube on a magnetic rack.

Enriching, sorting and/or detecting cells from a sample includes using monoclonal antibodies in conjunction with colloidal superparamagnetic microparticles having an organic coating of, for example, polysaccharides (e.g. magnetic-activated cell sorting (MACS) technology (Miltenyi Biotec, Bergisch Gladbach, Germany)). Particles (e.g., nanobeads or MicroBeads) can be either directly conjugated to monoclonal antibodies or used in combination with anti-immunoglobulin, avidin, or antihapten-specific Micro-Beads, or coated with other mammalian molecules with selective binding properties.

Magnetic particle selection technologies such as those described above, allows cells to be positively or negatively separated by incubating them with magnetic nanoparticles coated with antibodies or other moieties directed against a particular surface marker. This causes the cells expressing this marker to attach to the magnetic nanoparticles. Afterwards the cell solution is placed within a solid or flexible container in a strong magnetic field. In this step, the cells attach to the nanoparticles (expressing the marker) and stay on the column, while other cells (not expressing the marker) flow through. With this method, the cells can be separated positively or negatively with respect to the particular marker(s).

In case of a positive selection the cells expressing the marker(s) of interest, which attached to the magnetic column, are washed out to a separate vessel, after removing the column from the magnetic field.

In case of a negative selection the antibody or selective moiety used is directed against surface markers(s) which are known to be present on cells that are not of interest. After application of the cells/magnetic nanoparticles solution onto the column the cells expressing these antigens bind to the column and the fraction that goes through is collected, as it contains the cells of interest. As these cells are non-labelled by the selective antibodies or moiety(s) coupled to nanoparticles, they are "untouched". The known manual or semi-automated solid tissue processing steps are labor-intensive and require a knowledge of the art.

In addition, where the material is used for therapeutic purposes, the processing requires strict regulated environmental conditions during handling of the cell cultures, for example tissue processing as a part of or prior to disaggregation, enzymatic digestion and transfer into storing devices, or incubation conditions for disaggregation/cellularization and viable tissue yields. Typically, this process would require multiple pieces of laboratory and tissue processing equipment, and personnel with the skills and knowledge of the scientific art with critical stages contained within either hazard containment or tissue processing facility(s) aseptic environment(s) in order to perform the same activity safely and also minimize the risk of contamination(s).

Viability and recovery of a desired product from tissue may be affected by the conditions during tissue collection, disaggregation, and harvesting of cells. The invention arises from a need to provide improved tissue processing, including an apparatus/device that undertakes said processing that achieves the unmet need described above.

Citation or identification of any document in this application is not an admission that such document is available as prior art to the present invention.

SUMMARY OF THE INVENTION

The present invention relates to a method for isolating a therapeutic population of tumor infiltrating lymphocytes (TIL) which may comprise:

(a) resecting a tumor from a subject;
(b) storing the resected tumor in a single use aseptic kit, wherein the aseptic kit comprises:
a disaggregation module for receipt and processing of material comprising solid mammalian tissue;
an optional enrichment module for filtration of disaggregated solid tissue material and segregation of non-disaggregated tissue and filtrate; and a stabilization module for optionally further processing and/or storing disaggregated product material,
wherein each of the modules comprises one or more flexible containers connected by one or more conduits adapted to enable flow of the tissue material there between; and
wherein each of the modules comprises one or more ports to permit aseptic input of media and/or reagents into the one or more flexible containers;
(c) aseptically disaggregating the resected tumor in the disaggregation module thereby producing a disaggregated tumor;
(d) performing a first expansion by culturing the disaggregated tumor in a cell culture medium comprising IL-2 to produce a first population of UTILs;
(e) performing a second expansion by culturing the first population of UTILs with additional 1L-2, OKT-3, and antigen presenting cells (APCs), to produce a second population of TILs;
(f) harvesting and/or cryopreserving the second population of UTILs. In some embodiments, step a) is optional.

The present invention relates to a method for isolating a therapeutic population of cryopreserved tumor infiltrating lymphocytes (TIL) which may comprise:
(a) resecting a tumor from a subject;
(b) storing the resected tumor in a single use aseptic kit, wherein the aseptic kit comprises:
a disaggregation module for receipt and processing of material comprising solid mammalian tissue;
an optional enrichment module for filtration of disaggregated solid tissue material and segregation of non-disaggregated tissue and filtrate; and a stabilization module for optionally further processing and/or storing disaggregated product material,
wherein each of the modules comprises one or more flexible containers connected by one or more conduits adapted to enable flow of the tissue material there between; and
wherein each of the modules comprises one or more ports to permit aseptic input of media and/or reagents into the one or more flexible containers;
(c) aseptically disaggregating the resected tumor in the disaggregation module thereby producing a disaggregated tumor, wherein the resected tumor is sufficiently disaggregated if it can be cryopreserved with a minimum of cell damage;
(d) cryopreserving the disaggregated tumor in the stabilization module;
(e) performing a first expansion by culturing the disaggregated tumor in a cell culture medium comprising IL-2 to produce a first population of UTILs;
(f) performing a second expansion by culturing the first population of UTILs with additional IL-2, OKT-3, and antigen presenting cells (APCs), to produce a second population of TILs;
(g) harvesting and/or cryopreserving the second population of UTILs. In some embodiments, step a) is optional.

The disaggregation may comprise physical disaggregation, enzymatic disaggregation, or physical and enzymatic disaggregation. In an advantageous embodiment, the disaggregated tumor is cellularized or purified.

In the present invention, sets of containers, which are interconnected and have specific separate functions maintain an aseptically closed system to process, optionally enrich but stabilize the disaggregated and cellularized tumor. Essentially the invention provides a rapid pre-sterilized environment to minimize the time required and risk of contamination or operator exposure during the processing of the resected tumor.

The aseptic kit allows for closed solid tissue processing, eliminating the risk of contamination of the final cellularized product compared to standard non-closed tissue processing, especially when the process is performed within a tissue retrieval/procurement site and requires storage prior to final cell processing for its ultimate utility. In addition, safety of the operator is increased due to reduction of direct contact with biological hazardous material, which may contain infectious organisms such as viruses. The kit also enables either all of or a portion of the finally processed cellularized material to be stabilized for either transport or storage prior to being processed for its ultimate utility.

The invention will enable the resected tumor to be processed at the time of resection, or later if required, without impact upon the retrieval procedure or the viability of the cellularized tumor.

In some embodiments, an optional enrichment via a form of physical purification to reduce impurities such as no longer required reagents; cell debris; non-disaggregated tumor tissue and fats can be employed. The aseptic kit can have an optional enrichment module, prior to stabilization, for this purpose. A single cell or small cell number aggregates can be enriched for stabilization after disaggregation by excluding particles and fluids of less than 5 μm or incompletely disaggregated material of or around 200 μm across or larger but this will vary upon the tissue and the efficiency of disaggregation and various embodiments in the form of tissue specific kits may be employed depending upon the tissue or ultimate utility of the disaggregated tumor.

In another embodiment, a single cell suspension is provided after step (c).

In another embodiment, the first population of UTILs requires about 1-20 million UTILs.

In another embodiment, step (e) may further comprise growth of the UTILs out of the resected tumor starting material followed by the rapid expansion of step (0.

In another embodiment, step (e) may be performed for about two weeks and step (f) may be performed for about two weeks.

In another embodiment, additional step (h) involves suspending the second population of UTILs. The suspending may be in buffered saline, human serum albumin, and/or dimethylsulfoxide (DMSO).

The present invention also may comprise a therapeutic population of cryopreserved UTILs obtained by any of the herein disclosed methods. The therapeutic population may comprise about $5\times10^9$ to $5\times10^{10}$ of T cells.

The present invention also encompasses a cryopreserved hag of the herein disclosed therapeutic population. The cryopreserved bag may be for use in intravenous infusion.

The present invention also encompasses a method for treating cancer which may comprise administering the herein disclosed therapeutic population or the herein disclosed cryopreserved bag. The present invention also encompasses the herein disclosed therapeutic population, pharmaceutical composition or cryopreserved bag for use in the treatment of cancer. The cancer may be bladder cancer, breast cancer, cancer caused by human papilloma virus, cervical cancer, head and neck cancer (including head and neck squamous cell carcinoma (HNSCC), lung cancer, melanoma, ovarian cancer, non-small-cell lung cancer (NSCLC), renal cancer, or renal cell carcinoma.

In another embodiment, the one or more flexible containers of the aseptic kit comprise a resilient deformable material.

In another embodiment, the one or more flexible containers of the disaggregation module of the aseptic kit comprises one or more sealable openings. The one or more flexible containers of the disaggregation module and/or the stabilization module may also comprise a heat sealable weld.

In another embodiment, the one or more flexible containers of the aseptic kit comprises internally rounded edges.

In another embodiment, the one or more flexible containers of the disaggregation module of the aseptic kit comprises disaggregation surfaces adapted to mechanically crush and shear the solid tumor therein.

In another embodiment, the one or more flexible containers of the enrichment module of the aseptic kit comprises a filter that retains a retentate of cellularized disaggregated solid tumor.

In another embodiment, the one or more flexible containers of the stabilization module of the aseptic kit comprises media formulation for storage of viable cells in solution or in a cryopreserved state.

In another embodiment, the aseptic kit further comprises a digital, electronic, or electromagnetic tag identifier. The tag identifier can relate to a specific program that defines a type of disaggregation and/or enrichment and/or stabilization process, one or more types of media used in said processes, including an optional freezing solution suitable for controlled rate freezing.

In another embodiment, the same flexible container can form part of one or more of the disaggregation module, the stabilization module, and the optional enrichment modules.

In another embodiment, the disaggregation module of the aseptic kit comprises a first flexible container for receipt of the tissue to be processed.

In another embodiment, the disaggregation module of the aseptic kit comprises a second flexible container comprising the media for disaggregation.

In another embodiment, the optional enrichment module of the aseptic kit comprises the first flexible container and a third flexible container for receiving the enriched filtrate.

In another embodiment, both the disaggregation module and the stabilization module of the aseptic kit comprise the second flexible container and the second flexible container comprises digestion media and stabilization media.

In another embodiment, the stabilization module of the aseptic kit comprises a fourth flexible container comprising stabilization media.

In another embodiment, the stabilization module of the aseptic kit also comprises the first flexible container and/or third flexible container for storing and/or undergoing cryopreservation.

The present invention also provides for a method for isolating a therapeutic population of cryopreserved UTILs comprising:
  (a) resecting a tumor from a subject;
  (b) storing the resected tumor in a single use aseptic kit, wherein the aseptic kit comprises: a disaggregation module for receipt and processing of material comprising solid mammalian tissue;
    an optional enrichment module for filtration of disaggregated solid tissue material and segregation of non-disaggregated tissue and filtrate; and a stabilization module for optionally further processing and/or storing disaggregated product material,
    wherein each of the modules comprises one or more flexible containers connected by one or more conduits adapted to enable flow of the tissue material there between; and
    wherein each of the modules comprises one or more ports to permit aseptic input of media and/or reagents into the one or more flexible containers;
  (c) aseptically disaggregating the resected tumor in the disaggregation module thereby producing a disaggregated tumor, wherein the resected tumor is sufficiently disaggregated if it can be cryopreserved without cell damage;
  (d) cryopreserving the disaggregated tumor in the stabilization module;
  (e) performing a first expansion by culturing the disaggregated tumor in a cell culture medium comprising IL-2 to produce a first population of UTILs;
  (f) performing a second expansion by culturing the first population of UTILs with additional IL-2, OKT-3, and antigen presenting cells (APCs), to produce a second population of TILs;
  (g) harvesting and/or cryopreserving the second population of UTILs. In some embodiments, step a) is optional.

In another embodiment, the automated device further comprises a radio frequency identification tag reader for recognition of the aseptic kit so that it may be scanned and recognized during automated processing, such as within the automated device in embodiments of the present invention. Crucially the tag provides information about the conditions and steps required to be auto processed, so simply by scanning the kit, any automated system used with the kit to process the tissue can be undertaken without further intervention or contamination. Once the tissue sample has been placed in the disaggregation module, it can for example be sealed, manually or automatically, before processing begins.

The programmable processor of the automated device can also recognize the aseptic kit via the tag and subsequently can execute the kit program defining the type of disaggregation, enrichment, and stabilization processes, and the respective media types required for said processes, which include an optional freezing solution suitable for controlled rate freezing. The programmable processor of the automated device is adaptable to communicate with and control the disaggregation module, the enrichment module, and/or the stabilization module. Put another way, the kit is therefore readable by an automated device used to execute a specific fully automatic method for processing the tumor when inserted into such a device.

The programmable processor of the automated device can control the disaggregation module to enable a physical and/or biological breakdown of the solid tissue material. This breakdown can be a physical or enzymatic breakdown of the solid tissue material. Enzymatic breakdown of the solid tissue material can be by one or more media enzyme solutions selected from the group consisting of collagenase, trypsin, lipase, hyaluronidase, deoxyribonuclease, Liberase HI, pepsin, and mixtures thereof.

In another embodiment, the programmable processor controls disaggregation surfaces within the disaggregation flexible containers that mechanically crush and shear the solid tissue. In some embodiments, the disaggregation surfaces are controlled by mechanical pistons.

In another embodiment, the programmable processor controls the stabilization module to cryopreserve the enriched disaggregated solid tissue in the container. This may be achieved using a programmable temperature setting, a condition which is determined by reading the tag of the kit inserted in the device.

In another embodiment, to undertake different functions of the process, one or more of the additional components of the device and/or kit are provided and may be available in any combination. This may include: sensors capable of recognizing whether a disaggregation process has been completed in the disaggregation module prior to transfer of the disaggregated solid tissue to the optional enrichment module; weight sensors to determine an amount of media required in the containers of one or more of the disaggregation module; the enrichment module; and/or the stabilization module and control the transfer of material between respective containers; sensors to control temperature within the containers of the one or more of the disaggregation module; the enrichment module; and/or the stabilization module; at least one bubble sensor to control transfer of media between the input and output ports of each container in the module; at least one pump, optionally a peristaltic pump, to control transfer of media between the input and output ports; pressure sensors to assess the pressure within the enrichment module; one or more valves to control a tangential flow filtration process within the enrichment module; and/or one or more clamps to control the transfer of media between the input and output ports of each module.

In another embodiment, the programmable processor of the automated device is adapted to maintain an optimal storage temperature range in the stabilization module until the container is removed; or executes a controlled freezing step. This allows the UTILs to be stored for short periods (minutes to days) or stored for long periods (multiple days to years) prior to their ultimate utility depending on the type or stabilization process used with the stabilization module.

In another embodiment, the automated device further comprises a user interface. The interface can comprise a display screen to display instructions that guide a user to input parameters, confirm pre-programmed steps, warn of errors, or combinations thereof.

In another embodiment, the automated device is adapted to be transportable and thus may comprise dimensions that permit easy maneuverability and/or aid movement such as wheels, tires, and/or handles.

The present invention also provides a semi-automatic aseptic tissue processing method for isolating a therapeutic population of cryopreserved UTILs comprising the steps of:

(a) automatically determining aseptic disaggregation tissue processing steps and their associated conditions from a digital, electronic, or electromagnetic tag identifier associated with an aseptic processing kit, wherein the aseptic kit comprises:
 a disaggregation module for receipt and processing of material comprising solid mammalian tissue;
 an optional enrichment module for filtration of disaggregated solid tissue material and segregation of non-disaggregated tissue and filtrate; and a stabilization module for optionally further processing and/or storing disaggregated product material,
 wherein each of the modules comprises one or more flexible containers connected by one or more conduits adapted to enable flow of the tissue material there between; and
 wherein each of the modules comprises one or more ports to permit aseptic input of media and/or reagents into the one or more flexible containers;

(b) resecting a tumor from a subject;
(c) placing the tumor into the flexible plastic container of the disaggregation module of the aseptic kit;
(d) processing the tumor by automatically executing the one or more tissue processing steps by communicating with and controlling:
 the disaggregation module; wherein the resected tumor is aseptically disaggregated thereby producing a disaggregated tumor, wherein the resected tumor is sufficiently disaggregated if it can be cryopreserved without cell damage;
 the optional enrichment module wherein the disaggregated tumor is filtered to remove disaggregated solid tissue material and to segregate non-disaggregated tissue and filtrate;
 the stabilization module wherein the disaggregated tumor is cryopreserved;
(e) performing a first expansion by culturing the disaggregated tumor in a cell culture medium comprising IL-2 to produce a first population of UTILs;
(f) performing a second expansion by culturing the first population of UTILs with additional IL-2, OKT-3, and antigen presenting cells (APCs), to produce a second population of TILs;
(g) harvesting and/or cryopreserving the second population of UTILs. In some embodiments, step b) is optional.

Flexible containers such as bags, may be used to process tissue materials. Processing may include treatments that may separate or breakdown tissue, for example, physical breakdown may be accomplished using agitation, e.g., gentle agitation, a biological and/or enzymatic breakdown may include enzymatic digestion, and/or extraction of components of the tissue materials in the bag.

A flexible container, such as a bag, for processing tissue may include one or more layers made of a sealable polymer having at least three edges of the flexible container which are sealed during manufacturing and an open edge on the flexible container through which tissue material is inserted during use. One or more connectors may be used to couple the flexible container to at least one element through tubing. After tissue is placed in the flexible container, a section of the flexible container proximate the open edge may be sealed or welded to form a seal. The seal may have a width of at least a three mm and be positioned substantially parallel to the open edge and spaced away from the open edge of the flexible container. In some instances, the seal may have a width greater than about five mm. For example, a bag may be sealed after tissue is placed inside to have a seal of least 5 mm positioned proximate the open edge of the bag. The seal may be parallel to the open edge and spaced away from the open edge of the bag.

The flexible container may be further secured using a clamp having protrusions and positioned proximate the seal and spaced further from the open edge of the flexible container than the seal.

In some instances, the seal and the flexible container are constructed such that the flexible container can withstand a 100 N force applied to the flexible container during use. Using a clamp in conjunction with such a seal may be advantageous in some instances depending on the type of material used and/or a structure of the seal. Thus, during use of a flexible container, such as a bag, a combination of a seal and a clamp may be capable of withstanding a 100 N force applied to the flexible container.

In some instances, the seal and the flexible container are constructed such that the flexible container can withstand a 75 N force applied to the flexible container during use. Using a clamp in conjunction with such a seal may be advantageous in some instances depending on the type of material used and/or a structure of the seal. Thus, during use of a flexible container, such as a bag, a combination of a seal and a clamp may be capable of withstanding a 75 N force applied to the flexible container.

A flexible container may be used to hold tissue during processing such as disaggregation of the tissue material.

In some embodiments, a flexible container, such as a bag, may be used for disaggregation of the tissue material, filtration of disaggregated tissue material, and/or segregation of non-disaggregated tissue and filtrate.

Flexible containers such as bags may be formed from a resilient deformable material. Materials for use in flexible containers, such as bags may be selected for one or more properties including but not limited to sealability such as sealability due to heat welding, or use of radio frequency energy, gas permeability, flexibility for example low temperature flexibility (e.g., at −50° C., or −195° C.), elasticity for example low temperature elasticity, chemical resistance, optical clarity, biocompatibility such as cytotoxicity, hemolytic activity, resistance to leaching, having low particulates, high transmissions rates for particular gases (e.g., Oxygen and/or Carbon dioxide), and/or complying with regulatory requirements.

Flexible containers, such as bags, may include indicators. Indicators may be used to identify samples, patients from whom the samples were derived, and/or to track progress of a particular sample through a treatment process. In some instances, indicators may be scanned by an automated or semi-automated system to track progress of a sample.

Marks may be used on a flexible container, such as a bag, to identify where the bag should be placed, treated, sealed, or any other action that may be taken with respect to a bag that includes tissue. Each bag may include multiple marks for sealing.

An open end of the bag may be sealed after tissue is inserted in the bag. Any seal may be formed using a sealing device (e.g., heater sealer) operating at a predetermined pressure, a predetermined temperature, and predetermined time frame.

In some instances, a flexible container, such as a hag may be used as a disaggregation container for use as part of a disaggregation element that may also include a disaggregation device. In some embodiments, media and/or enzymes may be added to the a bag within a disaggregation element of a device. For example, a bag may be used with a device that mechanically crushes tissue material placed in the flexible container.

In some embodiments, tissue in a flexible container such as a bag may be sheared during disaggregation. In particular, the flexible container may be configured to shear the tissue material.

Flexible containers may be used in a semi-automated or an automated process for the aseptic disaggregation, stabilization and/or optional enrichment of mammalian cells or cell aggregates.

A kit for extraction of a desired material from tissue may include a disaggregation element in which at least some tissue is treated to form a processed fluid, an enrichment element (e.g., a filter) capable of enriching at least some of the processed fluid to form the desired material, a stabilization element capable of storing a portion of the desired material, and an indicator tag positioned on at least one of the disaggregation element, the enrichment element, or the stabilization element capable of providing at least one of a source of tissue, a status of the tissue with respect to the process, or a identifier.

The desired material may be biological material or components of a particular size. For example, the desired material may be tumor infiltrating lymphocytes (TILs).

Different types of media may be used in the various processes conducted by the disaggregation element and the stabilization element. For example, a cryopreservation media may be provided to the kit and used in the stabilization element to control a rate freezing.

Kit for use in a device where a disaggregation element may include a first flexible container and the stabilization element may include a second flexible container.

An automated device for semi-automated aseptic disaggregation and/or enrichment and/or stabilization of cells or cell aggregates from mammalian solid tissue may include a programmable processor and a kit that includes the flexible container described herein. The automated device may further include an indicator tag reader. For example, an indicator tag reader may be positioned at any element (e.g., disaggregation, enriching, or stabilization of tissue material in the kit).

In some instances, an automated device may further include radio frequency identification tag reader to recognize samples in flexible containers in the kit.

An automated device may include a programmable processor that is capable of recognizing indicators positioned on components of the kit such as a bag via an indicator tag such as a QR code. After determining which sample is in the bag, the programmable processor subsequently executes a program defining the type of disaggregation, enrichment, and stabilization processes and provides the respective media types required for those processes.

A kit for use in an automated device may include a disaggregation flexible container or bag. The programmable processor may control a disaggregation element and disaggregation flexible container to enable a physical and/or biological breakdown of the solid tissue.

A programmable processor may control elements of an automated device such that disaggregation surfaces positioned proximate a disaggregation flexible container may mechanically crush and shear the solid tissue in the disaggregation flexible container, optionally wherein the disaggregation surfaces are mechanical pistons.

Disaggregation elements of a system may be controlled by a processor such that tissue in the disaggregation flexible container to enable a physical and enzymatic breakdown of the solid tissue. One or more media enzyme solutions selected from collagenase, trypsin, lipase, hyaluronidase, deoxyribonuclease, Liberase HI, pepsin, or mixtures thereof may be provided to the disaggregation flexible container to aid in enzymatic breakdown of tissue.

A system may include a kit that includes a disaggregation flexible container and a stabilization flexible container and a programmable processor. The programmable processor may be adapted to control one or more of: the disaggregation element; the enrichment element; and the stabilization element.

A programmable processor may control a stabilization element to cryopreserve the enriched disaggregated solid tissue in the stabilization container. In some embodiments, a predetermined temperature may be programmed.

An automated device may include additional components in a multitude of combinations. Components may include sensors capable of recognizing whether a disaggregation process has been completed in the disaggregation module prior to transfer of the disaggregated solid tissue to the optional enrichment element, weight sensors to determine an amount of media required in the containers of one or more of the disaggregation element, an enrichment element, and/or the stabilization element and control the transfer of material between respective containers, sensors to control temperature within the containers of the one or more of the disaggregation element; the enrichment element; and/or the stabilization element; at least one bubble sensor to control the transfer of media between the input and output ports of each container in the element; at least one pump, optionally a peristaltic pump, to control the transfer of media between the input and output ports; pressure sensors to assess the pressure within the enrichment element; one or more valves to control a tangential flow filtration process within the enrichment element; and/or one or more clamps to control the transfer of media between the input and output ports of each element.

An automated device may include a programmable processor is adapted to maintain an optimal storage temperature range in the stabilization module until the container is removed. In an embodiment, the programmable processor may execute a controlled freezing step.

In some instances, an automated device may include a user interface. An interface of an automated device may include a display screen to display instructions that guide a user to input parameters, confirm pre-programmed steps, warn of errors, or combinations thereof.

An automated device as described herein may be adapted to be transportable.

An automatic tissue processing method may include automatically determining conditions for processing steps and the associated conditions from a digital, electronic or electromagnetic tag indicator associated with a component of a kit. During use a tissue sample may be placed into a flexible container of the kit having at least one open edge. After positioning tissue in the flexible container, the open edge may be sealed. During use tissue may be processed by automatically executing one or more tissue processing steps by communicating information associated with the indicator and controlling conditions near the flexible container and/or positions of the flexible container. Further, addition of materials to the kit may be controlled based on information associated with indicators. At least some of the processed tissue may be filtered such that a filtered fluid is generated. At least some of the filtered fluid may be provided to a cryopreservative flexible container to stabilize the desired material present in the filtered fluid.

Processing as described herein may include agitation, extraction, and enzymatic digestion of at least a portion of the tissue sample in the flexible container. In some instances, this processing of tissue may result in the extraction of a desired material from a tissue sample. For example, tumor infiltrating lymphocytes (TILs) may be extracted from a tissue sample.

Flexible containers, such as bags, for use in the methods described herein may include heat-sealable material.

Tissue processing and extraction from the tissue materials using a cryopreservation kit may result isolation of the desired material. In particular, materials such as tumor infiltrating lymphocytes (TILs) may be the desired material.

In some instances, a cryopreservation kit and/or components thereof described herein may be single use in an automated and/or a semi-automated process for the disaggregation, enrichment, and/or stabilization of cells or cell aggregates. In some embodiments, bags for use in a cryopreservation kit such as a collection bag may in some embodiments be used for multiple processes. For example, collection bags may be repeatedly sealed in different locations to create separate compartments for processing of a tissue sample such as a biopsy sample and/or solid tissue.

Flexible containers, such as bags, for use in the invention described herein include a collection bag and a cryopreservation bag may include at least a portion made from a predetermined material such as a thermoplastic, polyolefin polymer, ethylene vinyl acetate (EVA), blends such as copolymers, for example, a vinyl acetate and polyolefin polymer blend (i.e., OriGen Biomedical EVO film), a material that includes EVA, and/or coextruded layers of sealable plastics. A collection bag, such as a tissue collection bag of the invention may include a bag for receiving tissue made from a predetermined material such as ethylene vinyl acetate (EVA) and/or a material including EVA. Materials for use in the bag may be selected for specific properties. In an embodiment, bags, including collection bags may be made substantially from a vinyl acetate and polyolefin polymer blend. For example, a property of interest that may be used to select a material for cryopreservation kit component such as a collection bag and/or the associated tubing may relate to heat sealing.

Materials for use in the bag may be selected for a specific property and/or a selection of properties, for example, sealability such as heat sealability, gas permeability, flexibility for example low temperature flexibility, elasticity for example low temperature elasticity, chemical resistance, optical clarity, biocompatibility such as cytotoxicity, hemolytic activity, resistance to leaching, having low particulates.

In some embodiments, materials may be selected for specific properties for use in a coextruded material to form at least one layer of a bag. Layers may be constructed such that when constructed an interior layer of the bag is relatively biocompatible, that is the material on an inner surface of the bag is stable and does not leach into the contents of the bag.

For example, a property of interest that may be used to select a material for kit component such as a collection bag, a cryopreservation bag, and/or the associated tubing may relate to sealing, for example heat sealing.

Bags, such as collection bags and/or cryopreservation bags, and any associated tubing may be generally clear, transparent, translucent, any color desired, or a combination thereof. Tissue collection bags and/or tubing may be generally fabricated in ways analogous to the fabrication of closed and/or sealed blood and/or cryopreservation bags and the associated tubing. Tubing in the invention may be constructed from any desired material including, but not limited to polyvinyl chloride (PVC). For example, PVC may be a desired material as PVC is advantageous for welding and/or sealing.

In some embodiments, at least one end of a collection bag may be open for receiving tissue. In particular, in an embodiment, a tissue sample, for example from a biopsy may be placed in the bag through the open end, for example, a top end. In some cases, the biopsy sample may be cancerous tissue from an animal (e.g., domestic animal such as dog or cat) or a human.

After tissue is positioned in the bag, the bag may be sealed, and then may be processed. Processing may include agitation, e.g., gentle agitation, extraction, and/or enzymatic digestion of the tissue in the bag. Tissue processing and extraction of a desired material, such as tumor infiltrating lymphocytes (TILs), can be in a closed system. Advantageous or preferred embodiments may include indicators to identify the patient from whom the tissue was collected and/or marks to show where the collection bag may be clamped, sealed, acted upon by a device, and/or affixed in place in an instrument.

In some embodiments, bag may be formed from a sealable material. For example, bag may be formed from materials including, but not limited to polymers such as synthetic polymers including aliphatic or semi-aromatic polyamides (e.g., Nylon), ethylene-vinyl acetate (EVA) and blends thereof, thermoplastic polyurethanes (TPU), polyethylenes (PE), a vinyl acetate and polyolefin polymer blends, and/or combinations of polymers. Portions of a bag may be sealed and/or welded with energy such as heat, radio frequency energy, high frequency (HF) energy, dielectric energy, and/or any other method known in the art.

A collection bag may be used as a processing and/or disaggregation bag. Collection bags may have width in a range from about 4 cm to about 12 cm and a width in a range from about 10 cm to about 30 cm. For example, a collection bag for use in processing may have a width of about 7.8 cm and a length of about 20 cm. In particular, a bag may be heat sealable, for example, using an EVA polymer or blends thereof, a vinyl acetate and polyolefin polymer blend, and/or one or more polyamides (Nylon).

Indicators may include, but are not limited to codes, letters, words, names, alphanumeric codes, numbers, images, bar codes, quick response (QR) codes, tags, trackers such as smart tracker tags or bluetooth trackers, and/or any indicator known in the art. In some embodiments, indicators may be printed on, etched on, and/or adhered to a surface of a component of a kit. Indicators may also be positioned on a bag using an adhesive, for example, a sticker or tracker may be placed on a bag and/or on multiple bags. Collection bags and/or cryopreservation kit may include multiple indicators such as numeric codes and/or QR codes.

Indicators, for example QR codes, tags such as smart tags, and/or trackers may be used to identify a sample within a bag as well as to instruct a device's processor such that the device runs a specific program according to a type of disaggregation, enrichment, and/or stabilization processes that are conducted in cryopreservation kits. Different types of media may be used in these processes, for example, enzyme media, tumor digest media and/or cryopreservation media which may allow for a controlled rate of freezing. In some embodiments, cryopreservation kit and/or components thereof may include indicators that may be readable by an automated device. The device may then execute a specific fully automatic method for processing tissue when inserted to such a device. The invention is particularly useful in a sample processing, particularly automated processing. In some instances, the cryopreservation kit and/or components thereof described herein may be single use in an automated and/or a semi-automated process for the disaggregation, enrichment, and/or stabilization of cells or cell aggregates. In some embodiments, bags for use in a cryopreservation kit such as a collection bag may in some embodiments be used for multiple processes. For example, collection bags may be repeatedly sealed in different locations to create separate compartments for processing of a tissue sample such as a biopsy sample and/or solid tissue.

Further, marks may be placed at various locations on bags, such as tissue collection bags to indicate where the bags may be sealed, clamped, and/or affixed to an object. In some embodiments, marks showing where a bag may be clamped, sealed, and/or affixed to an object, such as instrument, may be positioned on the bag prior to use. For example, one or more marks may be positioned on a bag during manufacturing.

Positioners may be used to ensure that tissue material in bags can be treated properly during use, for example, positioning proximate an instrument. In some systems, the positioners may facilitate the use of the bags described herein in automated systems. In particular, positioners may be used to move bag through an automated system.

Use of an indicator, such as a QR code may allow for tracking of process steps for a specific sample such that it is possible to follow the sample through a given process.

The invention involves and provides therapeutic cell populations as discussed in the following numbered paragraphs:

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 3A is a schematic diagram of a flexible container for stabilization of cells following disaggregation of the solid tissue material and/or enrichment of cells.

FIG. 13A shows a front view of an embodiment of a collection bag.

FIG. 13B shows a front view of an embodiment of a collection bag.

FIG. 13C shows a front view of an embodiment of a collection bag.

FIG. 16A shows a top view of an embodiment of a collection bag.

FIG. 16B shows a bottom view of an embodiment of a collection bag.

FIG. 17A shows a top view of an embodiment of a partially open tissue collection bag for sealing tissue therein for processing of the invention where the bag has sealed edges.

FIG. 17B shows a bottom view of an embodiment of an open tissue collection bag for sealing tissue therein for processing of the invention where the bag has sealed edges.

FIG. 20A shows a front view of an embodiment of a collection bag.

FIG. 20B shows a front view of an embodiment of a collection bag.

FIG. 20C shows a front view of an embodiment of a collection bag.

FIG. 36A shows a front view of an embodiment of a cryopreservation kit that includes a collection bag, a filter, and a cryopreservation bag.

FIG. 36B shows a side view of an embodiment of a collection bag secured using a clamp, hinge, and latch as well as a bar positioned to proximate a surface of the collection bag during use.

FIG. 36C shows an exploded view of a clamp positioned on a collection bag.

FIG. 50, FIG. 51A, FIG. 51B, and FIG. 51C show alternative ways of sealing the sample bag.

FIG. 70 compares temperatures recorded from sample bags following a protocol that held the material at 4° C. for 10 minutes, then decreased the temperature at a rate of −1° C./min or decreased from 35° C. to −80° C. directly at a rate of −2° C./min.

FIG. 71A Disaggregator speed setpoint; FIG. 71B Disaggregator speed record; FIG. 71C Temperature setpoint (disaggregation); FIG. 71D Cryo-plate temperature record (disaggregation);

FIG. 71E Temperature setpoint (cryopreservation); FIG. 71F Temperature record (cryopreservation); FIG. 71G Setpoint cooling rate; FIG. 71H Cryo-plate cooling rate record.

FIG. 72A Disaggregator speed setpoint; FIG. 72B Disaggregator speed record; FIG. 72C Temperature setpoint (disaggregation); FIG. 72D Cryo-plate temperature record (disaggregation); FIG. 72E Temperature setpoint (cryopreservation);

FIG. 72F Temperature record (cryopreservation); FIG. 72G Setpoint cooling rate; FIG. 72H Cryo-plate cooling rate record.

FIG. 73A Disaggregator speed setpoint; FIG. 73B Disaggregator speed record; FIG. 73C Temperature setpoint (disaggregation and cryopreservation); FIG. 73D Cryo-plate temperature record (disaggregation and cryopreservation); FIG. 73E Cooling rate setpoint (disaggregation and (cryopreservation); FIG. 73F Cryo-plate cooling rate record (disaggregation and (cryopreservation).

FIG. 75A The median overall survival (OS) time with all 21 treated patients was 21.3 months. FIG. 75B The median OS time of 15 patients with quantitative response data was 16 months. FIG. 75C The median OS time for nonresponders (N=7) was 6.5 months. The median OS time for responders (per quantitative response only, N=8) was not reached.

DETAILED DESCRIPTION OF THE INVENTION

Figure 1:
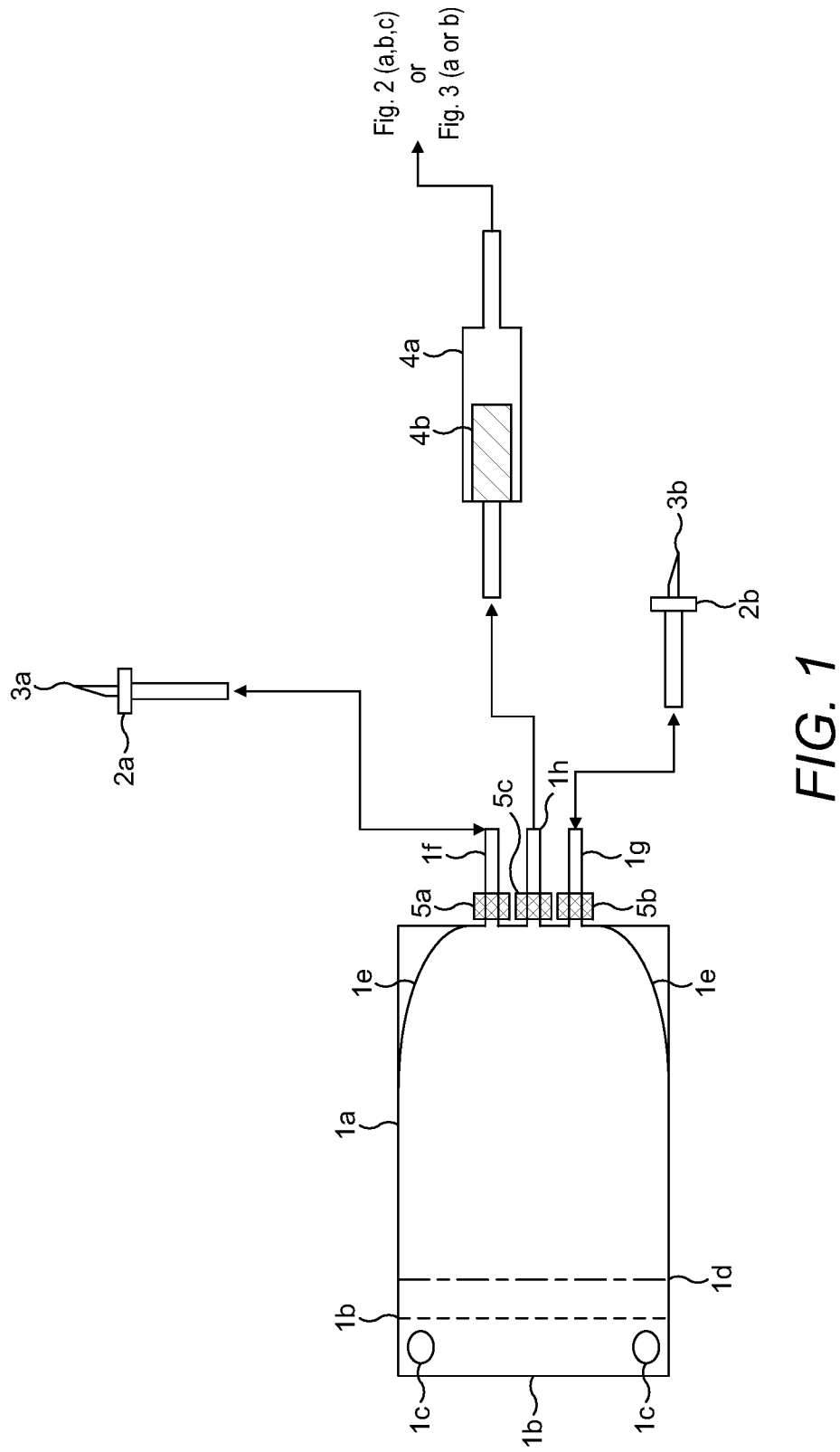
FIG. 1 is a schematic diagram of a flexible container for disaggregation and digestion of the solid tissue material.

Unless defined otherwise, all technical and scientific terms used herein have the same meaning as is commonly understood by one of skill in the art to which this invention belongs.

The term "anti-CD3 antibody" refers to an antibody or variant thereof, e.g., a monoclonal antibody and including human, humanized, chimeric, murine or mammalian antibodies which are directed against the CD3 receptor in the T cell antigen receptor of mature human T cells. Anti-CD3 antibodies include OKT-3, also known as muromonab. Anti-CD3 antibodies also include the UHCT1 clone, also known as T3 and CD3.epsilon. Other anti-CD3 antibodies include, for example, otelixizumab, teplizumab, and visilizumab.

When "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the tumor infiltrating lymphocytes (e.g. secondary TILs or genetically modified cytotoxic lymphocytes) described herein may be administered at a dosage of $10^4$ to $10^{11}$ cells/kg body weight (e.g., $10^5$ to $10^6$, $10^5$ to $10^{10}$, $10^5$ to $10^{11}$, $10^6$ to $10^{10}$, $10^6$ to $10^{11}$, $10^7$ to $10^{11}$, $10^9$ to $10^{10}$, $10^8$ to $10^{11}$, $10^8$ to $10^{10}$, $10^9$ to $10^{11}$, or $10^9$ to $10^{10}$ cells/kg body weight), including all integer values within those ranges. Tumor infiltrating lymphocytes (including in some cases, genetically modified cytotoxic lymphocytes) compositions may also be administered multiple times at these dosages. The tumor infiltrating lymphocytes (including in some cases, genetically) can be administered by using infusion techniques that are commonly known in immunotherapy (see, e.g., Rosenberg et al., New Eng. J. of Med. 319: 1676, 1988). The optimal dosage and treatment regime for a particular patient can readily be determined by one skilled in the art of medicine by monitoring the patient for signs of disease and adjusting the treatment accordingly.

The terms "co-administration," "co-administering," "administered in combination with," "administering in combination with," "simultaneous," and "concurrent," as used herein, encompass administration of two or more active pharmaceutical ingredients (in a preferred embodiment of the present invention, for example, at least one potassium channel agonist in combination with a plurality of TILs) to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present are preferred.

"Cellularized or cellularization" as used herein refers to the process of disaggregation where by the solid tissue a multicellular material generally made up of multiple cell lineages/types is broken down into small numbers of cells including but not limited to one cell but could be multiple cells of various lineages or cell types in very small numbers i.e. clump of cells or cell aggregates.

"Closed system" as used herein refers to a system that is closed to the outside environment. Any closed system appropriate for cell culture methods can be employed with the methods of the present invention. Closed systems include, for example, but are not limited to closed G-Rex containers or cell culture bags. Once a tumor segment is added to the closed system, the system is not open to the outside environment until the TILs are ready to be administered to the patient. In an advantageous embodiment, the closed system is the system disclosed in PCT Publication No. WO 2018/130845.

"Cryopreservation media" or "cryopreservation medium" as used herein refers to any medium that can be used for cryopreservation of cells. Such media can include media comprising 2% to 10% DMSO. Exemplary media include CryoStor CS10, HypoThermosol, Bloodstor BS-55 as well as combinations thereof.

The term "Cryopreserved TILs" herein is meant that TILs, either primary, bulk, or expanded (REP TILs), are treated and stored in the range of about −190° C. to −60° C. General methods for cryopreservation are also described elsewhere herein, including in the Examples. For clarity, "cryopreserved TILs" are distinguishable from frozen tissue samples which may be used as a source of primary TILs.

"Depletion" as used herein refers to a process of a negative selection that separates the desired cells from the undesired cells which are labelled by one marker-binding fragment coupled to a solid phase.

"Disaggregation or disaggregate" as used herein refers to the transformation of solid tissue into a single cells or small cell number aggregates where a single cell as a spheroid has a diameter in the range of 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, or more, wherein this is more usually between 7 to 20 µm.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, or the manner of administration. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

"Engineered" as used herein refers to either addition of nucleic material or factors, which change the tissue derived cell function from their original function to have a new or improved function for its ultimate utility.

"Enzyme Media" as used herein refers to media having enzymatic activity such as collagenase, trypsin, lipase, hyaluronidase, deoxyribonuclease, Liberase HI, pepsin, or mixtures thereof.

"Filtrate" as used herein refers to the material that passes through a filter, mesh or membrane.

"Flexible container" as used herein refers to a flexible packaging system in multiple formats with one or more different types of film. Each film type is selected to provide specific characteristics to preserve the physical, chemical, and functional characteristics of the sterile fluids, solid tissue derived cellular material and the container integrity depending upon the step of the process.

"Freezing solution" or "cryopreservation solution" also referred in the field to as the cryoprotectant is a solution that contains cryoprotective additives. These are generally permeable, non-toxic compounds which modify the physical stresses cells are exposed to during freezing in order to minimize freeze damage (i.e. due to ice formation) and are most commonly a % vol/vol of one or more of the following: dimethylsulphoxide (DMSO); ethylene glycol; glycerol; 2-methyl-2,4-pentanediol (MPD); propylene glycol; sucrose; and trehalose.

The term "hematological malignancy" refers to mammalian cancers and tumors of the hematopoietic and lymphoid tissues, including but not limited to tissues of the blood, bone marrow, lymph nodes, and lymphatic system. Hematological malignancies are also referred to as "liquid tumors." Hematological malignancies include, but are not limited to, acute lymphoblastic leukemia (ALL), chronic lymphocytic lymphoma (CLL), small lymphocytic lymphoma (SLL), acute myelogenous leukemia (AML), chronic myelogenous leukemia (CML), acute monocytic leukemia (AMoL), Hodgkin's lymphoma, and non-Hodgkin's lymphomas. The term "B cell hematological malignancy" refers to hematological malignancies that affect B cells.

The term "IL-2" (also referred to herein as "IL2") refers to the T cell growth factor known as interleukin-2, and includes all forms of IL-2 including human and mammalian forms, conservative amino acid substitutions, glycoforms, biosimilars, and variants thereof. IL-2 is described, e.g., in Nelson, J. Immunol. 2004, 172, 3983-88 and Malek, Annu. Rev. Immunol. 2008, 26, 453-79, the disclosures of which are incorporated by reference herein. The amino acid sequence of recombinant human IL-2 suitable for use in the invention is given in Table 2 (SEQ ID NO: 3). For example, the term IL-2 encompasses human, recombinant forms of IL-2 such as aldesleukin (PROLEUKIN, available commercially from multiple suppliers in 22 million IU per single use vials), as well as the form of recombinant IL-2 commercially supplied by CellGenix, Inc., Portsmouth, N.H., USA (CELLGRO GMP) or ProSpec-Tany TechnoGene Ltd., East Brunswick, N.J., USA (Cat. No. CYT-209-b) and other commercial equivalents from other vendors. Aldesleukin (des-alanyl-1, serine-125 human IL-2) is a nonglycosylated human recombinant form of IL-2 with a molecular weight of approximately 15 kDa. The term IL-2 also encompasses pegylated forms of 1L-2, as described herein, including the pegylated IL2 prodrug NKTR-214, available from Nektar Therapeutics, South San Francisco, Calif., USA. NKTR-214 and pegylated IL-2 suitable for use in the invention is described in U.S. Patent Application Publication No. US 2014/0328791 A1 and International Patent Application Publication No. WO 2012/065086 A1. Alternative forms of conjugated IL-2 suitable for use in the invention are described in U.S. Pat. Nos. 4,766,106, 5,206,344, 5,089,261 and 4,902,502. Formulations of IL-2 suitable for use in the invention are described in U.S. Pat. No. 6,706,289.

The term "IL-4" (also referred to herein as "IL4") refers to the cytokine known as interleukin 4, which is produced by Th2 T cells and by eosinophils, basophils, and mast cells. IL-4 regulates the differentiation of naive helper T cells (Th0 cells) to Th2 T cells. Steinke and Borish, Respir. Res. 2001, 2, 66-70. Upon activation by IL-4, Th2 T cells subsequently produce additional IL-4 in a positive feedback loop. IL-4 also stimulates B cell proliferation and class II MI-IC expression, and induces class switching to IgE and IgG1 expression from B cells. Recombinant human IL-4 suitable for use in the invention is commercially available from multiple suppliers, including ProSpec-Tany TechnoGene Ltd., East Brunswick, N.J., USA (Cat. No. CYT-211) and ThermoFisher Scientific, Inc., Waltham, Mass., USA (human IL-15 recombinant protein, Cat. No. Gibco CTP0043).

The term "IL-7" (also referred to herein as "IL7") refers to a glycosylated tissue-derived cytokine known as interleukin 7, which may be obtained from stromal and epithelial cells, as well as from dendritic cells. Fry and Mackall, Blood 2002, 99, 3892-904. IL-7 can stimulate the development of T cells. IL-7 binds to the IL-7 receptor, a heterodimer consisting of TL-7 receptor alpha and common gamma chain receptor, which in a series of signals important for T cell development within the thymus and survival within the periphery. Recombinant human 1L-7 suitable for use in the invention is commercially available from multiple suppliers, including ProSpec-Tany TechnoGene Ltd., East Brunswick, N.J., USA (Cat. No. CYT-254) and ThermoFisher Scientific, Inc., Waltham, Mass., USA (human IL-15 recombinant protein, Cat. No. Gibco PHC0071).

The term "IL-12" (also referred to herein as "IL12") refers to the T cell growth factor known as interleukin-12. Interleukin (IL)-12 is a secreted heterodimeric cytokine comprised of 2 disulfide-linked glycosylated protein subunits, designated p35 and p40 for their approximate molecular weights. IL-12 is produced primarily by antigen-presenting cells and drives cell-mediated immunity by binding to a two-chain receptor complex that is expressed on the surface of T cells or natural killer (NK) cells. The IL-12 receptor beta-1 (IL-12Rpi) chain binds to the p40 subunit of IL-12, providing the primary interaction between IL-12 and its receptor. However, it is IL-12p35 ligation of the second receptor chain, IL-12RP2, that confers intracellular signaling. IL-12 signaling concurrent with antigen presentation is thought to invoke T cell differentiation towards the T helper 1 (Th1) phenotype, characterized by interferon gamma (IFNy) production. Th1 cells are believed to promote immunity to some intracellular pathogens, generate complement-fixing antibody isotypes, and contribute to tumor immunosurveillance. Thus, IL-12 is thought to be a significant component to host defense immune mechanisms. IL-12 is part of the IL-12 family of cytokines which also includes IL-23, TL-27, IL-35, IL-39.

The term "IL-15" (also referred to herein as "IL15") refers to the T cell growth factor known as interleukin-15, and includes all forms of IL-15 including human and mammalian forms, conservative amino acid substitutions, glycoforms, biosimilars, and variants thereof. IL-15 is described, e.g., in Fehniger and Caligiuri, Blood 2001, 97, 14-32, the disclosure of which is incorporated by reference herein. IL-15 shares 13 and y signaling receptor subunits with IL-2. Recombinant human IL-15 is a single, non-glycosylated polypeptide chain containing 114 amino acids (and an N-terminal methionine) with a molecular mass of 12.8 kDa. Recombinant human IL-15 is commercially available from multiple suppliers, including ProSpec-Tany TechnoGene Ltd., East Brunswick, N.J., USA (Cat. No. CYT-230-b) and ThermoFisher Scientific, Inc., Waltham, Mass., USA (human IL-15 recombinant protein, Cat. No. 34-8159-82).

The term "IL-18" (also referred to herein as "IL18") refers to the T cell growth factor known as interleukin-15. Interleukin-18 (IL-18) is a proinflammatory cytokine that belongs to the 1L-1 cytokine family, due to its structure, receptor family and signal transduction pathways. Related cytokines include IL-36, IL-37, IL-38.

The term "1L-21" (also referred to herein as "IL21") refers to the pleiotropic cytokine protein known as interleukin-21, and includes all forms of IL-21 including human and mammalian forms, conservative amino acid substitutions, glycoforms, biosimilars, and variants thereof. 1L-21 is described, e.g., in Spolski and Leonard, Nat. Rev. Drug. Disc. 2014, 13, 379-95, the disclosure of which is incorporated by reference herein. IL-21 is primarily produced by natural killer T cells and activated human CD4+ T cells. Recombinant human IL-21 is a single, non-glycosylated polypeptide chain containing 132 amino acids with a molecular mass of 15.4 kDa. Recombinant human 1L-21 is commercially available from multiple suppliers, including ProSpec-Tany TechnoGene Ltd., East Brunswick, N.J., USA (Cat. No. CYT-408-b) and ThermoFisher Scientific, Inc., Waltham, Mass., USA (human IL-21 recombinant protein, Cat. No. 14-8219-80).

The term "liquid tumor" refers to an abnormal mass of cells that is fluid in nature. Liquid tumor cancers include, but are not limited to, leukemias, myelomas, and lymphomas, as well as other hematological malignancies. TILs obtained from liquid tumors may also be referred to herein as marrow infiltrating lymphocytes (MILs).

"Magnetic" in "magnetic particle" as used herein refers to all subtypes of magnetic particles, which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

"Marker" as used herein refers to a cell antigen that is specifically expressed by a certain cell type. Preferentially, the marker is a cell surface marker, so that enrichment, isolation and/or detection of living cells can be performed.

"Marker-binding fragment" as used herein refers to any moiety that binds preferentially to the desired target molecule of the cell, i.e. the antigen. The term moiety comprises, e.g., an antibody or antibody fragment. The term "antibody" as used herein refers to polyclonal or monoclonal antibodies which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labelled antibodies). The term "antibody" comprises both intact molecules and antibody fragments, such as Fab, Fab', F(ab')2, Fv and single-chain antibodies. Additionally, the term "marker-binding fragment" includes any moiety other than antibodies or antibody fragments that binds preferentially to the desired target molecule of the cell. Suitable moieties include, without limitation, oligonucleotides known as aptamers that bind to desired target molecules (Hermann and Pantel, 2000: Science 289: 820-825), carbohydrates, lectins or any other antigen binding protein (e.g. receptor-ligand interaction).

"Media" means various solutions known in the art of cell culturing, cell handling and stabilization used to reduce cell death, including but not limited to one or more of the following media Organ Preservation Solutions, selective lysis solutions, PBS, DMEM, HBSS, DPBS, RPMI, Iscove's medium, X-VIVO™, Lactated Ringer's solution, Ringer's acetate, saline, PLASMALYTE™ solution, crystalloid solutions and IV fluids, colloid solutions and IV fluids, five percent dextrose in water (D5W), Hartmann's Solution. The media can be standard cell media like the above mentioned-media or special media for e.g. primary human cell culture (e.g. for endothelia cells, hepatocytes, or keratinocytes) or stem cells (e.g. dendritic cell maturation, hematopoietic expansion, keratinocytes, mesenchymal stem cells or T cell expansion). The media may have supplements or reagents well known in the art, e.g. albumins and transport proteins, amino acids and vitamins, antibiotics, attachments factors, growth factors and cytokines, hormones, metabolic inhibitors or solubilizing agents. Various media are commercially available e.g. from ThermoFisher Scientific or Sigma-Aldrich.

The term "microenvironment," as used herein, may refer to the solid or hematological tumor microenvironment as a whole or to an individual subset of cells within the microenvironment. The tumor microenvironment, as used herein, refers to a complex mixture of "cells, soluble factors, signaling molecules, extracellular matrices, and mechanical cues that promote neoplastic transformation, support tumor growth and invasion, protect the tumor from host immunity, foster therapeutic resistance, and provide niches for dominant metastases to thrive," as described in Swartz, et al., Cancer Res., 2012, 72, 2473. Although tumors express antigens that should be recognized by T cells, tumor clearance by the immune system is rare because of immune suppression by the microenvironment.

The term "negatively separated" as used herein refers to the active separation of cells which are bound by one marker-binding fragment coupled to a solid phase and these cells are not the required population of cells.

"Non-labelled" or "untouched" as used herein refers to the cells which are not bound by one marker-binding fragment coupled to a solid phase. The non-labelled, untouched cell fraction contains the desired target cells.

"Non-target cells" as used herein refers to cells which are specifically bound by one marker-binding fragment which is coupled to a solid phase that is used to remove an unwanted cell type.

"OKT-3" (also referred to herein as "OKT3") refers to a monoclonal antibody or biosimilar or variant thereof, including human, humanized, chimeric, or murine antibodies, directed against the CD3 receptor in the T cell antigen receptor of mature T cells, and includes commercially-available forms such as OKT-3 (30 ng/mL, MACS GMP CD3 pure, Miltenyi Biotech, Inc., San Diego, Calif., USA) and muromonab or variants, conservative amino acid substitutions, glycoforms, or biosimilars thereof.

"Particle" as used herein refers to a solid phase such as colloidal particles, microspheres, nanoparticles, or heads. Methods for generation of such particles are well known in the field of the art. The particles may be magnetic particles or have other selective properties. The particles may be in a solution or suspension or they may be in a lyophilized state prior to use in the present invention. The lyophilized particle is then reconstituted in convenient buffer before contacting the sample to be processed regarding the present invention.

The terms "peripheral blood mononuclear cells" and "PBMCs" refers to a peripheral blood cell having a round nucleus, including lymphocytes (T cells, B cells, NK cells) and monocytes. Preferably, the peripheral blood mononuclear cells are irradiated allogeneic peripheral blood mononuclear cells. PBMCs are a type of antigen-presenting cell.

The terms "pharmaceutically acceptable carrier" or "pharmaceutically acceptable excipient" are intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

The term "population of cells" (including TILs) herein is meant a number of cells that share common traits. In general, populations generally range from $1\times10^6$ to $1\times10^{12}$ in number, with different TIL populations comprising different numbers.

"Positively separated" as used herein refers to the active separation of cells which are bound by one marker-binding fragment coupled to a solid phase and these cells are the required population of cells.

"Negatively separated" as used herein refers to the active separation of cells which are bound by one marker-binding fragment coupled to a solid phase and these cells are not the required population of cells.

"Purity" as used herein refers to the percentage of the target population or populations desired from the original solid tissue.

"Rapid expansion" means an increase in the number of antigen-specific TILs of at least about 3-fold (or 4-, 5-, 6-, 7-, 8-, or 9-fold) over a period of a week, more preferably at least about 10-fold (or 20-, 30-, 40-, 50-, 60-, 70-, 800-, or 90-fold) over a period of a week, more preferably at least about 100-fold (or 200-, 300-, 400-, 500-, 600-, 700-, 800-, or 900-fold) over a period of a week, or most preferably at least about 1000-fold or 2000-, 3000-, 4000-, 5000-, 6000-, 7000-, 8000-, or 9000-fold) over a period of a week. A number of rapid expansion protocols are outlined below.

"Regenerative medicine(s)", "adoptive cell therapy(ies)" or "advanced therapy medicinal product(s)" are used interchangeably herein to refer to cellular material that is used for therapeutic purposes of one or more mammals either by: the action of a part of or all of the cellular material; the supportive actions of a part of or all of the cellular material with the aim to improve the wellbeing of the mammal after application. The therapeutic cells can either be used directly or may require further processing, expansion and/or engineering to provide these actions.

"Sample" as used herein refers to a sample containing cells in any ratio. Preferentially, these cells are viable. In some instances, these cells can also be fixed or frozen cells which may be used for subsequent nucleic acids or protein extraction. The samples may be from animals, especially mammals such as mouse, rats, or humans. Any compressible solid tissue that contains cells can be used. The invention is illustrated mainly through the isolation of hematopoietic and cancer cells from solid tumor tissue. However, the invention relates to a method for isolation of a breadth of cells from any mammalian solid tissue.

"Solid phase" as used herein refers to the coupling of the marker-binding fragment, e.g. an antibody, bound to another substrate(s), e.g. particles, fluorophores, haptens like biotin, polymers, or larger surfaces such as culture dishes and microtiter plates. In some cases, the coupling results in direct immobilization of the antigen-binding fragment, e.g. if the antigen-binding fragment is coupled to a larger surface of a culture dish. In other cases, this coupling results in indirect immobilization, e.g. an antigen-binding fragment coupled directly or indirectly (via e.g. biotin) to a magnetic bead is immobilized if said bead is retained in a magnetic field. In further cases the coupling of the antigen-binding fragment to other molecules results not in a direct or indirect immobilization but allows for enrichment, separation, isolation, and detection of cells according to the present invention, e.g. if the marker-binding fragment is coupled to a chemical or physical moiety which then allows discrimination of labelled cells and non-labelled cells, e.g. via flow cytometry methods, like FACS sorting, or fluorescence microscopy.

"Solid tissue" as used herein refers to a piece or pieces of animal derived mammalian solid tissue which by its three dimensions i.e. length, breadth and thickness as a geometrical body is larger than the size of multiple individual cell based units and often contains connective materials such as collagen or a similar matrix that make up structure of the tissue whereby said solid tissue cannot flow through tubes or be collected by a syringe or similar small conduit or receptacle and is i.e. with dimensions in the range of 500 µm, 1 mm, 2 mm, 3 mm, 4 mm, 5 mm, 1 cm, 2 cm, 3 cm, 4 cm, 5 cm, 10 cm, 20 cm, 30 cm, or more.

"Solid tumor" refers to an abnormal mass of tissue that usually does not contain cysts or liquid areas. Solid tumors may be benign or malignant. The term "solid tumor cancer" refers to malignant, neoplastic, or cancerous solid tumors. Solid tumor cancers include, but are not limited to, sarcomas, carcinomas, and lymphomas, such as cancers of the lung, breast, prostate, colon, rectum, and bladder. The tissue structure of solid tumors includes interdependent tissue compartments including the parenchyma (cancer cells) and the supporting stromal cells in which the cancer cells are dispersed and which may provide a supporting microenvironment. In some embodiments, the cancer is selected from cervical cancer, head and neck cancer (including, for example, head and neck squamous cell carcinoma [HN-SCC]) glioblastoma, ovarian cancer, sarcoma, pancreatic cancer, bladder cancer, breast cancer, triple negative breast cancer, and non-small cell lung carcinoma. The tissue structure of solid tumors includes interdependent tissue compartments including the parenchyma (cancer cells) and the supporting stromal cells in which the cancer cells are dispersed and which may provide a supporting microenvironment.

By "thawed cryopreserved TILs" herein is meant a population of TILs that was previously cryopreserved and then treated to return to room temperature or higher, including but not limited to cell culture temperatures or temperatures wherein TILs may be administered to a patient.

The terms "treatment", "treating", "treat", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

By "tumor infiltrating lymphocytes" or "TILs" herein is meant a population of cells originally obtained as white blood cells that have left the bloodstream of a subject and migrated into a tumor. TILs include, but are not limited to, CD8+ cytotoxic T cells (lymphocytes), Thi and Thi 7 CD4+ T cells, natural killer cells, dendritic cells, and Ml macrophages. TILs include both primary and secondary TILs. "Primary TILs" are those that are obtained from patient tissue samples as outlined herein (sometimes referred to as "freshly harvested"), and "secondary TILs" are any TIL cell populations that have been expanded or proliferated as discussed herein, including, but not limited to hulk TILs and expanded TILs ("REP TILs" or "post-REP TILs"). TIL cell populations can include genetically modified TILs. TILs can generally be defined either biochemically, using cell surface markers, or functionally, by their ability to infiltrate tumors and effect treatment. TILs can be generally categorized by expressing one or more of the following biomarkers: CD4, CD8, TCR αβ, CD27, CD28, CD56, CCR7, CD45Ra, CD62L, CD95, PD-1, and CD25. Additionally and alternatively, TILs can be functionally defined by their ability to infiltrate solid tumors upon reintroduction into a patient. TILS may further be characterized by potency—for example, TILS may be considered potent or functional if in response to TCR engagement they produce, for example, interferon (IFN) release is greater than about 50 pg/mL, greater than about 100 pg/mL, greater than about 150 pg/mL, or greater than about 200 pg/mL, or more preferably individual cells can be Potency through intracellular staining for CD137, CD107a, INF-y TNF-a, and IL-2 following TCR induced stimulation by flow cytometry.

"Retentate" as used herein refers to the material that does not pass through a filter, mesh or membrane.

"Ultimate utility" as used herein refers to manufacture of or direct use in regenerative medicines, adoptive cell therapies, ATMPs, diagnostic in vitro studies or scientific research.

The present invention relates to tumor infiltrating lymphocytes (TILs) in particularly unmodified TILS (UTILs), which may be isolated from tumors of a metastatic cancer patient, involving autologous TILs generated from and returned to the same cancer patient. The present invention also relates to methods for isolating a therapeutic population of cryopreserved TILs or UTILs and to TILs and UTILs obtained or obtainable via use of a device comprising a single use aseptic kit for processing of a resected tumor by the methods described herein.

In general, TILs are initially obtained from a patient tumor sample ("primary TILs") and then expanded into a larger population for further manipulation as described herein, cryopreserved, restimulated as outlined herein and optionally evaluated for phenotype and metabolic parameters as an indication of TIL health.

A patient tumor sample may be obtained using methods known in the art, generally via surgical resection, needle biopsy or other means for obtaining a sample that contains a mixture of tumor and TIL cells. In general, the tumor sample may be from any solid tumor, including primary tumors, invasive tumors or metastatic tumors. The tumor sample may also be a liquid tumor, such as a tumor obtained from a hematological malignancy. The solid tumor may be of any cancer type, including, but not limited to, breast, ovary, cervical, pancreatic, prostate, colorectal, lung, brain, renal, stomach, and skin (including but not limited to squamous cell carcinoma, basal cell carcinoma, and melanoma). In some embodiments, TILs are obtained from malignant melanoma tumors, as these have been reported to have particularly high levels of TILs.

The production generally involves a two-stage process. In stage 1, initial tumor material is dissected, placed in the aseptic kit having a disaggregation module, enzymatically digesting and/or fragmenting, and homogenizing the tumor in the disaggregation module to provide a single cell suspension. While the homogenized cells can be further purified within the aseptic kit in a separate enrichment module to remove components such as no longer required reagents; cell debris; non-disaggregated tissue, the cells can be directly cryopreserved to stabilize the starting material for TIL manufacture and storage in the stabilization module of the aseptic kit until Stage 2 is required. Stage 2 generally involves growth of the TILs out of the resected tumor starting material (2 weeks), followed by a rapid expansion process of the TIL cells (rapid expansion protocol "REP"—2 weeks). The final product is washed and harvested prior to suspension in buffered saline, 8.5% HAS and 10% DMSO and cryopreserved to form a solid aseptic product that is thawed prior to infusion as a single dose with no further modification.

There are three separate elements to the treatment that potentially contribute to therapeutic activity. The core element is the TILs i.e. tumor-derived T cells, which can target and eliminate tumor cells by a variety of methods utilized by T cells as a part of their normal function. These methods include direct methods (i.e. perforin-mediated cytotoxicity) and indirect methods (i.e. cytokine production). Which of these methods is the most important to in vivo anti-tumor effects is unclear although mouse models suggest that the production of interferon gamma is critical for effective therapy. The two other elements which contribute to the therapy are pre-conditioning chemotherapy and high dose intravenous IL-2. These two elements are thought to act by supporting engraftment of T cells in the patient after infusion: initially through conditioning chemotherapy which removes competing and regulating immune cells; followed by the IL-2 component which supports survival of T cells.

The structure of the cell therapy product is created by growing the TIL directly out of an enzyme digested tumor mass by means of growth supporting cell culture media and a T cell supporting growth factor Interleukin-2 (IL-2). This enables tumor specific T cells to selectively survive and grow out of the tumor cell mixture, while T cells that do not recognize tumor antigens will not be stimulated and be selectively lost. The product comprises an autologous T-cell based product where the T cells have been derived from a patient's own cancer tissue and rapidly expanded to form a pure T cell population and T cells as defined by CD3 surface marker.

In brief, TILs, in particular UTILs, may be produced in a two-stage process using a tumor biopsy as the starting material: Stage 1 (generally performed over 2-3 hours) initial collection and processing of tumor material using dissection, enzymatic digestion and homogenization via use of a kit and a semi-automatic device to produce a single cell suspension which can be directly cryopreserved using the stabilization module of the kit to stabilize the starting material for subsequent manufacture and Stage 2 which can occur days or years later. Stage 2 may be performed over 4 weeks, which may be a continuous process starting with thawing of the product of Stage 1 and growth of the TIL out of the tumor starting material (about 2 weeks) followed by a rapid expansion process of the TIL cells (about 2 weeks) to increase the amount of cells and therefore dose. The TILs, in particular UTILs, are concentrated and washed prior to formulation as a liquid suspension of cells. The aseptic drug product may be cryopreserved in a bag that will be thawed prior to intravenous infusion as a single dose with no further modification.

In one embodiment, a bag of the invention is a collection bag and/or a cryopreservation bag. Bags and any associated tubing may be generally clear, transparent, translucent, any color desired, or a combination thereof. Tissue collection bags and/or tubing may be generally fabricated in ways analogous to the fabrication of closed and/or sealed blood and/or cryopreservation bags and the associated tubing. Tubing in the invention may be constructed from any desired material including, but not limited to polyvinyl chloride (PVC). For example, PVC may be a desired material as PVC is advantageous for welding and/or sealing.

A collection bag, such as a tissue collection bag of the invention may include at least a portion of the bag for receiving tissue made from a predetermined material such as a polyolefin polymer, ethylene vinyl acetate (EVA), copolymers such as vinyl acetate and polyolefin polymer blend (i.e., OriGen Biomedical EVO film), and/or a material including EVA. Materials for use in the bag may be selected for a specific property and/or a selection of properties, for example, salability such as heat sealability, gas permeability, flexibility for example low temperature flexibility, elasticity for example low temperature elasticity, chemical resistance, optical clarity, biocompatibility such as cytotoxicity, hemolytic activity, resistance to leaching, having low particulate.

Seals may be formed during use with energy, for example, heat to create a weld zone. Seals formed during use may be have a width in a range from about 2.5 mm to about 7.5 mm. Generally, seal 140 is formed after tissue material is placed in bag 140 and may have a width of about 5 mm. Seals may be tested for strength using a seal peel test (i.e., ASTM F88/F88M), and/or a burst test (i.e., ASTM F1140/F1140M or ASTM F2051/F2054M).

In some embodiments, a bag or a flexible container may withstand a force of 100 Newtons during use when properly sealed and further secured with a clamp when positioned within a device for treatment and/or processing. A bag or a flexible container embodiment may be constructed to withstand a force of 75 Newtons during use when properly sealed and further secured with a clamp when positioned within a device for treatment and/or processing.

When forming seals or welds on a flexible container such as a bag, for example, a collection bag and/or a cryopreservation bag, a sealing device may be used to apply heat and/or pressure at a predetermined temperature, pressure, and amount of time depending on the material used in the bag. For example, some heat sealers may require application of heat and pressure for about eight seconds. After 8 seconds, heat may be turned off on the device, however, pressure may be applied for an additional 2 to 3 seconds.

In some embodiments, bags may have a length in a range from about 10 cm to about 50 cm. In particular, bags for use in the invention described herein may have a length in a range from about 15 cm to about 30 cm. For example, bags may have a length in a range from about 18 cm to about 22 cm.

Some of the tubing may be weldable. Weldable tubing may be made from a polymer material, for example, polyvinyl chloride (PVC).

Valves including, but not limited to needle free valves may be used at points along the tubing. In some embodiments, bags may have a length in a range from about 10 cm to about 40 cm. In particular, bags for use in the invention described herein may have a length in a range from about 15 cm to about 30 cm. For example, bags may have a length in a range from about 18 cm to about 22 cm.

Cryopreservation bags may need to be suitable for cryopreservation with a cryoprotectant such as dimethyl sulfoxide ("DMSO"). In some embodiments, cryopreservation bags may be constructed so that the bags may hold a volume of material in a range from about 5 ml to about 45 ml. In particular, a cryopreservation bag may include accommodate a volume of material in a range from about 10 ml to about 35 ml. For example, some embodiments include cryopreservation bags that may accommodate a volume of material to be stored in a range from about 15 ml to about 30 ml. A cryopreservation bag may have sized such that a desired predetermined volume is achieved. In some embodiments, a cryopreservation bag may have a width in a range from about 4 cm to about 11 cm and a length in a range from about 10 cm to about 18 cm. For example, a cryopreservation bag may have a width in a range from about 5.8 cm to about 9.8 cm and a length in a range from about 12 cm to about 16 cm. In particular, an embodiment of a cryopreservation bag may have a width of about 7.8 cm and length of about 14 cm.

Prior to use, the cryopreservation kit and/or specific components thereof may be sterilized. Materials used to form bags may be heat sealable. Materials for use in the bags may include, but is not limited to polymers such as EVA, polyamides (e.g., nylons), and combinations thereof. Open bags may be used for processing and/or disaggregation after closing the bag using a seal and/or a clamp.

A filter may be an inline filter, a blood filter, such as a blood administration filter, a biological filter, and/or an in-line clump removal filter. The filter may be configured to remove materials from the processed tissue above a predetermined size to form a desired material. For example, lumps of tissue may be separated from the disaggregated tissue using the filter. In particular, a tissue composition entering tubing after being filtered may have constituents having an average size of less than about 200 pm such that a desired material is formed. For example, the desired material may include TILs (tumor infiltrating lymphocytes) having an average size of less than about 170 pm.

A filter may be selected such that the processed tissue composition entering from tubing may be enriched such that after the filter the desired material flows into tubing in the direction of the stabilization element having constituents having a size in a range from about 15 pm to about 500 pm. In some embodiments, a filter may be configured such that a tissue composition entering tubing in the direction of the stabilization element after being filtered has constituents having a size in a range from about 50 pm to about 300 pm. For example, a filter may, in an embodiment, be configured such that a tissue composition entering tubing after being filtered has constituents having a size in a range from about 150 pm to about 200 pm.

In some embodiments, a filter of the enrichment element may remove materials from the processed tissue outside of a predetermined size range from about 5 pm to about 200 pm to form a desired material. For example, the desired material may include TILs having an average size in a range from about 5 pm to about 200 pm. Valves may be placed a predetermined distance from a collection bag. For example, a needle free valve may be positioned about 20 cm from a collection bag. Valves such as needle free valves may be used to add materials to a collection bag. For example, enzyme media may be inserted into a needle free valve in order to add the media to a collection bag. Materials to be provided via valves include, for example, tumor digest media and/or a cryoprotectant or cryopreservation media such as DMSO and/or solutions thereof, such as 55% DMSO and 5% Dextran cryopreservation media (e.g., BloodStor 55-5).

Syringes may be used to provide tumor digest media and a 55% DMSO solution, such as 55% DMSO and 5% Dextran cryopreservation media, respectively, through needle free valves 290, 292. During processing materials may be selectively provided to the cryopreservation kit at predetermined times. Further, clamps may be used to control the flow of provided materials such as tumor digest media and/or a cryoprotectant, such as a DMSO solution may be provided to the devices such as the collection bag, the filter, and/or the cryopreservation bag at predetermined times.

In some embodiments, after such a valve there may be a predetermined amount of tubing to allow space to weld on additional components for the cryopreservation kit. For example, after some valves at least ten (10) cm of tubing may be positioned before next element. Tubing 199 may be sealable and/or weldable. For example, materials for tubing may include, but is not limited to PVC (polyvinyl chloride), and/or other materials known in the art. In some embodiments, tubing may be sized to fit connectors. For example, tubing may have an inner diameter in a range from about 1.5 mm to about 4.5 mm and an outer diameter in a range from about 2.1 mm to about 6.1 mm. For example, an embodiment of a cryopreservation kit may include tubing having an inner diameter in a range from about 2.9 mm to about 3.1 mm and having an outer diameter in a range from about 4.0 mm to about 4.2 mm. Tubing used in cryopreservation kit 191 may vary in length with individual tubing elements having a length in a range from about 1 cm to about 30 cm.

Clamps may be used to inhibit and/or prevent movement of enzyme media and/or digested tissue into the filter. For example, a clamp may be used to inhibit and/or prevent movement of enzyme media and/or digested tissue into the filter prior to a desired filtration step. Another clamp 198 inhibit and/or prevent undesired movement of the cryoprotective agent into the filter.

Two or more bags may be coupled together to ensure that disaggregated product material may be properly stored in a particular embodiment.

In some embodiments, the invention may include an automated device for semi-automated aseptic disaggregation, enrichment, and/or stabilization of cells and/or cell aggregates from tissue, for example a solid mammalian tissue. An automated device for use with the invention may include a programmable processor and a cryopreservation kit. In some embodiments, the cryopreservation kit may be single use. The invention further relates to a semi-automatic aseptic tissue processing method.

In some embodiments, bags such as a collection bag may be used in a collection kit. Bags have an open end allowing for the addition of a sample, such as a tissue sample. A connector may couple the bag to tubing in a collection kit. Tubing material may be sealable and/or weldable. For example, the tubing may be sealed using energy such as heat, radio frequency, etc. The tubing material may be made from PVA.

In some embodiments, tubing may be coupled to a valve to allow addition of one or more media enzyme solutions including, but not limited to collagenase, trypsin, lipase, hyaluronidase, deoxyribonuclease, Liberase HI, pepsin, or mixtures thereof. For example, the valve may be a needle free valve. Tubing used in the cryopreservation kit may include tubing having an outer diameter in a range from about 3.0 mm to about 5.0 mm with an inner diameter of the tubing in a range from about 2.0 mm to about 4 mm. In particular, tubing may have an outer diameter of 4.1+/−0.1 mm and an inner diameter of about 3.0+/−0.1 mm. The length of tubing may depend on the configuration of the collection kit. For example, an embodiment of a collection kit may include tubing having a length in a range from about 10 cm to about 20 cm.

In some embodiments of the collection kit prototype may include one or more clamps to inhibit and/or prevent movement of tissue and/or enzyme media. In particular, enzyme media and/or tissue may be inhibited from moving into a filter before a filtration step.

There are three separate elements to the treatment that may potentially contribute to therapeutic activity. The core elements are TILs, such as UTILs, which have the potential to eliminate tumor cells by a variety of mechanisms utilized by T-cells as part of their normal function.

These mechanisms include: direct cytotoxicity by [a] releasing cytotoxins (e.g. perforin, granzymes, and granulysin), which enter target cells by close engagement and induce cell death; and by [b] cell-surface interactions between T cell and target such as binding FAS Ligand mediated cytotoxicity inducing apoptosis; and indirect methods (e.g. cytokine production) that have the ability to recruit and stimulate secondary effector cells to engage and induce tumor cell death.

TILs, in particular UTILs, are an autologous product; consequently, each batch manufactured provides a single dose for a specified patient. There are no sub-batches or pooling of batches. The drug product is a small aseptically prepared batch of T cells ($5 \times 10^9$ to $5 \times 10^{10}$) cryopreserved in a saline based solution with 8.5% human serum albumin and 10% DMSO of between 125-270 mL for a single intravenous infusion after thawing.

There are several advantages in the present invention as compared to U.S. Pat. No. 10,398,734 ("the '734 patent"). The first step in the '734 patent is transforming the tumor bulk into fragments from which TILs are cultured. In contrast, the present invention liberates TILs from the tumor, which was preserved and disaggregated under aseptic conditions following resection in the aseptic kit, from which a cell suspension is prepared, and cryopreserves the resulting TILs by freezing. The present invention provides a diverse population of TILs representing the diversity that exists inside the tumor. And because they are a homogenous suspension, the TILs that are expanded in the culture will retain that diversity, which gives the greatest chance of addressing the diverse population of cancer cells that reside within the tumor.

In contrast, the manufacturing process of the '734 patent starts with fragments of tissue that have already experienced deterioration of the internal cell population during shipping and any further delay before starting processing. In addition, TILs used for manufacturing will only be TIL that expand from the tissue fragments and not any TIL that are retained in the interior, so that the resulting cell population may not reflect the full diversity of tumor environment.

Another difference is that the entry into closed manufacturing processing occurs much sooner and with less chance of contamination in the process of the present invention than in the process of the '734 patent. In particular, the disruption of the tumor tissue occurs in a closed processing system in the present application, rather than the extensive fragmentation process which the '734 patent describes as occurring in an open operation in a biological safety cabinet.

Because the starting material for the present invention is preserved under aseptic conditions in the aseptic kit, the full manufacturing process, which can be run on a cryopreserved tumor cell suspension, can be scheduled and run at high capacity and efficiency. In contrast, because the '734 patent starts with unfrozen tissue, the fragmentation and "growth-out" steps are run on a stand-by basis with lower efficiency of capacity utilization. Removing this intermediate freezing step, in the '734 patent, shortens the manufacturing process overall, but means that the entire process is run on a stand-by basis, meaning that manufacturing down time has significant consequences to the manufacturing facility of the '734 patent as there cannot be any delays and planning a down period for manufacturing requires will require all products in process to be completed and new surgeries to be stopped.

The advantage of the process of the present application is that tissue, in the form of a resected tumor, can be collected in advance of a requirement for TIL therapy, transported, processed, cryopreserved and stored in the aseptic kit until and if manufacturing is needed so patients with earlier stage disease can be harvested and stored while they have alternative therapies. Consequently, there is little or no impact upon the timing or geolocation of tumor collection and subsequent manufacturing. Whereas in the '734 patent, this is not possible and full manufacturing of a drug product has to occur before cells can be frozen and held.

As mentioned above, these are very different culture processes that will generate different populations of cells from which to initiate the REP culture, as reflected in the very different numbers of cells needed to seed the REP culture, 1-20 million (the present invention) versus 25-200 million (the '734 patent). In the present invention during the initial TIL expansion the culture seeding uses a cell suspension (i.e. cells that grow out of the disaggregated and cryopreserved cells which will be a mixture of resident and emergent T cells) versus outgrowth from the chunks (i.e. emergent cells); this means the REP is not just seeded with emergent T cells. In addition, the present invention can utilize both solid and flexible closed containers where flexible containers enable a more optimal environment based on the amount of tumor suspension derived rather than a number of chunks as defined in the '734 patent].

Metastatic tumor material is surgically removed using standard surgical practice within a surgical operating room. Prior to disaggregation extraneous material is removed (i.e. non-tumor material as defined macroscopically) and the tumor material is transferred into a sterile bag.

The following may be involved in tumor starting material acceptance testing. First, the source tissue is confirmed to be tumor material. Second, a representative sample of the disaggregated tissue is assessed for microbial load and where present antibiotic sensitivities defined (manufacturing may be performed at risk with antibiotics) but final material must be negative for microbial growth. Third, quantity and viability of TIL and tumor cells can be assessed by flow cytometry.

The methods of the invention comprise the step of aseptically disaggregating a tumor resected from a subject thereby producing a disaggregated tumor, wherein the resected tumor is sufficiently disaggregated if it can be cryopreserved without cell damage. In an advantageous embodiment, a programmable processor of a semi-automatic device may control disaggregation enabling the surfaces within disaggregation flexible containers to mechanically crush and shear the solid tissue (see, e.g., PCT Publication No. WO 2018/130845). Disaggregation surfaces may be controlled, for example, by mechanical pistons.

For enzymatic digestion, a cell suspension (containing both T cells and tumor cells) is generated from the resected metastatic tumor using an enzyme mixture of DNase 1 and Collagenase (Type IV). The combination of the repeated mechanical compression exposes additional surfaces for the enzymes to access and the enzymatic reaction speed up the process of turning a solid tissue into a cell suspension prior to optional cryopreservation. In one embodiment upon completion of the disaggregation step a DMSO based cryoprotectant is added just prior to a controlled rate freezing cycle. In some embodiments, the enzymatic breakdown of the solid tissue may be by the selection and provision of one or more media enzyme solutions such as collagenase, trypsin, lipase, hyaluronidase, deoxyribonuclease, Liberase HI, pepsin, or any mixture thereof. Enzymatic digestion of the resected metastatic tumor can occur in the disaggregation flexible containers of the semi-automatic device.

By way of example, in another embodiment of the method of the invention, where the disaggregation process is being supplemented with enzymatic digestion the media formulation for enzymatic digestion must be supplemented with enzymes that aid in protein breakdown causing the cell to cell boundaries to break down.

Various liquid formulations known in the art of cell culturing or cell handling can be used as the liquid formulation used for cell disaggregation and enzymatic digestion of solid tissues, including but not limited to one or more of the following media Organ Preservation Solutions, selective lysis solutions, PBS, DMEM, HBSS, DPBS, RPMI, Iscove's medium, XVIVO™, AIM-Vim, Lactated Ringer's solution, Ringer's acetate, saline, PLASMALYTE™ solution, crystalloid solutions and IV fluids, colloid solutions and IV fluids, five percent dextrose in water (D5W), Hartmann's SolutionDMEM, HBSS, DPBS, RPMI, AIM-V™, Iscove's medium, XVIVO™, each can be optionally supplemented with additional cell supporting factors e.g. with fetal calf serum, human serum or serum substitutes or other nutrients or cytokines to aid in cell recovery and survival or specific cell depletion. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cells). The media may have supplements or reagents well known in the art, e.g. albumins and transport proteins, amino acids and vitamins, metal-ion (s), antibiotics, attachments factors, de-attachment factors, surfactants, growth factors and cytokines, hormones or solubilizing agents. Various media are commercially available e.g. from ThermoFisher, Lonza, or Sigma-Aldrich or similar media manufacturers and suppliers.

The liquid formulation required for enzymatic digestion must have sufficient calcium ions present in the of at least 0.1 mM up to 50 mM with an optimal range of 2 to 7 mM ideally 5 mM.

The solid tissue to be digested can be washed after disaggregation with a liquid formulation containing chelating agents EGTA and EDTA to remove adhesion factors and inhibitory proteins prior to washing and removal of EDTA and EGTA prior to enzymatic digestion.

The liquid formulation required for enzymatic digestion is more optimal with minimal chelating agents EGTA and EDTA which can severely inhibit enzyme activity by removing calcium ions required for enzyme stability and activity.

In addition, β-mercaptoethanol, cysteine and 8-hydroxyquinoline-5-sulfonate are other known inhibitory substances.

Processing of tumor material using dissection, enzymatic digestion and homogenization produces a single cell suspension of TILs, in particular UTILs, which can be directly cryopreserved to stabilize the starting material for subsequent processing via the first expansion of the cell suspension of TILs, in particular UTILs, in IL-2 to obtain a first population of TILs, in particular UTILs.

The methods also comprise the step of cryopreserving the disaggregated tumor, e.g. the cell suspension. Cryopreserving the disaggregated tumor is carried out on the same day as carrying out the step of aseptically disaggregating a tumor resected from a subject thereby producing a disaggregated tumor, wherein the resected tumor is sufficiently disaggregated if it can be cryopreserved without cell damage. For example, cryopreserving is carried out 5, 10, 20, 30, 40, 50, 60, 70, 80, or 90 minutes, or 2, 4, 6, 8, 10, 12, 14, 16, 18, 20, or 22 hours following the step of disaggregating the tumor. Cryopreservation of the disaggregated tumor, as a single cell suspension obtained from the enzymatic disaggregation in the disaggregation module of the semi-automatic device, is carried out by cooling and/or maintaining the suspension at a temperature between 8° C. and at least −80° C. or below. Disaggregation could be as quick as 5 mins but most usually 45 mins to 1 hour and the cryopreservation can be a quick as 60 mins or up to 150 mins. In one embodiment, the methods include storing the cryopreserved disaggregated tumor. As described in preferred embodiments, the device comprises at least one cell container for cryopreservation wherein the containers are a flexible container manufactured from resilient deformable material. In this embodiment of the device, the final container is either transferred directly to a freezer −20 to −190° C. or more optimally located in the controlled rate freezing apparatus either associated with the device or supplied separately (manufactured by for example Planer Products or Asymptote Ltd) in which the temperature of the freezing chamber and the flexible storage container(s) employed to contain the enriched disaggregated solid tissue container is controlled either by: injecting a cold gas (normally nitrogen for example Planer products); or by removing heat away from the controlled cooling surface(s). Both methods result in the ability to accurately control with an error of less than 1° C. or more preferable 0.1° C. the freezing process at the required rate for the specific cell(s) to be frozen based on the freezing solution and the desired viability of the product. This cryopreservation process must take into account the ice nucleation temperature which is ideally as close as possible to the melting temperature of the freezing solution. Followed by crystal growth in an aqueous solution, water is removed from the system as ice, and the concentration of the residual unfrozen solution increases. As the temperature is lowered, more ice forms, decreasing the residual non-frozen fraction which further increases in concentration. In aqueous solutions, there exists a large temperature range in which ice co-exists with a concentrated aqueous solution. Eventually through temperature reduction the solution reaches the glass transition state at which point the freezing solution and cells move from a viscous solution to a solid-like state below this temperature the cells can undergo no further biological changes and hence are stabilized, for years potentially decades, until required.

Ice nucleation and crystal growth involves release of heat to the freezing solution and the cellular microenvironment and it is desirable to maintain cooling of cells and freezing solution even as the freezing fluid resists temperature changes while undergoing phase change. Depending on whether disaggregation includes enzymatic disaggregation, and what is the optimal temperature of enzymatic digestion for a given enzyme, enzyme concentration and tissue type, temperatures at the start of cryopreservation include, without limitation, 40° C., 39° C., 38° C., 37° C., 36° C., 35° C., 34° C., 33° C., 32° C., 31° C., 30° C., 29° C., 28° C., 27° C., 26° C., 25° C., 24° C., 23° C., 22° C., 21° C., and 20° C., i.e., temperatures ranging from a mammalian body temperature to room temperature, and further include lower refrigeration temperatures such as, without limitation, 10° C., 8° C., 6° C., 5° C., 4° C., 3° C., and 2° C. Target temperatures for cryogenic cooling include, without limitation, −60° C., −65° C., −70° C., −75° C., −80° C., −85° C., −90° C., and temperatures in between as well as colder temperatures down to the temperature of liquid nitrogen vapor storage (−195.79° C.). In certain embodiments, the methods and devices used according to the invention are designed or programmed to minimize the time from physiological temperature or digestion temperature to cryostorage temperature. In certain embodiments, the methods and devices used according to the invention for cryopreservation are advantageously designed and programmed for cooling under conditions whereby heat release to, into, around or in an environment including cells, as media crystalizes, is minimized or avoided. In certain embodiments, methods are designed and/or devices programmed for continuous cooling from disaggregation temperature down to a cryogenic target temperature. Exemplary programmed cooling rates include, without limitation, −0.5° C./min, −1° C./min, −1.5° C./min, −2° C./min, or −2.5° C./min. The cooling rates are program targets and may vary over a cooling cycle. The cooling rates may vary, for example by ±0.1° C./min, ±0.2° C./min, ±0.3° C./min, ±0.4° C./min, or ±0.5° C./min. In an embodiment of the invention, the cryopreservation temperature is −80° C.±10° C. and the device is programmed to reduce temperature by 1° C./min or 1.5° C./min or 2° C./min or 1° C./min±0.5° C./min or 1.5° C./min±0.5° C./min or 2° C./min±0.5° C./min.

In some embodiments, the present methods provide for obtaining young TILs, which are capable of increased replication cycles upon administration to a subject/patient and as such may provide additional therapeutic benefits over older TILs (i.e., TILs which have further undergone more rounds of replication prior to administration to a subject/patient). Features of young TILs have been described in the literature, for example Donia, at al., Scandinavian Journal of Immunology, 75:157-167 (2012); Dudley et al., Clin Cancer Res, 16:6122-6131 (2010); Huang et al., J Immunother, 28(3):258-267 (2005); Besser et al., Clin Cancer Res, 19(17):OF1-OF9 (2013); Besser et al., J Immunother 32:415-423 (2009); Robbins, et al., J Immunol 2004; 173: 7125-7130; Shen et al., J Immunother, 30:123-129 (2007); Zhou, et al., J Immunother, 28:53-62 (2005); and Tran, et al., J Immunother, 31:742-751 (2008), all of which are incorporated herein by reference in their entireties.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained by the present method exhibit an increase in the T-cell repertoire diversity as compared to freshly harvested TILs and/or TILs prepared using other methods than those provide. In some embodiments, the TILs obtained by the present method exhibit an increase in the T-cell repertoire diversity as compared to freshly harvested TILs and/or TILs. In some embodiments, the TILs obtained in the first expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRαβ).

The methods of the invention also comprise the step of performing a first expansion by culturing the disaggregated tumor in a cell culture medium comprising IL-2 to produce a first population of TILs, in particular UTILs. The cells resulting from the steps described above are cultured in serum containing IL-2 under conditions that favor the growth of TILs over tumor and other cells. In some embodiments, the tumor digests are incubated in 2 mL wells in media comprising inactivated human AB serum with 6000 IU/mL of IL-2. This primary cell population is cultured for a period of days, generally from 3 to 14 days, resulting in a bulk TIE population, generally about $1\times10^8$ bulk TIL cells. In some embodiments, this primary cell population is cultured for a period of 7 to 14 days, resulting in a bulk TIL population, generally about $1\times10^8$ bulk TIL cells. In some embodiments, this primary cell population is cultured for a period of 10 to 14 days, resulting in a bulk TIL population, generally about $1\times10^8$ bulk TIL cells. In some embodiments, this primary cell population is cultured for a period of about 11 days, resulting in a bulk TIL population, generally about $1\times10^8$ bulk TIL cells.

In a preferred embodiment, expansion of TILs may be performed using an initial bulk TIL expansion step as described below and herein, followed by a second expansion (including rapid expansion protocol (REP) steps and followed by restimulation REP steps) as described below and herein.

In an advantageous embodiment, the cryopreserved disaggregated tumor tissue is thawed and resuspended 1:9 in T cell media (T cell culture media contract manufactured for Immetacyte supplemented with the following additives 10% FBS and 3000 IU/mL IL-2) prior to filtration through an inline 100-270 μm filter and centrifugation in a 50 mL centrifuge tube prior to resuspension in 20 mL. A sample may be taken for flow cytometry analysis to quantify a number of HLA-A, B, C and CD58+, and DRAQ7− cells. In some embodiments this may be seeded using an alternative manual (such as but not limited to a haemocytometer) or alternative automated total viable cell counting device such as but not limited to NucleoCounter™; Guava®; automated blood analysis and counter; pipette based cell counter such as but not limited to Scepter™.

In one embodiment, resuspended cryopreserved disaggregated tumor tissue is cultured in serum containing IL-2 under conditions that favor the growth of TILs over tumor and other cells. In some embodiments, the tumor digests are incubated in 2 mL wells in media comprising inactivated human AB serum (or, in some cases, as outlined herein, in the presence of an artificial antigen-presenting [aAPC] cell population) with 6000 IU/mL of IL-2. This primary cell population is cultured for a period of days, generally from 10 to 14 days, resulting in a bulk TIL population, generally about $1\times10^8$ bulk TIL cells. In some embodiments, the growth media during the first expansion comprises IL-2 or a variant thereof. In some embodiments, the IL is recombinant human IL-2 (rhIL-2). In some embodiments the IL-2 stock solution has a specific activity of $20\text{-}30\times10^6$ IU/mg for a 1 mg vial. In some embodiments the IL-2 stock solution has a specific activity of $20\times106$ IU/mg for a 1 mg vial. In some embodiments the IL-2 stock solution has a specific activity of $25\times10^6$ IU/mg for a 1 mg vial. In some embodiments the IL-2 stock solution has a specific activity of $30\times10^6$ LU/mg for a 1 mg vial. In some embodiments, the 1L-2 stock solution has a final concentration of $4\text{-}8\times10^6$ IU/mg of IL-2. In some embodiments, the IL-2 stock solution has a final concentration of $5\text{-}7\times10^6$ IU/mg of IL-2. In some embodiments, the IL-2 stock solution has a final concentration of $6\times10^6$ IU/mg of IL-2. In some embodiments, the first expansion culture media comprises about 10,000 IU/mL of IL-2, about 9,000 IU/mL of IL-2, about 8,000 IU/mL of IL-2, about 7,000 IU/mL of IL-2, about 6000 IU/mL of IL-2 or about 5,000 IU/mL of IL-2. In some embodiments, the first expansion culture media comprises about 9,000 IU/mL of IL-2 to about 5,000 IU/mL of IL-2. In some embodiments, the first expansion culture media comprises about 8,000 IU/mL of IL-2 to about 6,000 IU/mL of IL-2. In some embodiments, the first expansion culture media comprises about 7,000 IU/mL of IL-2 to about 6,000 IU/mL of 1L-2. In some embodiments, the first expansion culture media comprises about 6,000 IU/mL of IL-2. In an embodiment, the cell culture medium further comprises IL-2. In some embodiments, the cell culture medium comprises about 3000 IU/mL of IL-2. In an embodiment, the cell culture medium further comprises IL-2. In a preferred embodiment, the cell culture medium comprises about 3000 IU/mL of IL-2. In an embodiment, the cell culture medium comprises about 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or about 8000 IU/mL of IL-2.

In some embodiments, first expansion culture media comprises about 500 IU/mL of IL-12, about 400 IU/mL of IL-12, about 300 IU/mL of IL-12, about 200 IU/mL of IL-12, about 180 IU/mL of IL-12, about 160 IU/mL of IL-12, about 140 IU/mL of IL-12, about 120 IU/mL of IL-12, or about 100 IU/mL of IL-12. In some embodiments, the first expansion culture media comprises about 500 IU/mL of IL-12 to about 100 IU/mL of IL-12. In some embodiments, the first expansion culture media comprises about 400 IU/mL of IL-12 to about 100 IU/mL of IL-12. In some embodiments, the first expansion culture media comprises about 300 IU/mL of IL-12 to about 100 IU/mL of IL-12. In some embodiments, the first expansion culture media comprises about 200 IU/mL of IL-12. In some embodiments, the cell culture medium comprises about 180 IU/mL of 1L-12. In an embodiment, the cell culture medium further comprises 1L-12. In a preferred embodiment, the cell culture medium comprises about 180 IU/mL of IL-12.

In some embodiments, first expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the first expansion culture media comprises about 500 IU/mL of IL-15 to about 100 IU/mL of IL-15. In some embodiments, the first expansion culture media comprises about 400 IU/mL of 1L-15 to about 100 IU/mL of IL-15. In some embodiments, the first expansion culture media comprises about 300 IU/mL of IL-15 to about 100 IU/mL of 1L-15. In some embodiments, the first expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, first expansion culture media comprises about 500 IU/mL of IL-18, about 400 IU/mL of IL-18, about 300 IU/mL of IL-18, about 200 IU/mL of IL-18, about 180 IU/mL of IL-18, about 160 IU/mL of IL-18, about 140 IU/mL of IL-18, about 120 IU/mL of IL-18, or about 100 IU/mL of IL-18. In some embodiments, the first expansion culture media comprises about 500 IU/mL of IL-18 to about 100 IU/mL of IL-18. In some embodiments, the first expansion culture media comprises about 400 IU/mL of IL-18 to about 100 IU/mL of IL-18. In some embodiments, the first expansion culture media comprises about 300 IU/mL of IL-18 to about 100 IU/mL of IL-18. In some embodiments, the first expansion culture media comprises about 200 IU/mL of IL-18. In some embodiments, the cell culture medium comprises about 180 IU/mL of IL-18. In an embodiment, the cell culture medium further comprises IL-18. In a preferred embodiment, the cell culture medium comprises about 180 IU/mL of IL-18.

In some embodiments, first expansion culture media comprises about 20 IU/mL of IL-21, about 15 IU/mL of IL-21, about 12 IU/mL of IL-21, about 10 IU/mL of 1L-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the first expansion culture media comprises about 20 IU/mL of IL-21 to about 0.5 IU/mL of IL-21. In some embodiments, the first expansion culture media comprises about 15 IU/mL of IL-21 to about 0.5 IU/mL of IL-21. In some embodiments, the first expansion culture media comprises about 12 IU/mL of IL-21 to about 0.5 IU/mL of 1L-21. In some embodiments, the first expansion culture media comprises about 10 IU/mL of IL-21 to about 0.5 IU/mL of IL-21. In some embodiments, the first expansion culture media comprises about 5 IU/mL of IL-21 to about 1 IU/mL of IL-21. In some embodiments, the first expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of 1L-21.

Also contemplated for the culture media are combinations of interleukins, such as but not limited to, IL-2, 1L-12, 1L-15, 1L-18 and 1L-21. Other cytokines are also contemplated, such as IL-23, IL-27, IL-35, IL-39, IL-18, IL-36, IL-37, IL-38, IFN-alpha, IFN-beta, IFN-gamma or a combination thereof along with IL-2, IL-12, IL-15, IL-18 and IL-21. Antibodies, such as Th2 blocking reagents, are also contemplated, such as but not limited to, IL-4 (aIL4), anti-IL-4 (aIL4R), anti-IL-SR (aIL5R), anti-IL-5 (aILS), anti-IL13R (aIL13R), or anti-IL13 (aIL13).

In some embodiments, the first TIL expansion can proceed for 1 day, 2 days, 3 days, 4 days, 5 days, 6 days, 7 days, 8 days, 9 days, 10 days, 11 days, 12 days, 13 days, or 14 days. In some embodiments, the first TIL expansion can proceed for 1 day to 14 days. In some embodiments, the first TIL expansion can proceed for 2 days to 14 days. In some embodiments, the first TIL expansion can proceed for 3 days to 14 days. In some embodiments, the first TIL expansion can proceed for 4 days to 14 days. In some embodiments, the first TIL expansion can proceed for 5 days to 14 days. In some embodiments, the first TIL expansion can proceed for 6 days to 14 days. In some embodiments, the first TIL expansion can proceed for 7 days to 14 days. In some embodiments, the first TIL expansion can proceed for 8 days to 14 days. In some embodiments, the first TIL expansion can proceed for 9 days to 14 days. In some embodiments, the first TIL expansion can proceed for 10 days to 14 days. In some embodiments, the first TIL expansion can proceed for 11 days to 14 days. In some embodiments, the first TIL expansion can proceed for 12 days to 14 days. In some embodiments, the first TIL expansion can proceed for 13 days to 14 days. In some embodiments, the first TIL expansion can proceed for 14 days. In some embodiments, the first TIL expansion can proceed for 1 day to 11 days. In some embodiments, the first TIL expansion can proceed for 2 days to 11 days. In some embodiments, the first TIL expansion can proceed for 3 days to 11 days. In some embodiments, the first TIL expansion can proceed for 4 days to 11 days. In some embodiments, the first TIL expansion can proceed for 5 days to 11 days. In some embodiments, the first TIL expansion can proceed for 6 days to 11 days. In some embodiments, the first TIL expansion can proceed for 7 days to 11 days. In some embodiments, the first TIL expansion can proceed for 8 days to 11 days. In some embodiments, the first TIL expansion can proceed for 9 days to 11 days. In some embodiments, the first TIL expansion can proceed for 10 days to 11 days. In some embodiments, the first TIL expansion can proceed for 11 days.

In some embodiments, a combination of IL-2, IL-7, IL-15, and/or IL-21 are employed as a combination during the first expansion. In some embodiments, 1L-2, 1L-7, 1L-15, and/or IL-21 as well as any combinations thereof can be included during the first expansion. In some embodiments, a combination of IL-2, IL-1S, and IL-21 are employed as a combination during the first expansion.

In some embodiments, the first expansion is performed in a closed system bioreactor. In some embodiments, a closed system is employed for the TIL expansion, as described herein. In some embodiments, a single bioreactor is employed. In some embodiments, the single bioreactor employed is example a G-REX-10 or a G-REX-100 or advantageously the device of WO 2018/130845. In some embodiments, the closed system bioreactor is a single bioreactor.

Advantageously, the TIL population obtained from the first expansion, referred to as the second TIL population, can be subjected to a second expansion (which can include expansions sometimes referred to as REP. Similarly, in the case where genetically modified TILs will be used in therapy, the first TIL population (sometimes referred to as the bulk TIL population) or the second TIL population (which can in some embodiments include populations referred to as the REP TIL populations) can be subjected to genetic modifications for suitable treatments prior to expansion or after the first expansion and prior to the second expansion.

Lentiviruses are efficient gene transfer vehicles due to their ability to transduce both dividing and nondividing cells. While the most thoroughly investigated of the lentiviral gene therapy vectors are derived from human immunodeficiency virus (HIV) type 1, gene therapy vectors based on other primate and non-primate lentiviruses have also been developed, including, HIV-2, SIV, feline immunodeficiency virus (FIV), equine infectious anemia virus (EIAV), caprine arthritis encephalitis virus (CAEV), visna virus, and Jembrana disease virus (JDV).

Replication-deficient viral vectors are essential in preventing infection of a patient with a potentially deadly virus. Lentiviral vectors have have been developed to become safer and more efficient. Recent third-generation vectors removed all accessory genes that aid in virulence and pathogenicity while splitting the remaining genes, which are vital for expression of a transgene across three plasmids. See, e.g., U.S. Patent Publication 2006/0024274.

EIAV gene transfer vectors were shown to be effective in transducing proliferating and Gi-arrested cells in vitro. Mitrophanous, et al., 1999. Stable gene transfer to the nervous system using a non-primate lentiviral vector. Gene Ther. 6: 1808-1818; Olsen, J. C., 1998, Gene transfer vectors derived from equine infectious anemia virus. Gene Ther. 5: 1481-1487; Olsen, J. C., 2001, E1AV, CAEV and Other Lentivirus Vector Systems, Somat Cell Mol Genet, Vol. 26, Nos. 1/6, 131-45.

Heemskerk, B. et al., 2008, Adoptive cell therapy for patients with melanoma, using tumor-infiltrating lymphocytes genetically engineered to secrete interleukin-2. Human gene therapy, 19(5), 496-510, describes TILs genetically engineered to express IL-2 to prolong TIL survival. Patient TIL was transfected during a first expansion with a retroviral vector based on Moloney murine leukemia virus (MMLV) followed by a second expansion to obtain sufficient numbers for treatment.

In brief, the SBIL2 vector, containing the MFG backbone derived from Moloney murine leukemia virus (MMLV) with a cDNA copy of the human IL-2 gene under the control of the 5' long terminal repeat (LTR) promoter, was pseudotyped in the PG13 packaging cell line, which provides the gibbon ape leukemia virus (GaLV) envelope protein. A stable producer clone (PGI3SBIL2 #3) was generated that contained three copies of the integrated retroviral IL-2 DNA. Clinical GMP-grade SBIL2 retroviral supernatant was produced by the National Gene Vector Laboratory at Indiana University (Indianapolis, Ind.). For TTL transduction, 6-well non-tissue-culture plates (Becton Dickinson, Franklin Lakes, N.J.) were coated with Retronectin (CH-296, 25 µg/ml in phosphate-buffered saline [PBS], GMP grade; Takara Bio, Otsu, Japan), blocked with PBS-2% human serum albumin (HSA), and preloaded for 4 hr with thawed SBIL2 viral supernatant (5 ml/well) at 32° C. and 10% $CO_2$. TILs were added at 3 nil/well for 18-24 hr at 37° C. and 5% $CO_2$, transferred to a second set of SBIL2-loaded plates, and cultured for an additional 18-24 hr, after which TILs were harvested and resuspended in fresh medium.

Zhang, L. et al., 2015, Tumor-infiltrating lymphocytes genetically engineered with an inducible gene encoding interleukin-12 for the immunotherapy of metastatic melanoma, Clinical Cancer Research 21(10), 2278-2288. describes TILs genetically engineered to secrete IL-12 selectively at a tumor site. TILs were transduced with a MSGV1 γ-retroviral vector carrying a gene encoding a single-chain IL-12 driven by a nuclear factor of activated T cells (NFAT) promoter. activated T cells promoter.

MSGV-1 is derived from the MSGV vector that utilizes the murine stem cell virus long terminal repeat and contains an extended gag region and Kozak sequence. The gene encoding human single chain IL-12 was synthesized with the order IL-12 p40, linker G6S and IL-12 p35 driven by an NFAT responsive promoter and inserted into the MSGV-1 vector reverse to the 5' LTR direction. A high-titer PG13 cell based producer cell line was generated and retroviral supernatant was produced by the NCI Surgery Branch Vector Production Facility (Bethesda, Md.) under good manufacturing practice (GMP) conditions. The vector supernatant was tested and passed all currently required US Food and Drug Administration guidelines for the production of recombinant gamma-retroviral vectors for clinical application.

The transduction procedure was initiated by stimulating tumor-infiltrating lymphocytes (TILs) with 30 ng/ml anti-CD3 mAb Orthoclone OKT3 (Centocor Ortho Biotech, Raritan, N.J.), 3000 IU/ml recombinant human IL-12 and 4 Gy irradiated allogeneic PBMC feeder cells at a ratio of 200 feeder cells for every TIL. Cells were harvested for transduction on day 4 and/or day 5 using RetroNectin (CH-296; Takara Bio Inc., Otsu, Japan) coated non-tissue culture 6-well plates. Vector supernatant was "spin loaded" onto coated plates by centrifugation at 2000 g for 2 hours at 32° C. Retroviral vector supernatant was aspirated from the wells and $2 \times 10^6$ stimulated TIL cells were added each well followed by centrifugation at 1000 g for 10 minutes. Plates were incubated at 37° C. overnight and cells were harvested for the 2nd transduction the following day. Cells for the first 21 patients underwent two transductions. Cells for patients 12 underwent only one transduction.

Jones, S. et al., 2009, Lentiviral vector design for optimal T cell receptor gene expression in the transduction of peripheral blood lymphocytes and tumor-infiltrating lymphocytes. Human gene therapy, 20(6), 630-640, describes development of promoters for use in lentiviral vectors to express genes in transduced T lymphocytes and construct effective antitumor T cells.

TILs were obtained from surgical specimens. PBLs were thawed from frozen stock stored at −180° C. and placed into culture in AIM-V and interleukin-2 (1L-2; Cetus, Emeryville, Calif.) at 300 IU/ml. For OKT3 stimulation, the cells were either initially place in medium with anti-CD3 antibody, OKT3 (Ortho Biotech, Bridgewater, N.J.) at 50 ng/ml, or were placed in OKT3 medium after transduction, at the initial changing of the culture medium. For transduction of the PBLs or TILs, 1×106 cells were adjusted to a final volume of 1 ml in a 24-well tissue culture-treated plate with the viral supernatant and Polybrene (final concentration, 8 m/ml). The cells were transduced by centrifugation of the plates for 1.5 hr at 1000×g, 32° C. The plates were placed in a 37° C., humidified 5% $CO_2$ incubator overnight, and the medium was replaced the next day. TILs were subject to the rapid expansion protocol (REP) as previously described, using OKT3 (50 ng/ml), 1L-2 (5000 µl/ml), and irradiated allogeneic peripheral blood mononuclear cells from three different donors (TIL:feeder ratio, 1:100). Six days post-REP, TILs were transduced as described and returned to culture.

Beane, J. D. et al., 2015, Clinical Scale Zinc Finger Nuclease-mediated Gene Editing of PD-1 in Tumor Infiltrating Lymphocytes for the Treatment of Metastatic Melanoma. Molecular therapy: 23(8), 1380-1390 describes clinical scale gene editing of PD-1 by electroporation of mRNA encoding PD-1 specific zinc finger nuclease (ZFN)-mediated gene editing.

In order to generate a sufficient number of transduced T cells for adoptive cell transfer, the TIL were induced to proliferate using a REP.46 Briefly, $1 \times 10^7$ TIL were combined with $1 \times 10^9$ allogeneic, irradiated (5,000 rad) peripheral blood mononuclear cells (PBMC), and these cells were suspended in 400 ml of T-cell media containing 30 ng/ml of OKT3. The cells were cultured in a G-Rex100 flask at 37° C. and 5% CO2. Five days later, 200 ml of media was aspirated and replaced. Seven days after the start of the REP, TIL were harvested and washed two times with Hyclone Electroporation Buffer (Hyclone Laboratories, Logan, Utah). Cells were then counted and resuspended in electroporation buffer at a concentration of $1 \times 108$/ml. Cells were then transferred to the MaxCyte CL-2 processing assembly and mixed with 120 µg/ml of PD-1 ZFN mRNA (or GFP mRNA for GFP transfected TIL/GFP). Electroporation was performed as per MaxCyte's protocol. Following electroporation, TIL were transferred from the processing assembly to a T-175 flask and placed in an incubator at 37° C. for 20 minutes. Following this incubation step, TIL were resuspended in AIM-V media at a concentration of $1 \times 10^6$/ml. Cells were then placed in an incubator set at 30° C. for an overnight low temperature incubation as previously described. The following day, TIE were transferred to a 37° C. incubator and left undisturbed until REP day 10 (3 days following electroporation).

In some embodiments, the TILs obtained from the first expansion are stored until phenotyped for selection. In some embodiments, the TILs obtained from the first are not stored and proceed directly to the second expansion. Thus, the methods comprise the step of performing a second expansion by culturing the first population of TILs, in particular UTILs, with additional IL-2, OKT-3, and antigen presenting cells (APCs), to produce a second population of TILs. In some embodiments, the TILs obtained from the first expansion are not cryopreserved after the first expansion and prior to the second expansion. In some embodiments, the transition from the first expansion to the second expansion occurs at about 3 days, 4, days, 5 days, 6 days, 7 days, 8 days, 9 days, 10 days, 11 days, 12 days, 13 days, or 14 days after the cryopreserved disaggregated tumor tissue is thawed. In some embodiments, the transition from the first expansion to the second expansion occurs at about 3 days to 21 days after the cryopreserved disaggregated tumor tissue is thawed. In some embodiments, the transition from the first expansion to the second expansion occurs at about 4 days to 14 days after the cryopreserved disaggregated tumor tissue is thawed. In some embodiments, the transition from the first expansion to the second expansion occurs at about 4 days to 10 days after the cryopreserved disaggregated tumor tissue is thawed. In some embodiments, the transition from the first expansion to the second expansion occurs at about 7 days to 14 days after the cryopreserved disaggregated tumor tissue is thawed. In some embodiments, the transition from the first expansion to the second expansion occurs at about 14 days after the cryopreserved disaggregated tumor tissue is thawed. In some embodiments the seeding of the REP culture occurs 3, 4, 5, 6, 7, 8, 9, 10, 11, 12, 13, 14, 15, 16, 17, 18, 19, 20 or 21 days after the cryopreserved disaggregated tumor tissue is thawed.

In some embodiments, the transition from the first expansion to the second expansion occurs at 1 day, 2 days, 3 days, 4 days, 5 days, 6 days, 7 days, 8 days, 9 days, 10 days, 11 days, 12 days, 13 days, or 14 days after the cryopreserved disaggregated tumor tissue is thawed. In some embodiments, the transition from the first expansion to the second expansion occurs 1 day to 14 days after the cryopreserved disaggregated tumor tissue is thawed. In some embodiments, the first TIL expansion can proceed for 2 days to 14 days. In some embodiments, the transition from the first expansion to the second expansion occurs 3 days to 14 days after the cryopreserved disaggregated tumor tissue is thawed. In some embodiments, the transition from the first expansion to the second expansion occurs 4 days to 14 days after the cryopreserved disaggregated tumor tissue is thawed. In some embodiments, the transition from the first expansion to the second expansion occurs 5 days to 14 days after the cryopreserved disaggregated tumor tissue is thawed. In some embodiments, the transition from the first expansion to the second expansion occurs 6 days to 14 days after the cryopreserved disaggregated tumor tissue is thawed. In some embodiments, the transition from the first expansion to the second expansion occurs 7 days to 14 days after the cryopreserved disaggregated tumor tissue is thawed. In some embodiments, the transition from the first expansion to the second expansion occurs 8 days to 14 days after the cryopreserved disaggregated tumor tissue is thawed. In some embodiments, the transition from the first expansion to the second expansion occurs 9 days to 14 days after the cryopreserved disaggregated tumor tissue is thawed. In some embodiments, the transition from the first expansion to the second expansion occurs 10 days to 14 days after the cryopreserved disaggregated tumor tissue is thawed. In some embodiments, the transition from the first expansion to the second expansion occurs 11 days to 14 days after the cryopreserved disaggregated tumor tissue is thawed. In some embodiments, the transition from the first expansion to the second expansion occurs 12 days to 14 days after the cryopreserved disaggregated tumor tissue is thawed. In some embodiments, the transition from the first expansion to the second expansion occurs 13 days to 14 days after the cryopreserved disaggregated tumor tissue is thawed. In some embodiments, the transition from the first expansion to the second expansion occurs 14 days after the cryopreserved disaggregated tumor tissue is thawed. In some embodiments, the transition from the first expansion to the second expansion occurs 1 day to 11 days after the cryopreserved disaggregated tumor tissue is thawed. In some embodiments, the transition from the first expansion to the second expansion occurs 2 days to 11 days after the cryopreserved disaggregated tumor tissue is thawed. In some embodiments, the transition from the first expansion to the second expansion occurs 3 days to 11 days after the cryopreserved disaggregated tumor tissue is thawed. In some embodiments, the transition from the first expansion to the second expansion occurs 4 days to 11 days after the cryopreserved disaggregated tumor tissue is thawed. In some embodiments, the transition from the first expansion to the second expansion occurs 5 days to 11 days after the cryopreserved disaggregated tumor tissue is thawed. In some embodiments, the transition from the first expansion to the second expansion occurs 6 days to 11 days after the cryopreserved disaggregated tumor tissue is thawed. In some embodiments, the transition from the first expansion to the second expansion occurs 7 days to 11 days after the cryopreserved disaggregated tumor tissue is thawed. In some embodiments, the transition from the first expansion to the second expansion occurs 8 days to 11 days after the cryopreserved disaggregated tumor tissue is thawed. In some embodiments, the transition from the first expansion to the second expansion occurs 9 days to 11 days after the cryopreserved disaggregated tumor tissue is thawed. In some embodiments, the transition from the first expansion to the second expansion occurs 10 days to 11 days after the cryopreserved disaggregated tumor tissue is thawed. In some embodiments, the transition from the first expansion to the second expansion occurs 11 days after the cryopreserved disaggregated tumor tissue is thawed.

In some embodiments, the TILs are not stored after the first expansion and prior to the second expansion, and the TILs proceed directly to the second. In some embodiments, the transition occurs in closed system, as described herein. In some embodiments, the TILs from the first expansion, the second population of TILs, proceeds directly into the second expansion with no transition period.

In some embodiments, the transition from the first expansion to the second expansion is performed in a closed system bioreactor. In some embodiments, a closed system is employed for the TIE expansion, as described herein. In some embodiments, a single bioreactor is employed. In some embodiments, the single bioreactor employed is for example a G-REX-10 or a G-REX-100 or Xuri WAVE bioreactor. In some embodiments, the closed system bioreactor is a single bioreactor.

In some embodiments, the TIL cell population is expanded in number after harvest and initial bulk processing. This further expansion is referred to herein as the second expansion, which can include expansion processes generally referred to in the art as a rapid expansion process. The second expansion is generally accomplished using a culture media comprising a number of components, including feeder cells, a cytokine source, and an anti-CD3 antibody, in a gas-permeable or gas exchanging container.

In some embodiments, the second expansion or second TIL expansion of TIL can be performed using any TIL culture flasks or containers known by those of skill in the art. In some embodiments, the second TIL expansion can proceed for 7 days, 8 days, 9 days, 10 days, 11 days, 12 days, 13 days, or 14 days. In some embodiments, the second TIL expansion can proceed for about 7 days to about 14 days. In some embodiments, the second TIL expansion can proceed for about 8 days to about 14 days. In some embodiments, the second TIL expansion can proceed for about 9 days to about 14 days. In some embodiments, the second TIL expansion can proceed for about 10 days to about 14 days. In some embodiments, the second TIL expansion can proceed for about 11 days to about 14 days. In some embodiments, the second TIL expansion can proceed for about 12 days to about 14 days. In some embodiments, the second TIL expansion can proceed for about 13 days to about 14 days. In some embodiments, the second TIL expansion can proceed for about 14 days.

In an embodiment, the second expansion can be performed in a gas permeable container using the methods of the present disclosure. For example, TILs can be rapidly expanded using non-specific T-cell receptor stimulation in the presence of interleukin-2 (IL-2) or interleukin-7 (IL-7) or interleukin-15 (IL-15); IL-12. The non-specific T-cell receptor stimulus can include, for example, an anti-CD3 antibody, such as about 30 ng/ml of OKT3, a mouse monoclonal anti-CD3 antibody (commercially available from Ortho-McNeil, Raritan, N.J. or Miltenyi Biotech, Auburn, Calif.) or UHCT-1 (commercially available from BioLegend, San Diego, Calif., USA). TILs can be expanded to induce further stimulation of the TILs in vitro by including one or more antigens during the second expansion, including antigenic portions thereof, such as epitope(s), of the cancer, which can be optionally expressed from a vector, such as a human leukocyte antigen A2 (ILA-A2) binding peptide, e.g., 0.3 µM MART-1:26-35 (27 L) or gpl 00:209-217 (210M), optionally in the presence of a T-cell growth factor, such as 300 IU/mL IL-2 or IL-15. Other suitable antigens may include, e.g., NY-ESO-1, TRP-1, TRP-2, tyrosinase cancer antigen, MAGE-A3, SSX-2, and VEGFR2, or antigenic portions thereof. TIL may also be rapidly expanded by re-stimulation with the same antigen(s) of the cancer pulsed onto HLA-A2-expressing antigen-presenting cells. Alternatively, the TILs can be further re-stimulated with, e.g., example, irradiated, autologous lymphocytes or with irradiated HLA-A2+ allogeneic lymphocytes and IL-2. In some embodiments, the re-stimulation occurs as part of the second expansion. In some embodiments, the second expansion occurs in the presence of irradiated, autologous lymphocytes or with irradiated HLA-A2+ allogeneic lymphocytes and IL-2.

In an embodiment, the cell culture medium further comprises IL-2. In some embodiments, the cell culture medium comprises about 3000 IU/mL of IL-2. In an embodiment, the cell culture medium comprises about 100 IU/mL, about 200 IU/mL, about 300 IU/mL, about 400 IU/mL, about 500 IU/mL, about 600 IU/mL, about 700 IU/mL, about 800 IU/mL, about 900 IU/mL, 1000 IU/mL, about 1500 IU/mL, about 2000 IU/mL, about 2500 IU/mL, about 3000 IU/mL, about 3500 IU/mL, about 4000 IU/mL, about 4500 IU/mL, about 5000 IU/mL, about 5500 IU/mL, about 6000 IU/mL, about 6500 IU/mL, about 7000 IU/mL, about 7500 IU/mL, or about 8000 IU/mL of IL-2. In an embodiment, the cell culture medium comprises between 1000 and 2000 IU/mL, between 2000 and 3000 IU/mL, between 3000 and 4000 IU/mL, between 4000 and 5000 IU/mL, between 5000 and 6000 IU/mL, between 6000 and 7000 IU/mL, between 7000 and 8000 IU/mL, or between 8000 IU/mL of IL-2.

In an embodiment, the cell culture medium comprises OKT3 antibody. In some embodiments, the cell culture medium comprises about 30 ng/mL of OKT3 antibody. In an embodiment, the cell culture medium comprises about 0.1 ng/mL, about 0.5 ng/mL, about 1 ng/mL, about 2.5 ng/mL, about 5 ng/mL, about 7.5 ng/mL, about 10 ng/mL, about 15 ng/mL, about 20 ng/mL, about 25 ng/mL, about 30 ng/mL, about 35 ng/mL, about 40 ng/mL, about 50 ng/mL, about 60 ng/mL, about 70 ng/mL, about 80 ng/mL, about 90 ng/mL, about 100 ng/mL, about 200 ng/mL, about 500 ng/mL, and about 1 µg/mL of OKT3 antibody. In an embodiment, the cell culture medium comprises between 0.1 ng/mL and 1 ng/mL, between 1 ng/mL and 5 ng/mL, between 5 ng/mL and 10 ng/mL, between 10 ng/mL and 20 ng/mL, between 20 ng/mL and 30 ng/mL, between 30 ng/mL and 40 ng/mL, between 40 ng/mL and 50 ng/mL, and between 50 ng/mL and 100 ng/mL of OKT3 antibody.

In some embodiments, a combination of IL-2, IL-7, IL-15, and/or IL-21 are employed as a combination during the second expansion. In some embodiments, IL-2, IL-7, IL-15, and/or IL-21 as well as any combinations thereof can be included during the second expansion. In some embodiments, a combination of IL-2, IL-15, and IL-21 are employed as a combination during the second expansion. In some embodiments, IL-2, IL-15, and IL-21 as well as any combinations thereof can be included.

In some embodiments, the second expansion can be conducted in a supplemented cell culture medium comprising IL-2, OKT-3, and antigen-presenting feeder cells. In some embodiments, the second expansion occurs in a supplemented cell culture medium. In some embodiments, the supplemented cell culture medium comprises IL-2, OKT-3, and antigen-presenting feeder cells. In some embodiments, the second cell culture medium comprises IL-2, OKT-3, and antigen-presenting cells (APCs; also referred to as antigen-presenting feeder cells). In some embodiments, the second expansion occurs in a cell culture medium comprising IL-2, OKT-3, and antigen-presenting feeder cells (i.e., antigen presenting cells).

In some embodiments, the second expansion culture media comprises about 500 IU/mL of IL-15, about 400 IU/mL of IL-15, about 300 IU/mL of IL-15, about 200 IU/mL of IL-15, about 180 IU/mL of IL-15, about 160 IU/mL of IL-15, about 140 IU/mL of IL-15, about 120 IU/mL of IL-15, or about 100 IU/mL of IL-15. In some embodiments, the second expansion culture media comprises about 500 IU/mL of IL-15 to about 100 IU/mL of IL-15. In some embodiments, the second expansion culture media comprises about 400 IU/mL of IL-15 to about 100 IU/mL of IL-15. In some embodiments, the second expansion culture media comprises about 300 IU/mL of IL-15 to about 100 IU/mL of IL-15. In some embodiments, the second expansion culture media comprises about 200 IU/mL of IL-15. In some embodiments, the cell culture medium comprises about 180 IU/mL of IL-15. In an embodiment, the cell culture medium further comprises IL-15. In a preferred embodiment, the cell culture medium comprises about 180 IU/mL of IL-15.

In some embodiments, the second expansion culture media comprises about 20 IU/mL of IL-21, about 15 IU/mL of IL-21, about 12 IU/mL of IL-21, about 10 IU/mL of IL-21, about 5 IU/mL of IL-21, about 4 IU/mL of IL-21, about 3 IU/mL of IL-21, about 2 IU/mL of IL-21, about 1 IU/mL of IL-21, or about 0.5 IU/mL of IL-21. In some embodiments, the second expansion culture media comprises about 20 IU/mL of IL-21 to about 0.5 IU/mL of IL-21. In some embodiments, the second expansion culture media comprises about 15 IU/mL of IL-21 to about 0.5 IU/mL of IL-21. In some embodiments, the second expansion culture media comprises about 12 IU/mL of IL-21 to about 0.5 IU/mL of IL-21. In some embodiments, the second expansion culture media comprises about 10 IU/mL of IL-21 to about 0.5 IU/mL of IL-21. In some embodiments, the second expansion culture media comprises about 5 IU/mL of IL-21 to about 1 IU/mL of IL-21. In some embodiments, the second expansion culture media comprises about 2 IU/mL of IL-21. In some embodiments, the cell culture medium comprises about 1 IU/mL of IL-21. In some embodiments, the cell culture medium comprises about 0.5 IU/mL of IL-21. In an embodiment, the cell culture medium further comprises IL-21. In a preferred embodiment, the cell culture medium comprises about 1 IU/mL of IL-21.

In some embodiments the antigen-presenting feeder cells (APCs) are PBMCs. In an embodiment, the ratio of TILs to PBMCs and/or antigen-presenting cells in the rapid expansion and/or the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to PBMCs in the rapid expansion and/or the second expansion is between 1 to 50 and 1 to 300. In an embodiment, the ratio of TILs to PBMCs in the rapid expansion and/or the second expansion is between 1 to 100 and 1 to 200.

In an embodiment, REP and/or the second expansion is performed in flasks with the bulk TILs being mixed with a 100- or 200-fold excess of inactivated feeder cells, 30 mg/mL OKT3 anti-CD3 antibody and 3000 IU/mL IL-2 in 150 ml media. Media replacement is done (generally ⅔ media replacement via respiration with fresh media) until the cells are transferred to an alternative growth chamber. Alternative growth chambers include G-REX flasks and gas permeable containers as more fully discussed below.

In some embodiments, the second expansion (which can include processes referred to as the REP process) is shortened to 7-14 days, as discussed in the examples and figures. In some embodiments, the second expansion is shortened to 11 days.

In an embodiment, REP and/or the second expansion may be performed using T-175 flasks and gas permeable bags as previously described (Tran, et al., J. Immunother. 2008, 31, 742-51; Dudley, et al., J. Immunother. 2003, 26, 332-42) or gas permeable cultureware (G-Rex flasks). In some embodiments, the second expansion (including expansions referred to as rapid expansions) is performed in T-175 flasks, and about $1\times10^6$ TILs suspended in 150 mL of media may be added to each T-175 flask. The TILs may be cultured in a 1 to 1 mixture of CM and AIM-V medium, supplemented with 3000 IU per mL of IL-2 and 30 ng per ml of anti-CD3. The T-175 flasks may be incubated at 37° C. in 5% CO2. Half the media may be exchanged on day 5 using 50/50 medium with 3000 IU per mL of IL-2. In some embodiments, on day 7 cells from two T-175 flasks may be combined in a 3 L bag and 300 mL of AIM V with 5% human AB serum and 3000 IU per mL of IL-2 was added to the 300 ml of TIL suspension. The number of cells in each bag was counted every day or two and fresh media was added to keep the cell count between 0.5 and $2.0\times10^6$ cells/mL.

In an embodiment, the second expansion may be performed in 500 mL capacity gas permeable flasks with 100 cm gas-permeable silicon bottoms (G-Rex 100, commercially available from Wilson Wolf Manufacturing Corporation, New Brighton, Minn., USA), $5\times10^6$ or $10\times10^6$ TIL may be cultured with PBMCs in 400 mL of 50/50 medium, supplemented with 5% human AB serum, 3000 IU per mL of IL-2 and 30 ng per ml of anti-CD3 (OKT3). The G-Rex 100 flasks may be incubated at 37° C. in 5% CO2. On day 5, 250 mL of supernatant may be removed and placed into centrifuge bottles and centrifuged at 1500 rpm (491×g) for 10 minutes. The TIL pellets may be re-suspended with 150 mL of fresh medium with 5% human AB serum, 3000 IU per mL of IL-2, and added back to the original G-Rex 100 flasks. When TIL are expanded serially in G-Rex 100 flasks, on day 7 the TIL in each G-Rex 100 may be suspended in the 300 mL of media present in each flask and the cell suspension may be divided into 3 100 mL aliquots that may be used to seed 3 G-Rex 100 flasks. Then 150 mL of AIM-V with 5% human AB serum and 3000 IU per mL of IL-2 may be added to each flask. The G-Rex 100 flasks may be incubated at 37° C. in 5% CO2 and after 4 days 150 mL of AIM-V with 3000 IU per mL of IL-2 may be added to each G-REX 100 flask. The cells may be harvested on day 14 of culture.

In an embodiment, the second expansion (including expansions referred to as REP) is performed in flasks with the bulk TILs being mixed with a 100- or 200-fold excess of inactivated feeder cells, 30 mg/mL OKT3 anti-CD3 antibody and 3000 IU/mL IL-2 in 150 ml media. In some embodiments, media replacement is done until the cells are transferred to an alternative growth chamber. In some embodiments, ⅔ of the media is replaced by respiration with fresh media. In some embodiments, alternative growth chambers include G-REX flasks and gas permeable containers as more fully discussed below.

In an embodiment, the second expansion (including expansions referred to as REP) is performed and further comprises a step wherein TILs are selected for superior tumor reactivity. Any selection method known in the art may be used. For example, the methods described in U.S. Patent Application Publication No. 2016/0010058 A1, may be used for selection of TILs for superior tumor reactivity.

Optionally, a cell viability assay can be performed after the second expansion (including expansions referred to as the REP expansion), using standard assays known in the art. For example, a trypan blue exclusion assay can be done on a sample of the bulk TILs, which selectively labels dead cells and allows a viability assessment. In some embodiments, TIL samples can be counted and viability determined using a Cellometer K2 automated cell counter (Nexcelom Bioscience, Lawrence, Mass.).

In some embodiments, the second expansion (including expansions referred to as REP) of TIL can be performed using T-175 flasks and gas-permeable bags as previously described (Tran K Q, Zhou J, Durflinger K H, et al., 2008, J Immunother., 31:742-751, and Dudley M E, Wunderlich J R, Shelton T E, et al. 2003, J lmmunother., 26:332-342) or gas-permeable G-Rex flasks. In some embodiments, the second expansion is performed using flasks. In some embodiments, the second expansion is performed using gas-permeable G-Rex flasks. In some embodiments, the second expansion is performed in T-175 flasks, and about $1\times10^6$ TIL are suspended in about 150 mL of media and this is added to each T-175 flask. The TIL are cultured with irradiated (50 Gy) allogeneic PBMC as "feeder" cells at a ratio of 1 to 100 and the cells were cultured in a 1 to 1 mixture of CM and AIM-V medium (50/50 medium), supplemented with 3000 IU/mL of IL-2 and 30 ng/mL of anti-CD3. The T-175 flasks are incubated at 37° C. in 5% CO2. In some embodiments, half the media is changed on day 5 using 50/50 medium with 3000 IU/mL of 1L-2. In some embodiments, on day 7, cells from 2 T-175 flasks are combined in a 3 L bag and 300 mL of AIM-V with 5% human AB serum and 3000 IU/mL of IL-2 is added to the 300 mL of TIL suspension. The number of cells in each bag can be counted every day or two and fresh media can be added to keep the cell count between about 0.5 and about $2.0\times10^6$ cells/mL.

In some embodiments, the second expansion (including expansions referred to as REP) are performed in 500 mL capacity flasks with 100 cm2 gas-permeable silicon bottoms (G-Rex 100, Wilson Wolf), about $5\times10^6$ or $10\times10^6$ TIL are cultured with irradiated allogeneic PBMC at a ratio of 1 to 100 in 400 mL of 50/50 medium, supplemented with 3000 IU/mL of IL-2 and 30 ng/mL of anti-CD3. The G-Rex 100 flasks are incubated at 37° C. in 5% CO2. In some embodiments, on day 5, 250 mL of supernatant is removed and placed into centrifuge bottles and centrifuged at 1500 rpm (491 g) for 10 minutes. The TIL pellets can then be resuspended with 150 mL of fresh 50/50 medium with 3000 IU/mL of IL-2 and added back to the original G-Rex 100 flasks. In embodiments where TILs are expanded serially in G-Rex 100 flasks, on day 7 the TIL in each G-Rex 100 are suspended in the 300 mL of media present in each flask and the cell suspension was divided into three 100 mL aliquots that are used to seed 3 G-Rex 100 flasks. Then 150 mL of AIM-V with 5% human AB serum and 3000 IU/mL of IL-2 is added to each flask. The G-Rex 100 flasks are incubated at 37° C. in 5% CO2 and after 4 days 150 mL of AIM-V with 3000 IU/mL of IL-2 is added to each G-Rex 100 flask. The cells are harvested on day 14 of culture.

The diverse antigen receptors of T and B lymphocytes are produced by somatic recombination of a limited, but large number of gene segments. These gene segments: V (variable), D (diversity), J (joining), and C (constant), determine the binding specificity and downstream applications of immunoglobulins and T-cell receptors (TCRs). The present invention provides a method for generating TILs which exhibit and increase the T-cell repertoire diversity. In some embodiments, the TILs obtained by the present method exhibit an increase in the T-cell repertoire diversity. In some embodiments, the TILs obtained in the second expansion exhibit an increase in the T-cell repertoire diversity. In some embodiments, the increase in diversity is an increase in the immunoglobulin diversity and/or the T-cell receptor diversity. In some embodiments, the diversity is in the immunoglobulin is in the immunoglobulin heavy chain. In some embodiments, the diversity is in the immunoglobulin is in the immunoglobulin light chain. In some embodiments, the diversity is in the T-cell receptor. In some embodiments, the diversity is in one of the T-cell receptors selected from the group consisting of alpha, beta, gamma, and delta receptors. In some embodiments, there is an increase in the expression of T-cell receptor (TCR) alpha and/or beta. In some embodiments, there is an increase in the expression of T-cell receptor (TCR) alpha. In some embodiments, there is an increase in the expression of T-cell receptor (TCR) beta. In some embodiments, there is an increase in the expression of TCRab (i.e., TCRαβ).

In some embodiments, the second expansion culture medium (e.g., sometimes referred to as CM2 or the second cell culture medium), comprises IL-2, OKT-3, as well as the antigen-presenting feeder cells (APCs).

In some embodiments, the second expansion is performed in a closed system bioreactor. In some embodiments, a closed system is employed for the TIL expansion, as described herein. In some embodiments, a single bioreactor is employed. In some embodiments, the single bioreactor employed is for example G-REX-10 or a G-REX-100 or advantageously the device of WO 2018/130845. In some embodiments, the closed system bioreactor is a single bioreactor.

In an embodiment, the second expansion procedures described herein, as well as those referred to as REP) require an excess of feeder cells during REP TIL expansion and/or during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation.

In general, the allogenic PBMCs are inactivated, either via irradiation or heat treatment, and used in the REP procedures, which provides an exemplary protocol for evaluating the replication incompetence of irradiate allogeneic PBMCs.

In some embodiments, PBMCs are considered replication incompetent and accepted for use in the TIL expansion procedures described herein if the total number of viable cells on day 14 is less than the initial viable cell number put into culture on day 0 of the REP and/or day 0 of the second expansion (i.e., the start day of the second expansion).

In some embodiments, PBMCs are considered replication incompetent and accepted for use in the TIL expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 30 ng/ml OKT3 antibody and 3000 IU/ml IL-2.

In some embodiments, PBMCs are considered replication incompetent and accepted for use in the TM expansion procedures described herein if the total number of viable cells, cultured in the presence of OKT3 and IL-2, on day 7 and day 14 has not increased from the initial viable cell number put into culture on day 0 of the REP and/or day 0 of the second expansion (i.e., the start day of the second expansion). In some embodiments, the PBMCs are cultured in the presence of 5-60 ng/ml OKT3 antibody and 1000-6000 IU/ml IL-2. In some embodiments, the PBMCs are cultured in the presence of 10-50 ng/ml OKT3 antibody and 2000-5000 IU/ml IL-2. In some embodiments, the PBMCs are cultured in the presence of 20-40 ng/ml OKT3 antibody and 2000-4000 IU/ml IL-2. In some embodiments, the PBMCs are cultured in the presence of 25-35 ng/ml OKT3 antibody and 2500-3500 IU/ml IL-2.

In some embodiments, the antigen-presenting feeder cells are PBMCs. In some embodiments, the antigen-presenting feeder cells are artificial antigen-presenting feeder cells. In an embodiment, the ratio of TILs to antigen-presenting feeder cells in the second expansion is about 1 to 25, about 1 to 50, about 1 to 100, about 1 to 125, about 1 to 150, about 1 to 175, about 1 to 200, about 1 to 225, about 1 to 250, about 1 to 275, about 1 to 300, about 1 to 325, about 1 to 350, about 1 to 375, about 1 to 400, or about 1 to 500. In an embodiment, the ratio of TILs to antigen-presenting feeder cells in the second expansion is between 1 to 50 and 1 to 300. In an embodiment, the ratio of TILs to antigen-presenting feeder cells in the second expansion is between 1 to 100 and 1 to 200.

In an embodiment, the second expansion procedures described herein require a ratio of about $2.5 \times 10^9$ feeder cells to about $100 \times 10^6$ TILs. In another embodiment, the second expansion procedures described herein require a ratio of about $2.5 \times 10^9$ feeder cells to about $50 \times 10^6$ TILs. In yet another embodiment, the second expansion procedures described herein require about $2.5 \times 10^9$ feeder cells to about $25 \times 10^6$ TILs.

In an embodiment, the second expansion procedures described herein require an excess of feeder cells during the second expansion. In many embodiments, the feeder cells are peripheral blood mononuclear cells (PBMCs) obtained from standard whole blood units from healthy blood donors. The PBMCs are obtained using standard methods such as Ficoll-Paque gradient separation. In an embodiment, artificial antigen-presenting (aAPC) cells are used in place of PBMCs.

In general, the allogenic PBMCs are inactivated, either via irradiation or heat treatment, and used in the TIL expansion procedure.

In an embodiment, artificial antigen presenting cells are used in the second expansion as a replacement for, or in combination with, PBMCs.

The expansion methods described herein generally use culture media with high doses of a cytokine, in particular IL-2, as is known in the art.

Alternatively, using combinations of cytokines for the rapid expansion and or second expansion of TILS is additionally possible, with combinations of two or more of IL-2, IL-15 and IL-21 as is generally outlined in International Publication No. WO 2015/189356 and W International Publication No. WO 2015/189357, hereby expressly incorporated by reference in their entirety. Thus, possible combinations include IL-2 and IL-15, IL-2 and IL-21, IL-15 and IL-21 and IL-2, IL-15 and IL-21, with the latter finding particular use in many embodiments. The use of combinations of cytokines specifically favors the generation of lymphocytes, and in particular T-cells as described therein.

In some embodiments, the culture media used in expansion methods described herein (including those referred to as REP) also includes an anti-CD3 antibody. An anti-CD3 antibody in combination with IL-2 induces T cell activation and cell division in the TIL population. This effect can be seen with full length antibodies as well as Fab and F(ab')2 fragments, with the former being generally preferred; see, e.g., Tsoukas et al., J. Immunol. 1985, 135, 1719, hereby incorporated by reference in its entirety.

As will be appreciated by those in the art, there are a number of suitable anti-human CD3 antibodies that find use in the invention, including anti-human CD3 polyclonal and monoclonal antibodies from various mammals, including, but not limited to, murine, human, primate, rat, and canine antibodies. In particular embodiments, the OKT3 anti-CD3 antibody is used (commercially available from Ortho-McNeil, Raritan, N.J. or Miltenyi Biotech, Auburn, Calif.).

After the second expansion step, cells can be harvested. In some embodiments the TILs are harvested after one, two, three, four or more expansion steps. In some embodiments the TILs are harvested after two expansion steps.

TILs can be harvested in any appropriate and sterile manner, including for example by centrifugation. Methods for TIL harvesting are well known in the art and any such know methods can be employed with the present process. In some embodiments, TILS are harvested using an automated system.

Cell harvesters and/or cell processing systems are commercially available from a variety of sources, including, for example, Fresenius Kabi, Tomtec Life Science, Perkin Elmer, and Inotech Biosystems International, Inc. Any cell based harvester can be employed with the present methods. In some embodiments, the cell harvester and/or cell processing systems is a membrane-based cell harvester. In some embodiments, cell harvesting is via a cell processing system, such as the LOVO system (manufactured by Fresenius Kabi). The term "LOVO cell processing system" also refers to any instrument or device manufactured by any vendor that can pump a solution comprising cells through a membrane or filter such as a spinning membrane or spinning filter in a sterile and/or closed system environment, allowing for continuous flow and cell processing to remove supernatant or cell culture media without pelletization. In some embodiments, the cell harvester and/or cell processing system can perform cell separation, washing, fluid-exchange, concentration, and/or other cell processing steps in a closed, sterile system.

In some embodiments, the harvest is performed from a closed system bioreactor. In some embodiments, a closed system is employed for the TIL expansion, as described herein. In some embodiments, a single bioreactor is employed. In some embodiments, the single bioreactor employed is for example G-REX-10 or a G-REX-100 or advantageously the device of WO 2018/130845. In some embodiments, the closed system bioreactor is a single bioreactor.

Cells are transferred to a container for use in administration to a patient. In some embodiments, once a therapeutically sufficient number of TILs are obtained using the expansion methods described above, they are transferred to a container for use in administration to a patient.

In an embodiment, TILs expanded using APCs of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic.

In an embodiment, TILs expanded using the methods of the present disclosure are administered to a patient as a pharmaceutical composition. In an embodiment, the pharmaceutical composition is a suspension of TILs in a sterile buffer. TILs expanded using PBMCs of the present disclosure may be administered by any suitable route as known in the art. In some embodiments, the T-cells are administered as a single intra-arterial or intravenous infusion, which preferably lasts approximately 30 to 60 minutes. Other suitable routes of administration include intraperitoneal, intrathecal, and intralymphatic administration.

Any suitable dose of TILs can be administered. In some embodiments, from about $2.3 \times 10^{10}$ to about $13.7 \times 10^{10}$ TILs are administered, with an average of around $7.8 \times 10^{10}$ TILs, particularly if the cancer is melanoma. In an embodiment, about $1.2 \times 10^{10}$ to about $4.3 \times 10^{10}$ of TILs are administered. In some embodiments, about $3 \times 10^{10}$ to about $12 \times 10^{10}$ TILs are administered. In some embodiments, about $4 \times 10^{10}$ to about $10 \times 10^{10}$ TILs are administered. In some embodiments, about $5 \times 10^{10}$ to about $8 \times 10^{10}$ TILs are administered. In some embodiments, about $6 \times 10^{10}$ to about $8 \times 10^{10}$ TILs are administered. In some embodiments, about $7 \times 10^{10}$ to about $8 \times 10^{10}$ TILs are administered. In some embodiments, the therapeutically effective dosage is about $2.3 \times 10^{10}$ to about $13.7 \times 10^{10}$. In some embodiments, the therapeutically effective dosage is about $7.8 \times 10^{10}$ TILs, particularly of the cancer is melanoma. In some embodiments, the therapeutically effective dosage is about $1.2 \times 10^{10}$ to about $4.3 \times 10^{10}$ of TILs. In some embodiments, the therapeutically effective dosage is about $3 \times 10^{10}$ to about $12 \times 10^{10}$ TILs. In some embodiments, the therapeutically effective dosage is about $4 \times 10^{10}$ to about $10 \times 10^{10}$ TILs. In some embodiments, the therapeutically effective dosage is about $5 \times 10^{10}$ to about $8 \times 10^{10}$ TILs. In some embodiments, the therapeutically effective dosage is about $6 \times 10^{10}$ to about $8 \times 10^{10}$ TILs. In some embodiments, the therapeutically effective dosage is about $7 \times 10^{10}$ to about $8 \times 10^{10}$ TILs.

In some embodiments, the number of the TILs provided in the pharmaceutical compositions of the invention is about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{10}$, $2 \times 10^{11}$ $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, and $9 \times 10^{13}$. In an embodiment, the number of the TILs provided in the pharmaceutical compositions of the invention is in the range of $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$, $1 \times 10^9$ to $5 \times 10^9$, $5 \times 10^9$ to $1 \times 10^{10}$, $1 \times 10^{10}$ to $5 \times 10^{10}$, $5 \times 10^{10}$ to $1 \times 10^{11}$, $5 \times 10^{11}$ to $1 \times 10^{12}$ $1 \times 10^{12}$ to $5 \times 10^{12}$, and $5 \times 10^{12}$ to $1 \times 10^{13}$.

In some embodiments, the concentration of the TILs provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v of the pharmaceutical composition.

In some embodiments, the concentration of the TILs provided in the pharmaceutical compositions of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of the TILs provided in the pharmaceutical compositions of the invention is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v or v/v of the pharmaceutical composition.

In some embodiments, the concentration of the TILs provided in the pharmaceutical compositions of the invention is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v or v/v of the pharmaceutical composition.

In some embodiments, the amount of the TILs provided in the pharmaceutical compositions of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the TILs provided in the pharmaceutical compositions of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

The TILs provided in the pharmaceutical compositions of the invention are effective over a wide dosage range. The exact dosage will depend upon the route of administration, the form in which the compound is administered, the gender and age of the subject to be treated, the body weight of the subject to be treated, and the preference and experience of the attending physician. The clinically-established dosages of the TILs may also be used if appropriate. The amounts of the pharmaceutical compositions administered using the methods herein, such as the dosages of TILs, will be dependent on the human or mammal being treated, the severity of the disorder or condition, the rate of administration, the disposition of the active pharmaceutical ingredients and the discretion of the prescribing physician.

In some embodiments, TILs may be administered in a single dose. Such administration may be by injection, e.g., intravenous injection. In some embodiments, TILs may be administered in multiple doses. Dosing may be once, twice, three times, four times, five times, six times, or more than six times per year. Dosing may be once a month, once every two weeks, once a week, or once every other day. Administration of TILs may continue as long as necessary.

In some embodiments, an effective dosage of TILs is about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$, $1\times10^{3}$, $2\times10^{13}$, $3\times10^{13}$, $4\times10^{13}$, $5\times10^{13}$, $6\times10^{13}$, $7\times10^{13}$, $8\times10^{13}$, and $9\times10^{13}$. In some embodiments, an effective dosage of TILs is in the range of $1\times10^6$ to $5\times10^6$, $5\times10^6$ to $1\times10^7$, $1\times10^7$ to $5\times10^7$, $5\times10^7$ to $1\times10^8$, $1\times10^8$ to $5\times10^8$, $5\times10^8$ to $1\times10^9$, $1\times10^9$ to $5\times10^9$, $5\times10^9$ to $1\times10^{10}$, $1\times10^{10}$ to $5\times10^{10}$, $5\times10^{10}$ to $1\times10^{11}$, $5\times10^{11}$ to $1\times10^{12}$, $1\times10^{12}$ to $5\times10^{12}$, and $5\times10^{12}$ to $1\times10^{13}$.

In some embodiments, an effective dosage of TILs is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg.

In some embodiments, an effective dosage of TILs is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg.

An effective amount of the TILs may be administered in either single or multiple doses by any of the accepted modes of administration of agents having similar utilities, including intranasal and transdermal routes, by infra-arterial injection, intravenously, intraperitoneally, parenterally, intramuscularly, subcutaneously, topically, by transplantation, or by inhalation.

The present invention also includes kits useful in performing diagnostic and prognostic assays using the TILs, in particular UTILs, of the present invention. Kits of the invention include buffers, cytokines, flasks, media, product containers, reagents and instructions.

A non-limiting multi-step embodiment is presented below to set up TIL growth out from a tumor, a setup of a rapid expansion process, confirmation that irradiated PBMC feeders are not expanding and a transfer of static culture to a WAVE bioreactor (see, e.g., https://www.gelifesciences.com/en/us/shop/cell-culture-and-fermentation/rocking-bioreactors/consumables-and-accessories/single-use-readytoprocess-wave-cellbag-bioreactors-p-00346#overview) and formulation and fill.

In step one (Day 0), the cryopreserved disaggregated tumor tissue is thawed and resuspended 1:9 in T cell culture media supplemented with 10% FBS and 3000 IU/mL IL-2 prior to filtration through an inline 100-270 μm filter and centrifugation in a 50 mL centrifuge tube prior to resuspension in 20 mL. A sample is taken for flow cytometry analysis SOP-to quantify a number of HLA-A, B, C and CD58$^+$, and DRAQ7$^-$ cells.

In step two, the cell suspension is then seeded at ≥0.25× $10^6$ to ≤0.75×$10^6$ HLA-A,B,C & CD58$^+$ and DRAQ7$^-$ cells/mL in CM-T (T cell media supplemented with 10% Fetal Bovine Serum) supplemented with added antibacterial and antifungal agents (Amphotericin B & Gentamicin) and interleukin-2 (IL-2) 1000 IU/ml in cell culture containers. The T cells are grown out over 2 week period in CM-T from day 5 half the media is removed and replaced with fresh media CM-T supplemented with 10% Fetal Bovine Serum, Amphotericin B & Gentamicin and IL-2. This is repeated every 2/3 days between day 5 and day 10 to ensure the cells are maintained at <0.1×$10^6$ to 2×$10^6$ CD45+CD3$^+$ Annexin-V$^{-ve}$ DRAQ7$^{-ve}$ cells/mL. A microbial examination test of TIL culture supernatant (Day 5-7) by PH Eur 2.6.27 confirms no microbial growth. Flow cytometry analysis (Day 7-10) quantifies a concentration of CD45$^+$ CD3$^+$ Annexin-V$^-$ & DRAQ7$^-$ cells.

In step three, isolate 4×$10^9$ irradiated PBMCs (25 to 50 Gy) with Ficoll (Density 1.078 g/ml) from multiple allogeneic donors (healthy blood donation derived Buffy coat). Flow cytometry analysis quantifies CD45$^+$ Annexin-V$^-$, and DRAQ7$^-$ cells. A microbial examination test of irradiated PBMCs determines microbial growth.

In step four, the amount of TIL available for the start of the rapid expansion process is quantified (Day-12). Flow cytometry analysis quantifies CD45$^+$ CD3$^+$ Annexin-V$^-$, and DRAQ7$^+$ cells.

In step 5, a culture mixture of feeders (Irradiated ficoll isolated PBMCs) is prepared and growth supplements in 3 L of T cell mixed media containing: ≥3 to <5×10$^9$ Irradiated PBMCs CD45$^+$ Annexin-V$^-$, and DRAQ7$^-$ cells, 7-9% human AB serum, 2000 to 4000 IU/mL IL-2 and 20 to 40 ng/ml OKT-3 antibody in a closed static cell culture bag.

In step 6, a representative sample of the culture mixture of feeders (Irradiated ficoll isolated PBMCs) is taken for a control flask prior to adding TIL.

In step 7, TIL is added to a REP culture: ≥1 to <20×10$^6$ Tumor derived TIL CD45$^+$ CD3$^+$ Annexin-V$^-$, and DRAQ7$^-$ cells.

In step 8, static culture is incubated between 35 to 38.5° C. with 3.5 to 6% Carbon dioxide in a dry incubator for 6 days. The number and viability of CD45$^+$ Annexin-V$^-$, and DRAQ7$^-$ cells are assessed in the Control flask (collected at Step 6) at Day 14 and 18 containing the REP mixture without TIL to ensure irradiated feeders are not expanding. Flow cytometry analysis quantifies CD45$^+$ Annexin-V$^-$, and DRAQ7$^-$ cells.

In step 9, a WAVE bioreactor bag is preconditioned for 1-2 hours at 35 to 38.5° C. with 3.5 to 6% carbon dioxide with 1.7 L of TCM supplemented with: 7-9% Human AB serum and 2000 to 4000 IU/mL IL-2.

In step 10, TIL is transferred and expanded in the WAVE bioreactor system.

In step 11, a perfusion feed 1×TCM 10 L bag supplemented with 2000 to 4000 IU/mL IL-2 is connected.

In step 12 (days 19-22), the perfusion rate between day 19 and day 22 is adjusted.

In step 13, (day 24), perfusion is stopped, and waste and feed is disconnected.

In step 14, TIL is concentrated and washed.

In step 15, a final drug formulation is made with cells suspended in PBS containing 10% DMSO and 8.5% HSA in a total volume range of 125 to 270 mL transfusion bag.

In step 16, a sample of the final product bag containing TIL is taken for QC assay and retention samples. The QC assays of the fresh drug product include microbial examination testing and color and visible particle testing. Retention samples are prepared for cell dose, viability phenotype and potency; microbial examination and endotoxin analysis.

In step 17, the final product container is labeled and overlapped with a final product label.

In step 18, there is cryopreservation by controlled rate freezing at −1° C./minute to −60° C. and a transfer to ≤−130° C. storage. QC assays for the cryopreserved drug product include mycoplasma testing by PCR, T cell dose and viability testing, endotoxin testing as measured using a kinetic chromogenic LAL test and potency testing to assess the CD2$^+$ Expressing CD45$^+$ DRAQ7$^-$ for a combination of CD137$^+$, IFN-γ$^+$, TNFα+, or CD107a$^+$ after co-culture with a cell line expressing an anti-CD3 fragment.

TABLE 1

Overview manufacture using static culture bags only

| CTU - TIL # (Sex) | Tumour derived TIL from first expansion (×10$^7$) | Viable CD3+ cells in second expansion (×10$^7$) | Fold Expansion* | Final Issue Viable CD3+ (×10$^{10}$) |
|---|---|---|---|---|
| 1 (F) | 2.1 | 1.5 | 690 | 1.0 |
| 3 (M) | 3.8 | 2.0 | 1100 | 2.2 |
| 5 (M) | 8.2 | 1.5 | 1281 | 2.0 |
| Mean ± SD | 6.0 ± 2.2 | 1.7 ± 0.23 | 1023 ± 303 | 1.7 ± 0.52 |

*Equals Final manufactured TIL/TIL used in REP

TABLE 2

Overview manufacture using perfusion bioreactor

| CTU - TIL # (Sex) | Tumour derived from first expansion (×10$^7$) | Viable CD3+ cells in second expansion (×10$^7$) | Fold Expansion* | Final Issue Viable CD3+ (×10$^{10}$) |
|---|---|---|---|---|
| 12 (F) | 5.4 | 2.0 | 1600 | 3.2 |
| 13 (M) | 14.0 | 2.0 | 1010 | 2.02 |
| 14 (M) | 5.8 | 2.0 | 2100 | 4.2 |
| 15 (M) | 5.1 | 2.0 | 3100 | 6.2 |
| 16 (M) | 3.0 | 1.8 | 3000 | 5.4 |
| 19 (M) | 7.6 | 2.0 | 3400 | 6.8 |
| 20 (M) | 1.4 | 1.1 | 5409 | 5.95 |
| 21 (M) | 1.4 | 1.4 | 3646 | 4.85 |
| 27 (M) | 5.1 | 2.0 | 1845 | 3.69 |
| 28 (F) | 8.9 | 2.0 | 1590 | 3.18 |
| 32 (F) | 34.0 | 2.0 | 1835 | 3.67 |
| 32 (F) | N/A ** | 2.0 | 1985 | 3.97 |
| 35 (M) | 8.6 | 2.0 | 3125 | 6.25 |
| 36 (M) | 3.2 | 1.6 | 2050 | 3.28 |
| 37 (F) | 4.0 | 2.0 | 1265 | 2.53 |
| 38 (M) | 0.55 | 0.32 | 3969 | 1.27 |
| 39 (M) | 0.83 | 0.83 | 1398 | 1.16 |
| 40 (F) | 1.4 | 0.71 | 7444 | 5.3 |
| 41 (M) | 9.0 | 2.0 | 1555 | 3.11 |
| 42 (M) | 9.8 | 2.0 | 1965 | 3.93 |
| 43 (F) | 25.0 | 2.0 | 2310 | 4.62 |
| 47 (F) | 2.67 | 2.0 | 1450 | 2.9 |
| 48 (F) | 2.73 | 2.0 | 1865 | 3.73 |
| 51 (M) | 4.1 | 2.0 | 1780 | 3.56 |
| 54 (M) | 27.5 | 2.0 | 395 | 7.9 |
| 57 (M) | 2.3 | 1.5 | 764 | 1.13 |
| 60 (F) | 3.1 | 1.1 | 1486 | 1.56 |
| 63 (M) | 0.84 | 0.89 | 5842 | 5.24 |
| 64 (M) | 0.72 | 0.72 | 2993 | 2.14 |
| 67 (M) | 0.38 | 0.37 | 7526 | 2.82 |
| Mean ± SD | 6.61 ± 8.2 | 1.56 ± 0.61 | 2650 ± 1770 | 3.52 ± 1.69 |

*Equals Final manufactured TIL/TIL used in REP
** Patient treated twice using original tumour derived TIL The present invention provides a disaggregation system or device. In some embodiments, the disaggregation device is in the form of a treading device for disaggregation of tissue into individual cells or cell clumps. In some embodiments, the disaggregation device provides thermal control during the disaggregation process. In some embodiments, the invention provides a cryopreservation system or device. In some embodiments, there is provided a device for disaggregation and cryopreservation and thermal control is provided. In another aspect, the invention provides one or more flexible containers, or a system containing a plurality of containers comprising one or more flexible containers adapted for disaggregation, cryopreservation, or both disaggregation and cryopreservation in a disaggregation/cryopreservation system or device of the invention. In some embodiments, the one or more containers or the plurality of containers are interconnected and suitable for use in a closed system. The above-mentioned aspects are represented in the claims appended herein. More advantages and benefits of the present invention will become readily apparent to the person skilled in the art in view of the detailed description below which provides examples of the invention.

In certain embodiments a disaggregator comprises one or more movable surfaces, for example plates and/or paddles, and is designed to apply compression and shear forces to a tissue sample. In an embodiment, the digester comprises a first surface and a second surface that are capable of moving relative to one another. In certain embodiments, the surfaces are opposing surfaces disposed to apply pressure to a sample. In an embodiment, at least one of the surfaces is moved in a direction perpendicular to the direction of the surfaces so as to apply pressure to a sample. In an embodiment, the surfaces are aligned in parallel and designed to move together and apart in a repeated or cyclical manner such that a sample is repeatedly compressed then relaxed between the surfaces in a cyclical manner. In embodiments of the invention, compression and relaxation of the sample results in shear forces in the sample.

In an embodiment, one of the first and second surfaces is held stationary while the other surface is moved. In another embodiment, both of the first and second surfaces are moved. In an embodiment, the tissue sample is contained in a flexible and/or elastic container which contains the tissue sample and optionally disaggregation fluid or solution. In certain embodiments, the container accommodates changes in volume between the first and second surfaces as the surfaces are moved. In certain embodiments, the container is elastic and confines the tissue sample and disaggregation fluid within the extent of the opposing surfaces. In certain embodiments, the container is flexible and surrounding air pressure assists confinement of tissue sample and disaggregation fluid within the extent of the opposing surfaces. In certain embodiments, the air pressure is ambient pressure. In certain embodiments, air pressure is applied in an enclosing chamber and the pressure is greater than ambient.

In certain embodiments, the disaggregation device comprises two or more sets of opposing surfaces, disposed side-by-side. In some such embodiments, one surface is common to the sets, for example a single plate, optionally held stationary, while the second surfaces of each set are located side-by-side and apply pressure against the stationary plate. The second surfaces may alternately apply pressure in a treading motion. In certain such embodiments, a flexible container is employed that confines the tissue sample and disaggregation fluid within the space between the stationary surface and the moving surfaces while allowing the contents of the container to flow back and forth between the moving surfaces. In certain embodiments, the container is adapted to limit or prevent such back-and-forth movement of the contents. In an embodiment, a seal across the container blocks flow of contents from one side to the other. In another embodiment, a baffle across the container limits flow of contents from one side to the other.

The treading surfaces can be actuated by any suitable mechanism. Disclosed herein as device 100 is an example of a lateral bar system designed to move treading surfaces alternately against a flexible container. The treading surfaces are sprung, the springs designed to press the treading surfaces against a container while allowing for variation in container thickness and particle size variation in the container. In certain embodiments, the springs are preloaded. Also disclosed herein as device 200 is an example of a cam actuated design that features two treading surfaces. In device 200, preloaded springs press treading surfaces against a flexible container and the cam mechanism cyclically raises one treading surface, then the other, away from the flexible container. In another embodiment, one or more rocker arms or levers is employed to lift treading surfaces away from the container. In yet another embodiment, the treading surfaces are raised and lowered hydraulically. In yet another embodiment, the treading surfaces are raised and lowered pneumatically. While in the 200 device, there are two treading surfaces alternately contacting the disaggregation container, in certain embodiments, the actuating mechanism allows all of the moving surfaces to apply pressure simultaneously including when the system is at rest. Such a feature is useful to empty the contents of the disaggregation container at the end of disaggregation process. For example, instead of treading surfaces being located at intermediate positions or one raised and one lowered, all of the treading surfaces are lowered against the disaggregation container, squeezing out its contents through attached tubing, optionally filtered, into a secondary receiving container, for example a cryopreservation container.

In a fully closed disaggregation and cryopreservation system exemplified herein, there is featured automated disaggregation followed by manual filtration and transfer by a sealed system of syringes and tubes to a cryopreservation container and automated cryopreservation. Advantageously, while disaggregated tumor tissue is manually transferred from a disaggregation container to a cryopreservation container, the disaggregation and cryopreservation steps are performed by the same automated device programmed to sequentially manage both steps. In other embodiments, the disaggregation procedure is designed such that at termination, the disaggregated tumor tissues is automatically moved from a disaggregation container to a cryopreservation container. In certain embodiments, a peristaltic pump and valves that contact the connecting tubes control flow of the contents. In certain embodiments, the treading surfaces of the disaggregator are disposed to push or squeeze the disaggregated tumor solution out of the disaggregation container, optionally through a filter, into a cryopreservation container, valves controlling flow of the contents. In such embodiments, disaggregation and cryopreservation along with any transfer of material in the closed system, are preferably controlled and performed by the same device as exemplified herein.

Several disaggregation systems have been tested and optimized with respect to variables including force, digestion time, and speed (RPM or cycles per minute). Results and projections using several tissue types were determined for combinations of force, time, and speed variables including forces up to and above 60 N, digestion times up to and above 60 min, and speeds up to and above 240 RPM. In certain embodiments of the invention, the force is from 20-200 N, or 30-120 N, or 30-90 N, or 40-60 N, or 10-20 N or 20-30 N, or 30-40 N, or 40-50 N, or 40-45 N, or 45-50 N, or 50-55 N, or 55-60 N, or 60-65 N, or 65-70 N, or 70-75 N, or 75-80 N. Typical treading feet have surfaces areas from about 20 to 50 cm$^2$. Based on a 30 cm$^2$ surface, the treading pressure is from 0.5-6.5 N/cm2, or 1-4 N/cm2, or 1-3 N/cm2, or 1-2 N/cm2, or 1.5-2.5 N/cm$^2$, or 2-3 N/cm$^2$, or 2.5-3.5 N/cm$^2$, or 1.5 N/cm$^2$ g 0.5 N/cm$^2$, or 2 N/cm$^2$±0.5 N/cm$^2$, or 2.5 N/cm$^2$ g 0.5 N/cm$^2$, or 3 N/cm$^2$±0.5 N/cm$^2$, or 4 N/cm$^2$±0.5 N/cm$^2$, or 5 N/cm$^2$±0.5 N/cm$^2$. Nominal pressure can be measured using a pressure sensor, preferably correcting for the thickness of a disaggregation container. In certain embodiments, the disaggregation device incorporates a pressure sensor. In certain embodiments of the invention, the digestion time is 90 min. or less, or 75 min. or less, or 60 min. or less, or 50 min. or less, or 5-120 min, or 15-100 min., or 30-90 min., or 40-60 min., or 5-10 min., or 10-20 min., or 20-30 min., or 30-40 min., or 40-45 min. or 45-50 min., or 50-60 min., or 60-65 min., or 65-70 min., or 40 min.±5 min. or 45 min.±5 min., or 50 min. 5 min., or 55 min.±5 min., or 60 min.±5 min., or 65 min.±5 min., or 70 min. 5 min. In certain embodiments, the disaggregation device operates at from 60-360 RPM. or 120-340 RPM, or 180-300 RPM, or 210-270 RPM, 80-160 RPM, or 120-200 RPM, or 160-240 RPM, or 200-280 RPM, or 240-320 RPM, or 280-360 RPM, or 60 RPM±20 RPM, or 80 RPM±20 RPM, or 100 RPM±20 RPM, or 120 RPM±20 RPM, or 140 RPM±20 RPM, or 160 RPM±20 RPM, or 180

RPM±20 RPM, or 200 RPM±20 RPM, or 220 RPM±20 RPM, or 240 RPM±20 RPM, or 260 RPM±20 RPM, or 280 RPM±20 RPM, or 300 RPM±20 RPM, or 320 RPM±20 RPM, or 340 RPM±20 RPM, or 360 RPM±20 RPM.

In certain embodiments, physical disaggregation is continuous. In certain embodiments, physical disaggregation is periodic or episodic. For example, when a temperature increase is observed in a disaggregation sample, it may be advantageous to briefly slow or halt physical disaggregation to reduce or prevent temperature increase or allow the temperature to equilibrate to a set point. Without being bound by theory, a temperature increase may occur through physical manipulation of a sample by a disaggregation device, heat transfer from an active treading mechanism of a device, reduced physical contact or heat transfer from sample to a refrigeration unit while the disaggregation process is active, or other reason. In certain embodiments, periodic or episodic disaggregation may be beneficial to the disaggregation device. In a cam driven device as disclosed herein, life expectancy of the cam mechanism may be improved by periodically reversing the direction of cam rotation from time to time, thus extending the life of the cam by distributing wear over both sides of the cam. In embodiments of the invention, activity periods of physical disaggregation include without limitation, 15-30 sec., 20-40 sec., 30-60 sec., 45-75 sec., 60-90 sec., at least 20 sec., at least 30 sec., at least 40 see, at least 1 min. at least 1.5 min., or at least 2 min. Durations of inactivity can be, without limitation, 1-10 sec, 10-20 sec., 20-30 sec., 30-40 sec. 40-60 sec., 5 sec., 10 sec., 20 sec., 30 sec., 40 sec., 60 sec., 90 sec. 120 sec. or durations in between. The duration of inactivity may be as short as is necessary for the disaggregation device to reverse direction.

In some embodiments, the surfaces are opposing surfaces disposed to move laterally with respect to one another. In certain such embodiments, the lateral motion comprises linear lateral motion. In certain such embodiments, the lateral motion comprises orbital lateral motion. In certain embodiment, there is both linear and orbital lateral motion.

In an embodiment, the opposing surfaces are flat. In an embodiment, at least one of the surfaces comprises a convex region and disposed to be moved in a rocking motion against the other surface. One aspect of a convex surface and rocking motion is to provide a peristalsis-like action.

According to the invention, the movement of the surfaces is controlled, such control comprising control of one or more aspect of surface movement, including but not limited to velocity, sample compression, system pressure, duration, and cycle frequency. In certain embodiments, one or more aspects of plate movement is constant. In certain embodiments, one or more aspect of plate movement depends on the state of disaggregation. In certain embodiments, the state of disaggregation is defined by the time of the disaggregation procedure, such as for example one or more predefined stages such as early, middle, late, or more precise time periods measured in hours, minutes and seconds. In certain embodiments, the state of disaggregation is defined by the size distribution of tumor pieces. For example, in an embodiment of the invention, pressure is increased as the size of tumor pieces is reduced.

Examples of Disaggregation Devices and Alternatives

Figure 41:
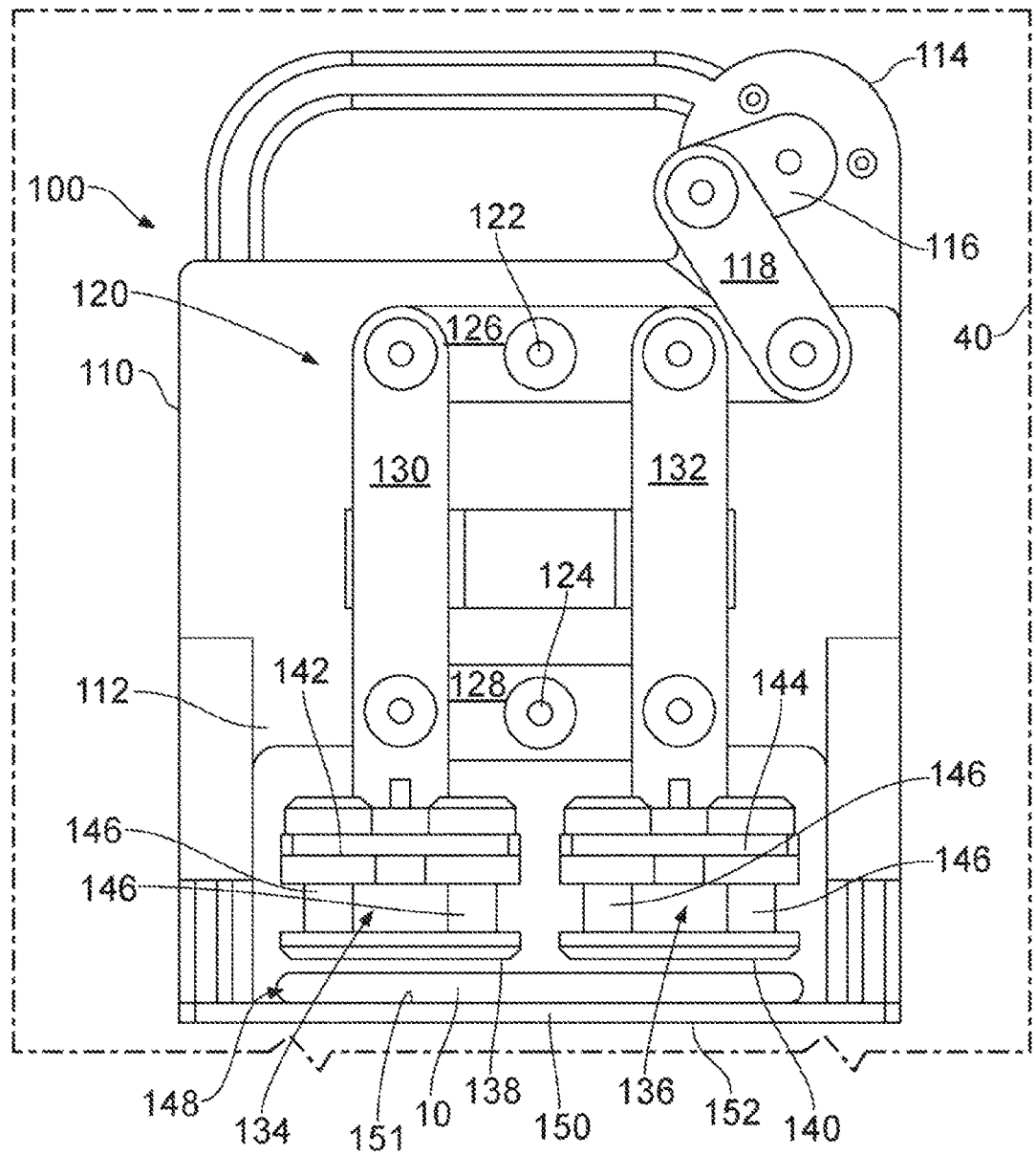
FIG. 41 shows a front view of a treading device for the disaggregation of tissue into individual cells or cell clumps within a closed sample container.

Referring to FIG. 41 there is shown a treading device 100 for the disaggregation of tissue into individual cells or cell clumps within a closed and at least initially aseptic generally flat-sided and relatively thin sample container bag 10. The device includes a housing 110 formed from an assembly of parts that can be removably inserted into a temperature controlled device such as a controlled temperature rate change freezer, thawer or warmer, for example a commercially available freezer known as Via Freeze™, or any other device which provides a controlled rate change in temperature, shown schematically in FIG. 41 and described herein generally as freezer 40. In practice the housing will include a cover, which is not illustrated. In use the device and bag provide a closed system, to disaggregate tissue e.g. excised tumours, parts of excised tumours or needle biopsies etc., and to then cryopreserve the resulting cell suspension for subsequent analysis without the need to transfer the disaggregated sample out of the bag 10.

The housing 110 has a chassis 112 to which is attached a motor unit 114 which includes an electric motor and gearbox, which has an output speed of 10-300 rpm. The output shaft of the motor and gearbox 114 has a crank 116 which drives a connecting rod 118, which in turn is pivotably connected to a treading mechanism 120, which will be moved through one treading cycle for each revolution of crank 116, i.e. a treading cycle between 0.2 and 6 seconds. In more detail this treading mechanism has a parallelogram four bar linkage, which includes two spaced pivots 122 and 124 rigidly mounted to the chassis 112 which pivotably mount two opposed parallel horizontal bars 126 and 128 respectively. Each of the horizontal bars has two parallel treading bars 130 and 132, pivotably connected thereto one on each side of the pivots 122 and 124, together forming the parallelogram linkage. The connecting rod 118 is conveniently pivotably held to an extension of the top horizontal bar, such that moving of that extension causes cyclic up and down motion (in the orientation shown) of the treading bars 130 and 132. To each treading bar 130 and 132 is connected a foot assembly 134 and 136 which, by virtue of the above-mentioned cyclic motion, will move up and down with motion of the crank 116, in a sequentially manner, i.e. when one foot is up the other will be down and vice versa.

The foot assemblies 134 and 136 each include a flat faced sole plate 138 and 140 each plate being spring-mounted to a upper foot frame 142 and 144 respectively, by coiled metal springs 146. In the arrangement described above, or an equivalent arrangement if used, the springs 146 are preloaded-. In this case the combined preload is preferably 40-80N, more preferably 30-70 N for each foot preferably about 60N. The combined spring rate is 1-5 N per mm of travel, preferably about 3N per mm, and the intended foot travel is about 8-12 mm, preferably about 10 mm. In addition the surface area of each foot is intended to be about 20 to 50 $cm^2$, preferably about 35 $cm^2$. This results in a notional pressure on the bag of between zero (when the foot lifts off the bag or has substantially no load, and up to about 6 $N/cm^2$ (about 9 psi). The preferred notional pressure is about 2$N/cm^2$ (about 3 psi). However, given that the bag may not, at least at the start of the treading process, contain a homogeneous material, then there will be lumps of material where the force exerted will be concentrated, and so the pressure is described as 'notional' which is the idealised situation, for example to provide a minimum pressure resistance of the bag 10 exerted toward the end of the treading process.

At the bottom of the chassis is a receiving area 148 for the flexible bag 10 and adjacent the receiving area 148 is heat transfer plate 150. The area 148 is large enough to admit the sample processing bag 10 slidable onto the plate 150 via the front of the chassis (the front being shown in FIG. 41). The plate includes an upper surface 151 on which the bag 10 sits, and a lower surface 152 which in use is exposed for externally influenced heating or cooling. The upper surface 151 is generally parallel to the sole plates 138 and 140 of each foot, so that the sole plates move generally parallel to the surface 151. Put another way, the flat sole plates move in a generally perpendicular direction to the surface 151, which prevents significant side forces on the mechanism 120. The plate 150 is formed from metal, preferably aluminium or copper or gold or silver, or alloys containing those metals. Heat conductance is preferably above 100 and more preferably above 200 W/m K measured at 20 degrees Celsius. The thickness of the plate 150 material is about 3 mm or less and provides low thermal mass and thus a quicker reaction of the contents of the bag 10 to follow temperature changes on the opposite side of the plate.

Figure 43:
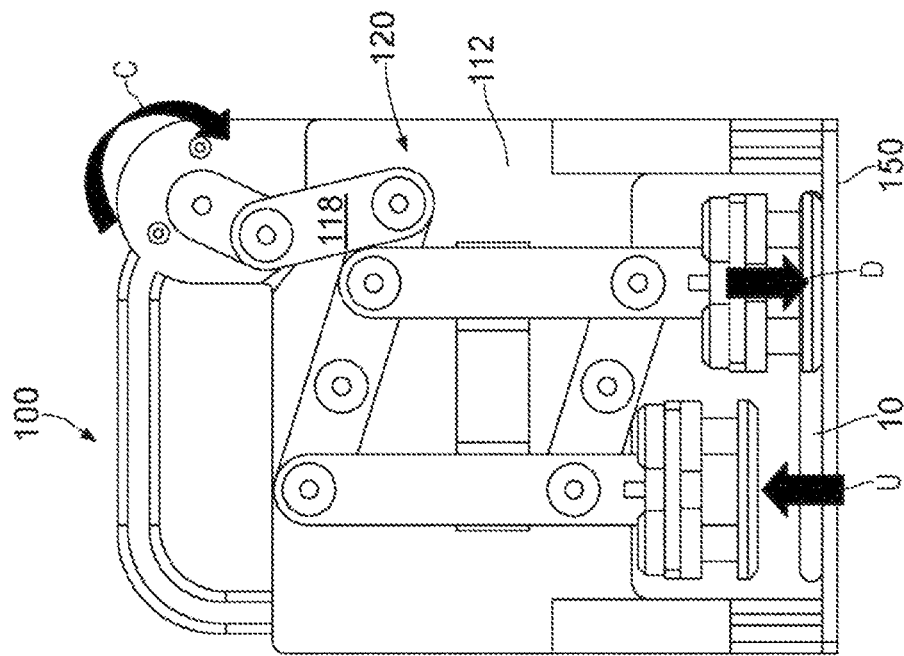
FIG. 42 and FIG. 43 show the device of FIG. 41 in two different respective operational positions.
Figure 42:
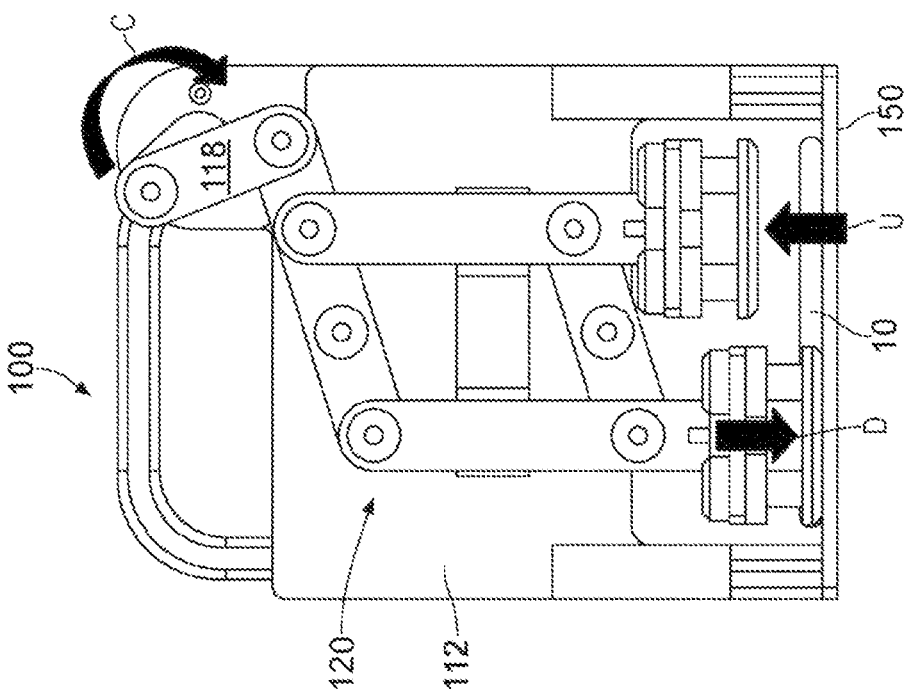

With reference additionally to FIGS. 42 and 43, the device is operated by supplying electrical current to the motor unit 114, to drive the crank 116, in this example clockwise as shown by arrows C. The crank causes the connecting rod 118 to operate the above described treading mechanism 120. It will be noted that the top and bottom of the stroke of the crank, where maximum force is applied to the mechanism 120 coincides with the lowermost position of each foot assembly 134 and 136. The foot assemblies move up and down in the direction of arrows U and D to massage the sample bag 10 sequentially, such that the contents of the bag 10 have an opportunity to move to one side away from the respective treading foot. Since the potentially solid tissue samples in the bag can move away from the treading foot, and because the sole plates 138 and 140 of each foot are spring loaded, with additional resilient travel being afforded to the feet even when they are at the bottom of their stroke, then there is less chance that the mechanism will jam when larger tissue masses are intended to be disaggregated. The sequential treading action also reduces the chances of the bag 10 rupturing.

Figure 44:
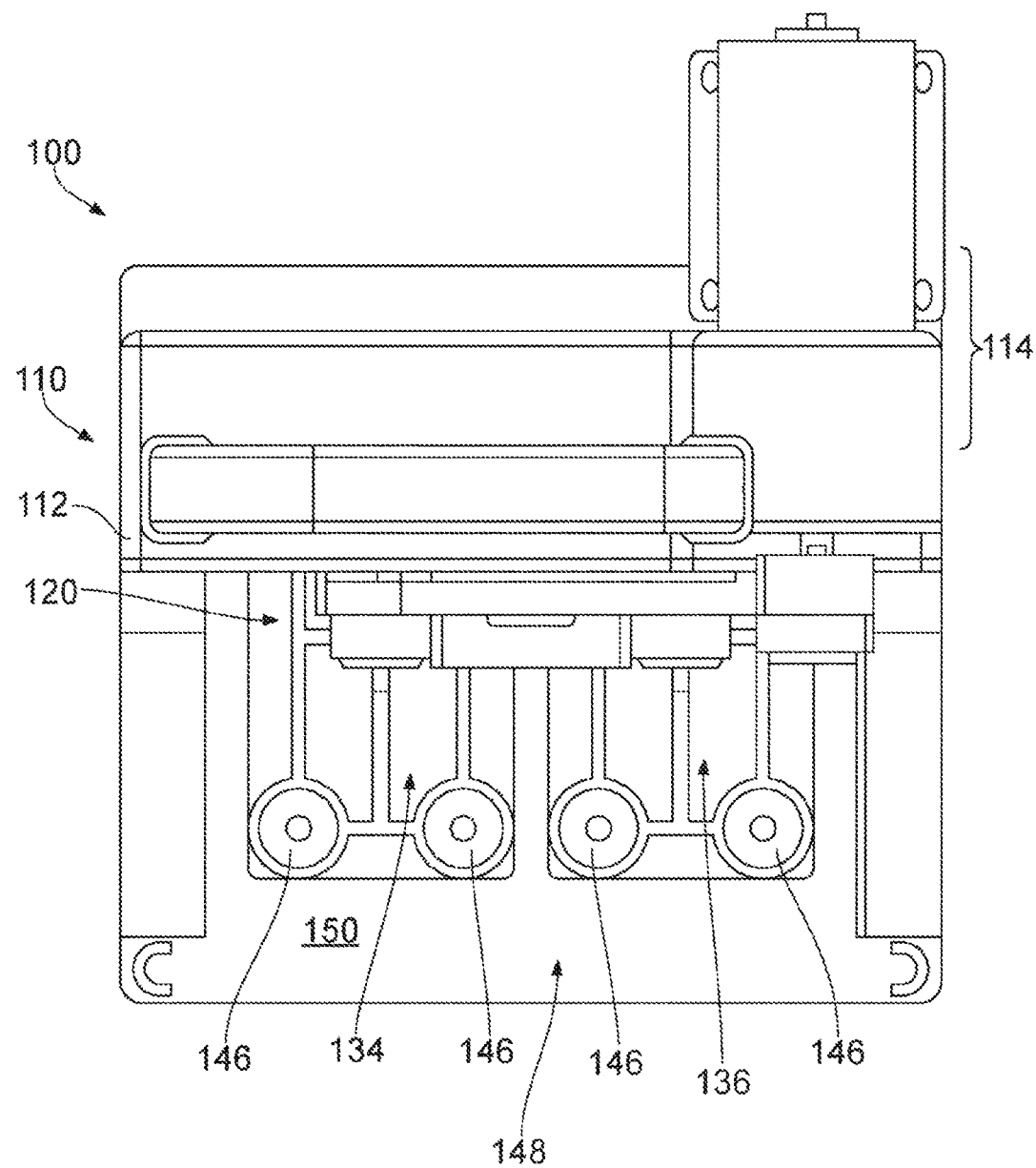
FIG. 44 shows a plan view of the device shown in the previous Figures.

FIG. 44 is a plan view of the device 100 described above, but no bag 10 is in place in this view. In particular, the relative side-by-side positions of the foot assemblies 134 and 136 can be seen, which are spaced and have a collective area viewed in plan, which area is about equal the area of the bag 10 when laid flat, but a difference in areas of about plus or minus 10% of the area of the bag 10 has utility.

Figure 45:
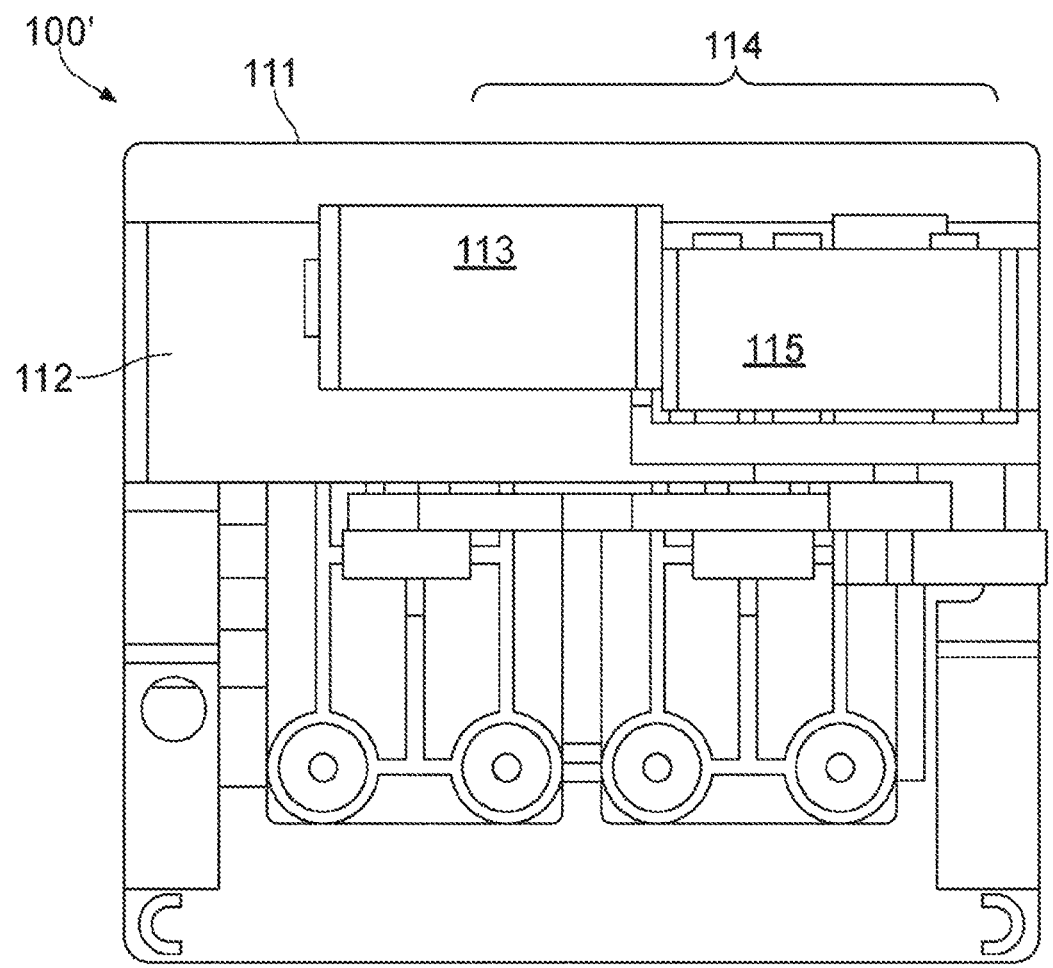
FIG. 45 shows another plan view of an alternative construction of the device.

FIG. 45 shows another plan view of a device 100' which is similar in construction to the device 100 described above, but in this alternative the motor 113 of the motor unit 114 is arranged transversely to the output shaft of its gearbox 115 by the use of a 90 degree gearbox 115, so that the motor 113 does not protrude beyond a backwall 111 of the device 100'. Thus, this device 100' can fit into a smaller freezer volume if needed.

During the above-mentioned disaggregation processing, the forces exerted by the foot assemblies 134 and 136 are reacted by the heat transfer plate 150. This means that the sample bag 10 is pressed against the contact surface 151 of the plate 150 during processing, providing good surface contact between the sample bag 10 and the plate's surface 151, and consequently improved heat energy transfer.

Figure 46:
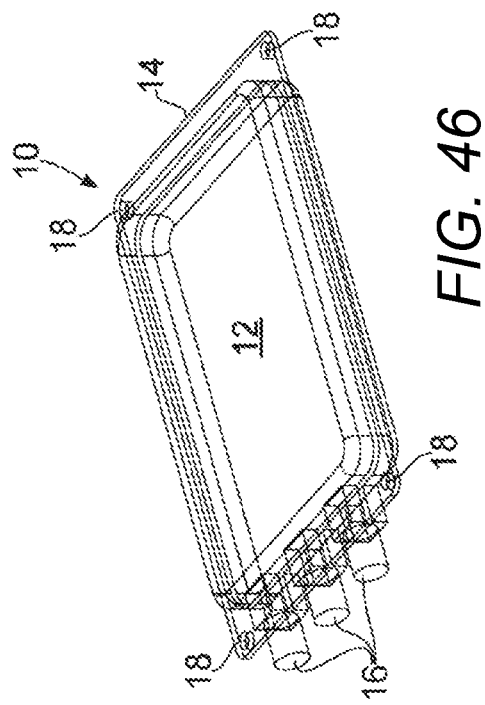
FIG. 46, FIG. 47 and FIG. 48 show three different constructions of a sample container suitable for use with the device of FIGS. 41 to 45.
Figure 47:
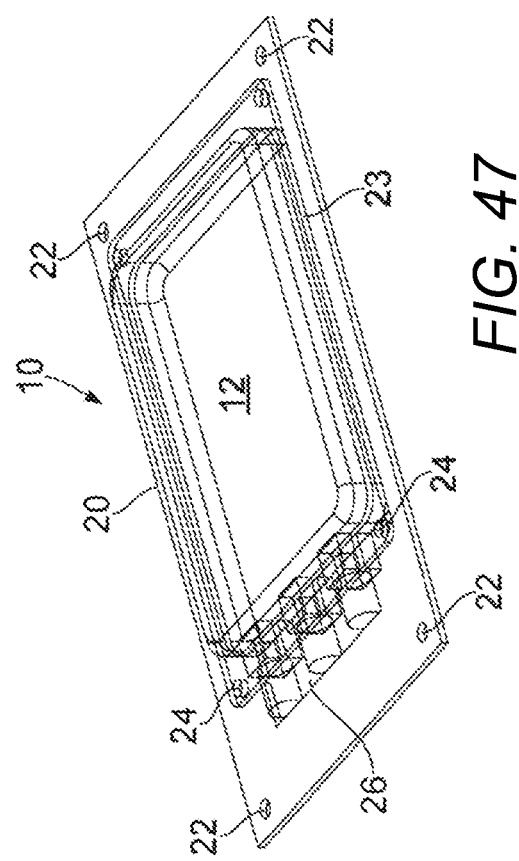
Figure 48:
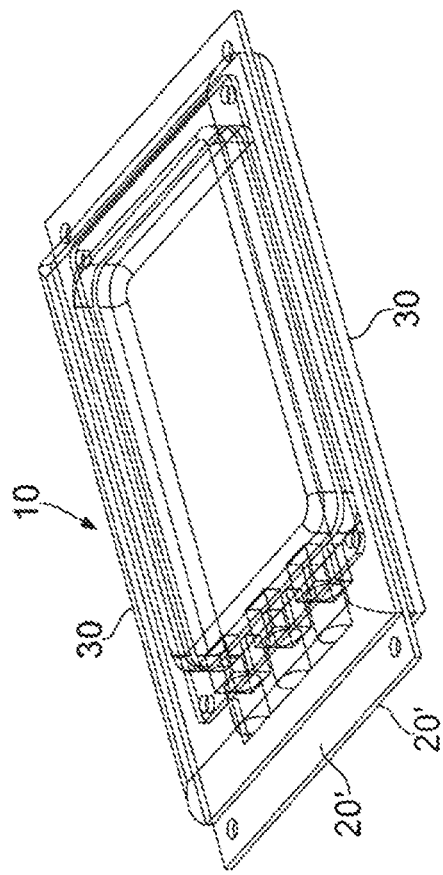

FIGS. 46, 47 and 48 show different embodiments of the flexible sample bag 10 mentioned above. The bag in use is slid into place in the receiving area 148 in the device 100 or 100' and sits under the two feet 134 and 136 mentioned. Thus, the bag has a generally flat construction, of about up to 12 mm thickness, with some additional compliance in order to fit tissue samples therein. As can be seen from FIG. 46 one construction of a bag 10 is shown formed from two layers of plastic material sealed only at their periphery 14 to form a central cavity 12, and ports 16 for access into the cavity 12. The bag may be formed from EVA. In use it is preferred that the ports 16, or at least one of them, is/are large enough, i.e. about 10 mm in diameter or larger, to accept a sample which if necessary has been chopped into small pieces and passed into the bag cavity 12 by means of a syringe. However, it is also possible to include a so called 'zip-lock' access at the end of the bag opposite the ports, such that large tissue samples can be put into the bag and the bag is then re-sealed. The 'zip-lock' can be folded over one or more times to make a seam, held folded inside a resilient channel or by means of another clamp or clamps (not shown) to reduce the chance of leakage. The bag 10 can, as an alternative, be opened and tissue can be added. The bag can then be heat sealed with its contents in place. The bag 10 includes corner apertures 18 for locating the bag in the device in use and holding it in place during treading. Whilst the drawings show a bag 10 with one cavity 12, it would be possible to provide a bag having more than one cavity, for example, two, three, four or five cavities, for example each of the plural cavities being elongate and having an initially open, heat sealable end, and a sealable port at its other end for the introduction of reagents such as a disaggregation enzyme, and for withdrawing the disaggregated sample once the disaggregation is complete or substantially complete.

FIG. 47 shows the bag 10 of FIG. 46 mounted in a locating frame 20 by means of pegs 24 on the frame which fit into the corner apertures 18. The frame 20 is an alternative way of locating and holding the bag 10 in place within the device 100/100'. The frame 20 includes location holes 22 which cooperate with the device for locating and holding the bag in place during treading. The frame has an inner open window 26 with a smooth rounded inner edge 23, to accommodate the cavity 12 and treading feet 134 and 136 in use. The frame 20 makes loading and unloading of the bag 10 into and out of the device 100/100' easier.

FIG. 48 shows an alternative frame 20' which has two generally symmetrical halves each similar to construction of frame 20. Each frame half has additionally a flexible shell 30 moulded to the frame 20', such that the two halves come together like a clam shell enveloping the bag 10. The top and bottom flexible shells act as a bund if the bag 10 inside ruptures in use. This feature is particularly useful for infectious tissue samples.

Yet another alternative, not shown, a simple bag-in-bag arrangement could be employed to contain leaks. In yet another alternative, the bag may include a base which has resilient (at least at room temperature) separate wells, such that aliquots of sample can be removed without using the whole sample, for example after freezing as described below. Alternatively, a sealable bag may be further heat sealed into portions for allowing the separation of the sample.

The processing of a sample put into the bag 10 can in one example largely follow the steps described in WO2018/130845. In this arrangement the sealed bag TO containing tissue is suspended in an aqueous solution which may contain digestive enzymes such as collagenases and proteases to accelerate the breakdown of the tissue, introduced into the bag via a port 16. The bag is here placed on the plate 150 and warmed from, for example, an external heat source to approximately 35° G to accelerate the rate of tissue digestion. One important difference proposed here is that a single sample processing bag is employed, and digestive enzymes can be introduced through one of the ports 16 in the bag prior to or during disaggregation. The heat transfer plate 150 can be used to introduce heat energy into the bag by heating the plate on its underside to provide the desired temperature in the bag for enzymatic action. That heat could conveniently come from an electrically heated warming plate, or electric heating elements in or on the plate 150. The amount of disaggregation action will depend on numerous parameters, for example the size, density and elasticity of the initial tissue sample, and so the time for disaggregation and the rate of treading will vary significantly. Too long or overly vigorous treading could lead to decreased cell viability. Thus, the motor unit speed and the disaggregation period is important. One option to address this problem is to time the processing according to a look-up table which includes times and output speeds required to disaggregate similar samples. Another option is to measure the instantaneous electrical power or electrical energy overtime needed to perform the disaggregation processing, or to measure the force or stress exerted on the pate 150 or another part of the mechanism, and to stop after a predetermined threshold has been reached, to indicate that the sample has been sufficiently disaggregated. As the power/forces/stresses reduce the disaggregation is closer to completion. Another option is to measure light absorbance through the bag—the greater the absorbance, the closer the sample is to complete disaggregation. Once disaggregation is complete the bag contents can be transferred, and the cells or other constituents of interest can be separated and put back into a fresh bag for freezing in the device 100/100'. Alternatively, and preferably the whole disaggregated materials can be left in the bag and device for freezing. A cryoprotectant is introduced in to the bag through a port 16.

Another difference between the present methodology and that described in WO2018/130845 is that once a cryoprotectant is introduced, the device with the disaggregated sample and cryoprotectant in the bag is mounted (or remains in) the device, and the whole device is mounted in the freezer 40 as described above. The base of the freezer is cold and so draws heat energy from the hag 10 via the heat transfer plate 150. To control the formation of ice and prevent supercooling of the sample while the bag it is being cooled, it can be massaged by the feet 134 and 136, in the manner described above, albeit at a slower rate than for disaggregation, to control ice nucleation and so increase the viability of the cells after thawing. Electrical energy can be supplied to the motor unit 114 via a wire conductor to maintain motion of the mechanism 120 inside the freezer, e.g. freezer 40 (FIG. 41).

Since the device is removeable from the freezer, cleaning after use is made easier.

When required for use, the frozen disaggregated samples in a bag 10 can be thawed rapidly in the device 100/100' by further external heating of the plate 150, and/or by partially immersing the device 100/100' in a warmed water bath, maintained at about 37° C., and the cryoprotectant removed. In each case the bag can be massaged during thawing. If the enzymes are still present, they too can be removed if needed, for example by means of filtering. Generally, they will have had little or no effect on the cells during cryopreservation because their action is halted at low temperatures. All the process manipulations, warming, disaggregation, cooling, freezing and then thawing occur with the sample in the same sealed flexible bag 10, and may be performed in a single device. This is not only time and space efficient, but it enables a single record to capture everything that happened to the sample during processing, e.g. temperatures, durations, disaggregation speed, freezing protocol, and lessens the chance for errors, such as a sample spending too much time in an uncontrolled environment between processing machines.

More specific examples of the apparatus and techniques used in tissue sample processing and freezing are given below.

Figure 49:
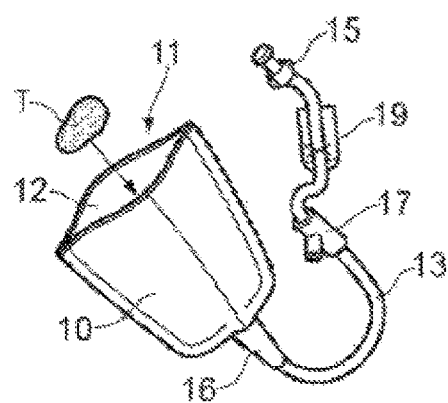
FIG. 49 shows a sample bag being prepared for use.

FIG. 49 shows an example of a bag 10 formed from a thermoplastic material such as EVA or PVG film and having an opening 11 for accepting the tissue sample T. The bag includes tubing 13 attached to the one or more ports 16 (FIG. 46) which tubing includes one or more branches 17, compression valves 19, and standard Luer-type connectors 15. The single tubing line shown is merely illustrative—the bag 10 may include additional parallel tubing connected via plural ports 16.

Figure 50:
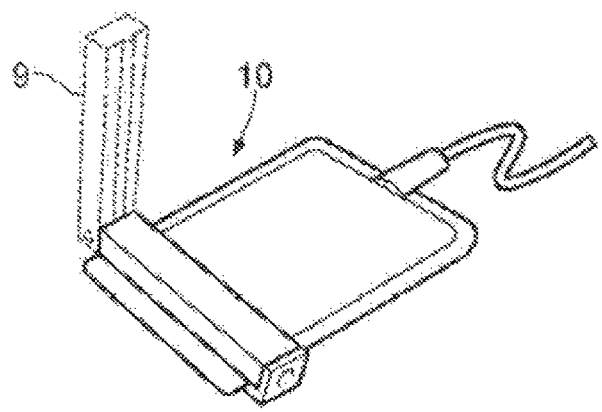
Figure 51A:
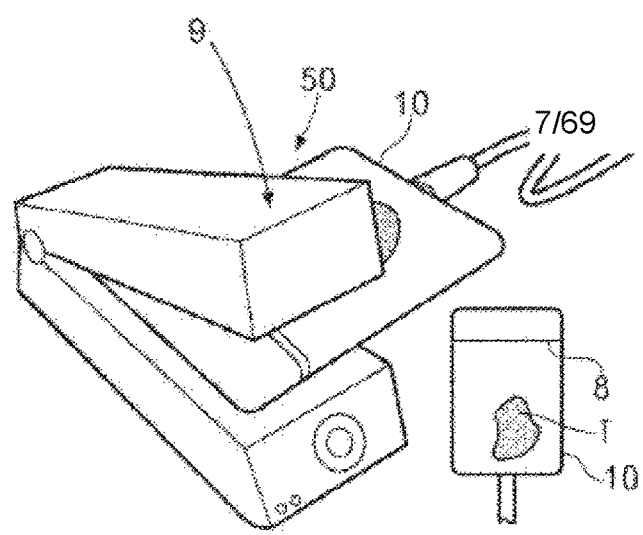

Once the tissue T is inside the bag 10. the opening 11 can be sealed by a mechanical clamping seal 9, shown closed and sealed in FIG. 50, and shown open in chain dotted lines in the same Figure, and/or by means of heat sealing using a heat sealing machine 50 as shown in FIG. 51*a*, to produce a heat-sealed closure strip or strips (for example plural parallel strips) 8, each method forming the sealed cavity 12 (FIGS. 46, 47 and 49).

An alternative or additional means for sealing a bag 10 is shown in FIGS. 51*b* and 51*c*. As shown in FIG. 51*c*, the bag 10 after heat sealing at seal 8 can be clamped in a two piece clamp 60, which comprises a top bar 62 and a bottom bar 64 forced together by a pair of screws 66. FIG. 51*b* shows the clamp 60 in an exploded condition, but in use the screws 66 need not be completely removed from the remaining clamp prior to insertion of the bag 10. The top bar 62 has a tapering recess 68, in which sits a complementary wedge shaped formation 61 when clamped. The recess and wedge concentrate the clamping forces at the apex of the wedge 65, providing higher clamping forces at the apex than could be achieved by flat clamping faces. For even more clamping force, the apex 65 has a small channel 67 at its peak, which is met in use by a complementary ridged formation 69, in the top bar. In certain embodiments, the forces are sufficient to negate the need for the heat seal 8. In certain embodiments, the heat seal or other bag sealing mechanism is desired, for example to provide for handling of a sample-containing bag outside of the disaggregator. In certain embodiments, the clamping device ensures the integrity of the seal. The clamping force is further enhanced by the thickness and stiffness of the top and bottom bar which do not readily bend, and so maintain the clamping force exerted by the screws 66. FIG. 51*c* shows the clamp 60 in a clamped condition. Protrusions 63 meet with features of the treading device 100/100' or 200 (as described below) to inhibit movement of the clamp, and consequently the clamped bag 10 during treading. The outer periphery and height of the clamp 60 is of a sized and shape to fit in a complementary part of the sample receiving area 148 (or 248 FIG. 62 et seq), and so afford further location of the clamped bag 10 during treading. Although not illustrated, the clamp 60 may incorporate also an additional frame 20, 20' as shown in FIGS. 47 and 48, and such that the clamp is rigidly mounted to one end of the frame and the port(s) 16 (FIGS. 46 and 49) are supported at the other end of the frame.

Figure 52:
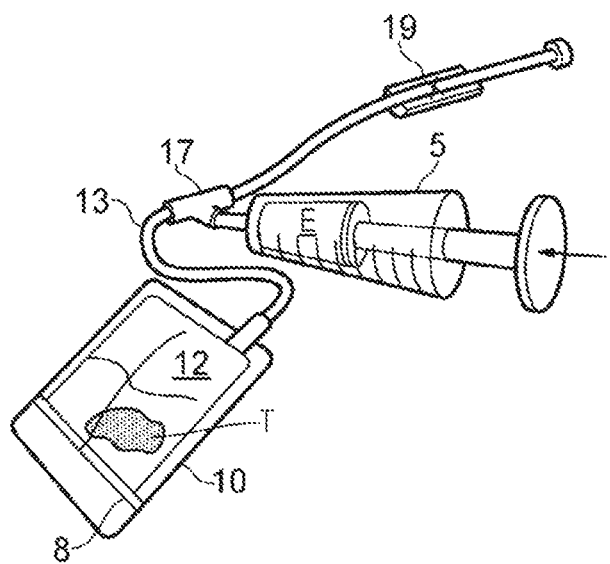
FIG. 52, FIG. 53, and FIG. 54 show apparatus and techniques for preparing the bag for use.
Figure 53:
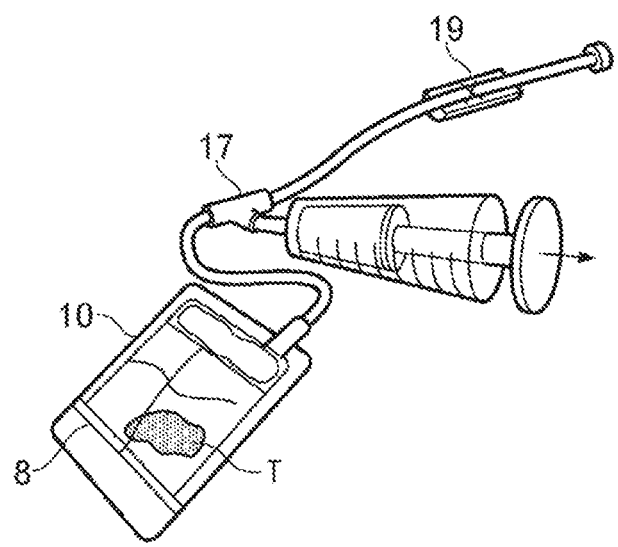
Figure 54:
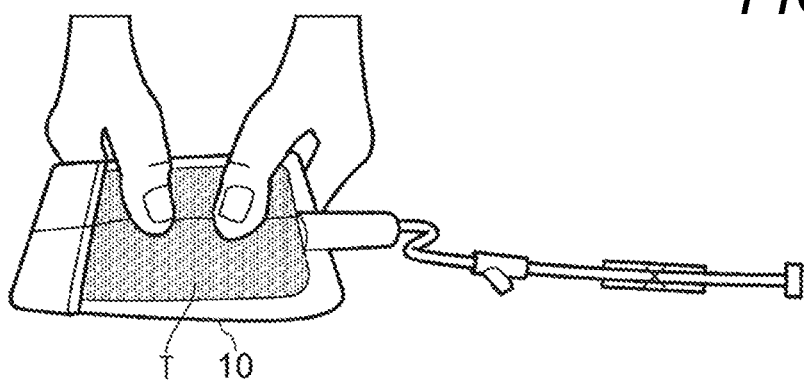

With reference to FIG. 52, in use, once sealed, a digestive enzyme E can be introduced into the cavity 12 via the tubing 13, for example by injecting the enzyme into the bag using a syringe 5 attached to the branch connection 17. By holding the bag in an upright orientation, air can then be removed from the cavity 12 by withdrawing the piston of the syringe 5 as shown in FIG. 53. Initial mixing of the enzyme E and tissue T can be made by hand as shown in FIG. 54.

Figure 55:
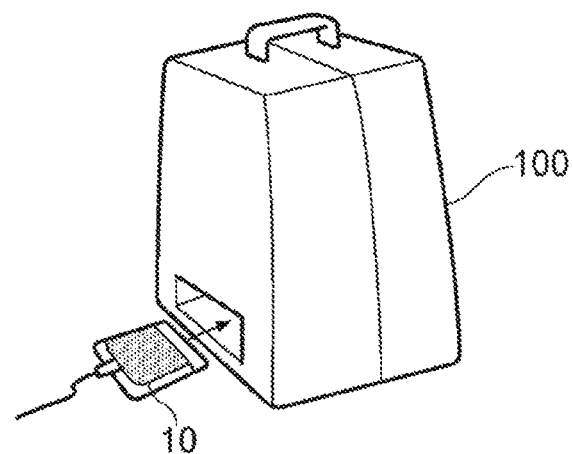
FIG. 55 shows loading of the sample bag or container into the treading device.

Loading of the bag 10 into the treading device 100 for disaggregation can then be commenced, either with or without the frame 20/20' and bunding cover 30, as illustrated in FIG. 55.

Figure 56:
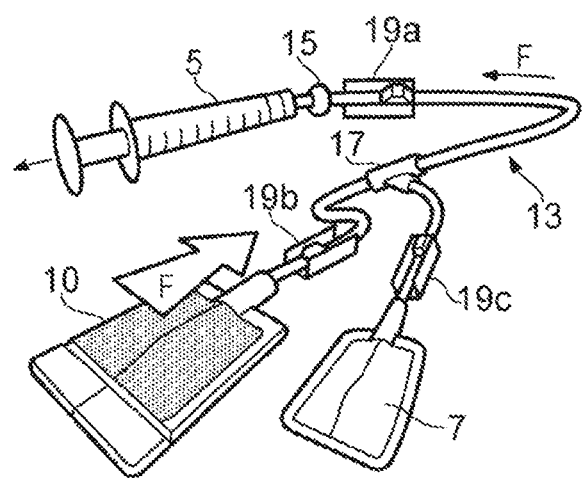
FIG. 56, FIG. 57, and FIG. 58 show apparatus for dividing a disaggregated sample.
Figure 57:
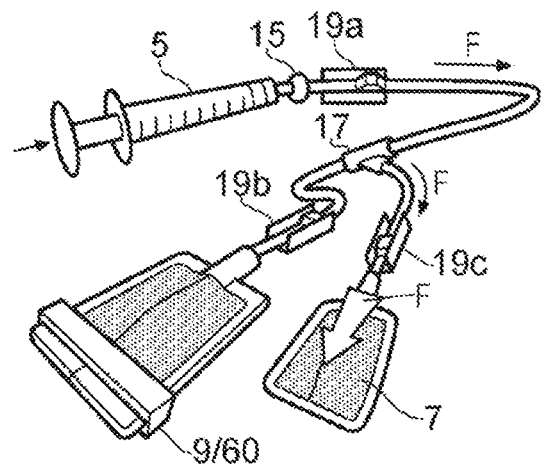
Figure 58:
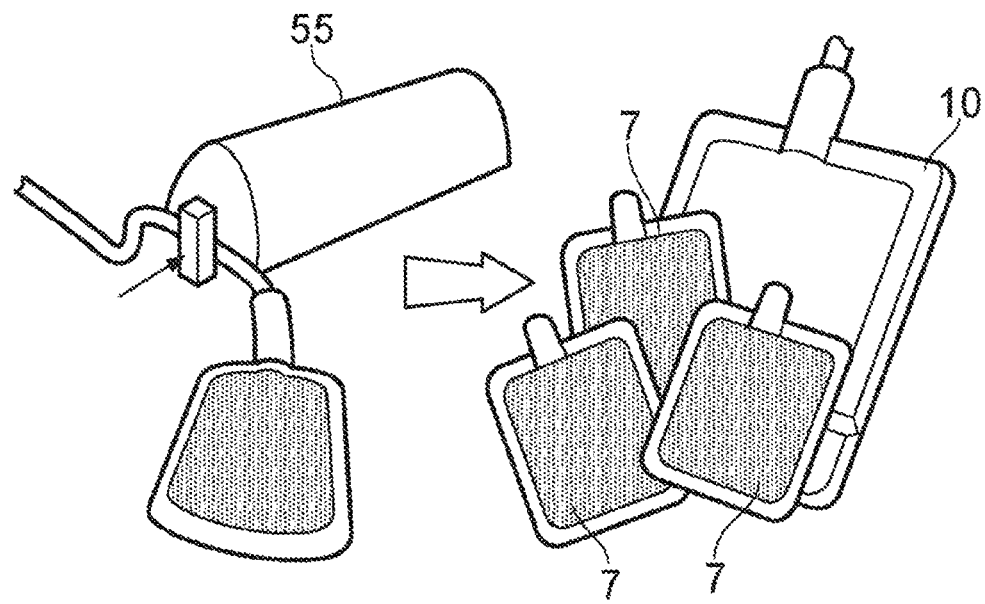

The disaggregation process then takes place as described above. Once complete, which may take between several minutes and several hours for example around 10 minutes to 7 hours, preferably 40 minutes to 1 hour, the disaggregated liquified sample may be subdivided in to aliquots, for example using the bag set described above, and an additional sample aliquot bag 7, as shown in FIG. 56, connected to the branch 17. In that instance a syringe 5 is used to draw the liquified sample out of the bag 10 in the direction of arrows F, valves 19a and 19b are open and valve 19c adjacent the sample aliquot bag 7 is closed. Once sufficient sample has been withdrawn into the syringe 5, valve 19b is closed, valve 19a remains open, and valve 19c is opened. The syringe is then used to force the liquids in the direction of arrow F in FIG. 57, into the sample aliquot bag 7. The tubing 13 of aliquot bag 7 can be heat sealed by means of a clamp heat seal machine 55 and shown in FIG. 58. That process can be repeated until sufficient aliquots are obtained or until the is no more sample left Bag may be partially divided already to make sealing off each compartment simpler.

Figure 59:
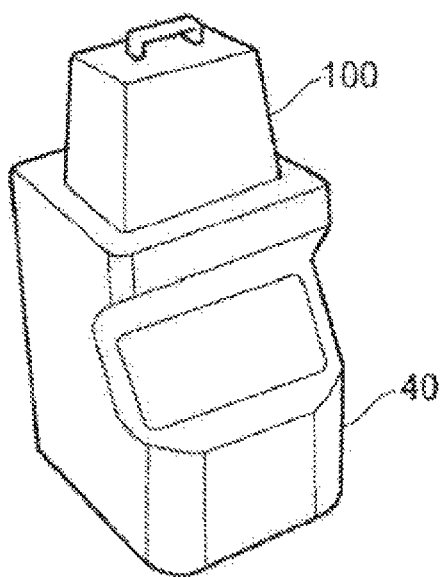
FIG. 59, FIG. 60, and FIG. 61 show apparatus for controlling the temperature of a sample or divided sample.
Figure 60:
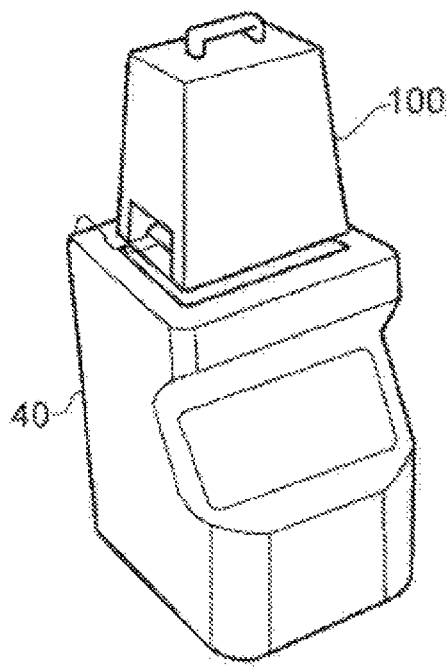
Figure 61:
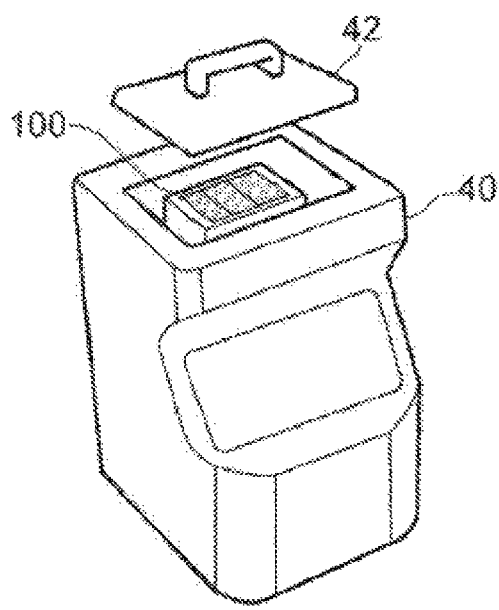

As described above, the sample bag 10, can remain in the treading device 100 (FIG. 55) and the treading device can then be loaded into a controlled rate temperature change device, in this case the freezer 40 as shown in FIG. 59. That technique allows treading to continue during freezing, to inhibit ice crystals forming, although in practice the bag 10 can be removed before freezing, and the freezer 40 then acts only to cool the sample through the heat transfer plate during treading. In the alterative, the aliquot sample bags 7 can take the place of the whole sample bag 10. In another alternative, the freezer 40 can be used to gently cool the unprocessed or processed sample to around 4 degrees Celsius by mounting the treading device 100 on top of the freezer 40 with its lid open so the base 150 is cooled, as shown in FIG. 60. In another alternative it is possible to remove the base 150 and put that into the freezer, with the freezer lid in place, as shown in FIG. 61. In yet another alternative, not shown, the bags 10, or 7 can be frozen directly in the freezer 40.

The invention is not to be seen as limited by the embodiments described above, but can be varied within the scope of the appended claims as is readily apparent to the person skilled in the art. For instance, the treading mechanism described above is preferred because it provides wholly pivoting mechanical interconnections which are less likely to jam in cold conditions than sliding surfaces, but that mechanism could be replaced with any mechanically equivalent means for treading two or more feet sequentially. The flat feet described may be replaced with roller feet, where the treading motion is from side to side rather than up and down. The treading described, or its mechanical equivalent, is preferably at a rate of 2 or 3 treads for each foot per second to optimise disaggregation and maximise cell recovery, and is a steady treading, but the treading could be quicker or slower, or intermittent, for different cell types.

Since the device 100/100' is intended to be placed in a freezer and subjected to extremely low temperatures (e.g. minus 80 degrees Celsius or lower), the use of metal parts, particularly those parts like springs 146 is preferred since polymeric parts become much more rigid at low temperatures. Also, tightly fitting parts, like pistons and cylinders, can become jammed or ill-fitting at very low temperatures so simple pivotable linkages like the mechanism 120 described are preferred.

Figure 62:
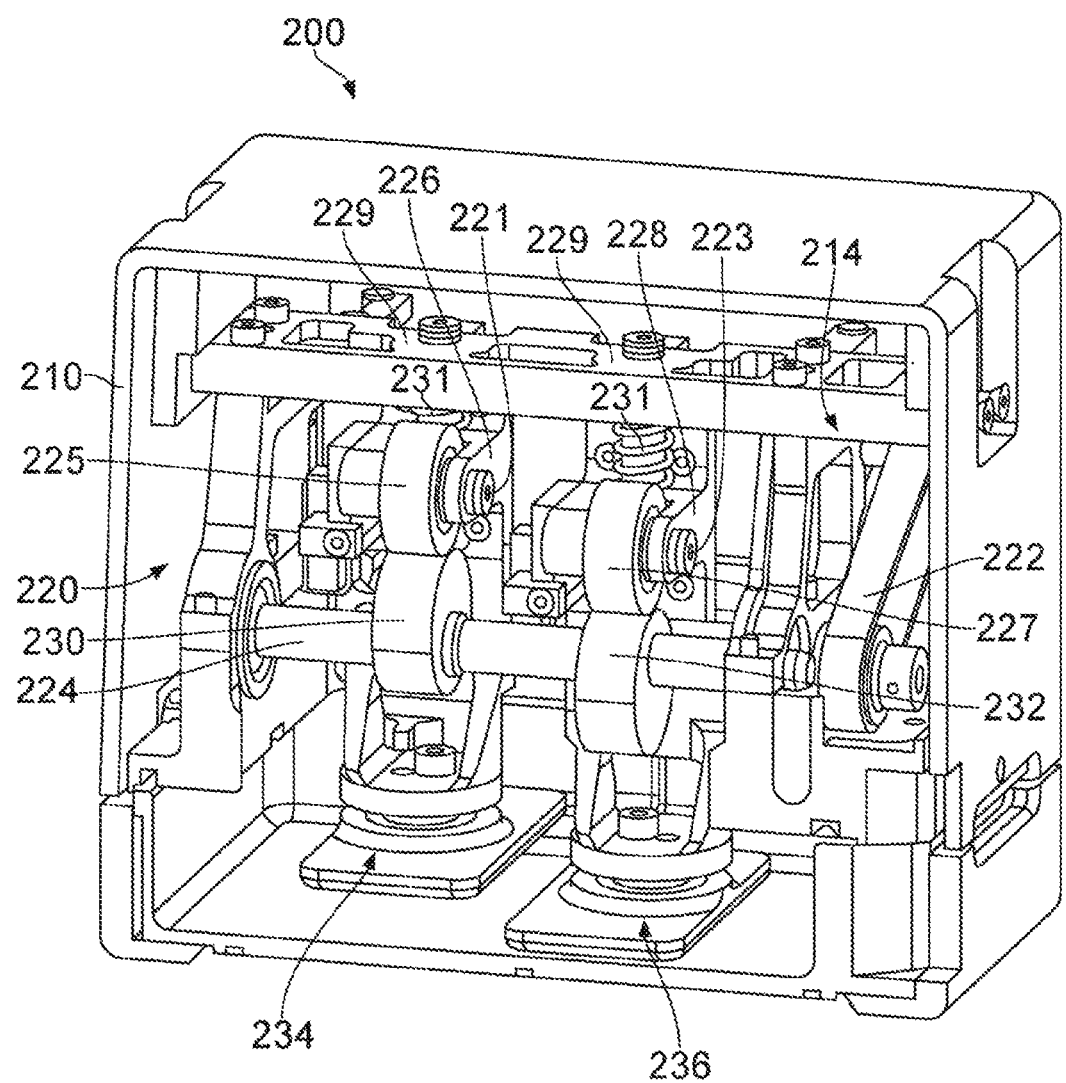
FIG. 62, FIG. 63, and FIG. 64 show a further embodiment of a treading device.
Figure 63:
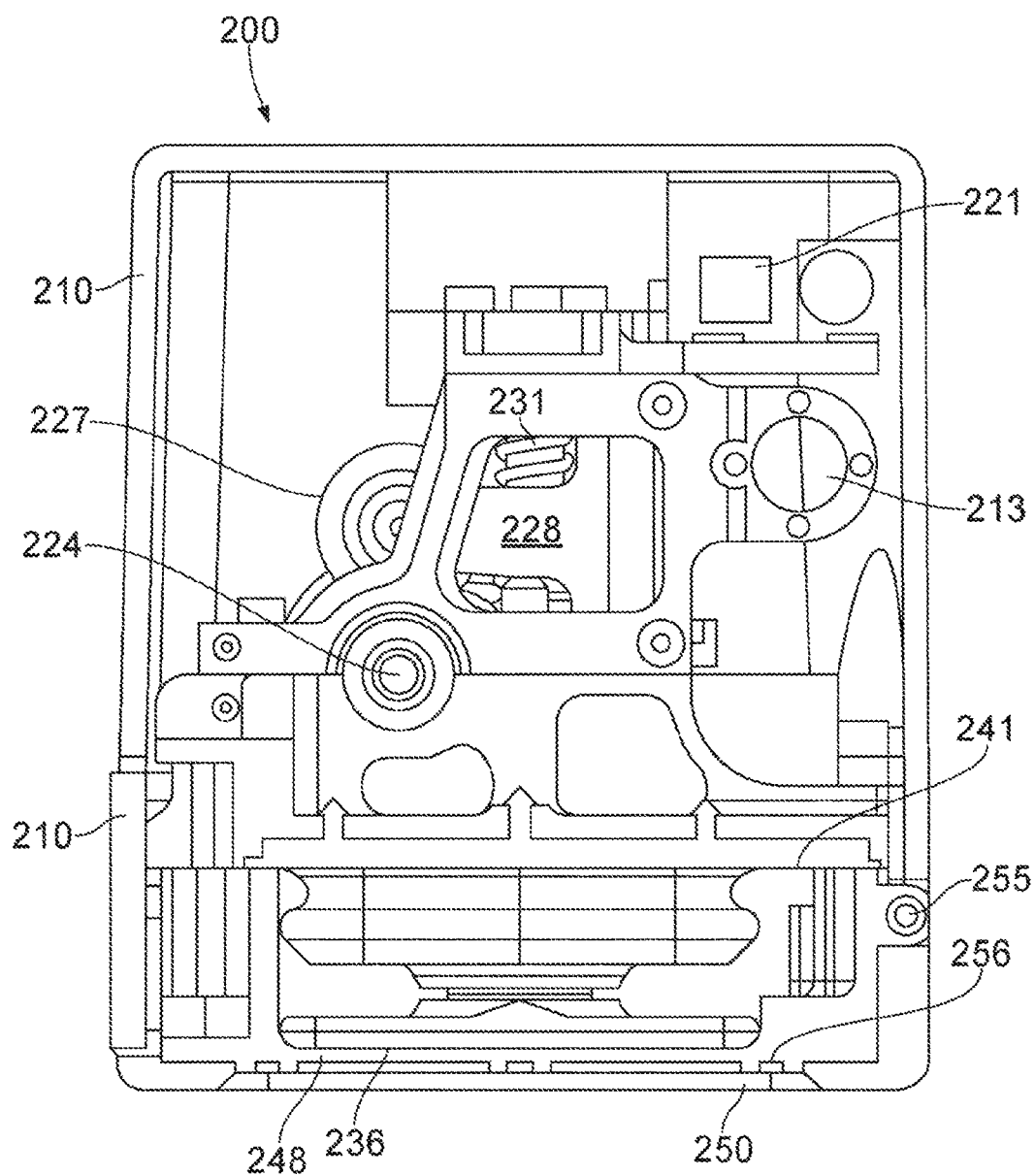
Figure 64:
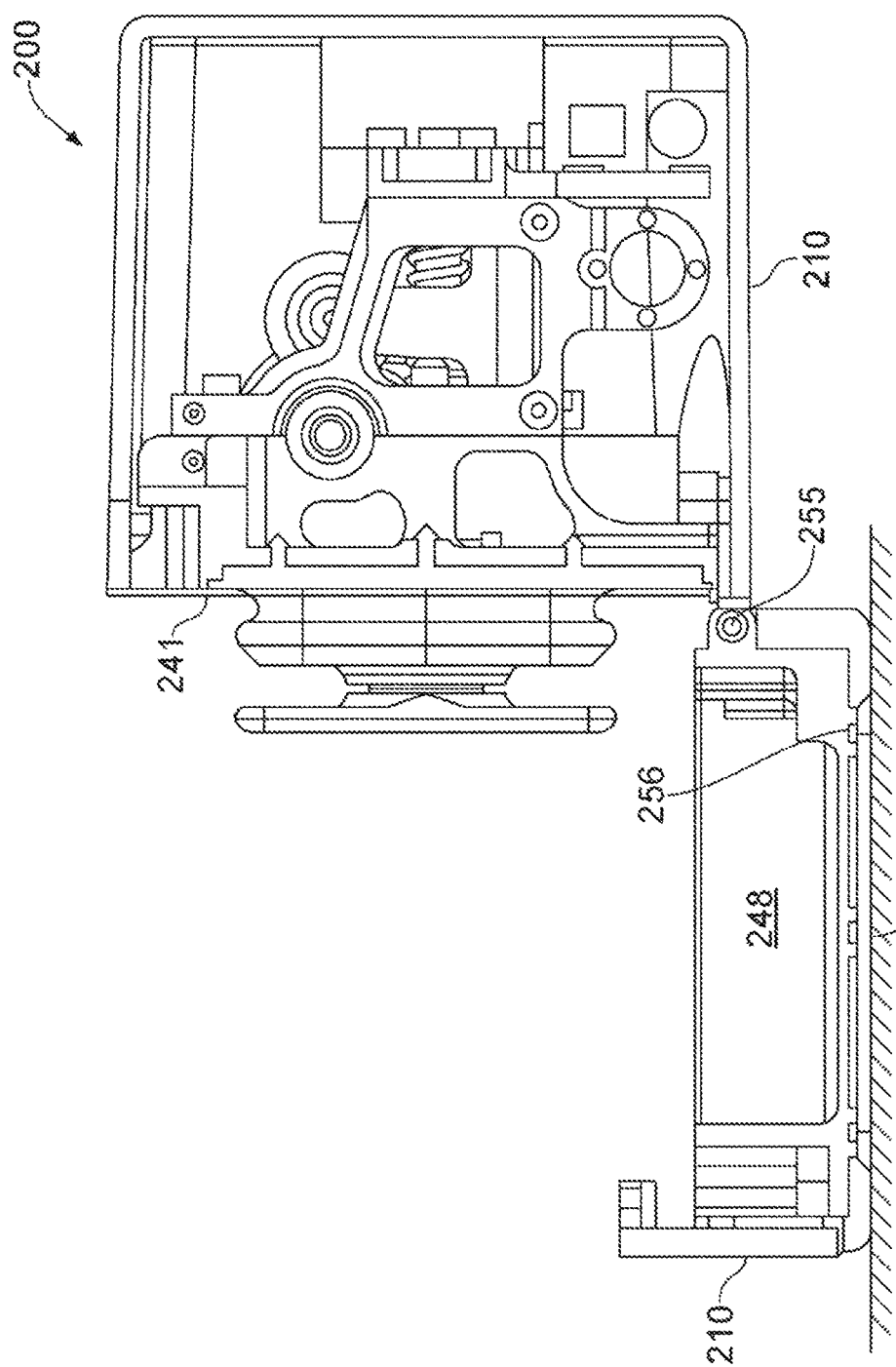

FIGS. 62, 63 and 64 show an alternative treading device 200, which is similar in size and function to the device 100 described above. The device 200 has certain differences which are described in more detail below.

Referring to FIG. 62, the principal difference between the device 100 and the device 200 is that the device 200 has a treading mechanism 220 which is different to the mechanism 120 of device 100. Two treading feet 234, 236 driven in a cyclic alternate treading motion, similar to the motion shown in FIGS. 42 and 43, by a 24 volt DC electric motor 213 (FIG. 63) which is part of an electric motor unit 214 which has a rotary encoder providing feedback to a controller 221 (FIG. 63) for monitoring and controlling the speed of the treading motion. The motor drives a cam shaft 224 via a toothed belt 222. The cam shaft includes a pair of cams 230, 232 offset at 180 degrees, in this instance, each profiled with a cycloidal shape to provide simple harmonic motion of the cam follower. Each cam is operable to move a cam follower assembly including an associated elastomeric follower wheel 225, 227 which rides over the cam's profile, a follower wheel axle 221, 223 in force transmitting relationship with a sprung follower carriage 226, 228. Each carriage 226,228 slides in a linear guide 229, and a respective foot 234, 236 is connected to the carriage. Each assembly is forced upwards in turn by a respective one of the follower wheels as it rides the cam profile away from a treading condition together with the foot, as the respective cam is rotated by the motor against the urging force of a return spring 231. As the cam is rotated further, and the cam profile recedes, the spring 231 associated with each follower assembly forces the assembly and foot downwards with a treading force.

Thereby, the treading force is limited to the spring rate of the associated follower assembly spring 231 and not the power of the drive motor. 1. The force applied to the hag is, in use, limited by the springs because the mechanism drives the feet up and the springs push them back down. This makes sure that:

a. the motor cannot stall (regardless of tumour size or texture);

b. the sample is not compressed with excessive force and the bag will not split;

c. the maximum pressure applied to the bag is lower than the pressure tested during bag manufacture; and d. As described below, a hinged bag receiving area 248 can accept a sample bag and any clamp used, without necessarily pre-positioning the feet. In other words, the feet can be in any position when accepting a bag, because the hinged sample area 248 is closed against the feet, and if needed any sample can at that time be compressed by the feet as the hinged area is closed against the feet.

Referring also to FIGS. 63 and 64, the device 200 further includes a flexible sealing membrane 241 extending from a device housing 210 to the upper parts of the two feet 234, 236 which provides a fluid resistant and dust seal between the soles of the feet and the remaining parts of the treading mechanism 220. That arrangement inhibits mechanism contamination, should the compressed bag split in service. Whilst a membrane 241 is preferred, the feet could slide in seals, such as lipped seals mounted to a partition dividing the mechanism 220 from the bag area 248, and achieving similar inhibition of contamination of the mechanism should that be needed.

The device 200 further includes heat transfer plate 250, which performs the same function as the heat transfer plate 150. This plate 250, however, is hinged to one side of the housing at hinge 255 (FIG. 64), so that insertion and removal of the bag to be trodden (as shown in FIGS. 46, 47 and 48) is easier. The heat transfer plate 250 includes a temperature sensor 256 which allows the temperature of the plate 250 and the bag receiving area 248 to be monitored and recorded by the controller, for quality control. The plate 250 has first and second surfaces 251 and 252 with the same function as the surfaces 151 and 152 described above.

Each foot is adjustable in height relative to a heat transfer plate 250 of the device 200 and an indication of its movement is monitored also by the controller. Thus, even though the rotary encoder may indicate that the motor is turning, a mechanical failure, such as a failure of the toothed belt 222, may still be detected by the controller, and a suitable action can be implemented, such as raising an alarm.

The device 200 has the same external dimensions as the device 100, and the device's housing 210 is intended to slide inside the controlled rate freezer 40 with the freezer lid in place as described above and illustrated in FIG. 61.

For convenience, terms such as upper, lower, up and down, and more descriptive terms such as feet, tread and treading have been used to describe the invention shown in the drawings, but in practice, the device shown could be oriented in any manner such that those terms become for example inverted or less descriptive in that new orientation. Therefore, no limitation as to orientation should be construed by such terms or equivalent terms.

The invention provides s device (100/100') for the disaggregation of tissue samples into individual cells or cell clumps in a closed flexible bag (10), the device including a mechanical disaggregation mechanism (120) and a tissue sample bag receiving area (148), said device further including a heat transfer plate (150) fortransferring heat energy to or from the area (148), the plate having a first plate surface (151) adjacent the area (148) and an opposing surface (152) exposed to external thermal influence which faces away from the area (148).

Cryopreservation of the tumor tissue at the time of collection resulted in the ability to separate manufacturing from tumor collection. This means UTIL manufacturing can be planned and performed as a single manufacturing process from thaw of the tumor digest through to final TIL harvest wash, drug product formulation, filling, labelling and cryopreservation.

Cryopreservation of the final product enabled all release testing to be performed prior to conditioning chemotherapy and patient treatment to be dislocated from final product manufacture.

Flow cytometry was used to characterize and quantify the manufactured products. TILd are defined as T cells that express the cell surface marker CD3 that have been culture derived from a metastatic Tumors by pathology assessment of a representative sample of the starting material. Viability is based on the percentage of all $CD3^+$ cells which do not bind the early cell death marker Annexin-V and/or the viability dye DRAQ7 (equivalent to Trypan blue or PI). Purity is defined as the percentage of viable T cells ($CD3^+$, Annexin-V-V-$^{ve}$, and DRAQ7-$^{ve}$) within the Viable Hematopoietic cell population ($CD45^+$, Annexin-V-$^{ve}$, and DRAQ7-$^{ve}$).

The vast majority of cells prior to the rapid expansion protocol (REP) are T cells expressing CD3. In research as well as clinical batches a variable distribution of CD3+ CD8+ and CD3+CD4+ TIL are observed and these will comprise of a subset containing the tumor-reactive cells. As the TILs are expanded in the REP with anti-CD3, the final product contains almost exclusively viable CD3+ T cells (>94%).

Theoretically, the end product could still contain tumor cells although this is very unlikely due to the culture conditions that strongly and selectively promote T cell growth and T cell-mediated killing of tumor cells. Clinical data of several hundred TIL infusions have shown no presence of tumor cells by cytology. In order to collate data to ultimately set a specification, a test has been incorporated to identify all viable cellular material that is not hematopoietic in origin IPC assay and will also test for a frequency of cancer biomarkers.

A TIL cell drug product is a suspension in approximately 125-270 ml of buffered isotonic saline containing 8.5% Human Serum Albumin and 10% DMSO. The number of cells present is dependent on the ability of each individual's TIL cells to be expanded in culture in conjunction with the culture conditions and the manufacturing reproducibility.

TABLE 3

Exemplary Drug Product Composition

| Component | Quantity (per infusion bag) | Function |
| --- | --- | --- |
| Tumor derived T cells | $5 \times 10^9$ to $5 \times 10^{10}$ $CD45^+$, $CD3^+$, Annexin-V-, DRAQ7- cells | Active |
| 20% Human Serum Albumin | 8.5% HSA W/V | Adsorbtion inhibitor |
| Phosphate buffered Saline | 125 to 270 ml | Isotonic diluent |
| DMSO | 10% V/V | Cryoprotectant |

With reference to FIG. 1 there is disclosed a disaggregation module of the device. The device may comprise a flexible container 1a for disaggregation and digestion in an embodiment involving enzymatic digestion. An open end 1b permits the transfer of solid tumor tissue material into the container 1a. Hanging holes 1c allow the container 1a to be hung and supported during transport or use. To maintain the aseptic conditions of the device, a target heat weld location 1d allows the container 1a to be sealed using a heat welder 13c or other comparable means. The container 1a can have rounded edges 1e on internal surfaces of container 1a to reduce losses, which may occur as part of the transfer to examples illustrated in FIGS. 2a-c or FIG. 3a or FIG. 3b. Tubing if enables media 3a to be transferred into container 1a via sterile filter 2a. Sterile filter 2a comprises a spike to permit puncture of the seal in a subsequent module to facilitate transfer of the media 3a. Tubing 1g enables digestion enzymes 3b to be transferred into container 1a via sterile filter 2b. Sterile filter 2b comprises a spike to permit puncture of a seal to facilitate transfer of the digestive enzymes 3b into the container 1a. After disaggregation of the solid tumor tissue, especially involving enzymatic digestion, the disaggregated mixture is transferred out of tubing 1h via filter unit 4a comprising sterile filter 4b prior to entering a phase of incubation. Filter unit 4a can be flexible to permit contortion without affecting the utility of the filtration process. A filter 4b removes the non-disaggregated tissue. Tubing clamp 5a allows the media 3a to enter the flexible container 1a via sterile filter 2a. In an embodiment involving enzymatic digestion, tubing clamp 5b allows the enzymes 3b to enter the flexible container 1a via sterile filter 2b. Tubing clamp 5c allows contents of flexible container 1a to pass via filter unit 4a into one or more examples identified in FIGS. 2a-c or FIG. 3a or FIG. 3b.

Figure 2A:
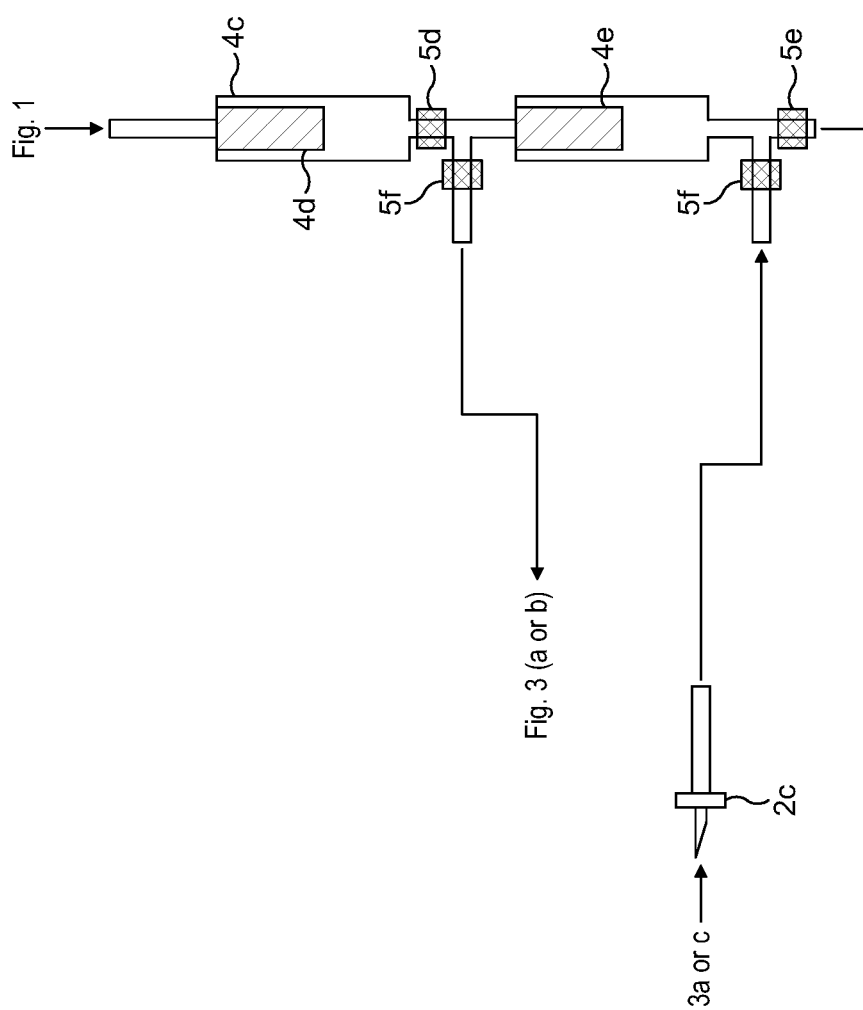
FIG. 2A is a schematic diagram of a series of filter modules that direct the digested solid tissue material to subsequent modules or a waste container.

According to FIG. 2a, sterile filter 2c permits the introduction of media 3a and/or a freezing solution 3c required for cryopreservation of the disaggregated tumor tissue. Filter 4*d* may be required for additional size segregation of cell/tissue clumps. Filter 4*d* is enclosed within filter unit 4*c*, which can be flexible to permit contortion without affecting the utility of the filtration process. In an embodiment, a filter 4*e* may be required to retain cells, but allow the media and cell fragments to be washed out. Filter 4*d* is similarly enclosed within filter unit 4*c*. In an embodiment, tubing clamp 5*d* is in place to stop material from container 1*a* that has passed through filter units 4*a* and 4*c* from returning back to container 1*a*. In an embodiment, tubing clamp 5*e* is in place to allow waste material from container 1*a* that has passed through filter units 4*a*, 4*c*, and 4*e* to enter waste container 6*a*, but stops media 3*a* or 3*c* from entering via sterile filter 2*c*. Tubing clamps 5*f* stop material from container 1*a* that has passed through filter units 4*a*, 4*c*, and 4*e* from returning to the source of the media 3*a* or 3*c* or transferring to one of the examples illustrated in FIG. 3*a* or FIG. 3*b* before the waste has passed into waste container 6*a* via tubing clamp 5*e*. Once the waste has been depleted, tubing clamps 5*e* and 5*d* are closed and tubing clamps 5*f* allow media 3*a* or 3*c* to transfer cells within filter 4*e* into one of the examples illustrated in FIG. 3*a* or FIG. 3*b*. The waste container 6*a* has hanging holes to support the waste container 6*a* during use and/or transport.

Figure 2B:
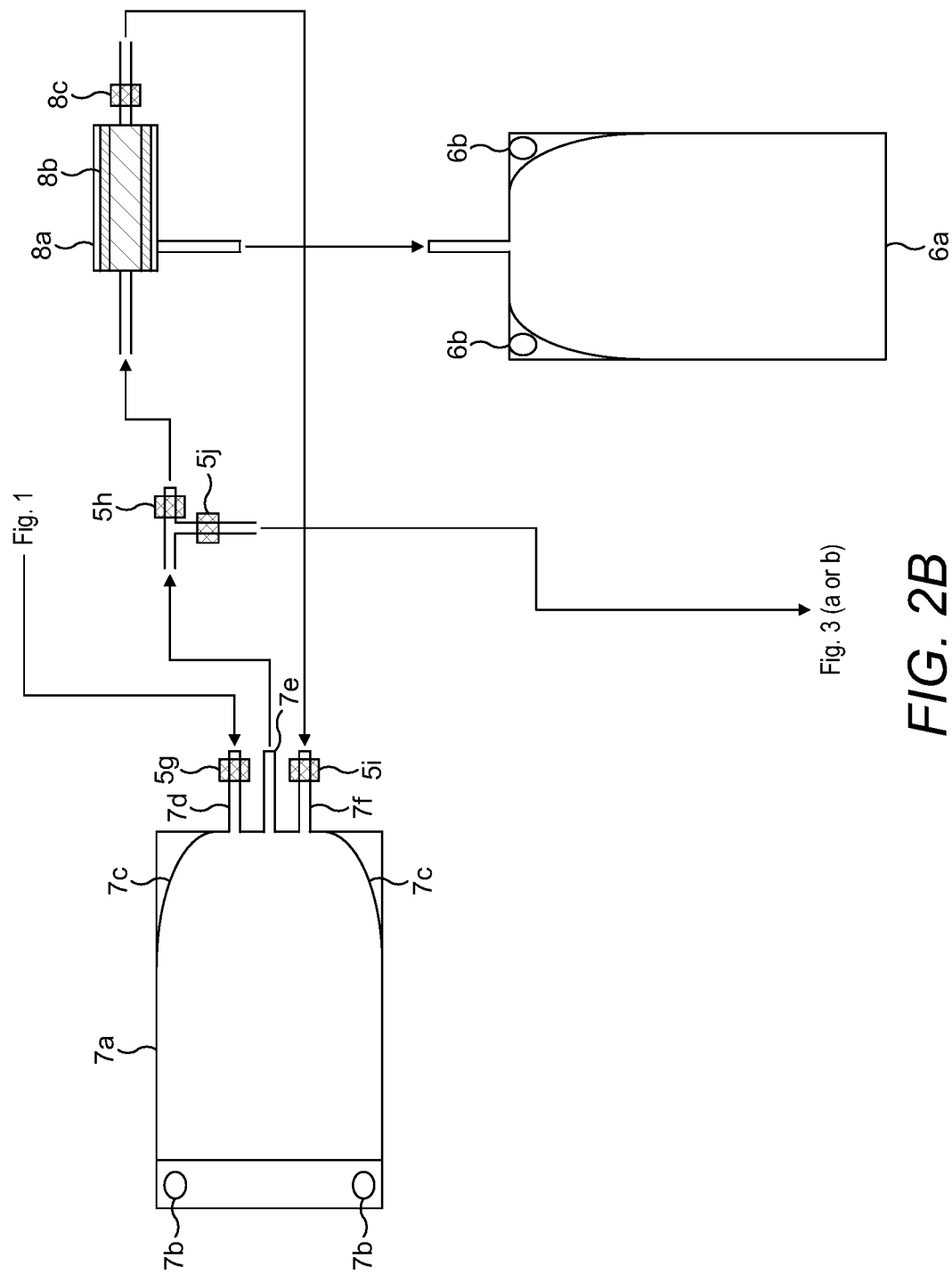
FIG. 2B is a schematic diagram of a flexible container for enrichment of cells following digestion and removal of waste material.

FIG. 2*b* illustrates the enrichment module of the device. Tubing clamp 5*g* allows the contents of container 1*a* to enter flexible container 7*a* of the enrichment module via filter unit 4*a*. Tubing clamp 5*h* allows contents of container 7*a* to pass through filter unit 8*a*, retaining and enriching cells, while allowing waste and debris to pass through filter 8*b* into waste container 6*a* with the pressure controlled by valve 8*c* before the enriched cells return to container 7*a* via open tubing clamp 5*i*. Tubing clamp 5*i* allows contents of container 7*a* via open tubing clamp 5*h* to pass through filter unit 8*a*, retaining and enriching cells while allowing waste and debris to pass through filter 8*b* with the pressure controlled by valve 8*c* before the enriched cells return to container 7*a*. After cell enrichment has occurred, tubing clamp 5*h* is closed and tubing clamp 5*j* is opened to allow the contents of container 7*a* to pass to one of the examples illustrated in FIG. 3*a* or FIG. 3*b*. The waste container 6*a* has hanging holes 6*b* to support the waste container 6*a* during use and/or transport. Container 7*a* of the enrichment module has hanging holes 7*b* to support the container 7*a* during use and/or transport. The container 7*a* can have rounded edges 7*c* on internal surfaces of container 7*a* to reduce losses, which may occur as part of the transfer to examples illustrated in FIG. 3*a* or FIG. 3*b*. Tubing 7*d* allows container 7*a* to receive the contents of container 1*a* via filter unit 4*a* and filter unit 8*a*. Tubing 7*e* allows the contents of container 7*a* to pass through filter unit 8*a*, retaining and enriching cells while allowing waste and debris to pass through filter 8*b* into waste container 6*a* with the pressure controlled by valve 8*c* before the enriched cells return to container 7*a* via open tubing clamp 5*i*. Tubing 7*f* allows the contents of container 7*a* to pass through filter unit 8*a*, retaining and enriching cells while allowing waste and debris to pass through filter 8*b* into waste container 6*a* with the pressure controlled by valve 8*c* before the enriched cells return to container 7*a*.

Figure 2C:
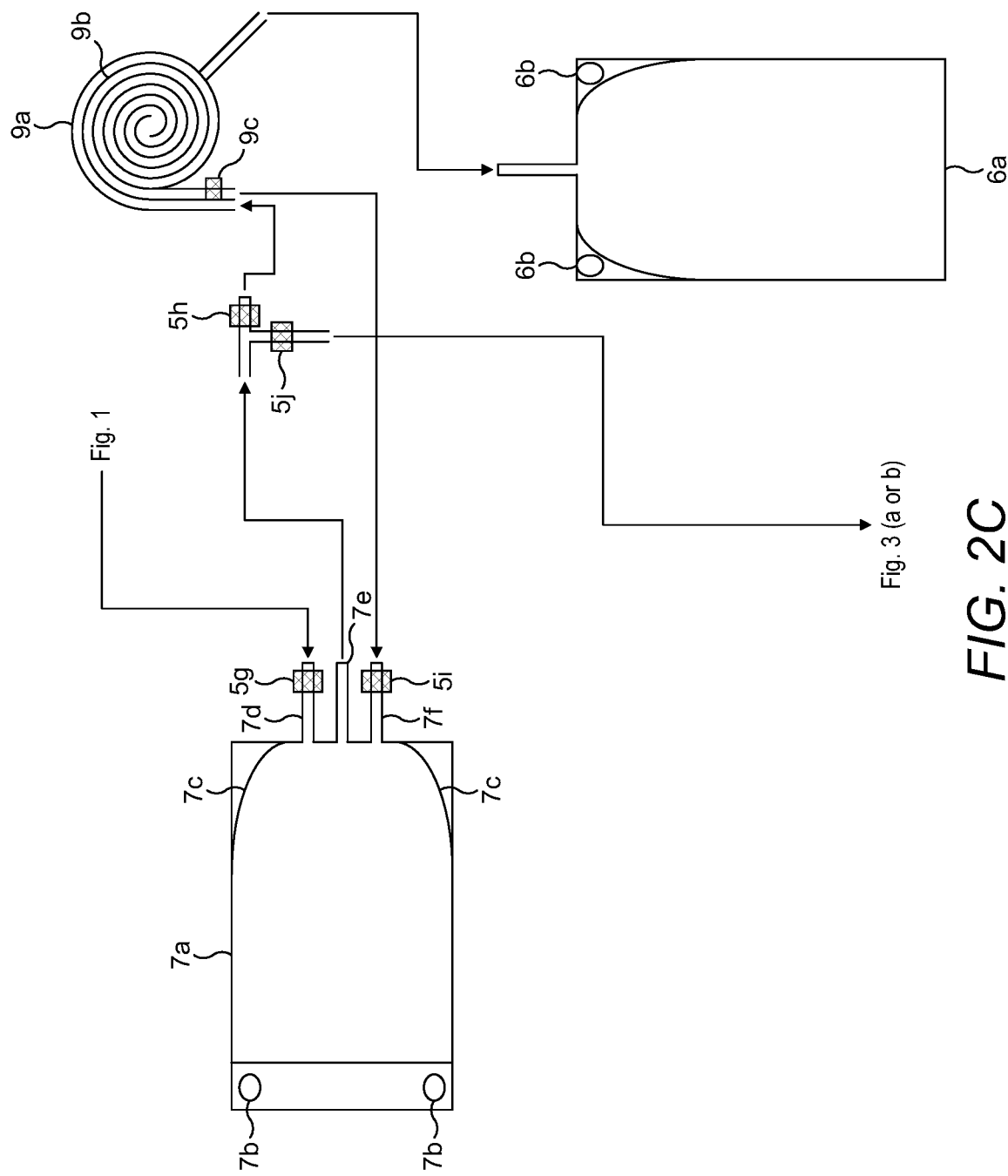
FIG. 2C is a schematic diagram of another embodiment of a flexible container for enrichment of cells following digestion and removal of waste material.

FIG. 2*c* illustrates another embodiment of the enrichment module. Tubing clamp 5*g* allows the contents of container 1*a* to enter the flexible container 7*a* via filter unit 4*a*. Tubing clamp 5*h* allows contents of container 7*a* to pass through filter unit 9*a*, retaining and enriching cells, while allowing waste and debris to pass through filter 9*b* into waste container 6*a* with the pressure controlled by valve 9*c* before the enriched cells return to container 7*a* via open tubing clamp 5*i*. Tubing clamp 5*i* allows contents of container 7*a* via open tubing clamp 5*h* to pass through filter unit 9*a*, retaining and enriching cells while allowing waste and debris to pass through filter 9*b* with the pressure controlled by valve 9*c* before the enriched cells return to container 7*a*. After cell enrichment has occurred, tubing clamp 5*h* is closed and tubing clamp 5*j* is opened to allow the contents of container 7*a* to pass to one of the examples illustrated in FIG. 3*a* or FIG. 3*b*. The waste container 6*a* has hanging holes 6*b* to support the waste container 6*a* during use and/or transport. Container 7*a* of the enrichment module has hanging holes 7*b* to support the container 7*a* during use and/or transport. The container 7*a* can have rounded edges 7*c* on internal surfaces of container 7*a* to reduce losses, which may occur as part of the transfer to examples illustrated in FIG. 3*a* or FIG. 3*b*. Tubing 7*d* allows container 7*a* to receive the contents of container 1*a* via filter unit 4*a* and filter unit 9*a*. Tubing 7*e* allows the contents of container 7*a* to pass through filter unit 9*a*, retaining and enriching cells while allowing waste and debris to pass through filter 9*b* into waste container 6*a* with the pressure controlled by valve 9*c* before the enriched cells return to container 7*a* via open tubing clamp 5*i*. Tubing 7*f* allows the contents of container 7*a* to pass through filter unit 9*a*, retaining and enriching cells while allowing waste and debris to pass through filter 9*b* into waste container 6*a* with the pressure controlled by valve 9*c* before the enriched cells return to container 7*a*. Filter unit 9*a* facilitates the filtration of the contents of container 7*a* to remove waste media and debris via filter 9*b* into waste container 6*a* with the pressure controlled by valve 9*c* before the enrich cells return to container 7*a*. Filter 9*b* can be wound into a coil to increase the distance that the waste must elute prior to reaching the waste container 6*a* for improved purification of the cell media, but facilitate transport and storage of the improved filter 9*b*.

FIG. 3*a* illustrates an example of the stabilization module. Tubing clamp 5*k* allows: the contents of container 1*a* as illustrated in FIG. 1 via filter unit 4*a*, or as illustrated in FIG. 2*a* via filter unit 4*c*; or the contents of container 7*a* as illustrated in FIG. 2*b* via filter unit 8*a*, or as illustrated in FIG. 2*c* via filter unit 9*a* to be transferred into container 10*a* of the stabilization module. Container 10*a* of the stabilization module has hanging holes 10*b* to support the container 10*a* during use and/or transport. The container 10*a* can have rounded edges 10*c* on internal surfaces of container 7*a* to reduce losses, which may occur as part of the transfer out of tubing 10*e* or 10*f*. Tubing 10*e* enables the contents of container 10*a* to be withdrawn via connector 10*h*. Tubing 10*f* contains a flexible membrane to enable a sterile spike to be introduced via an aseptic cover 10*g* to enable the contents of container 10*a* to be withdrawn.

Figure 3B:
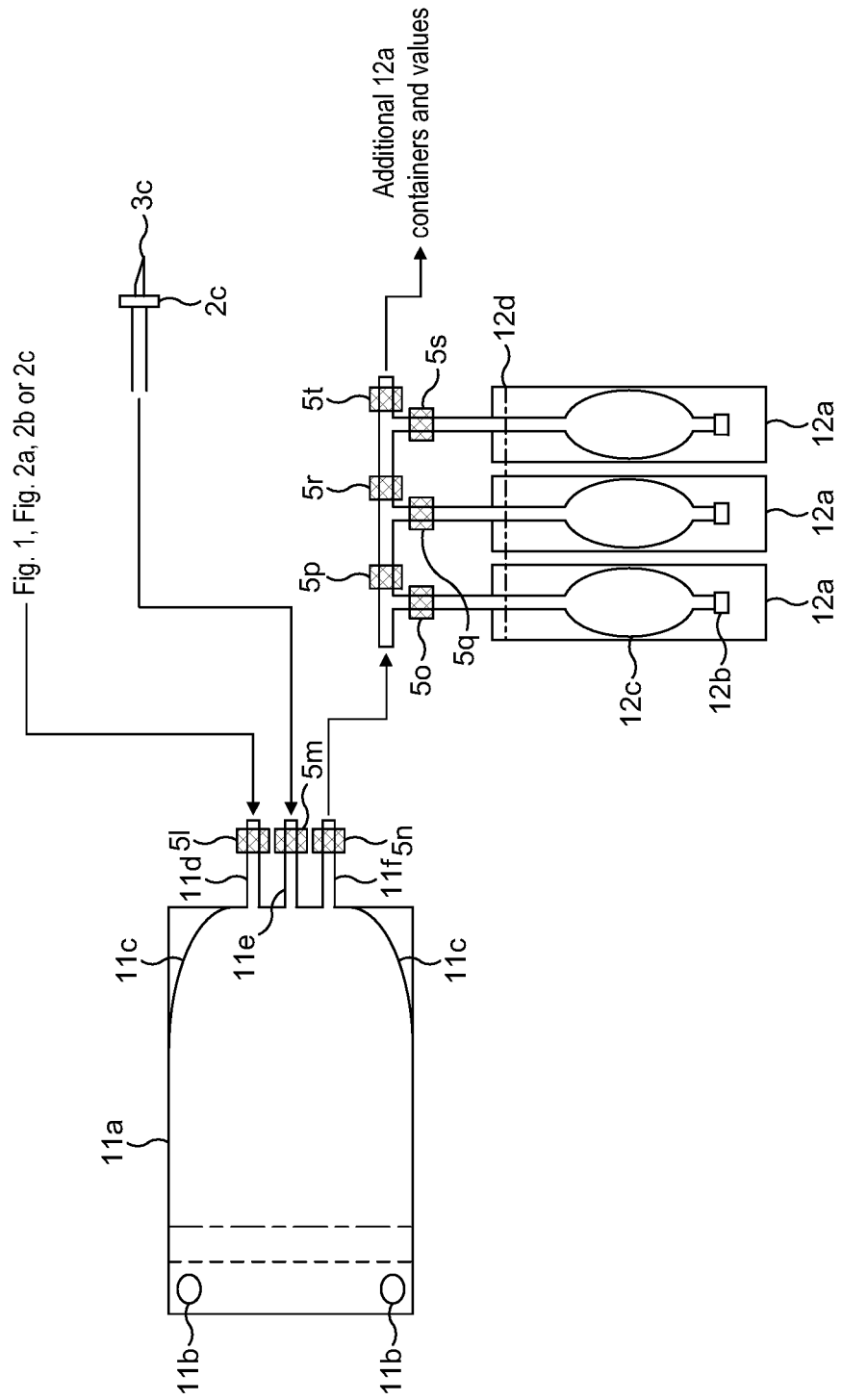
FIG. 3B is a schematic diagram of another embodiment of a flexible container containing connections to additional flexible containers for stabilization of cells through cryopreservation following the disaggregation of the solid tissue material and/or enrichment of cells.

FIG. 3*b* illustrates another embodiment of the stabilization module. Tubing clamp 5*l* allows: the contents of container 1*a* as illustrated in FIG. 1 via filter unit 4*a*, or as illustrated in FIG. 2*a* via filter unit 4*c*; or the contents of container 7*a* as illustrated in FIG. 2*b* via filter unit 8*a*, or as illustrated in FIG. 2*c* via filter unit 9*a* to be transferred into container 11*a* of the stabilization module. Container 11*a* of the stabilization module has hanging holes 11*b* to support the container 10*a* during use and/or transport. The container 10*a* can have rounded edges 10*c* on internal surfaces of container 7*a* to reduce losses, which may occur as part of the transfer out of tubing 11*f*. Tubing clamp 5*m* allows media 3*c* to enter the flexible container 11*a* via sterile filter 2*c*. Tubing clamp 5*n* allows the contents of container 11*a* to enter one of the cryopreservation containers 12*a* depending on the open or closed status of tubing clamps 5*o*, 5*p*, 5*q*, 5*r*, 5*s*, and 5t. Tubing clamps 5o, 5p, 5q, 5r, 5s, and 5t allow the contents of container 11a to enter one of the cryopreservation containers 12a. Tubing lid enables container 11a to receive: the contents of container 1a as illustrated in FIG. 1 via filter unit 4a, or as illustrated in FIG. 2a via filter unit 4c; or the contents of container 7a as illustrated in FIG. 2b via filter unit 8a, or as illustrated in FIG. 2c via filter unit 9a. Tubing 11e allows cryopreservation media 3c to be transferred into container 11a. Tubing 11f enables the contents of container 11a to be transferred to cryopreservation containers 12a, where the final disaggregated UTIL product as a single cell suspension is stored for future use in the rapid expansion process. Cryopreservation containers 12a have a fixtures 12b to allow aseptic transfer of the TILs out of the cryopreservation containers 12a. Cryopreservation containers 12a have a space 12c that is suitable for the volume of the UTIL cell suspension to be stored. The cryopreservation containers 12a also have a target location 12d for welding the tubing 11f to the cryopreservation containers 12a.

Figure 4:
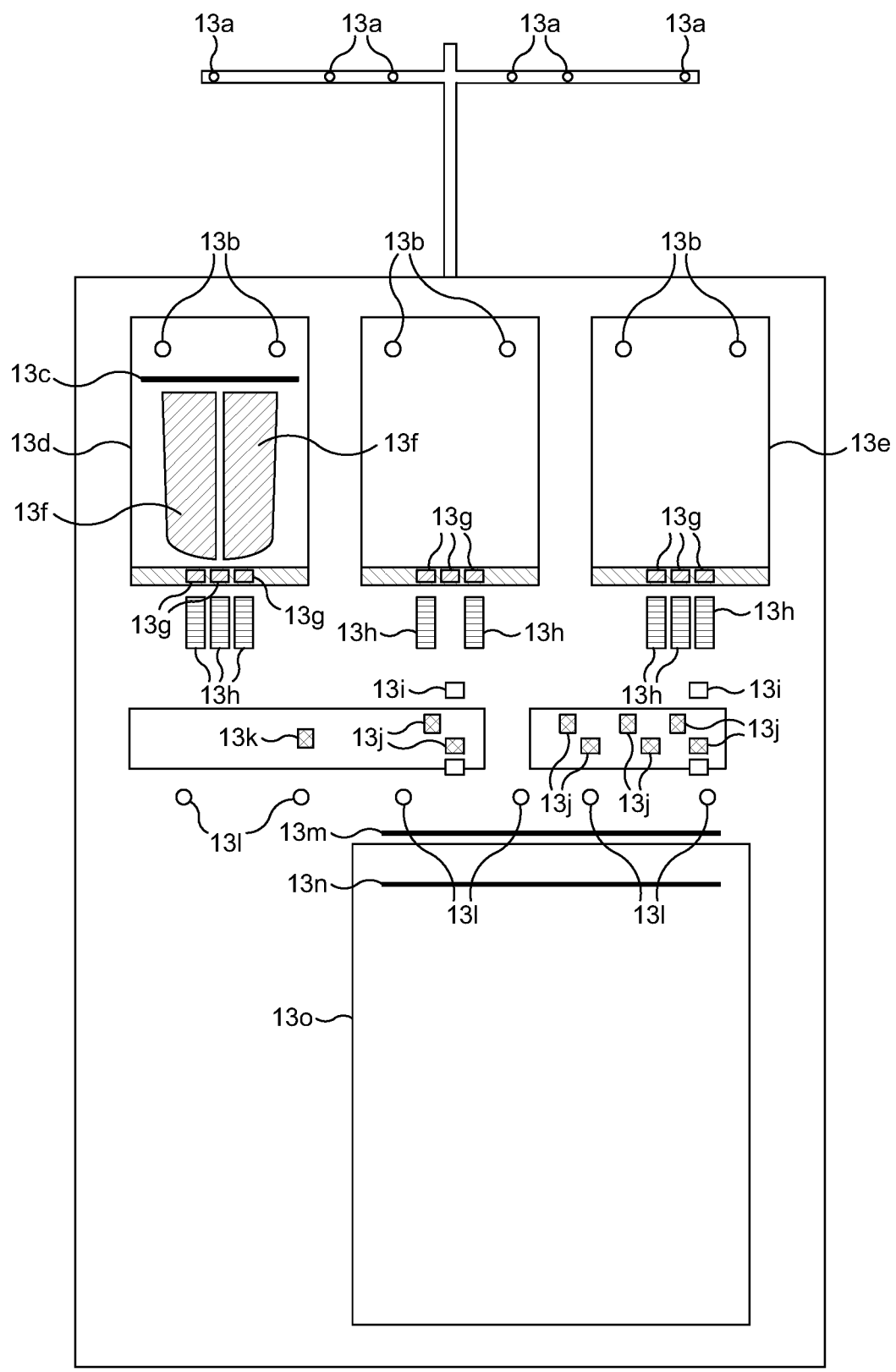
FIG. 4 is a schematic diagram of the aseptic kit.

FIG. 4 illustrates another example of the device and kit. Pegs 13a allow the media 3a, 3b, and 3c to be hung. Pegs 13b are connected to weight sensors for hanging container 1a and depending on the embodiment utilized, could include one or more of containers 7a, 10a, and/or 11a. The weight sensors are used to define decision stages to control the automated processing of the materials. A heat welder 13c can be used to seal container 1a at the target site following the introduction of the resected solid tumor tissue into container 1a. The disaggregation module 13d has an opening that can be closed and locked to enable disaggregation and can control the temperature to be between 0° C. and 40° C. to a tolerance of 1° C. to enable digestion where digestive enzymes are used for disaggregation of the solid tumor tissue. The disaggregation module 13d also has a built in sensor to assess the level of solid tissue disaggregation by determining the variation in light distribution against time to identify change and thereby identify completion of the disaggregation process, which occurs over a period of seconds to hours. Disaggregation module 13d may also comprise disaggregation surfaces 13f, which come directly into contact with container 1a and pushes against the back of the disaggregation module 13d enclosure, which can be closed and locked during disaggregation and digestion where enzymes are utilized. A final formulation module 13e has an enclosure that allows temperature control of either containers 10a or 11a depending on the embodiment utilized, which is capable of controlling temperatures between 0° C. and ambient environmental temperature to a tolerance of 1° C. Tubing clamps 13g and 13j act as input and output ports, disposed within tubing locators 13i, and facilitate transport of the disaggregated tumor product between the containers 1a, 10a, or 11a depending on the embodiment utilized. Peristaltic tubing pumps 13h control the transfer of the media 3a or 3c between the tubing clamps 13g and 13j that act as input and output ports. Tubing valve 13k assists in controlling the pressure via valves 8c and 9c in the enrichment module as illustrated in FIGS. 2b and 2c. Pegs 13l allow for the hanging of waste container 6a and/or cryopreservation containers 12a depending on the embodiment utilized. The embodiment can also include a tubing welder 13m required for connecting the cryopreservation containers 12a to the device as illustrated in FIG. 3b. The embodiment can also include a tubing cutter 13n for disconnecting the cryopreservation containers 12a to the device as illustrated in FIG. 3b. Controlled rate cooling module 13o is capable of cooling or maintaining any temperature between 8° C. and at least −80° C. to assist in the cryopreservation process.

The method of the invention is exemplified according to the following process. It is clearly stated that other than the essential features of the method, the various optional steps listed herein can be independently combined to achieve the relevant technical advantages associated with the type of sampling and result to be achieved.

A semi-automatic aseptic tissue processing method comprises: automatically determining aseptic disaggregation tissue processing steps and one or more further tissue processing steps and their associated conditions from a digital tag identifier on an aseptic processing kit, optionally in accordance with the kit described herein; placing a tissue sample into a flexible plastic container of the aseptic processing kit; and processing the tissue sample by automatically executing the one or more tissue processing steps by communicating with and controlling the disaggregation module; the optional enrichment module; and the stabilization module.

Essentially the process may comprise taking an open ended bag (first flexible container that is part of disaggregation module) that will receive the biopsy/tissue sample, preferably a resected tumor, which is already connected via one or more conduits to or can be connected via a manual operator controlled aseptic connection to I. a single container with digestion media (second flexible container that is part of the disaggregation module) and with or without a stabilization solution (same second flexible container is part of the stabilization module also)

II. one container with a digestion solution (second flexible container that is part of the disaggregation module) and another container with a stabilization solution (fourth flexible container is part of the stabilization module)

on addition of the biopsy and sealing of the open ended bag the digestion media can be added via the conduit or aseptic connections (conduit/ports claim 1) and the tissue material processed.

On completion of the digestion by which point the tissue is now a single or small number aggregate cellular suspension the cells can optionally be filtered prior to step 4 (optional enrichment module for filtration comprises the first flexible container containing sample and filtered to a third container for receiving the enriched filtrate).

Where the stabilization media is not present in the same flexible container, the container with stabilization solution is added by opening the attached conduit or manual operator controlled aseptically connection to be competed and said connection to be opened enabling in both cases the stabilization solution to be added before the process continues.

The single or small number aggregate cellular suspension in the original flexible container or which may be optionally subdivided into multiple storage stabilization containers thereafter are maintained in a stable state on the device and/or will undergo cryopreservation prior to removal for, transport, storage and or used in their ultimately utility. The stabilization module also comprises first or third container as used in storage/freezing/storage.

Figure 5:
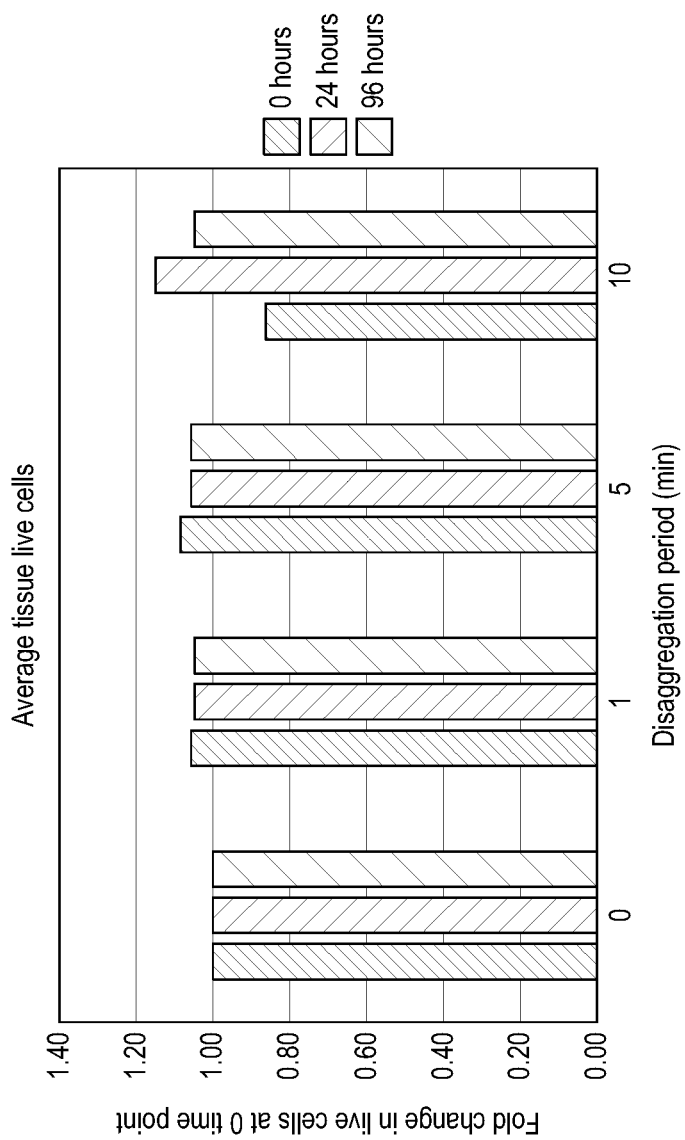
FIG. 5 is a bar graph indicating the observed fold change in a population of cells obtained from the disaggregation process for various disaggregation times ranging from a few seconds to several hours.

In one further non-limiting example of the process:

a) Collection of tissue sample by a separate procedure such as a biopsy or surgery to collect the required tissue material (not part of the invention) is placed into the initial flexible plastic container (see e.g., FIG. 1, container 1a).

b) Media (see e.g. FIG. 1, media 3a) is transferred into the disaggregation chamber, or in one example also enters and collects enzymes (see e.g. FIG. 1, enzymes 3b), prior to disaggregation using one or more of the following examples of the invention a mechanism such as weight sensors (see e.g. FIG. 1, 13b as part of module 13d) assesses the required amount of media to add either determined by: direct operator input or weight of solid tissue.

c) The single use flexible disaggregation container, solid tissue, media and in one example enzymes are combined during a physical disaggregation process for a minimum of a few seconds up to several hours with an optimal time of between 1 and 10 minutes required to break up the solid tissue until there is no visual change (See FIG. 5 and Table 1). The disaggregation device is designed to compress the tissues using a variable speed and time depending upon the time taken to disaggregate and feedback via sensors within the disaggregation module (see FIG. 1, 13d).

d) In one embodiment where enzymes are present this will require incubation periods at an optimal temperature of between 30 and 37° C. but could be as low as 0° C. up to 40° C. for at least 1 minute to several hours but more preferable 15 to 45 minutes.

e) Step c and in the embodiment where enzymes step d) can be repeated until the tissue stops changing or the see example has been disaggregated into a liquid cell suspension whichever comes 1st monitored by a sensor in the disaggregation module disaggregation module (see FIG. 1, 13d).

1) In one embodiment incompletely disaggregated tissues, associated material and impurities are removed enabling enrichment of the cell suspension by passing the disaggregated tissue and media using one or more of the following embodiments:

i. Direct pass through one or more mechanical filters with holes at least >0.1 μm to 1000 μm but most preferably between 50 and 250 μm and more preferably 100 μm to 200 μm (illustrated in FIG. 2a).

ii. Density based separation using centrifugation and/or sedimentation with or without a cell aligned density retention solution (e.g. Ficoll-paque GE Healthcare).

iii. Hydrodynamic filtration where fluid flow and flow obstructing materials enhance the resolution and fractionation of the cells and impurities based on size and shape iv. Field flow fractionation where an applied field (e.g. flow, electric, gravitational, centrifugal) acts in a perpendicular or reverse direction to the selection flow (e.g. Tangential flow filtration, Hollow fiber flow filtration, Asymmetric flow filtration, Centrifugal flow filtration). In which case: cells or impurities which are most responsive to the force are driven to the wall where flow is lowest and therefore a long retention time; while cells or impurities which are least responsive to the force remain laminar to the flow and elute quickly (tangential flow filtration illustrated in FIGS. 2b and c).

v. Acoustophoresis where one or more an acoustic frequency(ies) tuned to or harmonized with populations of cells or impurities is used to drive the required cells or impurities in a tangential path to the input stream.

g) In one embodiment the disaggregated enriched tissue product will be resuspended in a fresh media (FIG. 2a using media 3a) such as:

i. a cell enrichment media in order to undergo an independent targeted enrichment procedure as described previously ii. direct cell culture or cold storage media (such as HypoThermosol® from BioLife Solutions.

h) in the embodiment employed in g) the resuspended disaggregated solid tissue derived product is transferred to one of the embodiment final product containers (illustrated in FIG. 3a) for storage for hours to days prior to being used for its ultimate utility.

i) otherwise after step f) the embodiment applies (illustrated in FIG. 3h) will apply where the disaggregated solid tissue derived product undergoes re-suspension in a cryoprotectant (FIG. 3b, media 3c) a freezing solution for storage of the disaggregated solid tissue derived product for days to years such as CryoStor® Freezing solution from BioLife Solution.

j) At this stage the disaggregated solid tissue derived product is re-suspended in freezing solution (FIG. 4, module 13e) and transferred to one or more flexible cryopreservation container(s) (illustrated in FIG. 3a, container 12a) and in one embodiment of the device there is a controlled rate freezing process (FIG. 4, module 13o).

k) After which the bags can be separated from the device and aseptic processing kit for independent storage or distribution.

Figure 6:
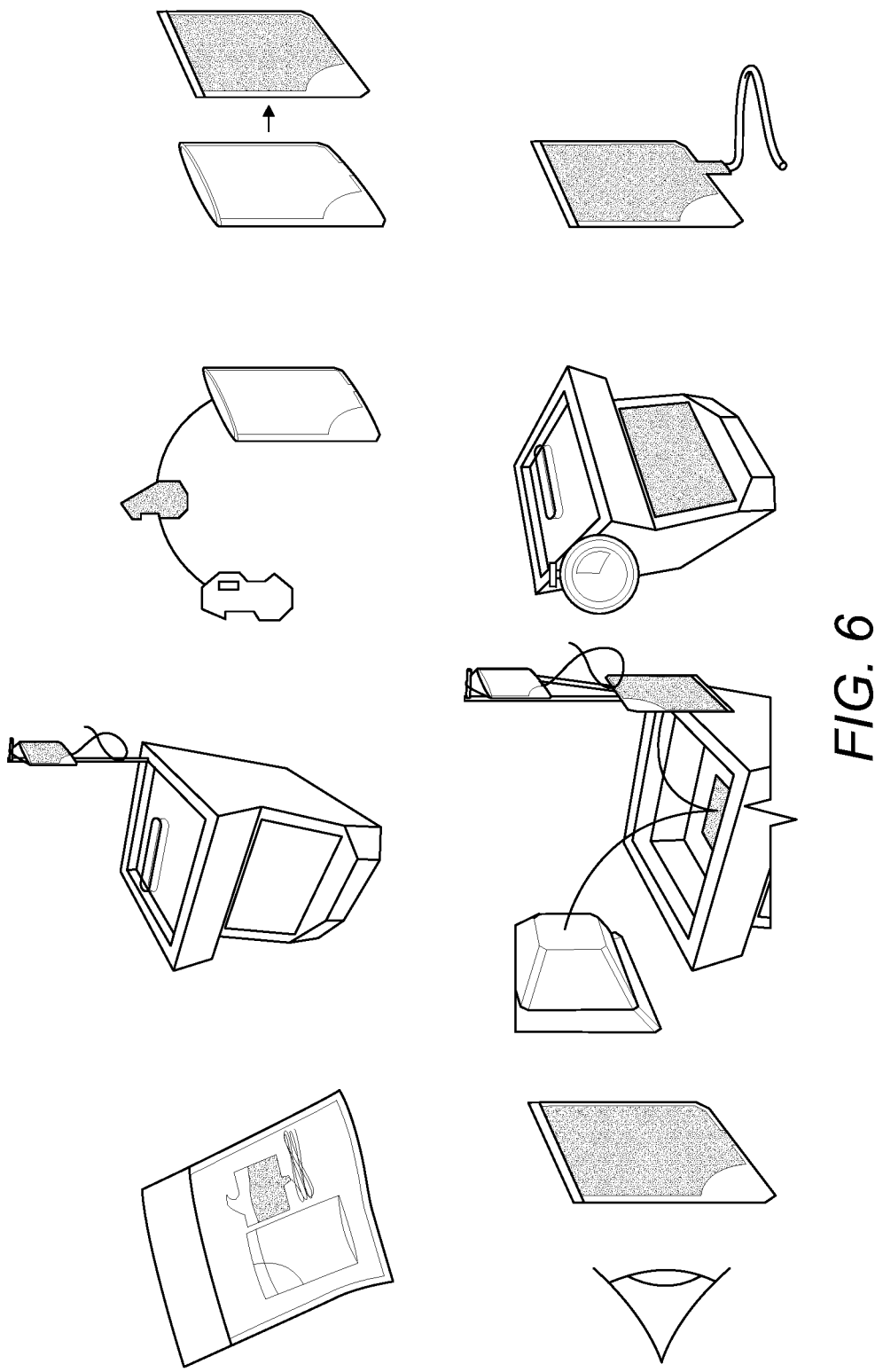
FIG. 6 is a diagram that describes the semi-automatic aseptic tissue processing method using multiple flexible containers for different starting solutions that are part of the modules of the process used for disaggregation and stabilization.
Figure 7:
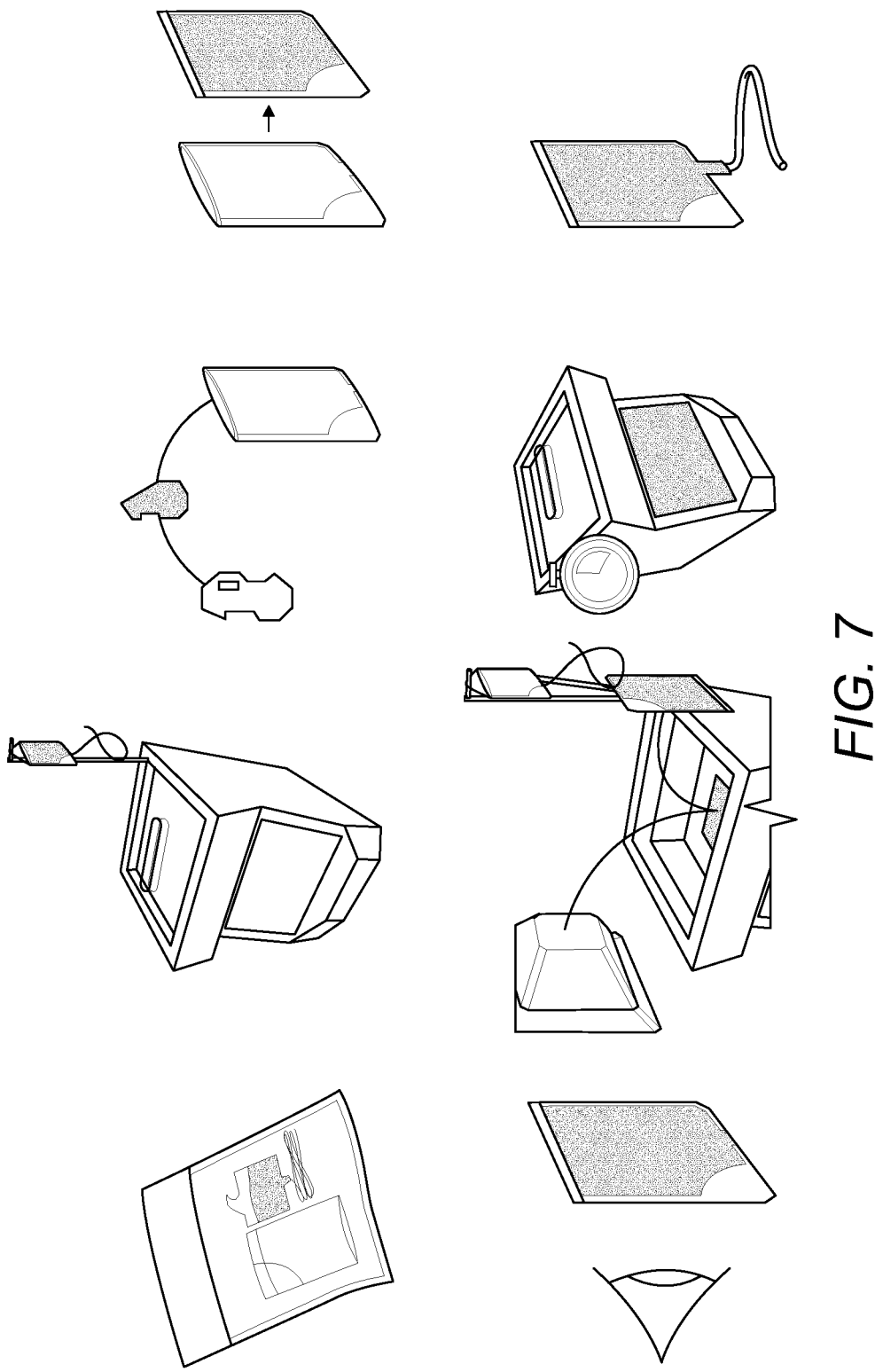
FIG. 7 is a diagram that describes how flexible containers comprising the media used in the process may be shared between the modules of the aseptic processing kit and method.
Figure 8:
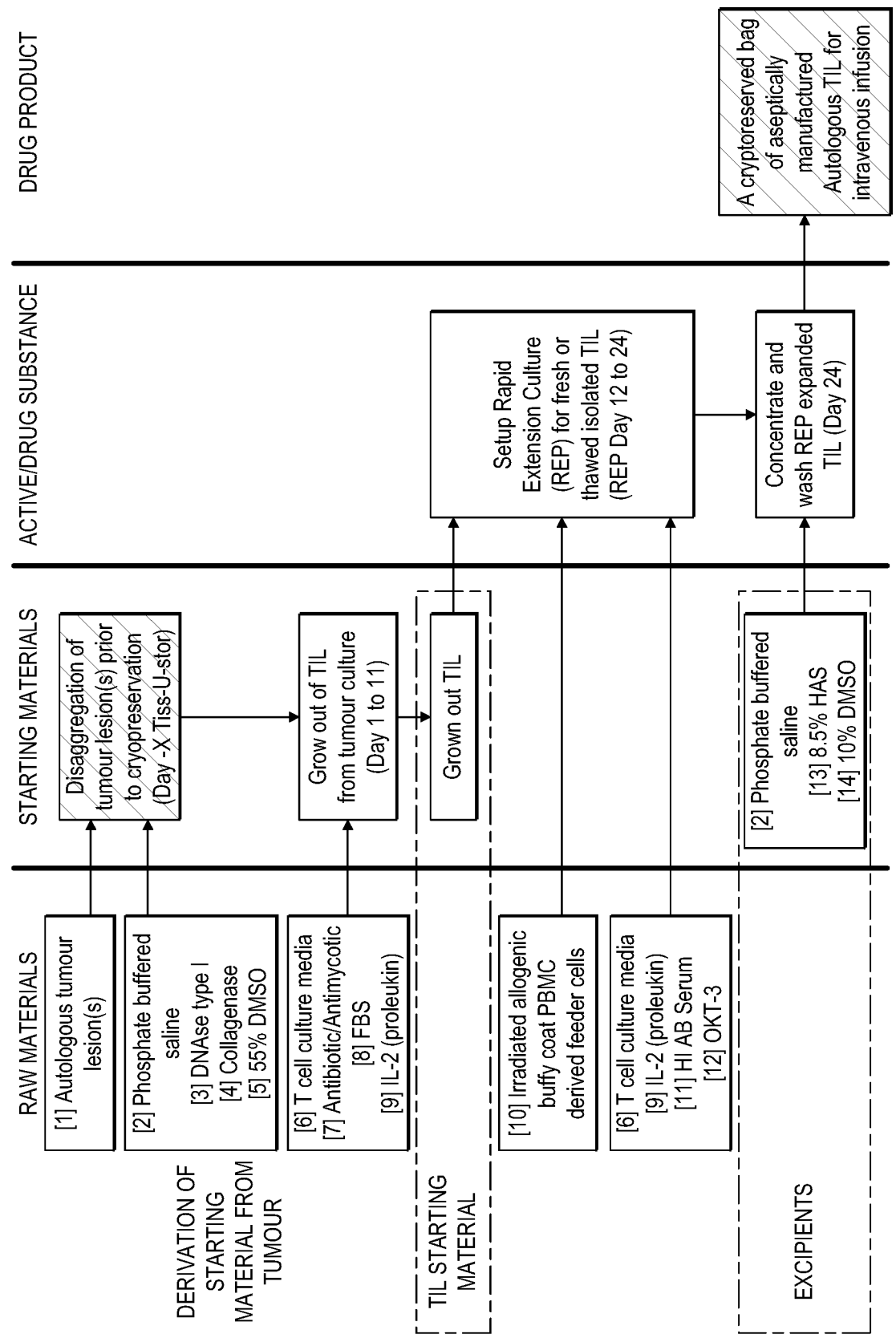
FIG. 8 depicts a general overview of the method for the generation of TILs.
Figure 9:
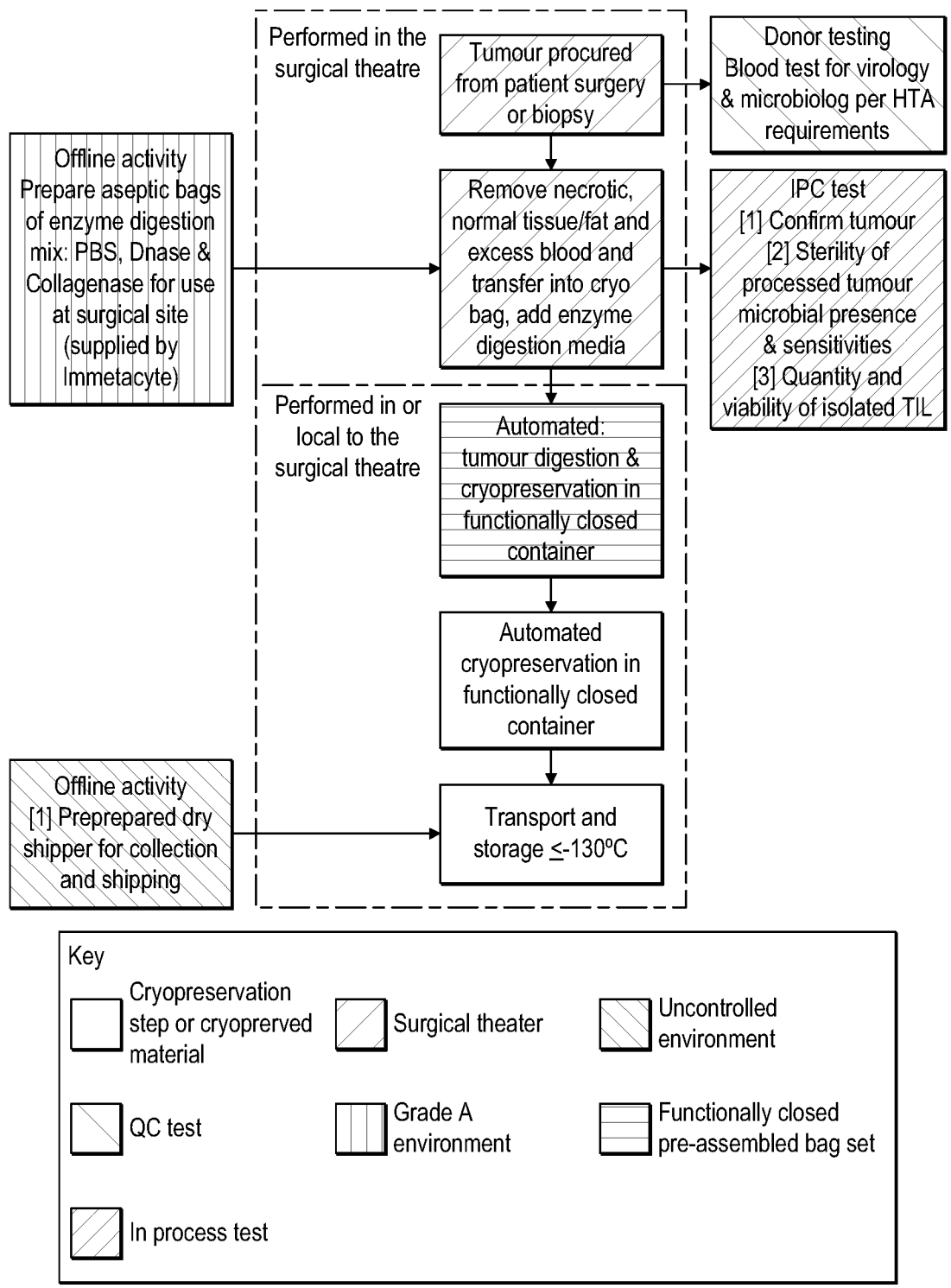
FIG. 9 depicts an overview of the collection and processing of the tumor starting material.
Figure 10:
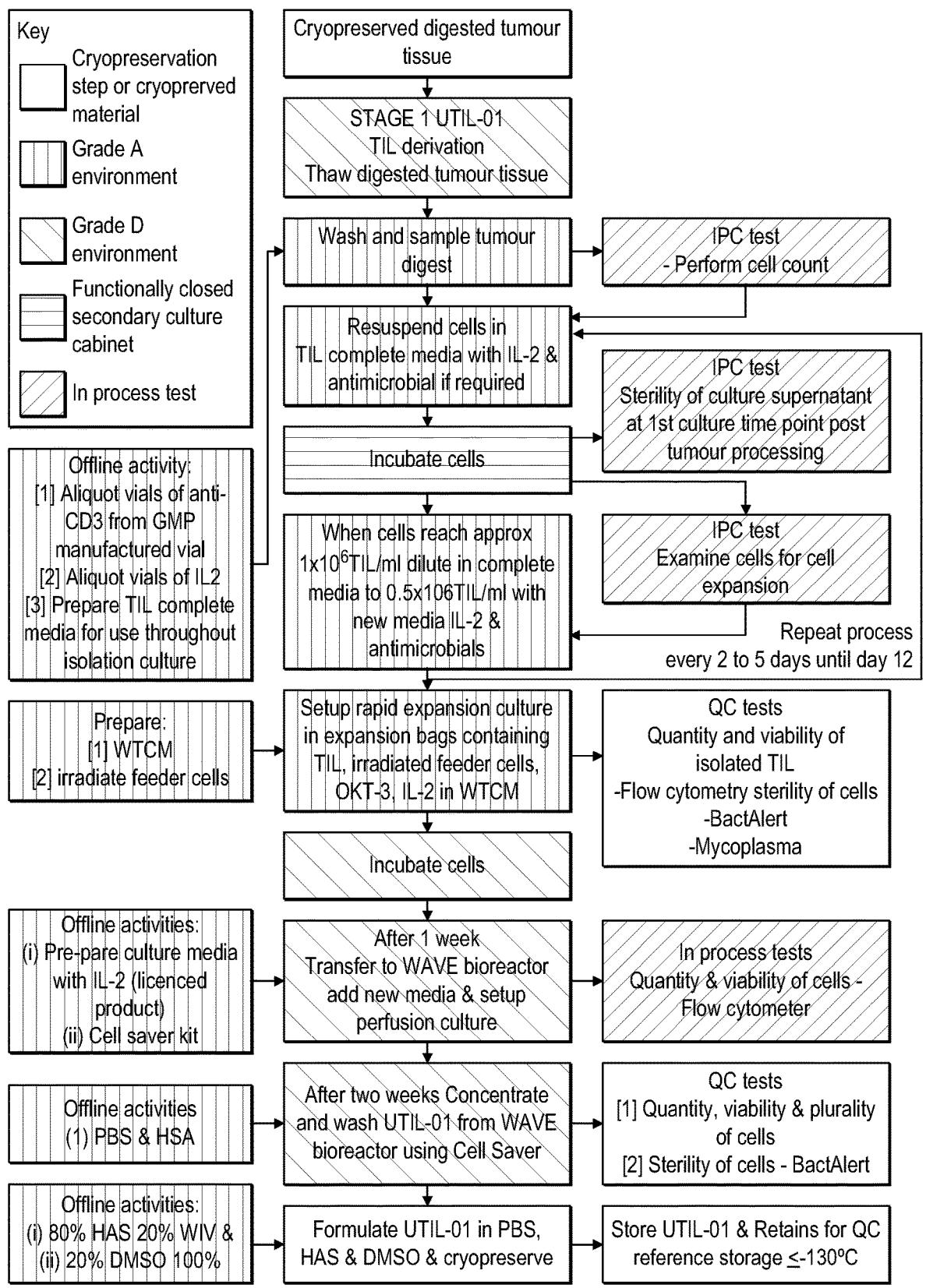
FIG. 10 depicts an overview of the TIL manufacturing process.

In further embodiments, a disposable kit of the invention can be used with an automatic device for semi-automatic aseptic processing of tissue samples. FIGS. 6 and 7 depict disposable kits of the invention.

FIG. 6 depicts a semi-automatic aseptic tissue processing method using multiple flexible containers for different starting solutions that are part of the modules of the process used for disaggregation and stabilization.

Process step 1—The user may login to device and scan the tag on the aseptic kit using the device to transfer the automatic processing steps to be used. The device processor recognizes the tag and is provided with information needed to carry out the specific processing instructions related to that particular kit.

Process step 2—The digestion media containing flexible hag (part of disaggregation module) and cryo/stabilization solution containing flexible bag (part of the stabilization module) are each hung or secured to the device.

Process step 3—The biopsy or tissue sample for processing may be placed into a flexible container (part of both modules) of the aseptic kit via an open end.

Process step 4—The flexible container comprising the sample may then be sealed using a heat weld to close the open end (used to add the sample during initial processing).

Process step 5—The user may then interact with the user interface of the processor to confirm the tissue sample is present and enter any further tissue material specific information, if required.

Process step 6—Digestion media and cryo/stabilization solution flexible containers are connected with the flexible container housing the sample, after which it may be placed into the device for automatic processing.

Process step 7—The device executes the cycles according to the kit information undertaking disaggregation of the sample and stabilization/cryo preservation of resulting cells.

Process step 8—When stabilized/frozen disconnect and discard used media and cryo/stabilization containers of kit. Tissue processed into single or multi-cell solution in flexible container is disconnected before transferring into storage or transport container prior to its ultimate utilization.

In another embodiment, FIG. 7 depicts flexible containers comprising the media used in the process may be shared between the modules of the aseptic processing kit and method.

Process step 1—The user may login to device and scan the tag on the aseptic kit using the device to transfer the automatic processing steps to be used.

Process step 2—A flexible bag (part of disaggregation/stabilization module) comprising both the media and cryo/stabilization solution is hung or otherwise secured to the device.

Process step 3—The biopsy or tissue sample for processing may be placed into a further flexible container (part of both modules) of the aseptic kit via an open end.

Process step 4—The flexible container comprising the sample may then be sealed using a heat weld to close the open end.

Process step 5—The user may then interact with the user interface of the processor to confirm the tissue sample is present and enter any tissue material specific information, if required.

Process step 6—Digestion media and cryo/stabilization solution flexible container is connected with the flexible container housing the sample, after which it may be placed into the device for automatic processing.

Process step 7—The device cycles to enable disaggregation of the sample and stabilization of resulting cells, optionally via cryopreservation.

Process step 8—When freezing/stabilizing is complete the user disconnects and discard used flexible containers of kit. Tissue processed into single or multi-cell solution in the remaining flexible container is disconnected before transferring into storage or transport container prior to its ultimate utilization.

By way of example, in another embodiment of the method of the invention, where the disaggregation process is being supplemented with enzymatic digestion the media formulation for enzymatic digestion must be supplemented with enzymes that aid in protein breakdown causing the cell to cell boundaries to breakdown as described above.

Various liquid formulations known in the art of cell culturing or cell handling can be used as the liquid formulation used for cell disaggregation and enzymatic digestion of solid tissues, including but not limited to one or more of the following media Organ Preservation Solutions, selective lysis solutions, PBS, DM EM, HBSS, DPBS, PM I, Iscove's medium, XVIVO™, AIM-V™, Lactated Ringer's solution, Ringer's acetate, saline, PLASMALYTE™ solution, crystalloid solutions and IV fluids, colloid solutions and IV fluids, five percent dextrose in water (D5W), Hartmann's Solution DM EM, HBSS, DPBS, RPMI, AIM-V™, Iscove's medium, XVIVO™, each can be optionally supplemented with additional cell supporting factors e.g. with fetal calf serum, human serum or serum substitutes or other nutrients or Cytokines to aid in cell recovery and survival or specific cell depletion. The media can be standard cell media like the above mentioned media or special media for e.g. primary human cell culture (e.g. for endothelia cells, hepatocytes or keratinocytes) or stem cells (e.g. dendritic cell maturation, hematopoietic expansion, keratonocytes, mesenchymal stem cells or T cells). The media may have supplements or reagents well known in the art, e.g. albumins and transport proteins, amino acids and vitamins, metal-ion(s), antibiotics, attachments factors, de-attachment factors, surfactants, growth factors and cytokines, hormones or solubilizing agents. Various media are commercially available e.g. from ThermoFisher, Lonza or Sigma-Aldrich or similar media manufacturers and suppliers.

The liquid formulation required for enzymatic digestion must have sufficient calcium ions present in the of at least 0.1 mM up to 50 mM with an optimal range of 2 to 7 mM ideally 5 mM.

The solid tissue to be digested can be washed after disaggregation with a liquid formulation containing chelating agents EGTA and EDTA to remove adhesion factors and inhibitory proteins prior to washing and removal of EDTA and EGTA prior to enzymatic digestion.

The liquid formulation required for enzymatic digestion is more optimal with minimal chelating agents EGTA and EDTA which can severely inhibit enzyme activity by removing calcium ions required for enzyme stability and activity. In addition, b-mercaptoethanol, cysteine and 8-hydroxyquinoline-5-sulfonate are other known inhibitory substances.

As described in preferred embodiments the final cell container for cryopreservation is a flexible container manufactured from resilient deform able material. In this embodiment of the device the final container is either transferred directly to a freezer −20 to −190° C. or more, optimally located in the controlled rate freezing apparatus either associated with the device or supplied separately (manufactured by for example Planer Products or Asymptote Ltd) in which the temperature of the freezing chamber and the flexible storage container(s) employed to contain the enriched disaggregated solid tissue container is controlled either by: injecting a cold gas (normally nitrogen for example Planer products); or by removing heat away from the controlled cooling surface(s). Both methods result in the ability to accurately control with an error of less than 1° C. or more preferable 0.1° C. the freezing process at the required rate for the specific cell(s) to be frozen based on the freezing solution and the desired viability of the product. This cryopreservation process must take into account the ice nucleation temperature which is ideally as close as possible to the melting temperature of the freezing solution. Followed by crystal growth in an aqueous solution, water is removed from the system as ice, and the concentration of the residual unfrozen solution increases. As the temperature is lowered, more ice forms, decreasing the residual non-frozen fraction which further increases in concentration. In aqueous solutions, there exists a large temperature range in which ice co-exists with a concentrated aqueous solution. Eventually through temperature reduction the solution reaches the glass transition state at which point the freezing solution and cells move from a viscous solution to a solid like state below this temperature the cells can undergo no further biological changes and hence are stabilized, for years potentially decades, until required.

The disaggregated cell products achieved by the method of the present invention can be cultured and/or analyzed (characterized) according to all methods known to the person skilled in the art.

The TILs obtainable by the methods disclosed herein may be used for subsequent steps such as research, diagnostics, tissue-banks, biobanks, pharmacological or clinical applications known to the person skilled in the art. TILs can then be taken into culture using a Medium optimized for this application, e.g. T cell Mixed Media (Cellular Therapeutics) usually containing but not limited to growth factors such as IL-2, IL-7, IL-15, IL-21 or stimulatory conditions such as plates or polystyrene beads coated with antibodies. In the present invention isolated cells were seeded into culture containers and maintained using procedures standardly used by a person skilled in the art such as a humidified atmosphere (1-20% usually 5% CO, 80 to 99% usually 95% air) at temperatures between 1 to 40° C., usually 37° C., for several weeks and supplements may be added supplemented with 10% FBS and 3000 IU/mL IL-2.

The enriched TILs could be used before and/or after cell culturing as a pharmaceutical composition in the therapy, e.g. cellular therapy, or prevention of diseases. The pharmaceutical composition can be used for the treatment and/or prevention of diseases in mammals, especially humans, possibly including administration of a pharmaceutically effective amount of the pharmaceutical composition to the mammal.

Such TIL cultures, in addition to being formulated as a drug product for the treatment of various cancers, can be used to study e.g. cell function, tumor cell killing, cell signaling, biomarkers, cell pathways, nucleic acids, and other cell or tissue related factors that may be used to identify donor, tissue, cell or nucleic acid status.

The disease may be any disease, which can be treated and/or prevented through the presence of solid tissue derived cells and/or through increasing the concentration of the relevant cells in/at the relevant place, i.e. the tumors or sites of disease. The treated and/or preventively treated disease may be any disorder, e.g. cancer or a degenerative disorder. The treatment may be the transplantation of enriched, engineered or expanded cells or any combination of these and either administered to the relevant part of the body or supplied systemically.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

As described herein the invention provides a kit that allows for the receipt, processing, storing, and/or isolating of material such as tissue, in particular mammalian tissue. Further, the invention provides components of the kit such as flexible containers, for example bags, filters, valves, brackets, clamps, connectors, and/or conduits such as tubing. In particular, bags may be coupled to one or more tubes or sections of tubing adapted to enable flow of tissue material between various components of a cryopreservation kit.

Processing of tissue to cells using a cryopreservation kit and/or a collection bag may include automated and/or semi-automated devices and methods.

Moreover, by utilizing the bags, kit, devices and processes described herein, in conjunction with ordinary skill in the art, further embodiments of the present disclosure can be readily identified. Those skilled in the art will readily understand known variations.

Design Patent Application Ser. No. 29/740,293 provides a tissue collection bag suitable for tissue collection. The top of the tissue collection bag of the invention is open, for receiving tissue, e.g., a tissue biopsy, such as animal (e.g., domestic animal such as dog or cat) or human cancerous tissue. The tissue collection bag is to be sealed with collected tissue therein, and for the tissue so sealed therein to be processed therein, e.g., processing can include agitation and/or compression, e.g., gentle agitation and/or compression, and/or enzymatic digestion of the tissue therein. Advantageously the tissue processing and extraction therein, from the desired material, such as tumor infiltrating lymphocytes (TILs), can be in a closed system. Advantageous or preferred embodiments can include indicia to indicate the patient from whom the tissue was collected and/or indicia to show where the collection bag may be clamped or affixed in place in an instrument for applying agitation and/or indicia to show where the collection bag may be sealed, e.g., by heat sealing (which may be part of the instrument for processing). Advantageously, prior to application of processing, the collection bag is clamped or affixed into an instrument for processing and/or sealed, e.g., heat sealed. In certain illustrations, tubing may be shown with dotted lines or stippling to show that the tubing is not necessarily considered part of the inventive design; but in certain embodiments may be considered part of the inventive design. The dotted lines or stippling is to be interpreted as the tubing may be present or absent and may be claimed as either or both, i.e.. throughout the drawings the tubing can form part of the inventive design (and also may not necessarily be part of the inventive design). In addition, while certain illustrations show no indicia, indicia that may indicate a patient from whom a sample was obtained, indicia that may indicate a patient from whom a sample was obtained and where the tissue collection bag may be clamped or affixed into an instrument, and indicia that may indicate a patient from whom a sample was obtained and where the tissue collection bag may be clamped or affixed into in an instrument and where the tissue collection bag may be sealed, e.g., heat sealed, it is to be understood that the inventive design can include variations thereof, e.g., the inventive design may include indicia that may indicate a patient from whom a sample was obtained and where the tissue collection bag may be heat sealed without also indicia showing where the tissue collection bag may be clamped or affixed into an instrument; and the inventive design may include indicia that may indicate where the tissue collection bag may be heat sealed and/or indicia showing where the tissue collection hag may be clamped or affixed into an instrument but without indicia indicating a patient from whom a sample was obtained (including as patient indicia may be imprinted onto the tissue collection bag as it is being used, whereas indicia as to clamping or affixing or heat sealing may already be on the tissue collection bag prior to being in use). The tissue collection bag including any associated tubing can be generally clear or transparent or translucent, or any color desired. The tissue collection bag including any associated tubing can be generally fabricated in ways analogous to the fabrication of: closed or sealed, blood collection, tissue culture, bio-processing or cryopreservation bags and associated tubing. The associated tubing in the invention may be constructed from any desired material, with polyvinyl chloride (PVC) or a material including PVC as a desired material as that is advantageous for welding and/or sealing. The portion of the tissue collection bag of the invention for receiving the tissue can be made from any desired material, with ethylene vinyl acetate (EVA) or a material including EVA as a desired material as that is advantageous for heat sealing.

Figure 11A:
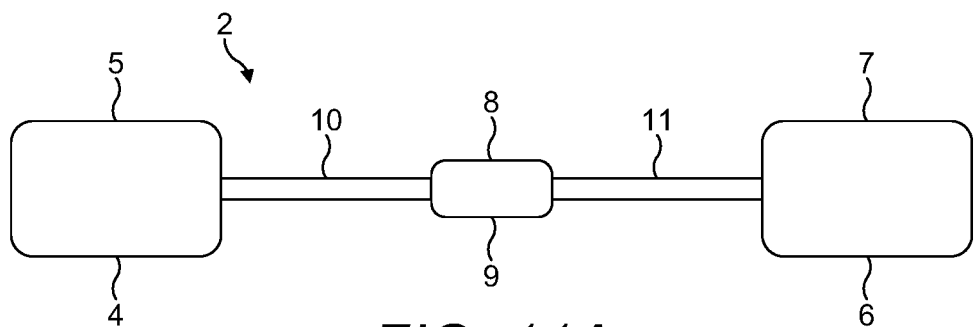
FIG. 11A shows a view of an embodiment of kit for processing and storing tissue materials.

As shown in FIG. 11A, an embodiment for kit 2 for treating tissue, for example, the disaggregation, enrichment, and/or stabilization of tissue. Tissue to be treated may include solid eukaryotic, in particular, mammalian tissue, such as tissue from a sample and/or a biopsy. Kit 2 includes components such as bags 4, 6, such as collection bag 4 and cryopreservation bag 6. Kits as depicted in FIG. 11A-D may be used in an automatic or a semi-automatic device for treatment.

In some embodiments, kit components may include indicators, such as codes, letters, words, names, alphanumeric codes, numbers, images, bar codes, quick response (QR) codes, trackers such as smart trackers and/or Bluetooth trackers, tags such as a radio frequency tag, and/or other digitally recognizable identification tag so that it may be scanned and recognized during automated and/or semi-automated treatment such as within an automated device in embodiments of the present invention. For example, a tag may provide information about the conditions and/or steps required to be automatically treated. For example, scanning a kit component such as a bag may allow an automated system used with the kit to treat tissue without further intervention and/or contamination. In particular, a tissue sample that has been placed in a collection bag for treatment in a disaggregation element of a device. The collection bag may be sealed before treatment begins. In some embodiments, a collection bag may be sealed manually and/or automatically using energy such as heat, radio frequency energy, high frequency (HF) energy, dielectric energy, and/ or any other method known in the art before treatment begins.

In some embodiments, a heat sealer (e.g., Van der Staehl MS-350, Uline H-190 Impulse Sealer, or similar sealers known in the art) with a heating bar the bar may be used to create a seal on a bag.

In a particular embodiment, when using a heat sealer it may be advantageous to form the seal at a temperature below about 100° C. and in at a pressure in a range from about 0.8 bar to about 2.8 bar. This elevated temperature and pressure may be applied for about eight seconds after which the temperature may be reduced but the pressure continues to be applied for about 2 to 3 seconds in some embodiments. The values for temperature, pressure, and time will vary based upon the formulation of the material forming the bag and in particular the material forming the seal. For example, another material may require that the sealer reach a temperature above about 210° F. (98.9° C.) for a minimum of about 3 seconds after which the heating bar may be allowed to cool for 5 seconds prior to removing the heating bar.

Positioning of the material to be sealed may be critical to the strength of the seal formed. For example, incomplete seals, folds, channels, and/or gaps in the material to be sealed may reduce the strength of the seal.

Seals may be tested for strength using a seal peel test (i.e., ASTM F88/F88M), and/or a burst test (i.e., ASTM F1140/F1140M or ASTM F2051/F2054M).

In some embodiments, a bag or a flexible container may withstand a force of 100 Newtons during use when properly sealed and further secured with a clamp when positioned within a device for treatment and/or processing. A bag or a flexible container embodiment may be constructed to withstand a force of 75 Newtons during use when properly sealed and further secured with a clamp when positioned within a device for treatment and/or processing.

As shown in FIG. 11A, kit 2 includes disaggregation element 4 where collection bag 5 may be treated, enrichment element 8 where filter 9 may be located, and stabilization element 6 where cryopreservation bag 7 is used to preserve the desired material. In a component of kit 2, such as collection bag 5, tissue is treated. For example, collection bag 5 may be used for the disaggregation of solid tissue derived from eukaryotic cells. Tissue may be treated in such manner that a majority of the resulting tissue after processing may be single cells and/or small cell number aggregates. Further, processing may occur in the kit and/or in the collection bag in particular.

Enrichment of the treated tissue may occur at enrichment element 8 in filter 9. Filter 9 may be selected such that the filtered composition (i.e., desired material) entering tubing 11 may have constituents having a predetermined size. Filter 9 may be selected such that the desired material composition entering tubing 11 may have constituents such as tumor infiltrating lymphocytes (TILs) having an average size of less than about 200 pm. In particular, in an embodiment the desired material may include tumor infiltrating lymphocytes (TILs) having an average size of less than about 170 pm.

In some embodiments, the desired material may include tumor infiltrating lymphocytes (TILs) in a range from about 15 pm to about 500 pm. For example, filter 9 may, in an embodiment, be configured such that a tissue composition entering tubing 11 has constituents having an average size of less about 200 pm. In particular, the desired material exiting the filter and entering the tubing 11 after being filtered may have constituents having an average size of less than about 170 pm.

In some embodiments, filter 9 is configured such that the filtered composition entering tubing 11 has constituents having a size in a range from about 50 pm to about 300 pm. For example, filter 9 may in an embodiment be configured such that a tissue composition entering tubing 11 has constituents having an average size in a range from about 150 pm to about 200 pm.

As shown in FIG. 11A, stabilization element 6 of the system for treating tissue is where cryopreservation bag 7 may be used to stabilize the tissue composition for storage and/or transport.

Figure 11B:
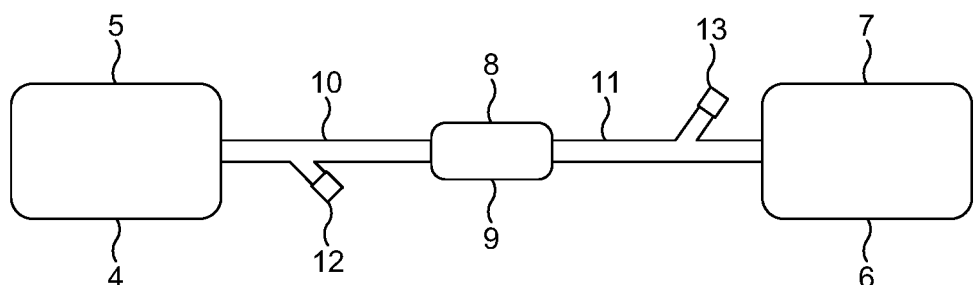
FIG. 11B shows a view of an embodiment of kit for processing and storing tissue materials.

FIG. 11B depicts kit 2 having valves 12, 13. Valves may be needle free valves. Valves 12, 13 may be used to provide enzyme media such as a tumor digesting media, cryoprotectant, and/or cryopreservation media. In particular, valve 12 may be used to provide an enzyme media to tubing 10. Enzyme media may travel to collection bag 4 to aid in the processing of tissue placed in bag 5.

Valve 13 may be used to provide a cryoprotectant such as a DMSO solution to tubing 11 such that the DMSO solution may travel to cryopreservation bag 7. In some embodiments, a cryoprotectant such as a DMSO solution may mix with the filtered material entering tubing 11 such that a combined composition of DMSO solution and filtered material enters cryopreservation bag 7. The filtered material entering tubing 11 may include constituents, such as tumor infiltrating lymphocytes (TILs) having a predetermined average size. For example, in some embodiments an average size of constituents in the filtered composition may be less than about 200 pm.

Figure 11C:
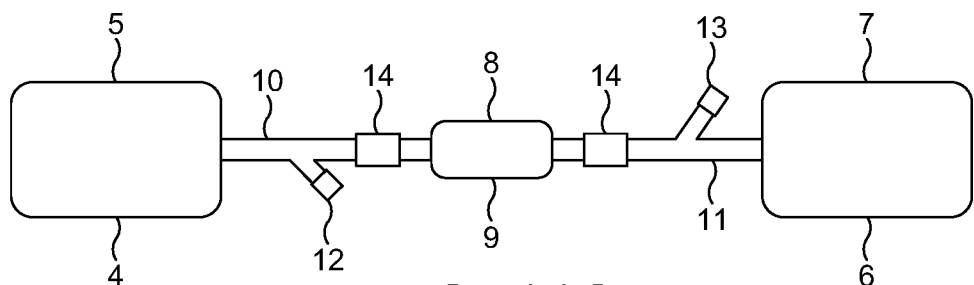
FIG. 11C shows a view of an embodiment of kit for processing and storing tissue materials.

In some embodiments, as shown in FIG. 11C, kit 2 includes clamps 14 around filter 9 to ensure that materials provided through valves 12, 13 are inhibited and/or prevented from flowing into filter 9. Valve 13 may be used to provide a cryoprotectant to tubing 11 such that the cryoprotectant may mix with the filtered material entering tubing 11 from filter 9. For example, clamp 14 may be positioned to inhibit and/or prevent flow of the cryoprotectant in the direction of filter 9. In some embodiments, after the filtered solution starts to flow from filter 9 clamp 14 will be released such that a combined composition of cryoprotectant and filtered material enters cryopreservation bag 7 at stabilization element 6. The filtered material entering tubing 11 may include constituents, such as tumor infiltrating lymphocytes (TILs) having a predetermined average size. For example, in some embodiments an average size of constituents in the filtered composition may be less than about 200 pm.

Figure 11D:
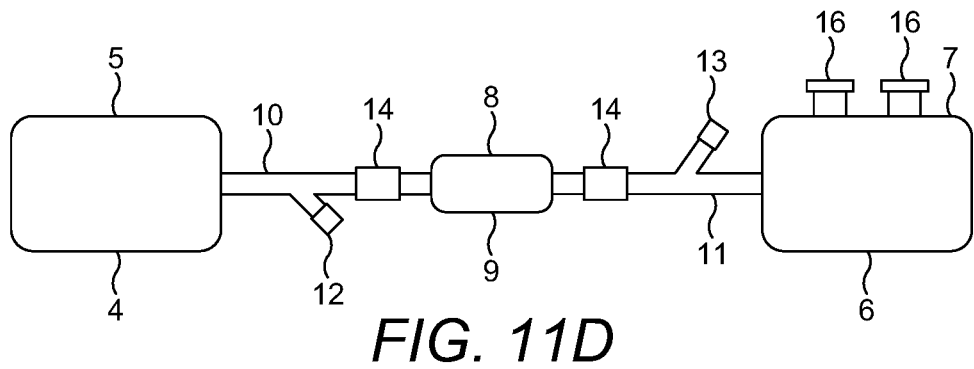
FIG. 11D shows a view of an embodiment of kit for processing and storing tissue materials.

An embodiment of kit 2 may include ports 16 on cryopreservation bag 7 as is shown FIG. 11D. Ports may be used to add and/or remove materials from cryopreservation bag 7. For example, test samples may be removed from cryopreservation bag.

Figure 12C:
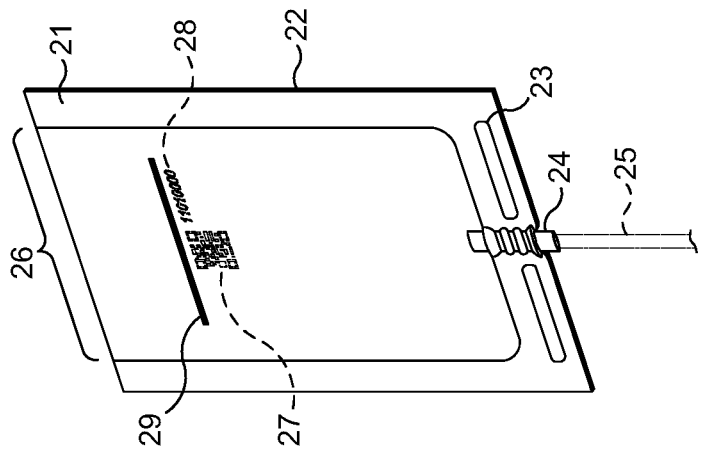
FIG. 12C shows a perspective view of an embodiment of a collection bag.
Figure 12B:
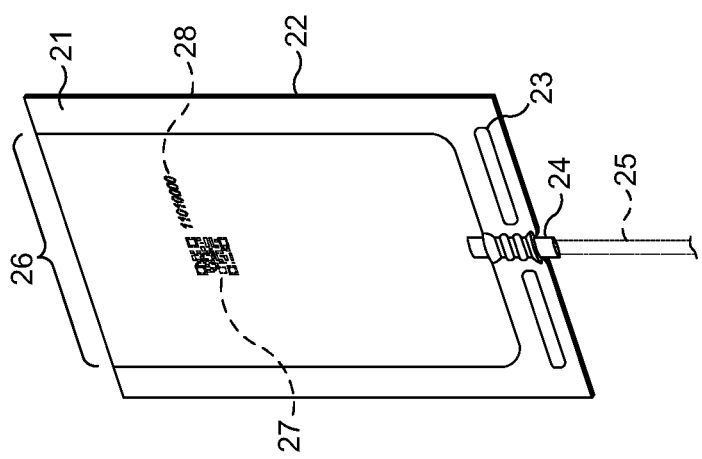
FIG. 12B shows a perspective view of an embodiment of a collection bag.
Figure 12A:
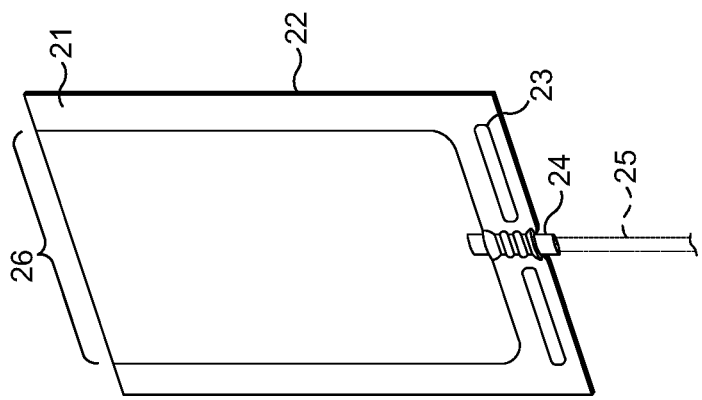
FIG. 12A shows a perspective view of an embodiment of a collection bag.

FIG. 12A shows a perspective view of an embodiment of bag 22 for use in a kit. Bag 22 may include connector 24, open section 26, sealed section 21, and positioners 23. Connector 24 may be used to couple bag 22 to tubing 25. Positioners 23 may be openings in bag 22.

Bags, such as collection bags and/or cryopreservation bags, and any associated tubing may be generally clear, transparent, translucent, any color desired, or a combination thereof. Bags, for example, collection bags and/or cryopreservation bags, and/or tubing may be generally fabricated in ways analogous to the fabrication of closed and/or sealed blood and/or cryopreservation bags and the associated tubing.

Bags for use in the invention described herein include a collection bag and a cryopreservation bag may include at least a portion made from a predetermined material such as a thermoplastic, polyolefin polymer, ethylene vinyl acetate (EVA), blends such as copolymers, for example, a vinyl acetate and polyolefin polymer blend (i.e., OriGen Biomedical EVO film), a material that includes EVA, and/or coextruded layers of sealable plastics.

Materials for use in the bag may be selected for a specific property and/or a selection of properties, for example, sealability such as sealability due to heat welding, or use of radio frequency energy, gas permeability, flexibility for example low temperature flexibility (e.g., at −150° C., or −195° C.), elasticity for example low temperature elasticity, chemical resistance, optical clarity, biocompatibility such as cytotoxicity, hemolytic activity, resistance to leaching, having low particulates, high transmissions rates for particular gases (e.g., Oxygen and/or Carbon dioxide), and/or complying with regulatory requirements. For example, materials used in the bag may be selected for having a tensile strength greater than about 2500 psi (172 bar) when tested according to the test method for tensile strength outlined in ASTM D-638. In particular, an embodiment of a flexible container, such as a bag, have use materials having a tensile strength greater than about 2800 psi (193 bar) when tested according to the test method for tensile strength outlined in ASTM D-638.

In some embodiments, materials may be selected for specific properties for use in a coextruded material to form at least one layer of a bag. Layers may be constructed such that when constructed an interior layer of the bag is relatively biocompatible, that is the material on an inner surface of the bag is stable and does not leach into the contents of the bag.

For example, a property of interest that may be used to select a material for kit component such as a collection bag, a cryopreservation bag, and/or the associated tubing may relate to sealing, for example heat sealing.

Seals may be tested for strength using a seal peel test (i.e., ASTM F88/F88M), and/or a burst test (i.e., ASTM F1140/F1140M or ASTM F2051/F2054M).

In some embodiments, a bag or a flexible container may withstand a force of 100 Newton's during use when properly sealed and further secured with a clamp when positioned within a device for treatment and/or processing. A bag or a flexible container embodiment may be constructed to withstand a force of 75 Newtons during use when properly sealed and further secured with a clamp when positioned within a device for treatment and/or processing.

Dimensions of bags, in particular collection bags and/or preservative bags, may be specific to the device used to conduct treatment and/or processing. Bag size should be adjusted based on the configuration and/or size of the device(s) used to conduct treatment. Particular care should be taken with placement and/or size of any component that extends beyond the border of a bag, for example, a port, connector or the like. Components such as ports may interfere with the operation of a device used to conduct treatment and/or processing. Further, care should be taken to ensure that a thickness of bags comports with the requirement of the machine, in particular with respect to sealed material such as the manufactured seal.

Tubing in the invention may be constructed from any desired material including, but not limited to polyvinyl chloride (PVC). For example, PVC may be a desired material as PVC is advantageous for welding and/or sealing.

In some embodiments, as depicted in FIGS. 12A-12E, 13A-13E, 14, 20A-20E, 21A-21E, 22A-22D, 27A, 28, 33, and 34 at least one end of a collection bag may be open for receiving tissue. In particular, in an embodiment, a tissue sample, for example from a biopsy may be placed in the bag through the open end, for example, a top end. In some cases, the biopsy sample may be cancerous tissue from an animal (e.g., domestic animal such as dog or cat) or a human.

As shown in FIG. 12A, bag 22 may be used as a tissue collection bag. For example, after tissue is positioned in the bag, the bag may be sealed, and then may be processed. Processing may include agitation, e.g., gentle agitation, extraction, and/or enzymatic digestion of the tissue in the bag. Tissue processing and extraction therefrom of desired material, such as tumor infiltrating lymphocytes (TILs), can be in a closed system. Advantageous or preferred embodiments may include indicators to indicate the patient from whom the tissue was collected and/or marks to show where the collection bag may be clamped, sealed, acted upon by a device, and/or affixed in place in an instrument.

In some embodiments, bag 22 may be formed from a sealable material. For example, bag 22 may be formed from materials including, but not limited to polymers such as synthetic polymers including aliphatic or semi-aromatic polyamides (e.g., Nylon), ethylene-vinyl acetate (EVA) and blends thereof, a vinyl acetate and polyolefin polymer blend, thermoplastic polyurethanes (TPU), polyethylene (PE) and/or combinations of polymers. Portions of a bag may be sealed and/or welded with energy such as heat, radio frequency energy, high frequency (HF) energy, dielectric energy, and/or any other method known in the art.

A collection bag may be used as a processing and/or disaggregation bag. Collection bags may have width in a range from about 4 cm to about 12 cm and a width in a range from about 10 cm to about 30 cm.

For example, a collection bag for use in processing may have a width of about 7.8 cm and a length of about 20 cm. In particular, a bag may be heat sealable, for example, using an EVA polymer and blends thereof, a vinyl acetate and polyolefin polymer blend, and/or one or more polyamides (Nylon).

As depicted in FIG. 12A, bag 22 may be used as a tissue collection bag for sealing tissue therein for processing of the invention.

FIG. 12B shows a perspective view of an embodiment of bag 22 for use as a tissue collection bag. Tissue may be sealed in the bag and then processed. Bag 22 as shown in FIG. 12B may be marked with indicators 27, 28, such as a patient identifier that can identify a patient from whom a tissue sample or biopsy has been taken or obtained.

Indicators may include, but are not limited to codes, letters, words, names, alphanumeric codes, numbers, images, bar codes, quick response (QR) codes, tags, trackers such as smart tracker tags or Bluetooth trackers, and/or any indicator known in the art. In some embodiments, indicators may be printed on, etched on, and/or adhered to a surface of a component of a kit. For example, indicators may be printed directly on a surface of at least one component of a kit as shown in FIG. 12B. Indicators may also be positioned on a bag using an adhesive, for example, a sticker or tracker may be placed on a bag and/or on multiple bags. For example, as shown FIG. 12B bag 22 includes multiple indicators 28 (numeric code), 27 (QR code).

FIG. 12C shows a perspective view of a bag for use as a tissue collection bag. Tissue may be inserted into bag 22 for processing. Indicators may be used to can identify a patient from whom a tissue sample and/or biopsy has been taken or obtained. As shown in FIG. 12C, indicators 27, 28 include a QR code and identifying number used to track a sample, locate a sample, and/or track status of a sample in a process. For example, in some embodiments indicators may be used locate a sample at any given position in a laboratory. Indicators may be placed on bag prior to and/or during use, for example, as the bag is being taken out for use with a sample, patient indicators may be imprinted onto the bag. Further, bag 22 may include mark 29. Marks may be used to show where seals, clamps, and/or instruments should be positioned.

Indicators, for example QR codes, tags such as smart tags, and/or trackers may be used to identify a sample within a bag as well as to instruct a device's processor such that the device runs a specific program according to a type of disaggregation, enrichment, and/or stabilization processes that are conducted in cryopreservation kits. Different types of media may be used in these processes, for example, enzyme media, tumor digest media and/or cryopreservation media which may allow for a controlled rate of freezing. In some embodiments, cryopreservation kit and/or components thereof may include indicators that may be readable by an automated device. The device may then execute a specific fully automatic method for processing tissue when inserted to such a device. The invention is particularly useful in a sample processing, particularly automated processing.

In some instances, the cryopreservation kit and/or components thereof described herein may be single use. Cryopreservation kits and/or components thereof may be used in an automated and/or a semi-automated process for the disaggregation, enrichment, and/or stabilization of cells or cell aggregates. In some embodiments, bags for use in a cryopreservation kit such as a collection bag may in some embodiments be used for multiple processes. For example, collection bags may be repeatedly sealed in different locations to create separate compartments for processing of a tissue sample such as a biopsy sample and/or solid tissue.

Further, marks may be placed at various locations on bags, such as tissue collection bags to indicate where the bags may be sealed, clamped, and/or affixed to an object. In some embodiments, marks showing where a bag may be clamped, sealed, and/or affixed to an object, such as instrument, may be positioned on the bag prior to use. For example, one or more marks may be positioned on a bag during manufacturing.

Seals may be formed during use with energy, for example, heat to create a weld zone. Seals formed during use may behave a width in a range from about 2.5 mm to about 7.5 mm. Generally, seal 140 is formed after tissue material is placed in bag 140 and may have a width of about 5 mm.

Seals may be tested for strength using a seal peel test (i.e., ASTM F88/F88M), and/or a burst test (i.e., ASTM F1140/F1140M or ASTM F2051/F2054M).

In some embodiments, a bag or a flexible container may withstand a force of 100 Newtons during use when properly sealed and further secured with a clamp when positioned within a device for treatment and/or processing. A bag or a flexible container embodiment may be constructed to withstand a force of 75 Newtons during use when properly sealed and further secured with a clamp when positioned within a device for treatment and/or processing.

When forming seals or welds on a flexible container such as a bag, for example, a collection bag and/or a cryopreservation bag, a sealing device may be used to apply heat and/or pressure at a predetermined temperature, pressure, and amount of time depending on the material used in the bag. For example, some heat sealers may require application of heat and pressure for about eight seconds. After 8 seconds, heat may be turned off on the device, however, pressure may be applied for an additional 2 to 3 seconds.

Figure 12E:
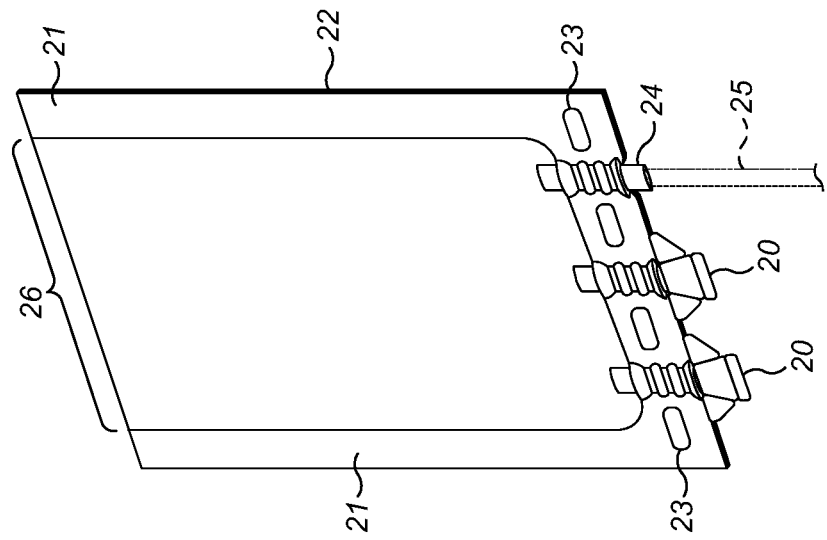
FIG. 12E shows a perspective view of an embodiment of a collection bag.
Figure 12D:
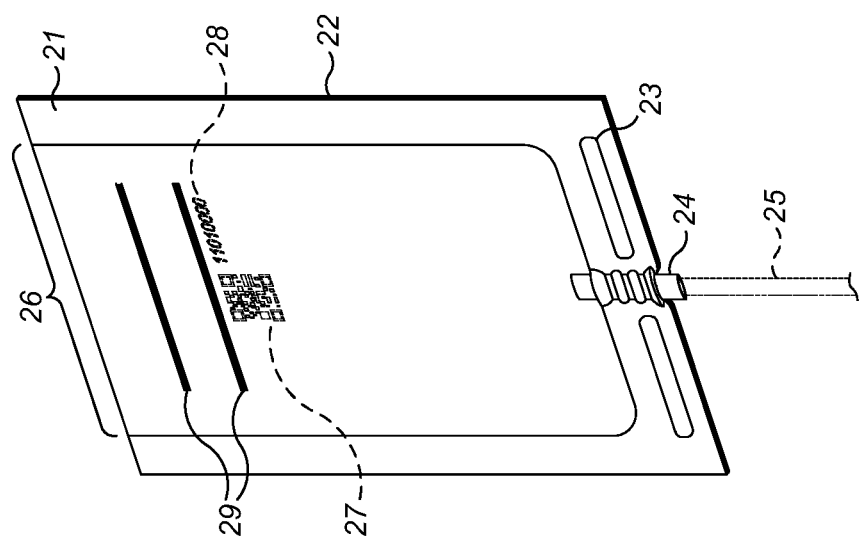
FIG. 12D shows a perspective view of an embodiment of a collection bag.

FIG. 12D shows a perspective view of an embodiment of a tissue collection bag for sealing tissue therein for processing of the invention. Indicators 27, 28 are positioned on bag 22 such that a user can easily identify a patient during use. Further, these indicators may be used to identify materials in the bags as well as track the progress during a particular method of treatment for the materials in the bags. In some embodiments, a bag holds a volume of media in a range from about 0.1 ml to about 25 ml and a volume of tissue in a range from about 0.1 ml to about 10 ml in the bag during treatment. A ratio volume of media to a volume of tissue in a bag during treatment should be in a range from about 1.0 to about 2.5. In some embodiments, a ratio of the volume of media to a volume of tissue is in a range from about 1.7 to about 2.3. In particular, a ratio of the volume of media to a volume of tissue is in a range from about 2.0 to about 2.2.

As shown in FIG. 12D, marks 29 are positioned proximate open end 26 of bag 22. During use marks 29 may be positioned on a bag based on a method used to treat a tissue sample and/or biopsy sample. Marks may be placed on a bag during use, for example, based on the processing method being used or to be used and/or the equipment to be used. In some embodiments, marks may be positioned on a bag during manufacturing. For example, positioning of marks for the locations of sealing and/or clamping may vary based on the processing method and/or volume of tissue to be treated.

FIG. 12E shows a perspective view of a tissue collection bag. Tissue may be sealed in bag 22 processing. Connector 24 may provide access to the bag. As shown connector 24 may be connected to other devices such as filter, bags, etc. using tubing 25. Ports 20 may be used to take samples from bag 22 and/or provide materials from bag 22 during use.

FIG. 13A shows a front view of a bag used for tissue collection. Tissue may be sealed within hag during use. Bag 30 may be manufactured having sealed edge 31. As shown in FIG. 13A, sealed edges 31 may be located on three edges and fourth edge may include open section 36.

Positioners 33 on bag 30 may be used to position a bag. For example, one or more positioners may be used to ensure that bag can be treated properly during use, for example, positioning proximate an instrument. In some systems, the positioners may facilitate the use of the bags described herein in automated systems. In particular, positioners may be used to move bag through an automated system.

As shown in FIG. 13B, bag 30 may have indicators 36, 37 used to identify a sample, for example, an indicator that identifies a patient from whom a tissue sample or biopsy has been taken or obtained. Use of an indicator 37 such as a QR code may allow for tracking of process steps for a specific sample such that it is possible to follow the sample through a given process.

FIG. 13C shows a front view of a tissue collection hag. Tissue may be sealed within a bag and treated and/or processed therein. Bag 30 may have indicators 37, 38 used to identify a sample, for example, an indicator that identifies a patient from whom a tissue sample or biopsy has been taken or obtained. Use of indicator 37 such as a QR code may allow for tracking of process steps for a specific sample such that it is possible to follow the sample through a given process. Positioners 33 may be used to position bag 30 for treatment. Connector 34 may allow tissue, treated tissues, etc. to couple to other device through tubing 35.

Figure 13E:
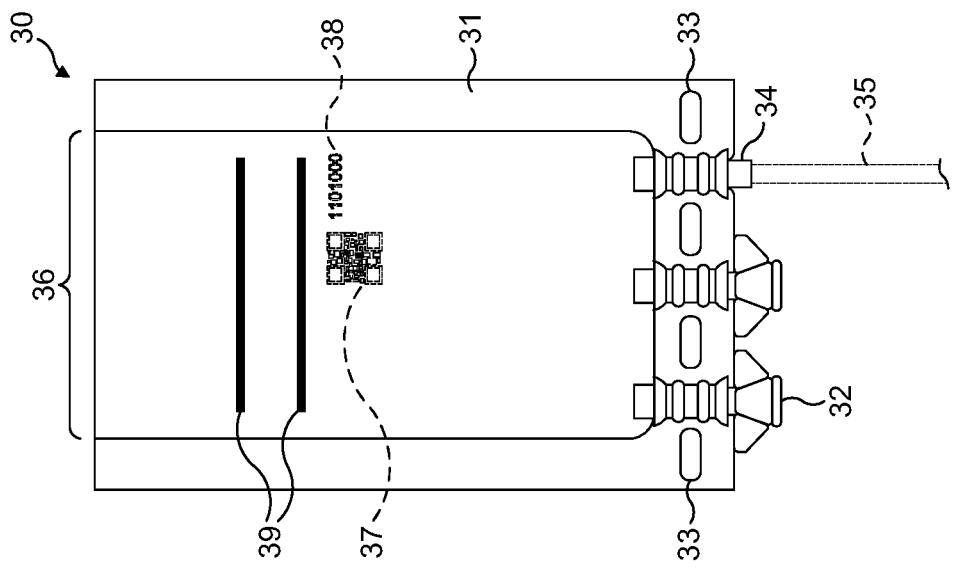
FIG. 13E shows a front view of an embodiment of a collection bag.
Figure 13D:
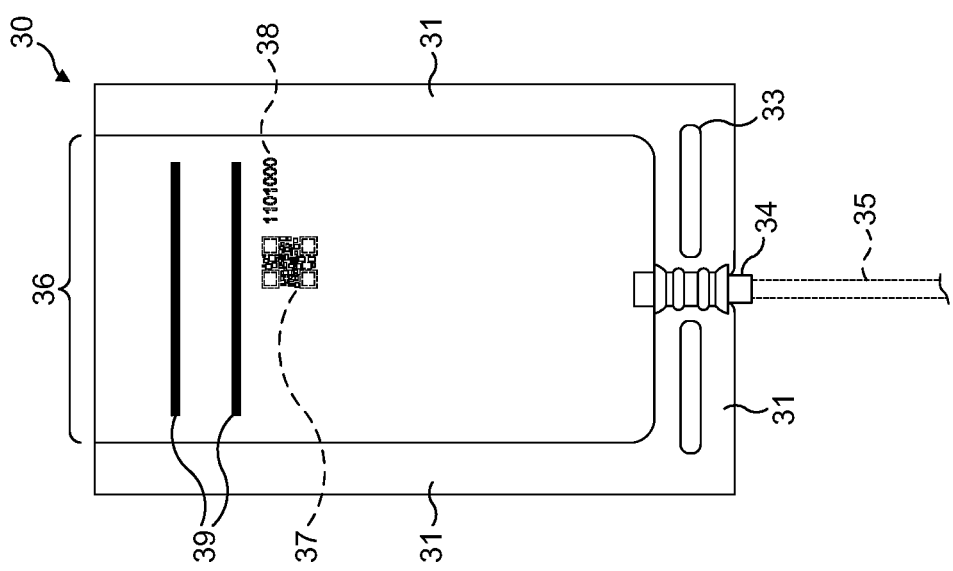
FIG. 13D shows a front view of an embodiment of a collection bag.

FIG. 13D depicts a front view of a tissue collection bag having indicators 37, 38 used to identify a sample. Use of an indicator 37 such as a QR code may allow for tracking of process steps for a specific sample such that it is possible to follow the sample through a given process. Marks 39 and/or positioners 33 may be used to control positioning of the bag during processing and/or treatment. Marks placed proximate an open end to indicate where to position, seal and/or clamp the bag during use. Bag 30 may be manufactured having sealed edges 3 L As shown in FIG. 13D, sealed edges 31 may be located on three edges and fourth edge may include open section 36.

FIG. 13E shows a front view of a tissue collection bag which is capable of being sealed after tissue is placed therein. Connectors 34 and ports 32 may provide access to the bag. One or more ports may be positioned on a collection bag such that the ports allow for input of media and/or reagents and/or extraction of sample from the bags.

As shown connector 34 may be coupled to other devices such as filter, bags, etc. using tubing 35. Marks and indicators may be placed one or more sides of the hag depending on use. In particular, as shown if FIG. 13E, positioners 33, marks 39, and/or indicators 37, 38 may be used to position bag 30 for processing such as applying agitation, sealing, e.g., by heat sealing (which may be part of the instrument for processing), addition of materials for processing and/or extraction. Advantageously, prior to application of processing, the collection bag is clamped or affixed into an instrument for processing and/or sealed, e.g., heat sealed.

Figure 14:
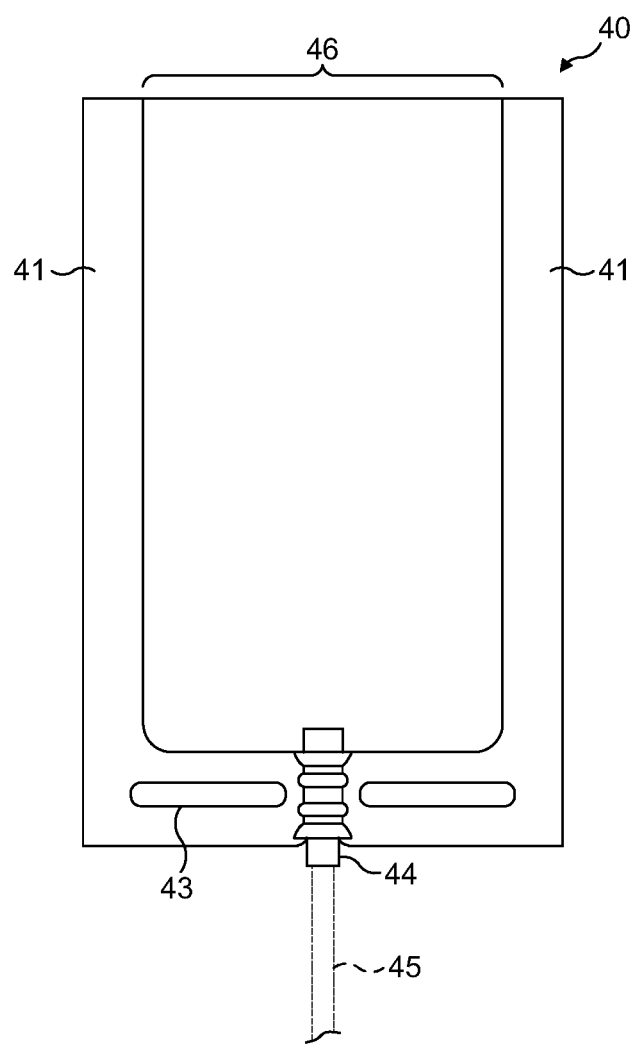
FIG. 14 shows a back view of an embodiment of a collection bag.

FIG. 14 shows a back view a bag for tissue collection. In particular, bag 40 is capable of being sealed with tissue positioned therein and processed. Seal may be positioned proximate open end 46 and substantially parallel thereto. As shown connector 44 may be connected to other devices such as filter, bags, etc. using tubing 46. Bag 40 may be manufactured having sealed edge 41. As shown in FIG. 14, sealed edges 41 may be located on three edges and fourth edge may include open section 46. Positioners 43 may be surrounded by manufactured sealed edge 41.

Figure 15:
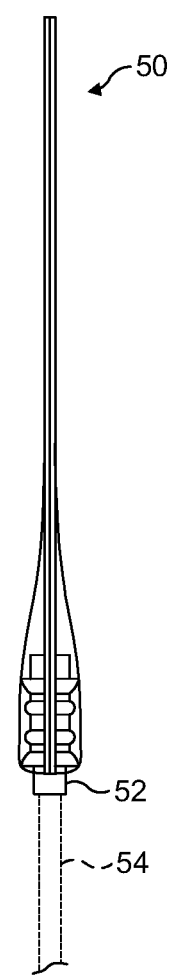
FIG. 15 shows a side view of an embodiment of a collection bag.

FIG. 15 depicts a side view of bag 50 for use in tissue collection capable of sealing tissue therein and allowing processing of the tissue during use of the bag. Bag 50 may be coupled to tubing 54 by connector 52.

FIG. 16A shows a top view of an unsealed tissue collection bag. Bag 60 may include sealed portions 66 and open portion 64. Connector 62 is visible through bag 60. After placing tissue in bag open portion of top of bag 60 may be sealed.

FIG. 16B shows a bottom view of the tissue collection bag 60 having sealed edges 66 for sealing tissue therein for processing. Connector 62 visible on bag 60.

FIG. 17A shows a top view of partially open bag. Bag 70 may include sealed portions 76 and open portion 74. Connector 72 is visible through bag 70. After placing tissue in bag open portion of top of bag 70 may be sealed.

FIG. 17B shows a bottom view of the tissue collection bag for sealing tissue therein for processing. Connector 72 is visible on bag 70.

Figure 18A:
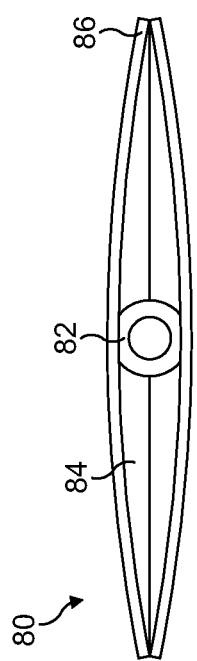
FIG. 18A shows a top view of an embodiment of a partially open tissue collection bag for sealing tissue therein for processing of the invention.

FIG. 18A depicts a top view of a partially open bag. Tissue may be inserted through open end 84 of bag 80. Connector 82 is shown positioned at the bottom of bag 80.

Figure 18B:
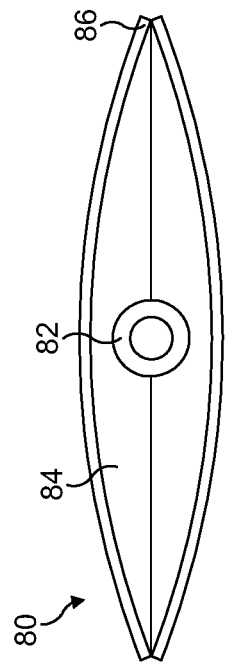
FIG. 18B shows a top view of an embodiment of a fully open tissue collection bag for sealing tissue therein for processing of the invention.

FIG. 18B shows a top view of a fully open bag for the collection and/or processing of tissue. Open end 84 of bag 80 may receive tissue for processing such as treatment, isolation, and/or separation. Sealed edges 86 may be created during manufacturing.

Figure 19A:
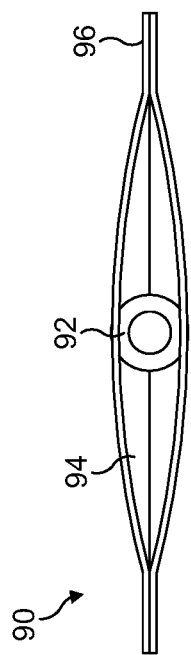
FIG. 19A shows a top view of an embodiment of a partially open tissue collection bag for sealing tissue therein for processing of the invention where the bag has sealed edges having a predetermined width.

FIG. 19A depicts a top view of partially open hag 90 having sealed edges 96 on the sides of the bag. As shown, tissue may be inserted through open end 94 of bag 90. Connector 92 is shown positioned at the bottom of bag 90.

Figure 19B:
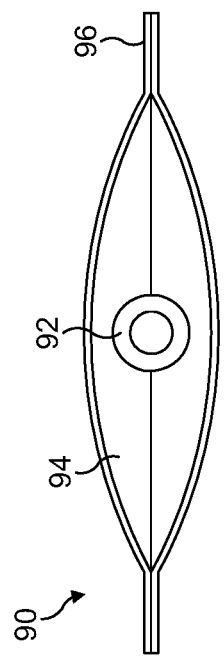
FIG. 19B shows a top view of an embodiment of a fully open tissue collection bag for sealing tissue therein for processing of the invention where the bag has sealed edges having a predetermined width.

FIG. 19B shows a top view of a fully open bag for the collection and/or processing of tissue having sealed edges 96 on the sides of the bag. Open end 94 of bag 90 may receive tissue for processing such as treatment, isolation, and/or separation. Connector 92 is shown positioned at the bottom of bag 94.

Figure 20E:
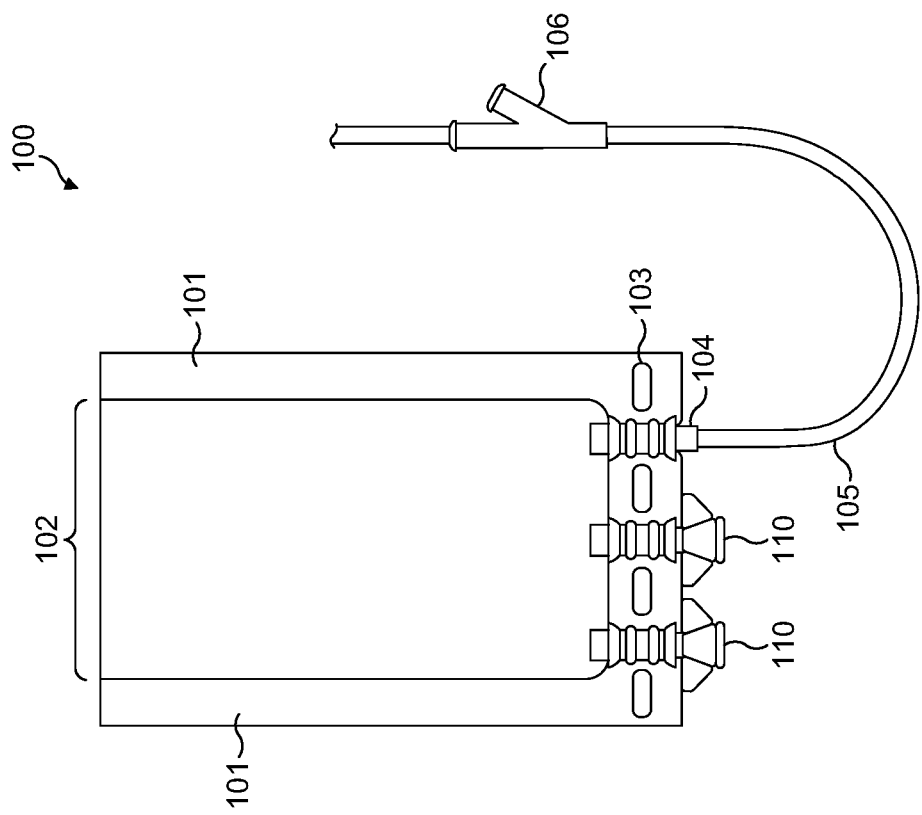
FIG. 20E shows a front view of an embodiment of a collection bag.

FIGS. 20A-20E show a front view of embodiments of tissue collection bags. As shown in FIG. 20A, bag 100 having sealed edges 101 and open end 102 may be connected to devices (not pictured) via tubing 105 and/or connectors 104. For example, connector 104 is positioned in bag 100 while y-connectors $10^6$ may be positioned along tubing. FIG. 20B shows a further embodiment of hag 100 including indicators 107, 108 such that a user can identify a patient from whom a tissue sample or biopsy has been taken or obtained.

Figure 20D:
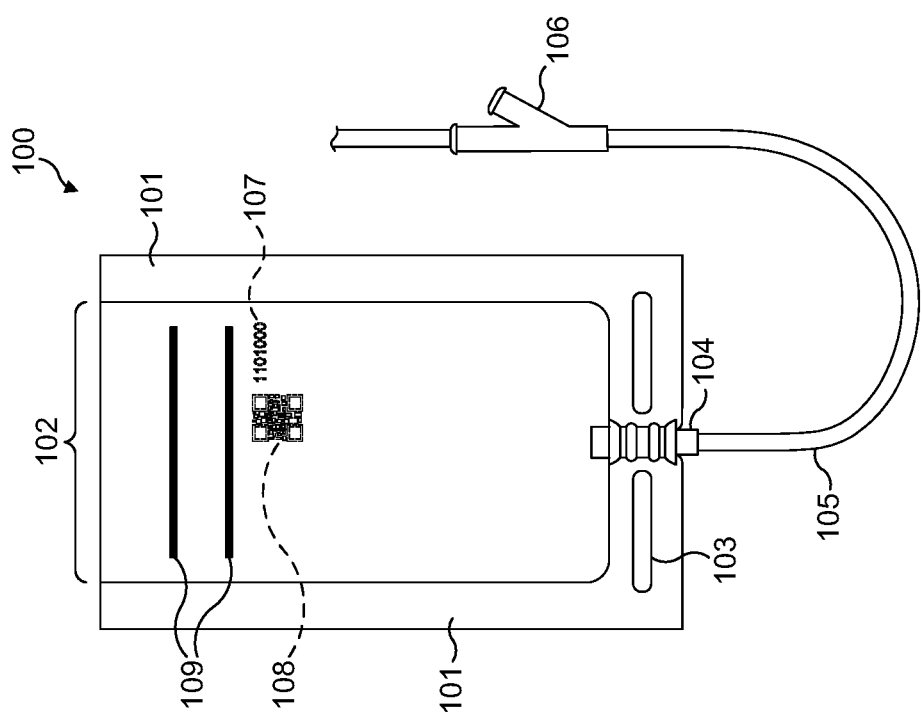
FIG. 20D shows a front view of an embodiment of a collection bag.

In addition, an embodiment of bag 100 that includes mark 109 and indicators 107, 108 is depicted in FIG. 20C. Use of positioners 103 may allow for consistent positioning of bags that allow for consistent processing of tissue within bags. Indicators 107, 108 identify samples with either sample and/or patient information. In some instances, indicators may be used to identify and/or track a sample, such as a tissue sample and/or biopsy sample. FIG. 20D depicts bag 100 having multiple indicators 107, 108 and marks 109. Marks may show locations where bag 100 is to be sealed. For example, marks 109 may indicate locations where bag 100 should be sealed, clamped, and/or couple to another device. Marks for sealing may be positioned proximate an open edge of the bag, for example, such marks may be positioned a predetermined distance from the open edge. Marks for sealing may be substantially parallel to the open edge in some embodiments. As shown bag 100 may include connector 104 and tubing 105.

In an embodiment as shown in FIG. 20E, bag 100 includes ports 110 and connector 104. Ports may allow for addition of materials and/or removal of material from the sample. For example, during processing of the tissue, samples may be taken at multiple times throughout processing. Further, ports 110 may allow aseptic input of media and/or reagents into bag 100.

Figures 21A, 21B, 21C:
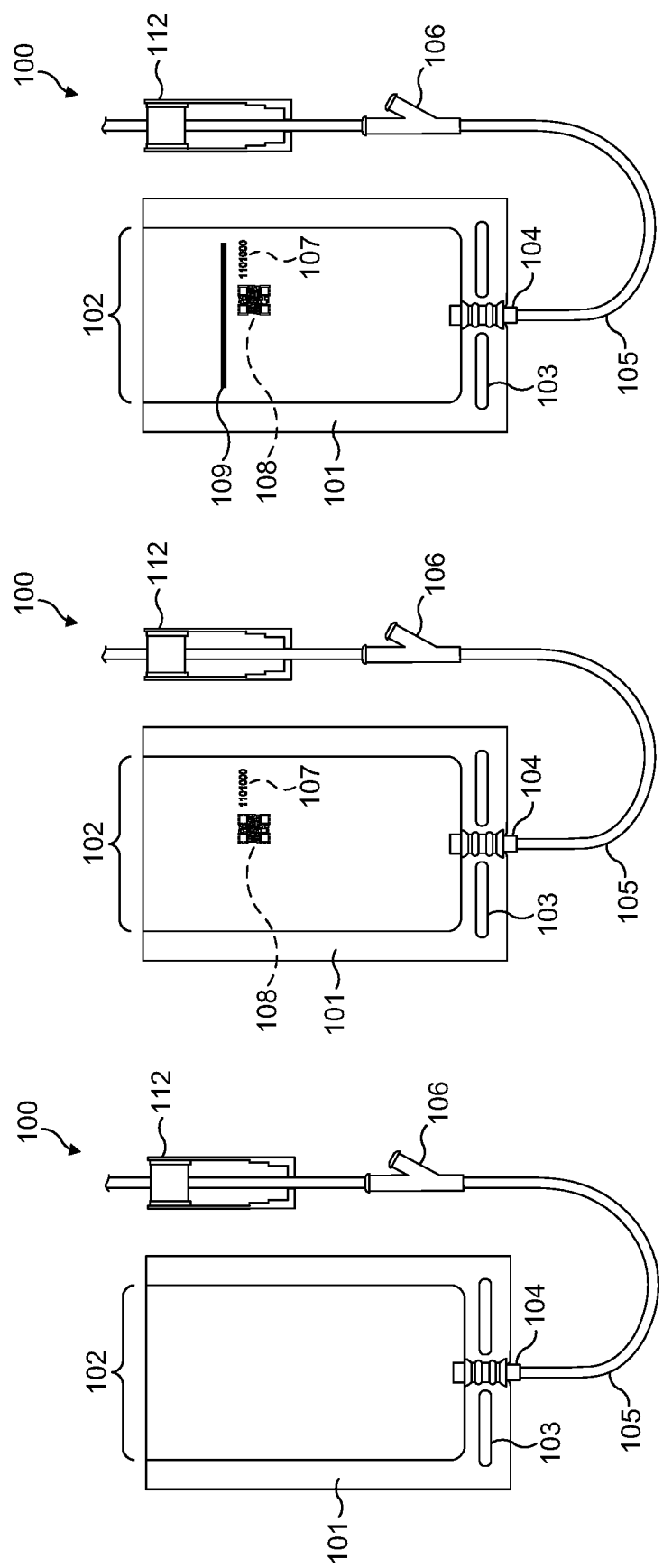
FIG. 21A shows a front view of an embodiment of a collection bag.
FIG. 21B shows a front view of an embodiment of a collection bag.
FIG. 21C shows a front view of an embodiment of a collection bag.

FIG. 21A shows a front view of bag 100 for the collection and/or processing of tissue. Tissue may be placed in bag 100 through open end 102. Connector 104 may be used to couple bag 100 with tubing 105, and clamp 112.

FIGS. 21B-21E show front views of additional embodiments of hag 100. FIGS. 21B-11D show various configurations including indicators 107, 108 and/or marks 109. Bags may include indicators such as codes, letters, words, names, alphanumeric codes, numbers, images, bar codes, quick response (QR) codes, tags, trackers such as smart tracker tags or Bluetooth trackers, and/or any indicator known in the art. In some embodiments, indicators may be printed on, etched on, and/or adhered to a surface of a component of a kit. Indicators may also be positioned on a bag using an adhesive, for example, a sticker or tracker may be placed on a bag and/or on multiple bags. Collection bags and/or cryopreservation kit may include multiple indicators such as numeric codes and/or QR codes.

Indicators, for example QR codes, tags such as smart tags, and/or trackers may be used to identify a sample within a bag as well as to instruct a device's processor such that the device runs a specific program according to a type of disaggregation, enrichment, and/or stabilization processes that are conducted in cryopreservation kits.

Figure 21E:
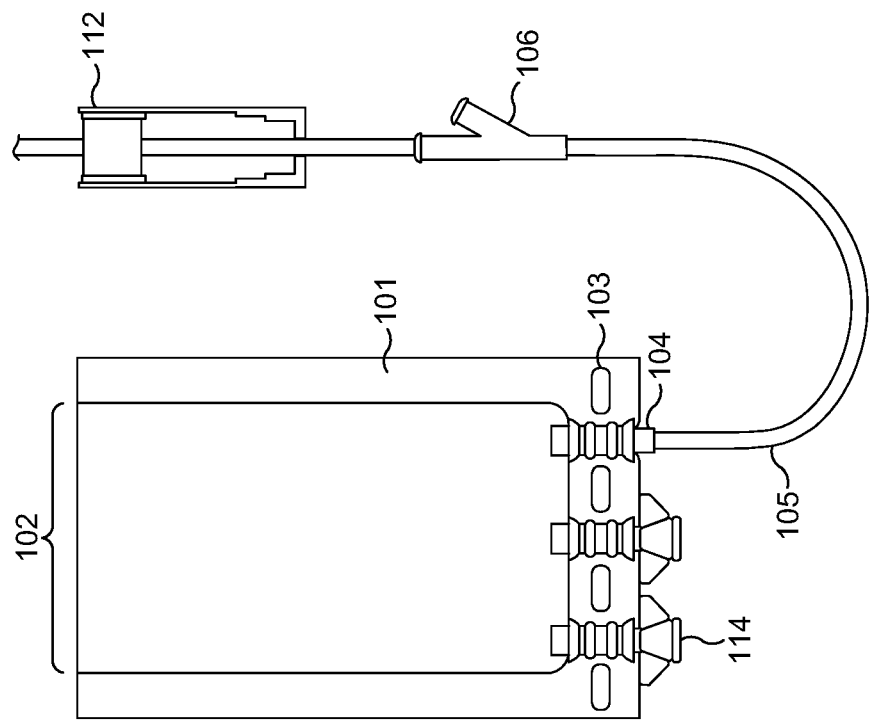
FIG. 21E shows a front view of an embodiment of a collection bag.
Figure 21D:
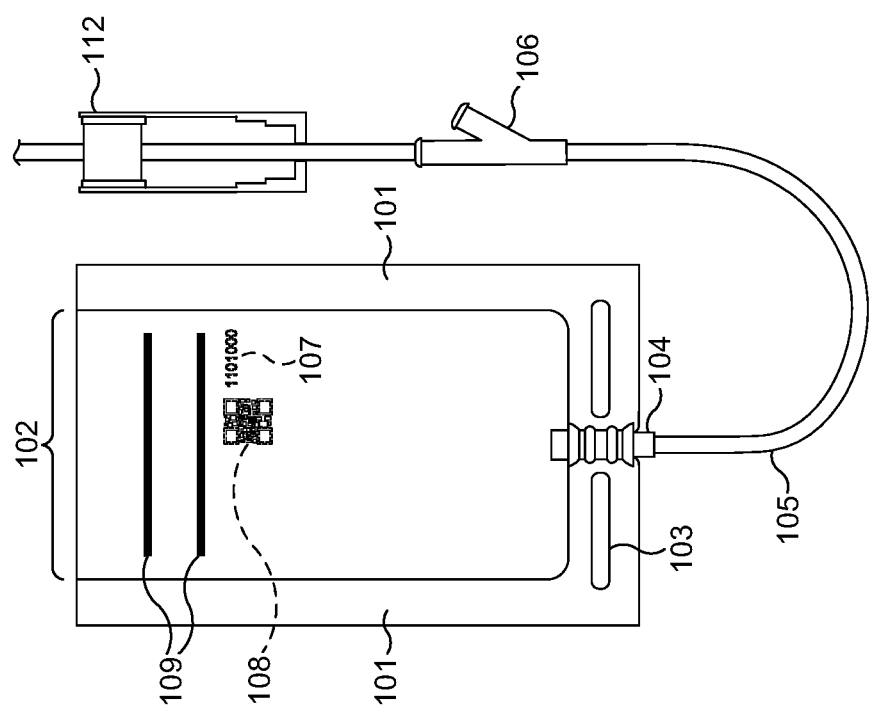
FIG. 21D shows a front view of an embodiment of a collection bag.

FIG. 21E depicts a front view of another embodiment of bag 100 used for collection, processing, treatment, and/or isolation of materials. Tissue to be treated may be sealed within bag 100. Tubing 105 may couple bag 100 through connector 104 to clamp 112. Ports 114 may allow for input and/or removal from bag 100. For example, ports may allow for sampling and/or allow for aseptic input of media and/or reagents into a flexible container, such as a bag of the cryopreservation kit.

Figure 22B:
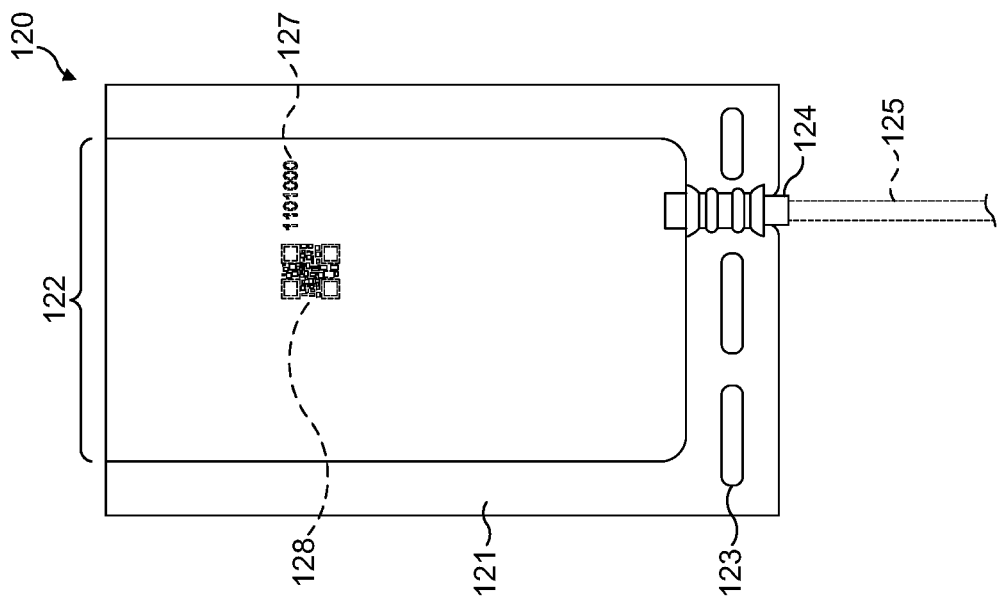
FIG. 22B shows a front view of an embodiment of a collection bag.
Figure 22A:
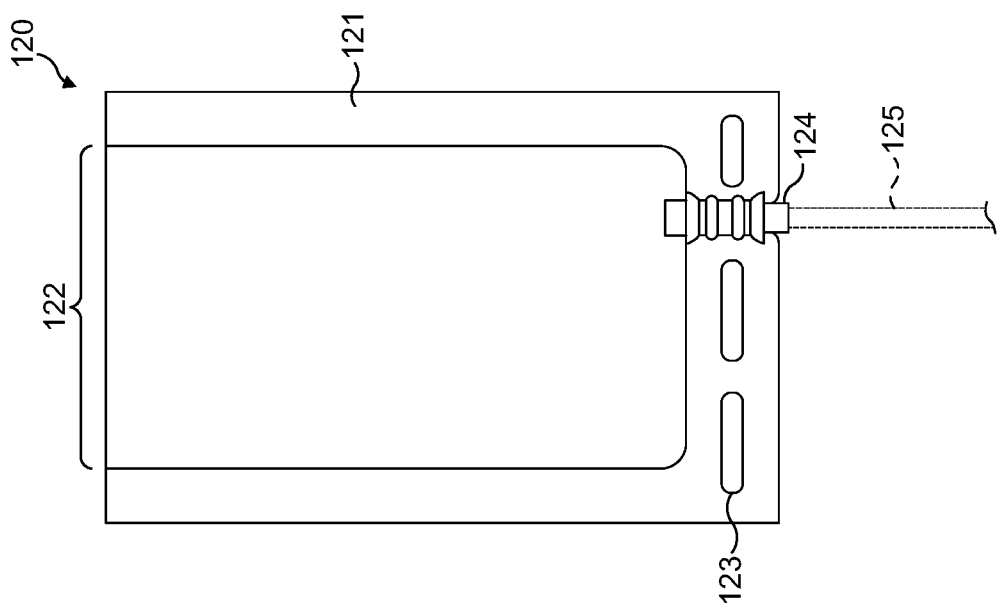
FIG. 22A shows a front view of an embodiment of a collection bag.

FIG. 22A shows a front view of another embodiment of a tissue collection bag 120 having sealed edge 121 for sealing tissue therein for processing. Bag 120 includes positioner 123 and connector 124 coupled to tubing 125.

FIG. 22B shows a front view of tissue collection bag 120 having sealed edges 121 and open end 122. Indicators 127, 128 may be positioned on bag 120 such that they can be easily accessed by an automated system. Openings defining positioners 123 may be surrounded by sealed edges 121. Indicators may be used to identify the patient from whom a tissue sample or biopsy has been taken or obtained.

Figure 22C:
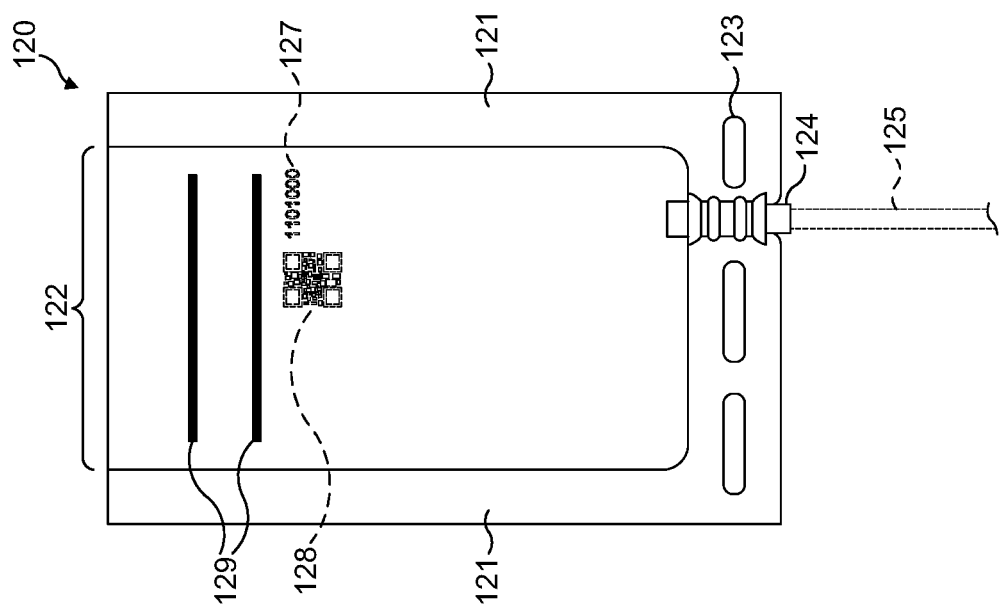
FIG. 22C shows a front view of an embodiment of a collection bag.
Figure 22D:
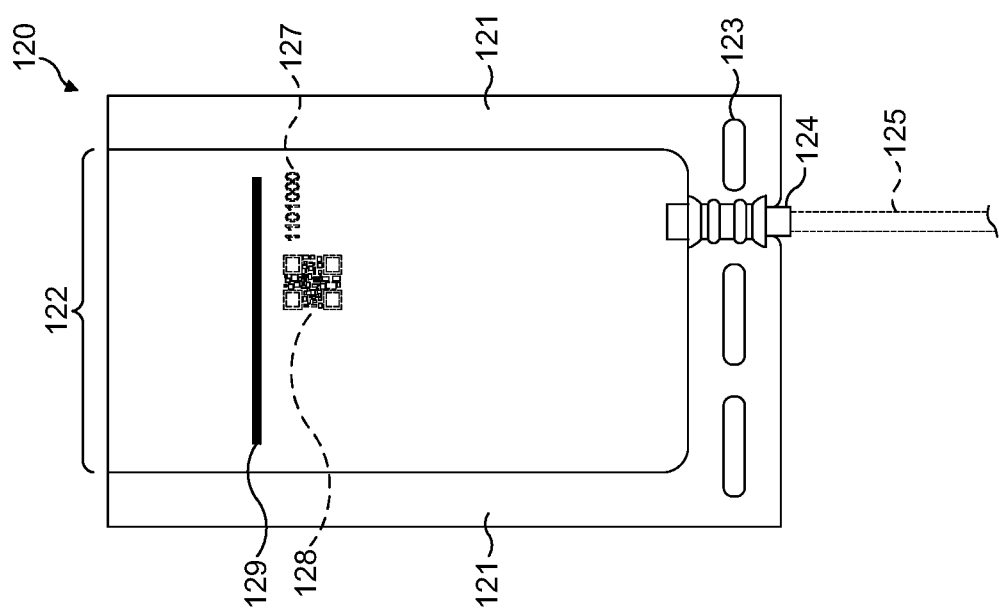
FIG. 22D shows a front view of an embodiment of a collection bag.

As shown in FIG. 22C, bag 120 includes indicators 127, 128 and mark 129. FIG. 22D depicts shows a collection bag 120 having multiple marks 129. Marks for sealing may be positioned proximate an open edge of the bag. Such marks may be positioned a predetermined distance from the open edge. Marks for sealing may be substantially parallel to the open edge in some embodiments.

Figure 23:
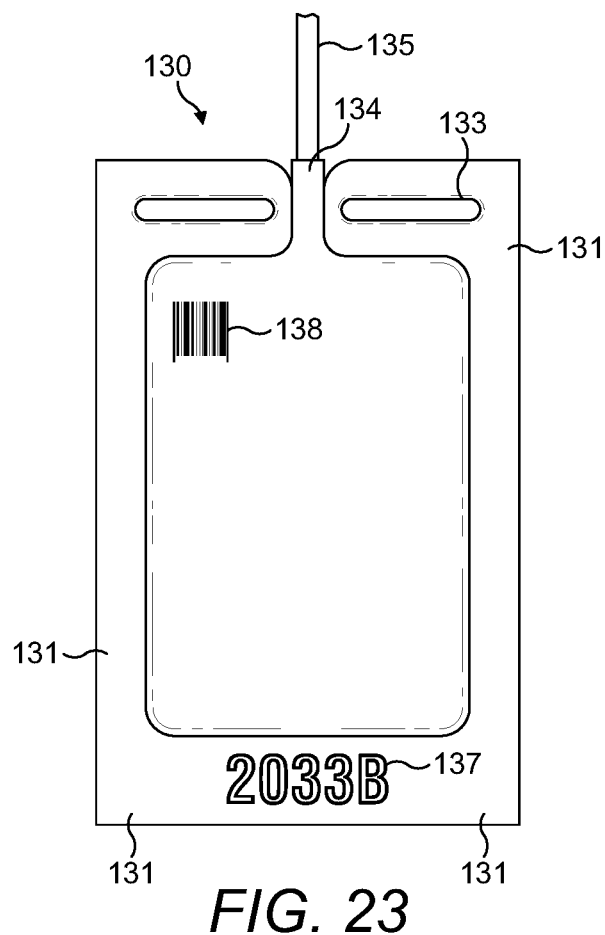
FIG. 23 shows a front view of an embodiment of a collection bag.

FIG. 23 depicts a front view of sealed bag 130 positioned such that the bottom of bag 130 is shown at the top of the page with tubing 135 emerging from connector 134. Bag 130 includes indicator 137 on sealed portion 131 of bag 130. An indicator on the sealed portion may be positioned during and/or after sealing of bag 130. Generally, the bag is sealed after tissue is provided. Indicator 138 on a surface of bag 130 may be a bar code. Positioners 133 may be positioned proximate connector 134.

Bags, such as collection bags and/or cryopreservation bags, and any associated tubing may be generally clear, transparent, translucent, any color desired, or a combination thereof. Tissue collection bags and/or tubing may be generally fabricated in ways analogous to the fabrication of closed and/or sealed blood and/or cryopreservation bags and the associated tubing. Tubing in the invention may be constructed from any desired material including, but not limited to polyvinyl chloride (PVC). For example, PVC may be a desired material as PVC is advantageous for welding and/or sealing.

A collection bag, such as a tissue collection bag of the invention may include at least a portion of the bag for receiving tissue made from a predetermined material such as a polyolefin polymer, ethylene vinyl acetate (EVA), copolymers such as vinyl acetate and polyolefin polymer blend (i.e., OriGen Biomedical EVO film), and/or a material including EVA. Materials for use in the bag may be selected for a specific property and/or a selection of properties, for example, salability such as heat sealability, gas permeability, flexibility for example low temperature flexibility, elasticity for example low temperature elasticity, chemical resistance, optical clarity, biocompatibility such as cytotoxicity, hemolytic activity, resistance to leaching, having low particulate.

Figure 24:
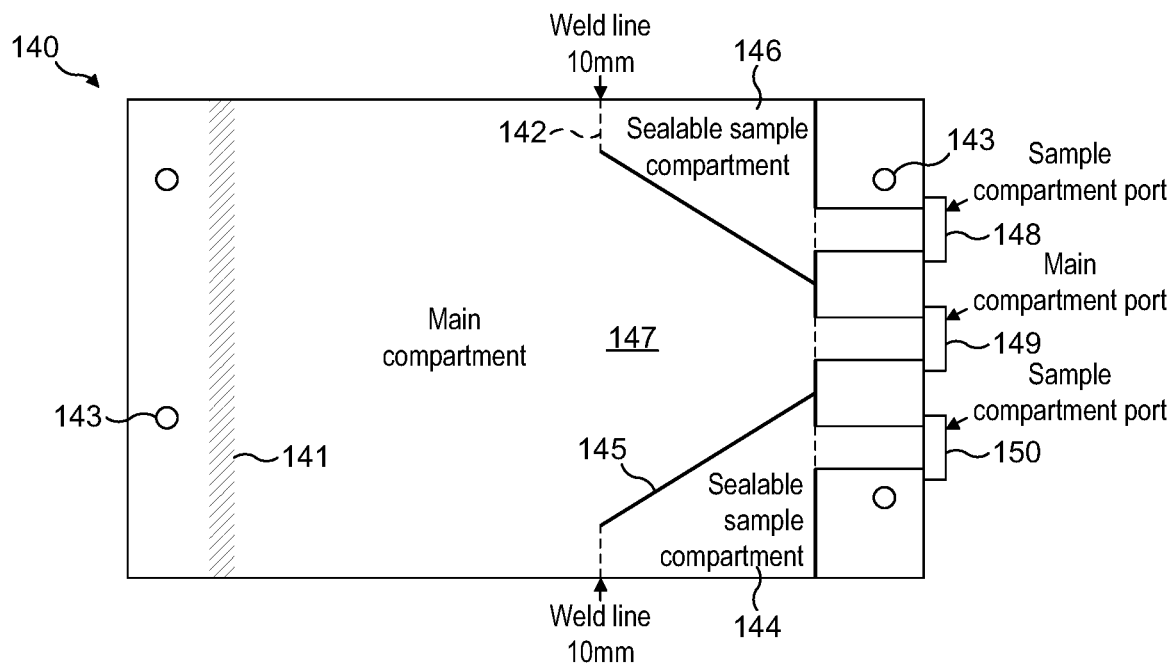
FIG. 24 shows a front view of an embodiment of a collection bag.

As shown in FIG. 24, bag 140 may include multiple marks 141, 142 that are placed such that if the areas including marks are sealed, compartments 143 may be formed in bag 140. Bag 140 has pre-welded sections 145 that are formed during manufacture of the bag that may be used in the formation of the compartments for samples during use. FIG. 24 depicts an embodiment of a collection bag that is capable of being formed such that it has multiple compartments. Each compartment may be formed in a bag by placement of multiple seals and/or welds (e.g., heat sealed). For example, after placing a tumor suspension in a collection bag the open end may be welded shut and additional marks 141 such as weld lines 142 may be welded using energy such as heat to form compartments.

Positioners 143 on bag 140 ensure that the bag is positioned correctly with respect to instruments, such as sealing devices like RF heat sealers and/or injectors.

Seals may be formed during use with energy, for example, heat to create a weld zone. Seals formed during use may behave a width in a range from about 2.5 mm to about 7.5 mm. Generally, seal 140 is formed after tissue material is placed in bag 140 and may have a width of about 5 mm.

Seals may be tested for strength using a seal peel test (i.e., ASTM F88/F88M), and/or a burst test (i.e., ASTM F1140/F1140M or ASTM F2051/F2054M).

In some embodiments, a hag or a flexible container may withstand a force of 100 Newtons during use when properly sealed and further secured with a clamp when positioned within a device for treatment and/or processing. A bag or a flexible container embodiment may be constructed to withstand a force of 75 Newtons during use when properly sealed and further secured with a clamp when positioned within a device for treatment and/or processing.

When forming seals or welds on a flexible container such as a bag, for example, a collection bag and/or a cryopreservation bag, a sealing device may be used to apply heat and/or pressure at a predetermined temperature, pressure, and amount of time depending on the material used in the bag. For example, some heat sealers may require application of heat and pressure for about eight seconds. After 8 seconds, heat may be turned off on the device, however, pressure may be applied for an additional 2 to 3 seconds.

In some systems, the positioners may facilitate the use of the bags described herein in automated systems. Thus, tissues that have been placed in bag 140 may be split into separate compartments 144, 146, 147. As shown, each compartment 144, 146, 147 includes ports 148, 149, 150, respectively. Each port may allow for direct access into compartments. This may allow for individualized additions, banking, and/or testing of samples. For example, a sealed collection bag may facilitate banking and testing of TIL for suitability and/or microbiological properties of complex samples. As this type of testing may require a small aliquot of the digested material to be frozen in the collection bag such that the small aliquot of the digested material can be thawed separately. In some embodiments, hag 140 as depicted in FIG. 24 may be used as a collection hag and/or a cryopreservation bag.

Figure 25:
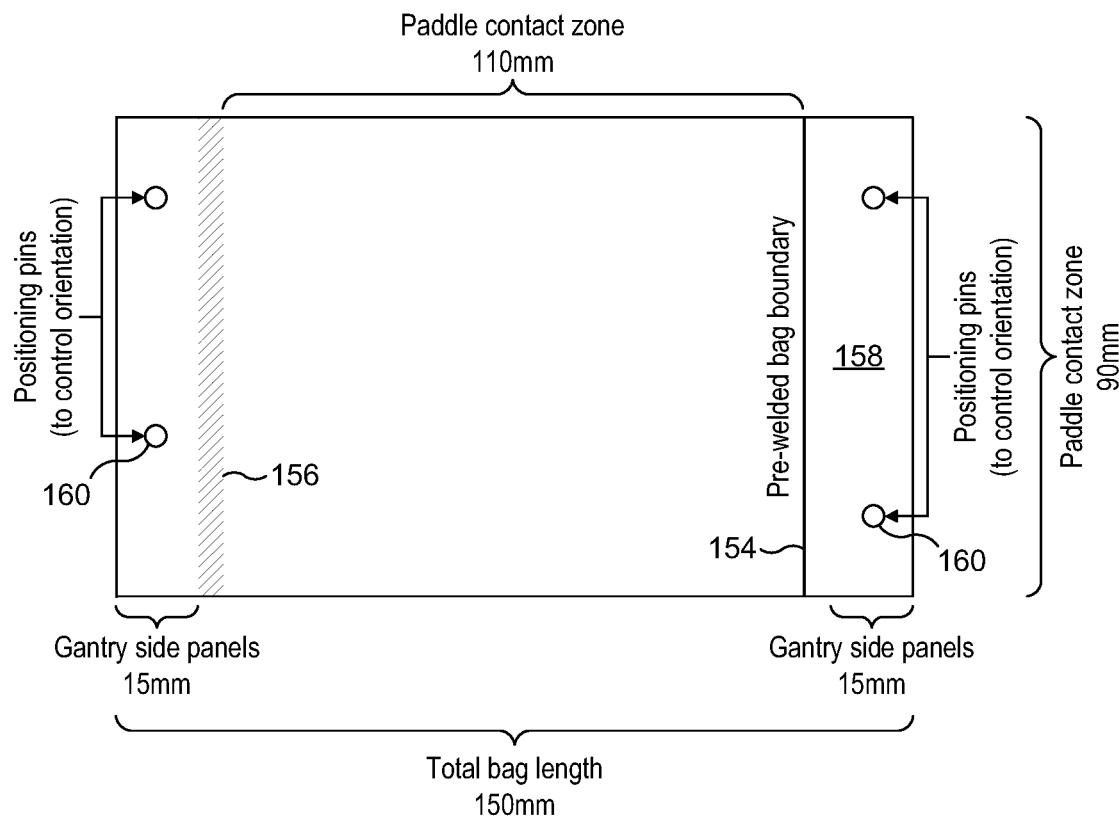
FIG. 25 shows a front view of an embodiment of a collection bag.

FIG. 25 shows a front view of an embodiment of a collection bag. In this embodiment, collection bag 152 has a length of about 150 mm (i.e., 15 cm) and a width of about 90 mm (i.e., 9 cm). Bag 152 includes openings acting as positioners 160. One or more positioners may be used to control the orientation of the bag to ensure that the bag is positioned properly for processing and/or treatment during use, for example, positioning proximate an instrument. In some systems, the positioners may facilitate the use of the bags described herein in automated systems. In particular, positioners may be used to move bag through an automated system. Seal 156 is about 5 mm. Seals may be formed during use using energy, for example, heat to create a weld zone. Seals may have a width in a range from about 2.5 mm to about 7.5 mm. Generally, seal 156 is formed after tissue material is placed in hag 152. As shown in FIG. 25, hag 152 has pre-welded sections 158 that are formed during manufacture of the bag.

Figure 26:
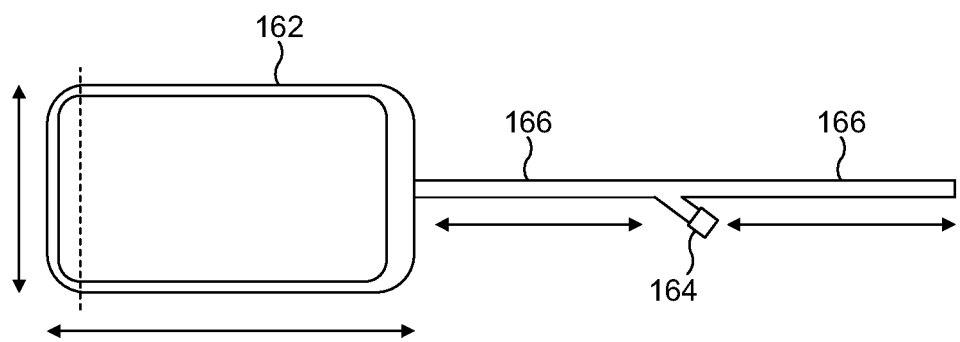
FIG. 26 shows a front view of an embodiment of a collection bag coupled to tubing and a port.

As shown in FIG. 26, a collection bag may be coupled to tubing and a valve. In some embodiments, bags may have a length in a range from about 10 cm to about 50 cm. In particular, bags for use in the invention described herein may have a length in a range from about 15 cm to about 30 cm. For example, bags may have a length in a range from about 18 cm to about 22 cm. Bag 162 as shown in FIG. 26 has a length of about 20 cm. Collection bags for use as described herein may have a width in a range from about 6.8 cm to about 8.8 cm. As shown in FIG. 26, collection bag 162 has a width of about 7.8 cm. Valves including, but not limited to needle free valves may be used at points along the tubing. For example, needle free valve 164 is positioned approximately 20 cm from bag 162 coupled by tubing 166. Tubing 166 extends from needle free valve 164 for at least 10 cm before another element or component is added.

Figure 27A:
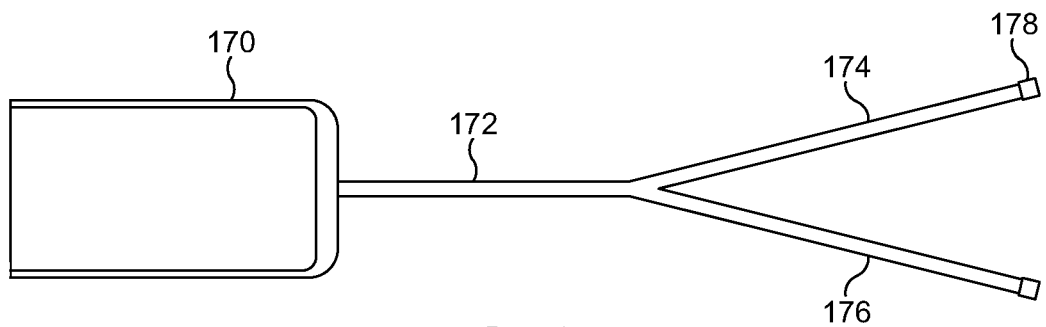
FIG. 27A shows a front view of an embodiment of a collection bag prior to use.

As depicted in FIG. 27A, open bag 170 is coupled to tubing 172, 174, 176 prior to use. Bag 170 may be constructed from a sealable material. In particular, the bags may be sealable using a heat sealer such as, for example, a benchtop heat-sealing device. Some of the tubing, for example tubing 174 may be non-weldable. Valves including but not limited to needle free valves may be used at points along the tubing. For example, needle free valves 178 are positioned at ends of tubing 174, 176.

In some embodiments, bags may have a length in a range from about 10 cm to about 50 cm. In particular, bags for use in the invention described herein may have a length in a range from about 15 cm to about 30 cm. For example, bags may have a length in a range from about 18 cm to about 22 cm. Bag 170 as shown in FIG. 27A has a length of about 20 cm.

Figure 27B:
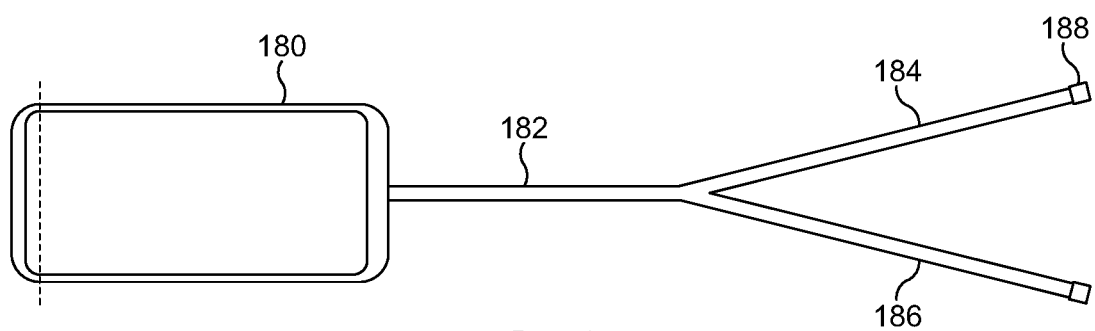
FIG. 27B shows a front view of an embodiment of a collection bag that has been sealed, for example, after deposition of material within the bag.

FIG. 27B shows a front view of an embodiment of a collection bag that has been sealed, for example, after deposition of material within the bag. Bag 180 is constructed from a sealable material. In particular, the bags may be sealable using a heat sealer such as, for example, a benchtop heat-sealing device. Seals may be positioned proximate an open edge of the bag, in some instances, marks may be positioned a predetermined distance from the open edge. Seals may be substantially parallel to the open edge in some embodiments.

Some of the tubing, for example tubing 182, 184, 186 may be weldable. Weldable tubing may be made from a polymer material, for example, polyvinyl chloride (PVC).

Valves including, but not limited to needle free valves may be used at points along the tubing. For example, needle free valves 188 are positioned at ends of tubing 184, 186. In some embodiments, bags may have a length in a range from about 10 cm to about 40 cm. In particular, bags for use in the invention described herein may have a length in a range from about 15 cm to about 30 cm. For example, bags may have a length in a range from about 18 cm to about 22 cm. Bag 180 as shown in FIG. 27A has a length of about 20 cm.

Figure 28:
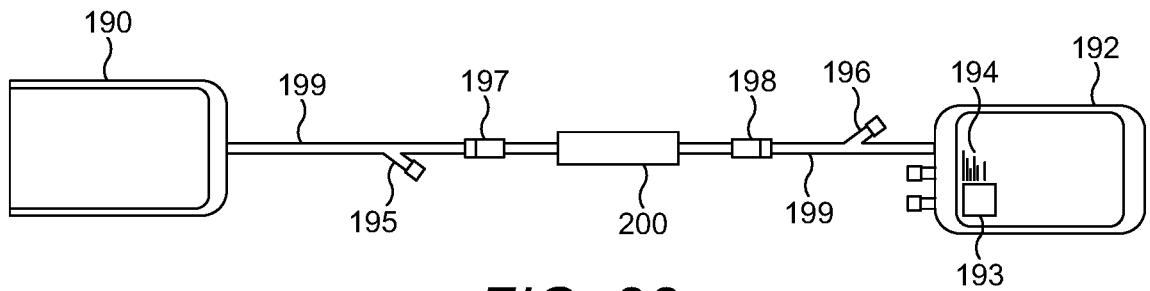
FIG. 28 shows a top view of an embodiment of a cryopreservation kit facing upwards including an open collection bag and a cryopreservation bag.

As shown in FIG. 28, an embodiment of a cryopreservation kit is shown facing upwards and includes open bag 190 and a cryopreservation bag 192. As shown cryopreservation bag 192 may include indicators 193, 194. Cryopreservation bags may need to be suitable for cryopreservation with a cryoprotectant such as dimethyl sulfoxide ("DMSO"). In some embodiments, cryopreservation bags may be constructed so that the bags may hold a volume of material in a range from about 5 ml to about 45 ml. In particular, a cryopreservation bag may include accommodate a volume of material in a range from about 10 ml to about 35 ml. For example, some embodiments include cryopreservation bags that may accommodate a volume of material to be stored in a range from about 15 ml to about 30 ml. Cryopreservation bag 192 may have sized such that a desired predetermined volume is achieved. In some embodiments, a cryopreservation bag may have a width in a range from about 4 cm to about 11 cm and a length in a range from about 10 cm to about 18 cm. For example, a cryopreservation bag may have a width in a range from about 5.8 cm to about 9.8 cm and a length in a range from about 12 cm to about 16 cm. In particular, an embodiment of a cryopreservation bag as depicted in FIG. 28 may have a width of about 7.8 cm and length of about 14 cm.

Prior to use the cryopreservation kit and/or specific components thereof may be sterilized. For example, bags 190, 192 may be sterilized. Materials used to form bags 190, 192 may be heat sealable. Materials for use in the bags may include, but is not limited to polymers such as EVA, polyamides (e.g., nylons), and combinations thereof. Open bag 190 may be used for processing and/or disaggregation after closing the bag using a seal and/or a clamp (not shown).

Kit 191 further includes valves 195, 196, clamps 197, 198, tubing 199, and filter 200. Filter 200 may be an inline filter, a blood filter, such as a blood administration filter, a biological filter, and/or an in-line clump removal filter. The filter may be configured to remove materials from the processed tissue above a predetermined size to form a desired material. For example, lumps of tissue may be separated from the disaggregated tissue using the filter. In particular, a tissue composition entering tubing after being filtered may have constituents having an average size of less than about 200 μm such that a desired material is formed. For example, the desired material may include TILs (tumor infiltrating lymphocytes) having an average size of less than about 170 pm.

A filter may be selected such that the processed tissue composition entering from tubing may be enriched such that after the filter the desired material flows into tubing in the direction of the stabilization element having constituents having a size in a range from about 15 pm to about 500 pm. In some embodiments, a filter may be configured such that a tissue composition entering tubing in the direction of the stabilization element after being filtered has constituents having a size in a range from about 50 pm to about 300 IJM. For example, a filter may, in an embodiment, be configured such that a tissue composition entering tubing after being filtered has constituents having a size in a range from about 150 pm to about 200 pm.

In some embodiments, a filter of the enrichment element may remove materials from the processed tissue outside of a predetermined size range from about 5 pm to about 200 pm to form a desired material. For example, the desired material may include TILs (tumor infiltrating lymphocytes) having an average size in a range from about 5 pm to about 200 pm. Valves 195, 196 may be placed a predetermined distance from a collection bag. For example, needle free valve 195 may be positioned about 20 cm from collection bag 190. Valves such as needle free valves may be used to add materials to collection bag 190. For example, enzyme media may be inserted into needle free valve 195 in order to add the media to collection bag 190.

In some embodiments, after such a valve there may be a predetermined amount of tubing to allow space to weld on additional components for the cryopreservation kit. For example, after some valves at least ten (10) cm of tubing may be positioned before next element. Tubing 199 may be sealable and/or weldable. For example, materials for tubing may include, but is not limited to PVC (polyvinyl chloride), and/or other materials known in the art. In some embodiments, tubing may be sized to fit connectors. For example, tubing may have an inner diameter in a range from about 1.5 mm to about 4.5 mm and an outer diameter in a range from about 2.1 mm to about 6.1 mm. For example, an embodiment of a cryopreservation kit may include tubing having an inner diameter in a range from about 2.9 mm to about 3.1 mm and having an outer diameter in a range from about 4.0 mm to about 4.2 mm. Tubing used in cryopreservation kit 191 may vary in length with individual tubing elements having a length in a range from about 1 cm to about 30 cm. For example, as depicted in FIG. 28 lengths of individual tubing elements may vary from about 5 cm to about 20 cm.

Clamps 197, 198 as depicted in FIG. 28 may be used to inhibit and/or prevent movement of enzyme media and/or digested tissue into the filter. For example, clamp 197 may be used to inhibit and/or prevent movement of enzyme media and/or digested tissue into the filter prior to a desired filtration step. Clamp 198 may inhibit and/or prevent undesired movement of the cryoprotective agent into the filter.

Figure 29:
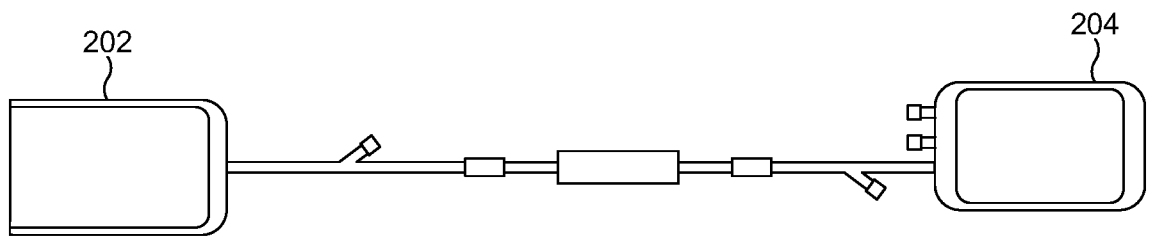
FIG. 29 shows a top view of an embodiment of a cryopreservation kit facing downwards including a collection bag indicating where it is to be closed and a cryopreservation bag.

FIG. 29 shows a top view of an embodiment of a cryopreservation kit similar to the kit 191 shown in FIG. 28, however kit 201 is facing downwards. FIG. 29 depicts a position at which collection bag 202 may be closed.

Figure 30:
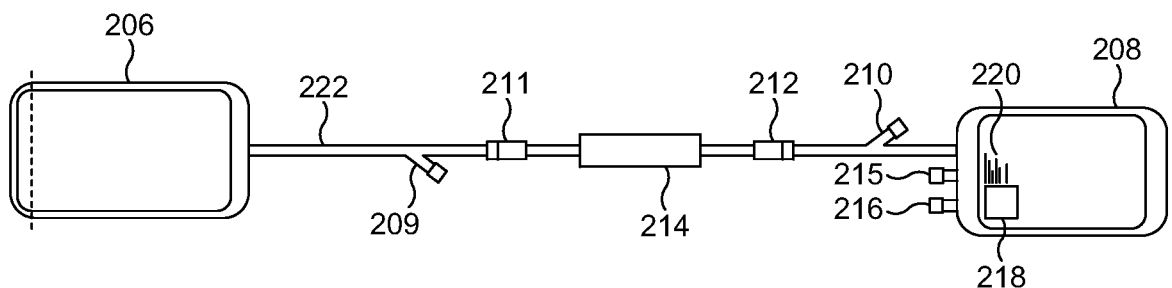
FIG. 30 shows a top view of an embodiment of a cryopreservation kit facing upwards including a closed collection bag and a cryopreservation bag.

FIG. 30 shows a top view of an embodiment of a cryopreservation kit facing upwards including closed collection bag 206 and cryopreservation bag 208. In some embodiments, cryopreservation bag 208 may include ports 215, 216 that allow for sampling, permit aseptic input of media and/or reagents into the cryopreservation bag. Cryopreservation kit 205 may include filter 214, valves 209, 210, clamps 211, 212 and tubing 222.

Filter 214 may be an inline filter, a biological filter, a blood filter such as a blood administration filter and/or an in-line clump removal filter. The filter may be configured to remove materials above a predetermined size. For example, lumps of tissue may be separated from the disaggregated tissue using the filter. A filter may be selected such that tissue composition entering tubing after the filter may have constituents having a size in a range from about 15 pm to about 500 μm. In some embodiments, a filter may be configured such that a tissue composition entering tubing after being filtered has constituents having a size in a range from about 50 pm to about 300 pm. For example, a filter may, in an embodiment, be configured such that a tissue composition entering tubing after being filtered has constituents having an average size in a range from about 150 pm to about 200 pm. In particular, a tissue composition entering tubing after being filtered may have constituents having an average size of less than about 170 μm.

Valves 209, 210 may be placed a predetermined distance from a collection bag. For example, needle free valve 209 may be positioned about 20 cm from collection bag 206. Valves such as needle free valves may be used to add materials to collection bag 206. For example, enzyme media may be inserted into needle free valve 209 in order to add the media to collection bag 206.

In some embodiments, after such a valve there may be a predetermined amount of tubing to allow space to weld on additional components for the cryopreservation kit. For example, after some valves at least ten (10) cm of tubing may be positioned before next element. Tubing 222 may be sealable and/or weldable. For example, materials for tubing may include, but is not limited to PVC and/or other materials known in the art. In some embodiments, tubing may be sized to fit connectors. For example, tubing may have an inner diameter in a range from about 1.5 mm to about 4.5 mm and an outer diameter in a range from about 2.1 mm to about 6.1 mm. For example, an embodiment of a cryopreservation kit may include tubing having an inner diameter in a range from about 2.9 mm to about 3.1 mm and having an outer diameter in a range from about 4.0 mm to about 4.2 mm. Tubing used in cryopreservation kit 205 may vary in length with individual tubing elements having a length in a range from about 1 cm to about 30 cm. For example, as depicted in FIG. 30 lengths of individual tubing elements may vary from about 5 cm to about 20 cm.

Clamp 211, 212 as depicted in FIG. 30 may be used to inhibit and/or prevent movement of enzyme media and/or digested tissue into the filter. For example, clamp 211 may be used to inhibit and/or prevent movement of media enzyme solution and/or digested tissue into the filter prior to a desired filtration step. Clamp 212 may inhibit and/or prevent undesired movement of the cryoprotective agent into the filter.

Figure 31:
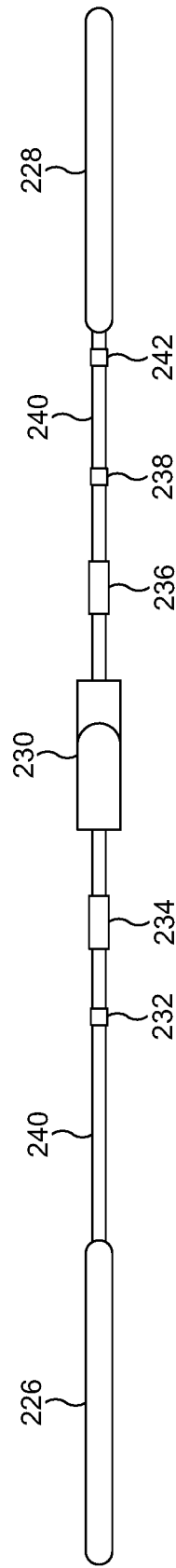
FIG. 31 shows a side view of an embodiment of a cryopreservation kit facing upwards including a closed collection bag and a cryopreservation bag.

FIG. 31 shows a side view of an embodiment of a cryopreservation kit facing upwards that includes closed collection bag 226 and cryopreservation bag 228. Cryopreservation bag 228 may include port 242. Port 242 provides access to cryopreservation hag 228. Valves 232, 238 and clamps 234, 236 may be positioned around filter 230 and used to control movement of the fluid within the cryopreservation kit 224.

Figure 32:
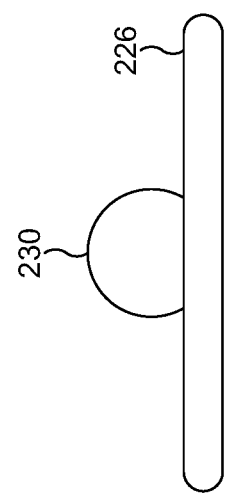
FIG. 32 shows an end view of an embodiment of a cryopreservation kit.

FIG. 32 shows an end view of an embodiment of a cryopreservation kit. Sealed bag 226 and filter 230 are visible. Sealed bag 226 may be coupled to filter 230 using tubing, valves, and/or clamps.

Figure 33:
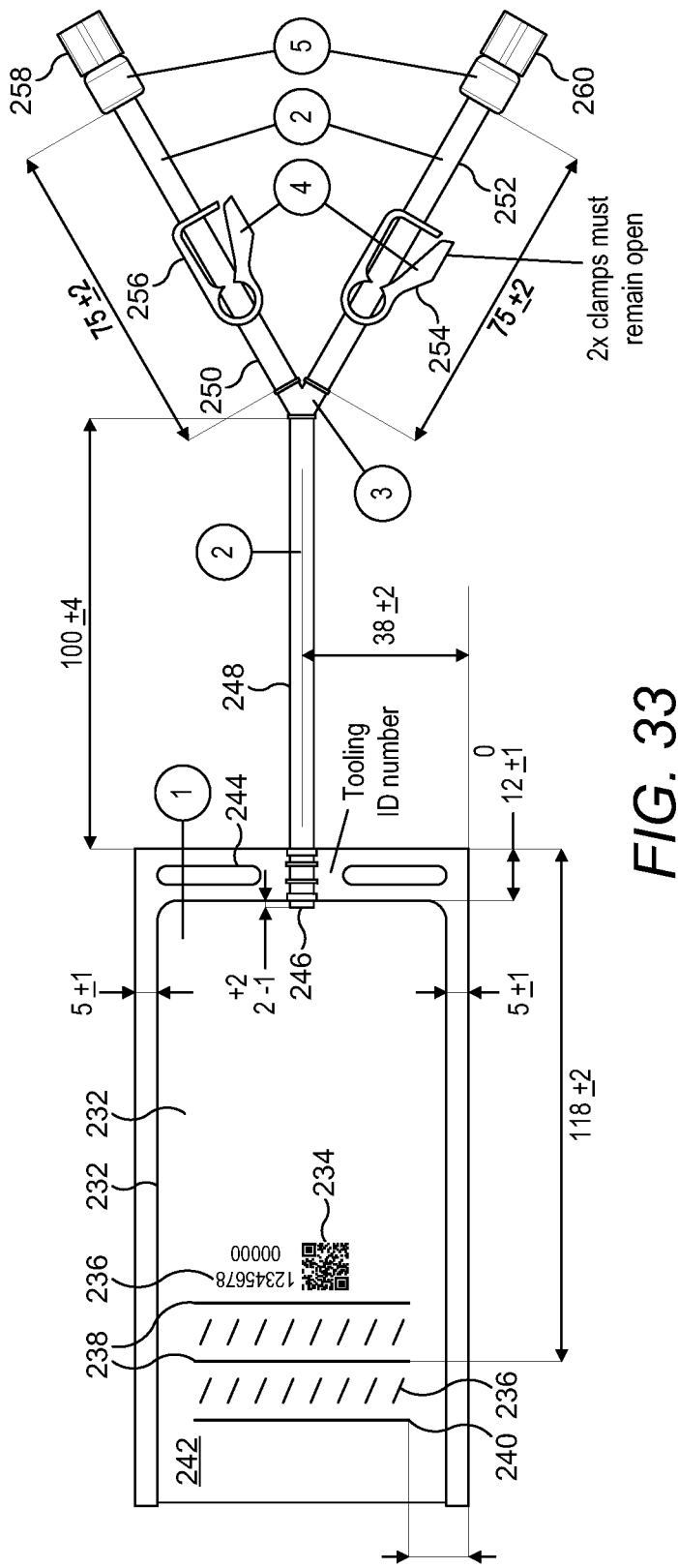
FIG. 33 shows a top view of an embodiment of a collection bag including indicia coupled to tubing.

FIG. 33 shows a top view of an embodiment of a collection bag. Bag 232 is shown as open and includes indicators 234, 236 and marks 238, 240. Marks may be used to show where portions of a bag should be sealed and/or clamped. Marks for sealing may be positioned proximate an open edge of the bag. Such marks may be positioned a predetermined distance from the open edge. Marks for sealing may be substantially parallel to the open edge in some embodiments.

Bag 232 includes positioners 244 and connector 246. Connector 246 couples hag 232 to tubing 248. Connecter 246 may allow tubing 248 to split into tubing 250, 252 that include clamps 254, 256 and/or ports 258, 260.

Figure 34:
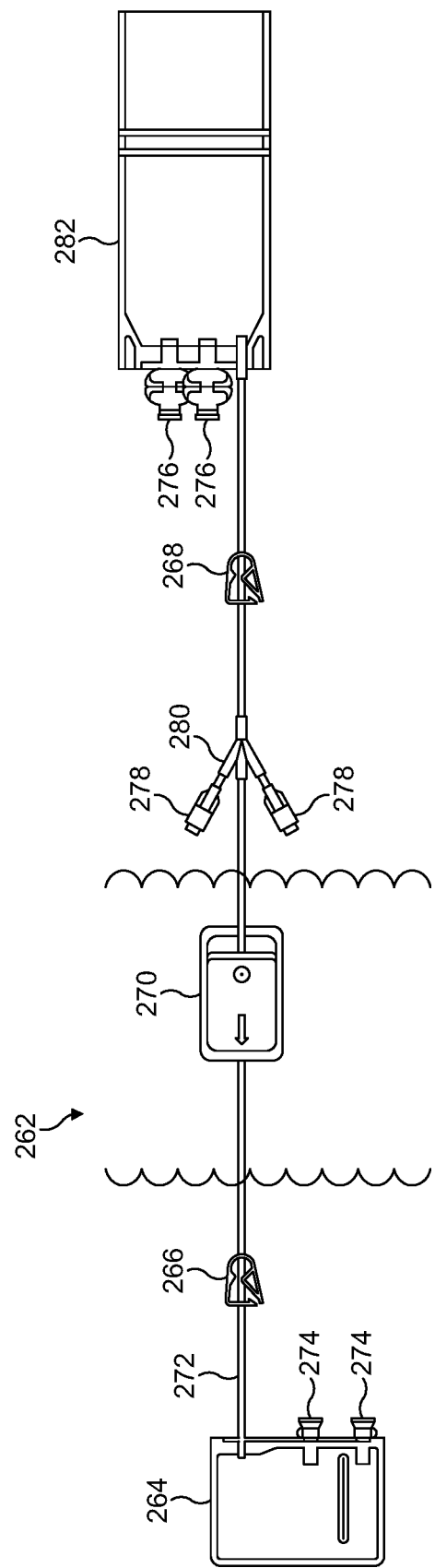
FIG. 34 shows a front view of an embodiment of a cryopreservation kit that includes a collection bag, a filter, and a cryopreservation bag.

FIG. 34 shows a front view of an embodiment of a cryopreservation kit that includes a collection bag 264, clamps 266, 268, filter 270, tubing 272, ports 274, 276, valves 278, connector 280, and cryopreservation bag 282. The collection bag and the associated tubing may be formed using at least some EVA material. In some embodiments, the collection bag and/or tubing may be formed from EVA. Clamps 266, 268 may be pinch clamps. Connector 280 is a four-way connector and may be used to couple tubing from filter 270 to valves 278, for example needle free valves, as well as to tubing coupled to cryopreservation bag 282.

Figure 35:
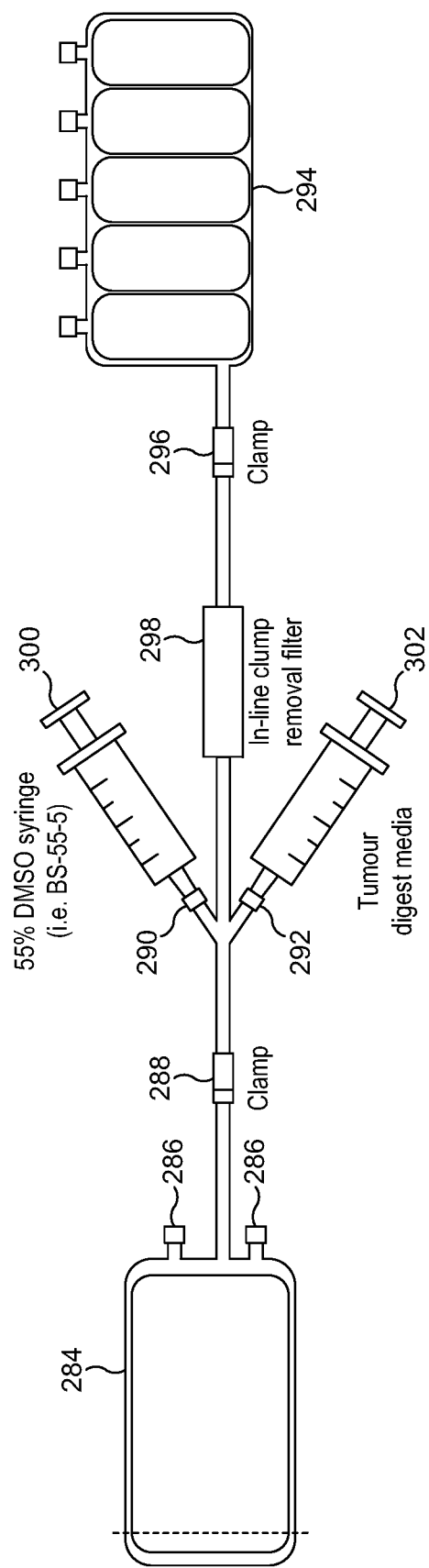
FIG. 35 shows a front view of an embodiment of a cryopreservation kit that includes a collection bag, a filter, and a cryopreservation bag.

FIG. 35 shows a front view of an embodiment of a cryopreservation kit that includes collection bag 284, ports 286, clamps 288, 296, valves 290, 292, filter 298, and cryopreservation bag 294. As depicted, valves 290, 292 may be needle free valves capable of receiving materials for use in the kit during processing. For example, materials to be provided via valves 290, 292 include, for example, tumor digest media and/or a cryoprotectant or cryopreservation media such as dimethyl sulfoxide ("DMSO") and/or solutions thereof, such as 55% DMSO and 5% Dextran cryopreservation media (e.g., BloodStor 55-5). Syringes 300, 302 may be used to provide tumor digest media and a 55% DMSO solution, such as 55% DMSO and 5% Dextran cryopreservation media, respectively, through needle free valves 290, 292. During processing materials may be selectively provided to the cryopreservation kit at predetermined times. Further, clamps may be used to control the flow of provided materials such as tumor digest media and/or a cryoprotectant, such as a DMSO solution may be provided to the devices such as the collection bag, the filter, and/or the cryopreservation bag at predetermined times.

FIG. 36A shows a front view of an embodiment of a cryopreservation kit that is capable of being secured in a device such as a digestor. As shown collection bag 304 is enclosed at least partially by bracket 306 during use. Bracket may position collection bag 304 such that processing can occur in an efficient manner. FIG. 36A depicts collection bag 304 that has weld 310 and utilizes clamp 312 proximate weld 310 during use to reduce pressure on weld 310. Tissue introduced during use may be distributed substantially evenly in collection bag 304 such that tissue may be treated using paddles 314, 316 from a device. Cryopreservation bag 330 has multiple sections 332 each having their own port 334.

A side view of an embodiment of a collection bag secured using a bracket is depicted in FIG. 36B. Bracket 336 may be used to secure a collecting bag. Bracket 336 includes hinge 338, top side 340, bottom side 342, clamp 344, protrusion 346 and latch 348. During use clamp 344 may be positioned proximate a weld on collection bag (FIG. 36A). Protrusion 346 on bracket 336 is constructed such that it would be positioned proximate a surface of the collection bag and protrude up into collection bag during use. In some embodiments, protrusion 346 may reduce and/or inhibit movement of tissue and/or media during use to ensure that processing of tissue is substantially similar along the length of the collection bag. For example, the protrusion may be constructed such that it reduces and/or inhibits sliding of tissues between paddles (shown in FIG. 36A). Bracket 336 may also include latch 348 to ensure that collection bag is secured.

FIG. 36C shows an exploded view of clamp 344 including ridges 350 for use with a collection bag. In particular, during use clamp 344 may be positioned proximate a weld on a collection bag to reduce the risk of weld and/or seal failures.

Figure 37:
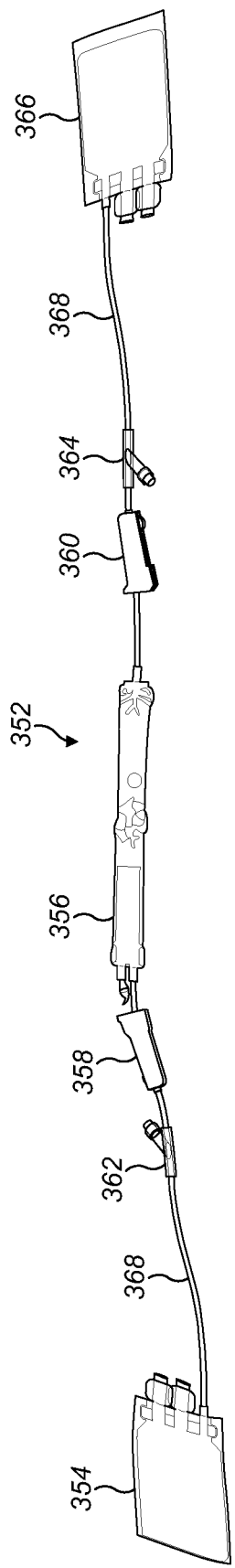
FIG. 37 shows a front view of an embodiment of a cryopreservation kit that includes a collection bag, a filter, and a cryopreservation bag.

FIG. 37 shows a top view of an embodiment of a cryopreservation kit that includes collection bag 354, filter 356, valves 362, 364, clamps 358, 360, tubing 368, and cryopreservation bag 366. Tubing length between various components of the cryopreservation kit 352 may vary.

Figure 38:
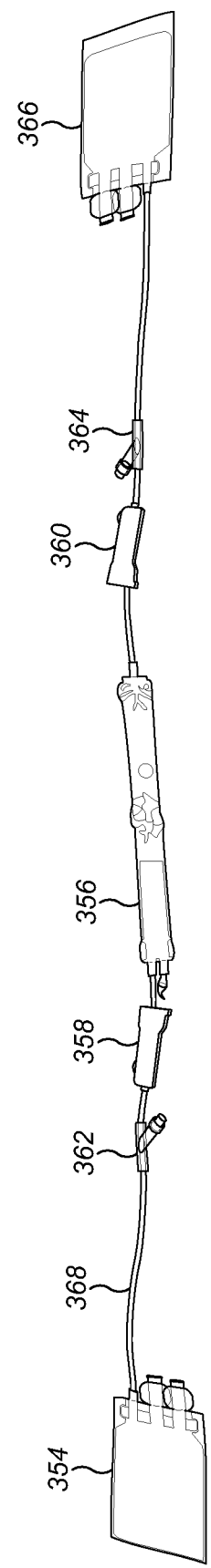
FIG. 38 shows a front view of an embodiment of a cryopreservation kit that includes a collection bag, a filter, and a cryopreservation bag.

FIG. 38 shows a view of an embodiment of a cryopreservation kit positioned face down that includes collection bag 354, filter 356, valves 362, 364, clamps 358, 360, tubing 368, and cryopreservation bag 366.

Two or more bags may be coupled together to ensure that disaggregated product material may be properly stored in a particular embodiment.

In some embodiments, the invention may include an automated device for semi-automated aseptic disaggregation, enrichment, and/or stabilization of cells and/or cell aggregates from tissue, for example a solid mammalian tissue. An automated device for use with the invention may include a programmable processor and a cryopreservation kit. In some embodiments, the cryopreservation kit may be single use. aseptic kit. The invention further relates to a semi-automatic aseptic tissue processing method.

In some embodiments, bags such as a collection bag may be used in a collection kit. Bags have an open end allowing for the addition of a sample, such as a tissue sample. A connector may couple the bag to tubing in a collection kit. Tubing material may be sealable and/or weldable. For example, the tubing may be sealed using energy such as heat, radio frequency, etc. The tubing material may be made from PV A.

In some embodiments, tubing may be coupled to a valve to allow addition of one or more media enzyme solutions including, but not limited to collagenase, trypsin, lipase, hyaluronidase, deoxyribonuclease, Liberase HI, pepsin, or mixtures thereof. For example, the valve may be a needle free valve.

Tubing used in the cryopreservation kit may include tubing having an outer diameter in a range from about 3.0 mm to about 5.0 mm with an inner diameter of the tubing in a range from about 2.0 mm to about 4 mm. In particular, tubing may have an outer diameter of 4.1+/−0.1 mm and an inner diameter of about 3.0+/−0.1 mm. The length of tubing may depend on the configuration of the collection kit. For example, an embodiment of a collection kit may include tubing having a length in a range from about 10 cm to about 20 cm.

In some embodiments of the collection kit prototype may include one or more clamps to inhibit and/or prevent movement of tissue and/or enzyme media. In particular, enzyme media and/or tissue may be inhibited from moving into a filter before a filtration step The invention is further described by the following numbered paragraphs:

1. A single use aseptic kit comprising: a disaggregation module for receipt and processing of material comprising solid mammalian tissue; an optional enrichment module for filtration of disaggregated solid tissue material and segregation of non-disaggregated tissue and filtrate; and a stabilization module for optionally further processing and/or storing disaggregated product material, wherein each of said modules comprises one or more flexible containers connected by one or more conduits adapted to enable flow of the tissue material there between; and wherein each of said modules comprises one or more ports to permit aseptic input of media and/or reagents into the one or more flexible containers.

2. The single use aseptic kit of paragraph 1, wherein the one or more flexible containers comprise a resilient deformable material.

3. The single use aseptic kit of paragraph 1 or 2, wherein the one or more flexible containers of the disaggregation module comprises one or more sealable openings.

4. The single use aseptic kit of paragraph 3, wherein the flexible container of the disaggregation module comprises a heat sealable weld.

5. The single use aseptic kit of any preceding paragraph, wherein the one or more flexible containers comprises internally rounded edges.

6. The single use aseptic kit of any preceding paragraph, wherein the one or more flexible containers of the disaggregation module comprises disaggregation surfaces adapted to mechanically crush and shear the solid tissue therein.

7. The single use aseptic kit of any preceding paragraph, wherein the one or more flexible containers of the enrichment module comprises filter which retains a retentate of cellularized disaggregated solid tissue.

8. The single use aseptic kit of any preceding paragraph, wherein the one or more flexible containers of the stabilization module comprises media formulation for storage of viable cells in solution or in a cryopreserved state.

9. The single use aseptic kit of any preceding paragraph, wherein the kit further comprises a digital, electronic or electromagnetic tag indicator.

10. The single use aseptic kit of paragraph 9, wherein the tag indicator relates to a specific a program that defines: a type of disaggregation and/or enrichment and/or stabilization process; one or more types of media used in those processes; including an optional freezing solution suitable for controlled rate freezing.

11. The single use aseptic kit of any preceding paragraph, wherein the same flexible container can form part of one or more disaggregation module, the stabilization module and the optional enrichment modules.

12. The single use aseptic kit of any preceding paragraph, wherein the disaggregation module comprises a first flexible container for receipt of the tissue to be processed.

13. The single use aseptic kit of any preceding paragraph, wherein the disaggregation module comprises a second flexible container comprising the media for disaggregation.

14. The single use aseptic kit of any preceding paragraph, wherein the optional enrichment module comprises the first flexible container and a third flexible container for receiving the enriched filtrate.

15. The single use aseptic kit of any preceding paragraph, wherein both the disaggregation module and the stabilization module comprise the second flexible container and wherein the second container comprises digestion media and stabilization media.

16. The single use aseptic kit of any preceding paragraph, wherein the stabilization module comprises a fourth flexible container comprising stabilization media.

17. The single use aseptic kit of any preceding paragraph, wherein the stabilization module also comprises the first flexible container and/or third flexible container for storing and/or undergoing cryopreservation.

18. Use of the single use aseptic kit according to any preceding paragraph in a semi-automated process for the aseptic disaggregation, stabilization and optional enrichment of mammalian cells or cell aggregates.

19. An automated device for semi-automated aseptic disaggregation and/or enrichment and/or stabilization of cells or cell aggregates from mammalian solid tissue comprising: a programmable processor; and the single use aseptic kit of any of paragraphs 1 to 17.

20. The automated device of paragraph 19, further comprising radio frequency identification tag reader to recognize the single use kit.

2 L The automated device of paragraph 19 or 20, wherein the programmable processor is capable of recognizing the single use aseptic kit via the tag and subsequently executes the kit program defining the type of disaggregation, enrichment and stabilization processes and the respective media types required for those processes.

22. The automated device of any preceding paragraph, wherein the programmable processor is adapted to communicate with and control one or more of: the disaggregation module; the enrichment module; and the stabilization module.

23. The automated device of paragraph 22, wherein the programmable processor controls the disaggregation module to enable a physical and/or biological breakdown of the solid tissue material.

24. The automated device of paragraph 23, wherein the programmable processor controls the disaggregation module to enable a physical and enzymatic breakdown of the solid tissue material.

25. The automated device of paragraph 24, wherein the enzymatic breakdown of the solid tissue material is by one or more media enzyme solutions selected from collagenase, trypsin, lipase, hyaluronidase, deoxyribonuclease, Liberase HI, pepsin, or mixtures thereof.

26. The automated device of any one of paragraphs 19-25, wherein the programmable processor controls disaggregation surfaces within the disaggregation flexible containers which mechanically crush and shear the solid tissue, optionally wherein the disaggregation surfaces are mechanical pistons.

27. The automated device of any one of paragraphs 19-25, wherein the programmable processor controls the stabilization module to cryopreserve the enriched disaggregated solid tissue in the container, optionally using a programmable temperature.

28. The automated device of any preceding paragraph wherein the device further comprises one or more of the additional components in any combination: sensors capable of recognizing whether a disaggregation process has been completed in the disaggregation module prior to transfer of the disaggregated solid tissue to the optional enrichment module; weight sensors to determine an amount of media required in the containers of one or more of the disaggregation module; the enrichment module; and/or the stabilization module and control the transfer of material between respective containers; sensors to control temperature within the containers of the one or more of the disaggregation module; the enrichment module; and/or the stabilization module; at least one bubble sensor to control the transfer of media between the input and output ports of each container in the module; at least one pump, optionally a peristaltic pump, to control the transfer of media between the input and output ports; pressure sensors to assess the pressure within the enrichment module; one or more valves to control a tangential flow filtration process within the enrichment module; and/or one or more clamps to control the transfer of media between the input and output ports of each module.

29. The automated device of any preceding paragraph, wherein the programmable processor is adapted to maintain an optimal storage temperature range in the stabilization module until the container is removed; or executes a controlled freezing step.

30. The automated device of any preceding paragraph, further comprising a user interface.

3L The automated device of paragraph 23, wherein the interface comprises a display screen to display instructions that guide a user to input parameters, confirm pre-programmed steps, warn of errors, or combinations thereof.

32. The automated device of any preceding paragraph, wherein the automated device is adapted to be transportable.

33. A semi-automatic aseptic tissue processing method comprising: automatically determining aseptic disaggregation tissue processing steps and their associated conditions from a digital, electronic or electromagnetic tag indicator associated with the aseptic processing kit, optionally in accordance with the kit according to any of paragraphs 1 to 17; placing a tissue sample into a flexible plastic container of the disaggregation module of the aseptic processing kit;

and processing the tissue sample by automatically executing the one or more tissue processing steps by communicating with and controlling the disaggregation module; the optional enrichment module; and the stabilization module.

Figure 65:
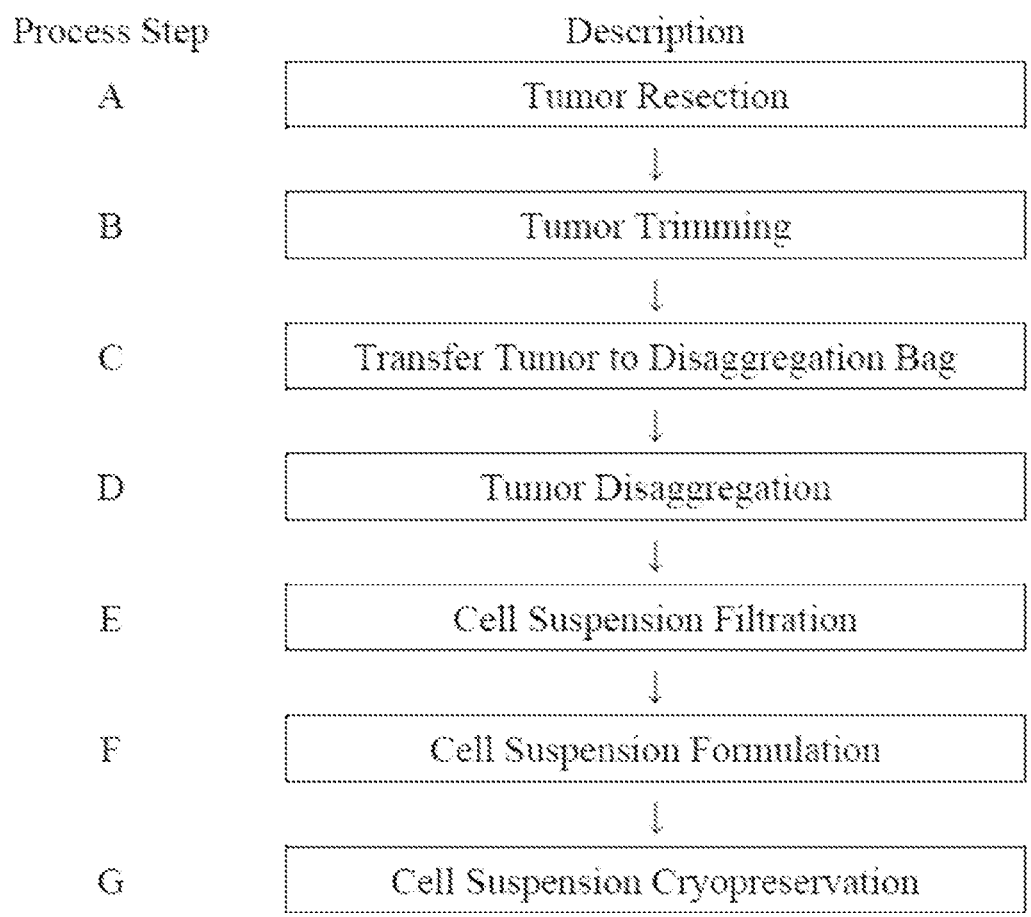
FIG. 65 is an exemplary flow diagram for collection, processing and cryopreservation of tumor tissue.

Procedures for Collection of Tumor Material, Cryopreseration, and TIL Manufacure The starting material for TIL manufacturing is a disaggregated and cryopreserved cell suspension containing autologous TIL and tumor cells from an eligible patient. An exemplary flow diagram is provided (FIG. 65) for collection and processing of the tumor starting material.

The tumor is surgically resected and then trimmed to remove visibly necrotic tissue, visibly healthy (non-cancerous) tissue, fat tissue, and excess blood. The trimmed tumor weight should be greater than or equal to 2 grams (≥2 grams). Tumors weighing over 7 g may be divided into smaller portions and individually disaggregated.

Each tumor fragment is placed into an individual sterile bag containing media, collagenase and DNAse. Exemplary reagents are shown in the following table:

TABLE 4

Disaggregation Media

| Raw Material | Animal/Human Derived | Supplier | Available Certificates |
|---|---|---|---|
| Phosphate buffered saline | No | Life Technologies Ltd | CoA |
| 2 mM Calcium Chloride | No | Sigma-Aldrich | CoA |
| DNAse 1 (dornase alfa) | Approved medical product in the US | Roche Products Ltd | CoA |
| Collagenase type IV | Bovine | Nordmark Arzneimittel GmbH &Co KG | CoA, CoO, TSE/BSE statement |
| BloodStor 55-5 (55% DMSO) | No | BioLife Solutions | CoA |

The bag is then heat sealed and its contents are disaggregated to generate a homogeneous cell suspension containing tumor and TIL. Disaggregation is performed by a device, such as the Tiss-U-Stor device described herein, which runs a program to deliver a defined number of repeated physical compression events, with a defined compression pressure over a defined duration to ensure enzyme access into the tumor tissue thereby accelerating enzymatic digestion. The number of cycles, pressure, temperature, and duration are recorded for each individual tumor.

The homogenized cell suspension is then aseptically filtered using a 200 pm filter (Baxter, RMC2159) and the filtrate passed aseptically into the cryopreservation bag. BloodStor 55-5 (Biolife Solutions, Bothell, Wash.) is aseptically added to achieve 5% DMSO. The cell suspension is then cryopreserved using the Tiss-U-Stor device with a defined cooling program, and the measured temperature profile is recorded for each individual cell suspension derived from each tumor portion. The cryopreserved cell suspension is stored in vapor-phase of liquid nitrogen.

The cryopreserved cell suspension recommended storage condition is ≤−130° C.

The cell suspension is transported from the clinical site to the GMP cell therapy manufacturing site by a qualified courier service packaged in a container validated to ensure the cryopreserved cell suspension is maintained at ≤−130° C.

(Tiss-u-Stor)

Resected tumors are evaluated for weight and condition. For each tumor fragment, extraneous material is removed and the fragment weighed. A CS50N bag is opened, up to about 7 g of tumor is added and the bag is then sealed. 15 ml of EDM digest medium is added to the bag with 2 gl gentamicin/amphotericin per ml EDM by syringe via needleless port followed by removal of air from the from the bag into the syringe.

The tumor tissue and disaggregation media in the disaggregation hag is placed in the temperature controlled tissue disaggregator. The temperature is increased from ambient temperature to 35° C. at a rate of 1.5° C./min and maintained at 35° C. for a total of about 45 minutes during which time the disaggretor is active at 240 cycles per minute.

Once disaggregated the tumor material is filtered through an inline filter into a secondary freezing bag. 1.5 ml of Blood stor (DMSO) is injected via a needleless port and air removed.

2 ml. of the suspension is withdrawn for testing.

For optional cryopreservation, the cryobag is loaded into a freezing cassette and the freezing cassette placed in the Via freeze. The Via freeze is then cooled to −80° C., preferably directly from 35° C. to −80° C. at a rate of −2° C./min.

The frozen cryobag is then transferred to liquid nitrogen storage.

TIL Manufacture

Autologous tissue used for culturing in the United Kingdom (UK) should conform to HTA-GD-20, Guide to Quality and Safety Assurance for Human Tissue and Cells for Patient Treatment, established by the UK's Human Tissue Authority with suitable consent, Chain of Identity, Chain of Custody and screening to confirm donors are negative for Hepatitis B virus, Hepatitis C virus, HIV-1 & 2, HTLV-1 & 2, and Syphilis.

Manufacturing involves outgrowth and expansion from a cryopreserved cell suspension containing TILs and tumor cells derived from a resected tumor. If the tumor is greater than about 7 g, the resection process generates multiple cryopreserved cell suspensions, where each cell suspension derives from a 2-7 g tumor fragment. Typically, only one cell suspension is needed to be thawed for 1 T1L outgrowth while the remaining cryopreserved cell suspensions remain in GMP control and held at the recommended storage condition (vapor phase of liquid nitrogen).

Figure 66:
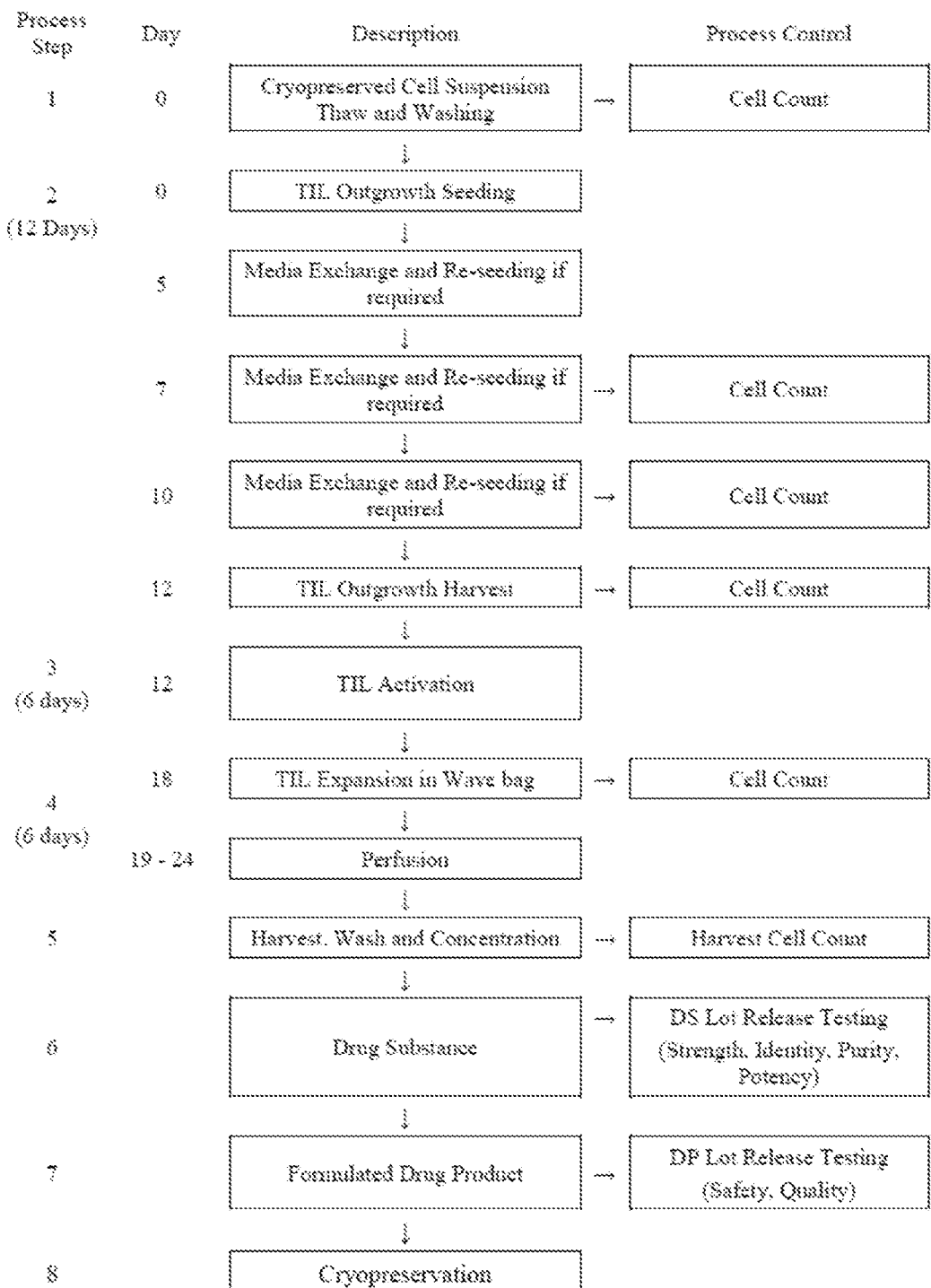
FIG. 66 is an exemplary flow diagram for TIL manufacture from processed and cryopreserved tumor tissue.

In certain embodiments the cell suspension has been filtered after disaggregation, prior to cryopreservation. An exemplary manufacturing procedure is shown in FIG. 66. Exemplary Manufacturing Raw Materials are provided in the following table:

TABLE 5

Raw Material Sourcing

| Raw Material | Human/Animal Derived | Supplier | Available Certificates |
|---|---|---|---|
| T Cell Medium | Human and Animal | ThermoFisher Scientific | CoA, CoO |

TABLE 5-continued

Raw Material Sourcing

| Raw Material | Human/Animal Derived | Supplier | Available Certificates |
|---|---|---|---|
| Fetal Bovine Serum (FBS) | Animal | Life Technologies | CoA, CoO |
| Gentamicin/ Amphotericin B. 500x | No | Life Technologies | CoA |
| IL-2 (aldesleukin) | Not Available | Clinigen | CoA |
| Human AB Serum | Human | Valley Biomedical | CoA with Origin |
| MACS GMP CD3 OKT3 antibody | No | Miltenyi Biotec | CoA |
| Irradiated Buffy Coat | Human | SNBTS | CoA |
| Phosphate buffered saline | No | Life Technologies | CoA |
| Albumin (human) 20% | Human | OctaPharma | CoA with Origin |
| CryoSure-DMSO | No | WAK - Chemie Medical GmbH | CoA, TSE |

T cell medium (TCM) contains Albumin (human), human Holo Transferrin, and animal origin cholesterol. The source plasma used to manufacture Albumin and Transferrin are sourced from the USA and the donors are tested for adventitious agents.

Cholesterol is sourced from sheep woolgrease originating in Australia/New Zealand, which complies with USDA regulations prohibiting ruminant original material from countries with reported cases of transmission spongiform encephalopathy (TSE).

Fetal Bovine Serum (FBS) is sourced from Australia/New Zealand in compliance with the USDA regulations prohibiting ruminant original material from countries with reported cases of transmission spongiform encephalopathy (TSE). The FBS is tested in compliance with 21 CFR part 113.47, specifically including: bluetongue virus, bovine adenovirus, bovine parvovirus, bovine respiratory syncytial virus, bovine viral diarrhea virus, rabies virus, reovirus, cytopathic agents, haemadsorbing agents. The FBS is heat inactivated at 56° C. for 30 minutes and triple 0.1 µm filtered to provide two orthogonal viral removal steps.

Human AB Serum is sourced from Valley Biomedical, an FDA registered establishment (1121958). Each donor unit is tested for Hepatitis B surface Antigen (HBsAg), Hepatitis B Virus (HBV) Nucleic acid Amplification Test (NAT), anti-Human Immunodeficiency Virus (HIV) type 1 and 2, HIV-1 NAT, anti-Hepatitis C Virus (HCV), HCV NAT, and a test for syphilis by FDA approved methods. The serum is heat inactivated at 56° C. for 30 minutes and 0.1 µm filtered.

Irradiated Buffy Coat sourcing, preparation, shipment and storage: The Scottish National Blood Transfusion Service (SNBTS) screens donors, collects the blood component, prepares and irradiates buffy coats. The SNBTS is licensed by the United Kingdom's Human Tissue Authority (license number 11018) in accordance with the Blood, Safety and Quality Regulations (2005) to procure, process, test, store and distribute blood, blood components and tissues.

Healthy donor screening meets or exceeds the requirements described in the United States Code of Federal Regulations (CFR) Title 21 Part 1271.75 with the exception that donors live in the United Kingdom. While this presents a theoretical risk of sporadic Creutzfeldt-Jakob Disease (sCJD) or variant Creutzfeldt-Jakob Disease (vCJD), the United Kingdom has a robust national surveillance program. The most recent annual report, covering May 1990 to Dec. 31, 2018 (National CJD Research & Surveillance Unit, 2018), confirms the incidence of sCJD in the UK is comparable to those observed elsewhere in the world, including countries that are free of bovine spongiform encephalopathy (BSE). There have been no reported cases of vCJD in 2017 through Apr. 5, 2020, and only two cases identified nationally since Jan. 1, 2012 (NCJDRSU Monthly Report, 2020). This rigorous surveillance network has eliminated transfusion transmitted vCJD infections with none reported since 2007 (National CJD Research & Surveillance Unit, 2018). Exemplary eligible donor testing (Table 7) meets 21 CFR Part 1271.85 requirements and adds Hepatitis E testing which is not required.

TABLE 6

Exemplary donor screening (NHSBT)

| Pathogen | Specification | Requirement |
|---|---|---|
| Hepatitis B, C & E virus | Not detected/Negative | Every donation |
| Human Immunodeficiency Virus (HIV) type 1 and 2 | Not detected/Negative | Every donation |
| Syphilis | Not detected/Negative | Every donation |
| Human T Lymphotrophic Virus (HTLV) type 1 and 2 | Not detected/Negative | 1st donation and in selected subsequent donations |
| Malaria | Not detected/Negative | Test performed depending on the donor's individual circumstances |
| T cruzi | Not detected/Negative or IgG positive | |
| West Nile Virus | Not detected/Negative | |
| Cytomegalovirus (CMV) | Not detected/Negative or IgG positive | |

The licensed blood establishment prepares clinical grade irradiated buffy coats which are suitable to treat patients with severe neutropenia. To prepare the buffy coats, blood is centrifuged to form three layers: the red blood cell layer, the buffy coat layer and the plasma layer. Buffy coats from 10 donors are irradiated with 25 to 50 Gy irradiation to arrest cell growth. The clinical grade irradiated buffy coats are prepared and shipped to the GMP manufacturing facility by overnight courier using a controlled temperature shipper including a temperature monitor. The shipment occurs one day before use in the manufacturing process.

Upon receipt, the buffy coats are held at 15-30° C. until use in manufacturing.

Irradiated Feeder Cell Preparation

Buffy coats from up to ten unique donors are pooled, then centrifuged by Ficoll gradient density centrifugation to harvest peripheral blood mononuclear cells (PBMCs). Approximately 4×10$^9$ viable white blood cells are resuspended in TCM supplemented with approximately 8% human AB serum, 3000 IU/mL IL-2 and 30 ng OKT-3 in a closed static cell culture bag. The PBMC are released per specification.

TABLE 7

Allogeneic PBMC stock specification

| Attribute | Test method | Acceptance criteria |
| --- | --- | --- |
| Appearance | Visual inspection | ID label |
| Identity | Flow cytometry | >85% viable CD45+ cells |
| Viability | Flow cytometry | Report results |
| Total viable leukocyte content | Flow cytometry | 2 to 4 × 10$^9$ |

The PBMC are also tested for sterility and mycoplasma. Immediately prior to starting step 3 (day 12, FIG. C), a sample of the formulated feeder cell, including media, IL-2 and OKT3, is removed. This sample is incubated and analyzed on days 13, 17 and 18 to confirm that the feeder cells do not expand.

Albumin (human), also known as Human Serum Albumin (HSA), is sourced from US donors. All plasma donations are individually tested and non-reactive to HBsAg, anti-HIV 1, anti-HIV 2, and anti-HCV antibodies. Each plasma pool is tested and found negative for HBsAg, anti-HIV 1, anti-HIV 2, and HCV-RNA by NAT. The HSA product is manufactured according to GMP regulations fulfilling the production and testing criteria of US and European Pharmacopoeia.

TIL Outgrowth

The cell suspension is seeded at approximately 0.25×10$^6$ to 0.75×10$^6$ viable cells/mL into TCM supplemented with 10% FBS, 0.25 μg/mL Amphotericin B with 10 μg/mL Gentamicin (Life Technologies, Grand Island, N.Y.), and interleukin-2 (IL-2; aldesluekin) 3000 IU/mL (Clinigen, Nurnberg, Germany) and cultured in standard cell culture conditions (37° C., 5% CO2).

On day 5, half of the media is removed and replaced with TCM supplemented with 10% FBS, 0.50 μg/mL Amphotericin B, 20 μg/mL Gentamicin and 6000 IU/mL IL-2.

On day 7, if the cell concentration is >1.5×10$^6$ viable cells/mL, the TIL outgrowth culture is diluted with three times the volume to maintain approximately 0.1×106 to 2.0×106 viable cells/mL. If the cell concentration is ≤1.5×106 viable cells/mL, half of the media is replaced. In either option, the media is TCM supplemented with 10% FBS, 0.50 μg/mL Amphotericin B, 20 μg/mL Gentamicin and 6000 IU/mL IL-2.

On day 10, if the cell concentration is >1.5×106 viable cells/mL, the TIL outgrowth culture is diluted with three times the volume to maintain approximately 0.1×106 to 2.0×106 viable cells/mL. If the cell concentration is ≤1.5×106 viable cells/mL, half of the media is replaced. In either option, the media added is TCM supplemented with 10% FBS, 0.50 μg/mL Amphotericin B, 20 μg/mL Gentamicin and 6000 IU/mL IL-2.

TIL Activation

TILs are activated using an anti-CD3 antibody (OKT3) to provide a CD3 specific stimulation when bound to the FC receptor of irradiated feeder cells from allogeneic peripheral blood mononuclear cells (PBMCs). The feeders provide a natural source of additional co-stimulation to support the added anti-CD3 (OKT-3).

On day 12, 1 to 20×106 viable T cells from the TIL outgrowth Step 2 are added to 2.0 to 4.0×109 viable irradiated feeder cells (Section 8.1.4.4) using approximately 30±10 ng/mL OKT3, approximately 8% Human AB Serum and 3000±1000 IU/mL IL-2. The TIL activation culture is incubated for 6 days at standard cell culture conditions.

TIL Expansion

On day 18, the activated TILs continue expansion by aseptically adding the activated TIL cell suspension into a bioreactor containing T cell media supplemented with approximately 8% Human AB Serum and 3000 IU/mL IL-2.

On day 19, the TIL expansion is provided a continuous feed of T cell media supplemented with 3000 IU/mL IL-2 until harvest.

TILs are harvested by washing the cells using SEFTA™. The cells are concentrated by centrifugation then washed 2-4 times using phosphate buffered saline (PBS) supplemented with 1% human serum albumin (HSA). The cells are then resuspended in PBS+1% HSA to approximately 50-60 mL.

The washed and concentrated cells are aseptically transferred into a cryobag and a portion removed for lot release testing and retained samples. Cryoprotectant is added to achieve a formulated product of >5×109 viable cells suspended in approximately 10% DMS0 and 8.5% HSA in PBS. A portion is removed for lot release testing and retained samples. The cryobag is cooled to −80° C.

TIL Manufacture Processes

The following table shows examples of process variations.

TABLE 8

Manufacturing Processes

| Process versions | v1.0 | v1.1 | v1.2 | ITIL-168 |
| --- | --- | --- | --- | --- |
| Tumor disaggregation | Manual Disaggregation | Manual Disaggregation | Tiss-U-Stor Disaggregation | Tiss-U-Stor Disaggregation |
| Starting Material | Fresh | Cryopreserved | Cryopreserved | Cryopreserved |
| TIL Outgrowth | 1-3 Weeks | 1-3 Weeks | 12 Days | 12 Days |
| Intermediate Hold Step | Cryopreserved | Cryopreserved | Not Applicable | Not Applicable |

TABLE 8-continued

Manufacturing Processes

| Process versions | v1.0 | v1.1 | v1.2 | ITIL-168 |
|---|---|---|---|---|
| TIL Recovery | 3 Days | 3 Days | Not Applicable | Not Applicable |
| Rapid Expansion Phase | 12 Days | 12 Days | 12 Days | 12 Days |
| Culture Extension | 0-2 Days | 0-2 Days | Not Applicable | Not Applicable |
| Final Product | Fresh | Fresh | Cryopreserved | Cryopreserved |

The following table shows Drug Product Data

TABLE 8

Drug Product Data

| Product Lot | Process Version | Yield ($\times 10^{10}$) | Viability | Percent $CD3^+$ Cells |
|---|---|---|---|---|
| TIL001 | 1.0 | 1.1 | 82 | N/A |
| TIL003 | 1.0 | 2.2 | 94 | 98 |
| TIL005 | 1.0 | 2.0 | 96 | N/A |
| TIL012 | 1.0 | 3.2 | 95 | 98 |
| TIL013 | 1.0 | 2.1 | 80 | 92 |
| TIL014 | 1.0 | 4.4 | 91 | 95 |
| TIL015 | 1.0 | 6.4 | 91 | 97 |
| TIL016 | 1.0 | 5.5 | 93 | 96 |
| TIL027 | 1.0 | 3.8 | 95 | 97 |
| TIL032 | 1.0 | 3.7 | 92 | 99 |
| TIL035 | 1.0 | 6.4 | 96 | 90 |
| TIL037 | 1.0 | 2.6 | 92 | 97 |
| TIL038 | 1.0 | 1.3 | 83 | 98 |
| TIL039 | 1.1 | 1.2 | 80 | 93 |
| TIL040 | 1.0 | 5.3 | 93 | 97 |
| TIL041 | 1.0 | 3.2 | 93 | 98 |
| TIL043 | 1.0 | 4.8 | 93 | 98 |
| TIL054 | 1.1 | 0.82 | 86 | 91 |
| TIL065 | 1.1 | 3.4 | 94 | 97 |
| TIL067 | 1.2 | 3.0 | 91 | 97 |
| TIL073 | 1.0 | 5.4 | 92 | 98 |
| TIL077 | 1.2 | 1.0 | 91 | 97 |
| TIL078 | 1.2 | 3.4 | 99 | 98 |
| E2 | 1.2 | 3.5 | 86 | 97 |
| E3 | 1.2 | 1.8 | 80 | 96 |
| E4 | 1.2 | 1.0 | 88 | 93 |
| E5 | 1.2 | 4.1 | 98 | 100 |

Figures 67A, 67B, 67C:
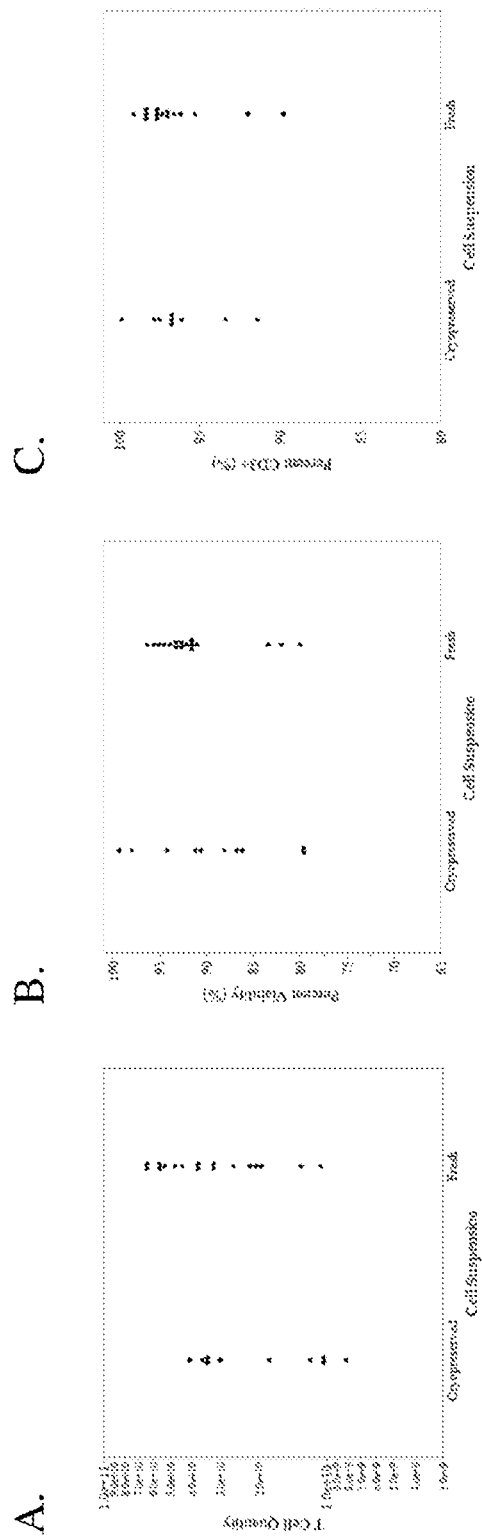
FIG. 67A-67C compare yield (FIG. 67A), percent viability (FIG. 67B), and percent CD3+ T cells (FIG. 67C) of cryopreserved and fresh disaggregated cell suspensions.

Comparing cryopreserved and fresh cell suspensions, representative yields were consistent as demonstrated by similar drug substance yield (FIG. 67A), viability (FIG. 67B), and percent T cells (FIG. 67C).

Figure 68A:
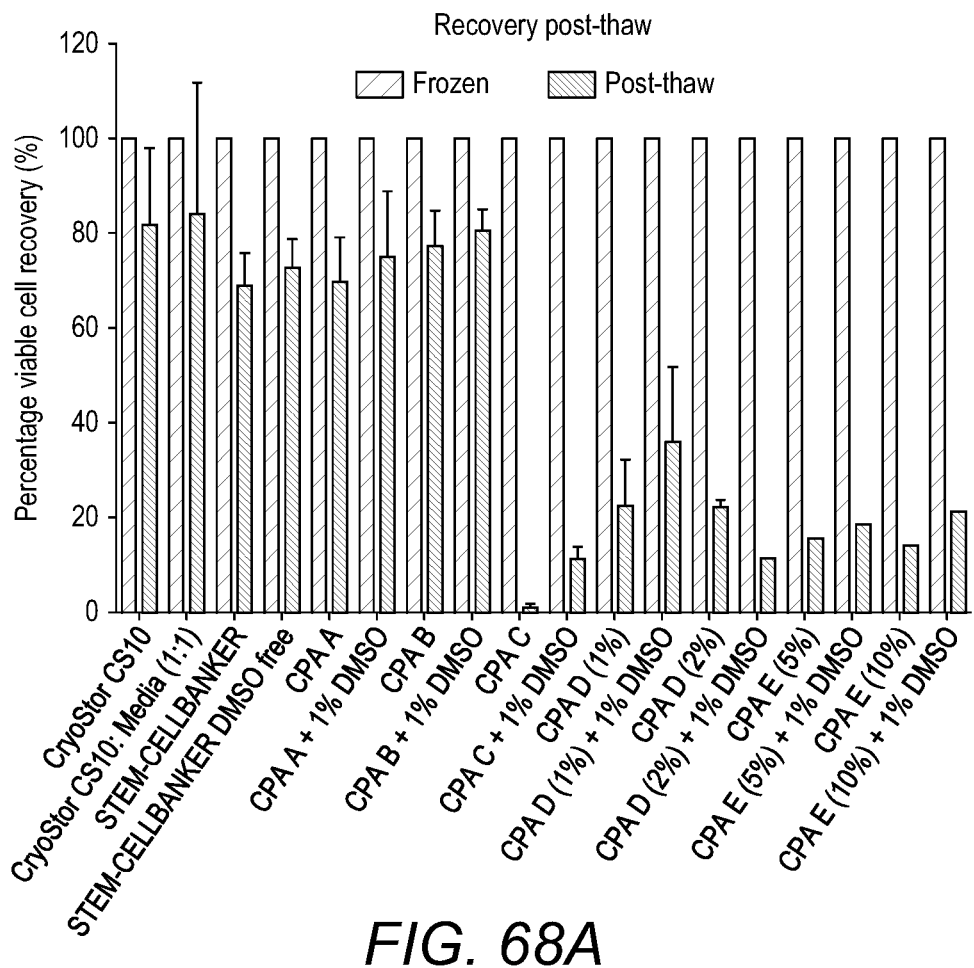
FIGS. 68A and 68B compare viability of PBMCs cryopreserved with commercially available cryopreservants.
Figure 68B:
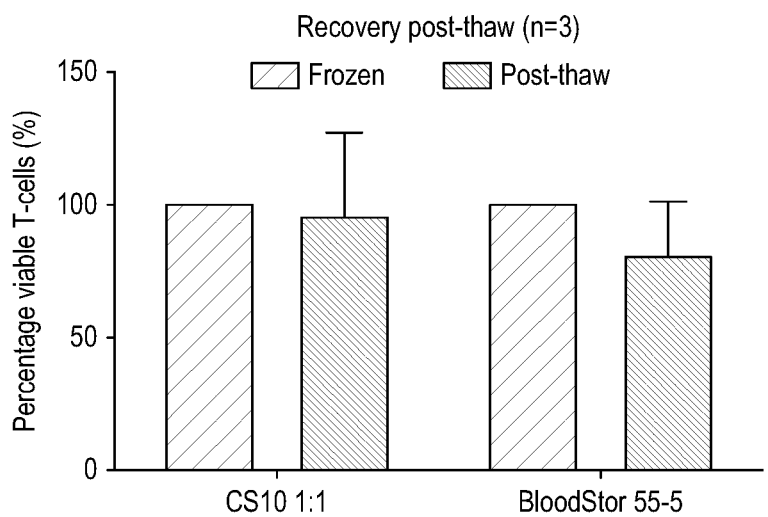
Figure 69:
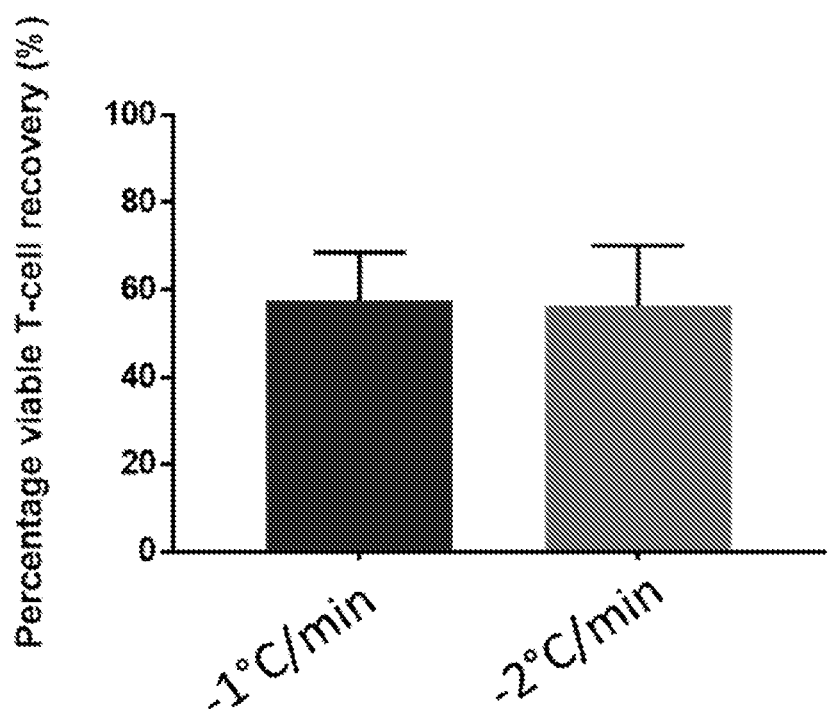
FIG. 69 compares viability of PBMCs digested then cryopreserved following a protocol that held the material at 4° C. for 10 minutes, then decreased the temperature at a rate of −1° C./min or decreased from 35° C. to −80° C. directly at a rate of −2° C./min.
Figure 71A:
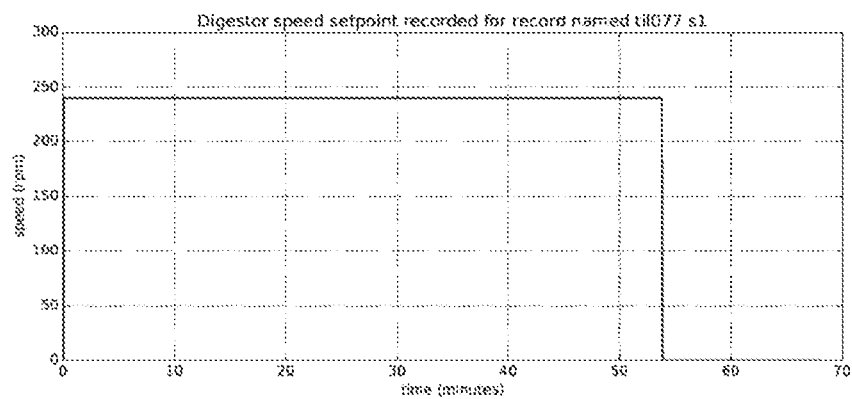
FIG. 71A-71D and FIG. 71E-71H depict disaggregation and cryopreservation of TIL077.
Figure 71B:
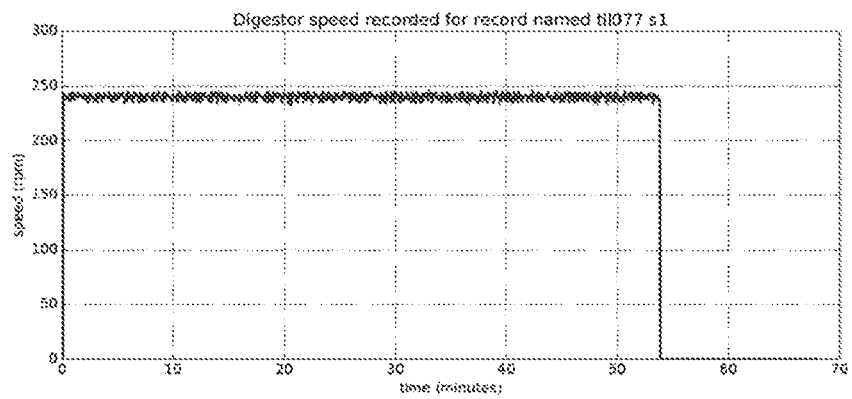
Figure 71C:
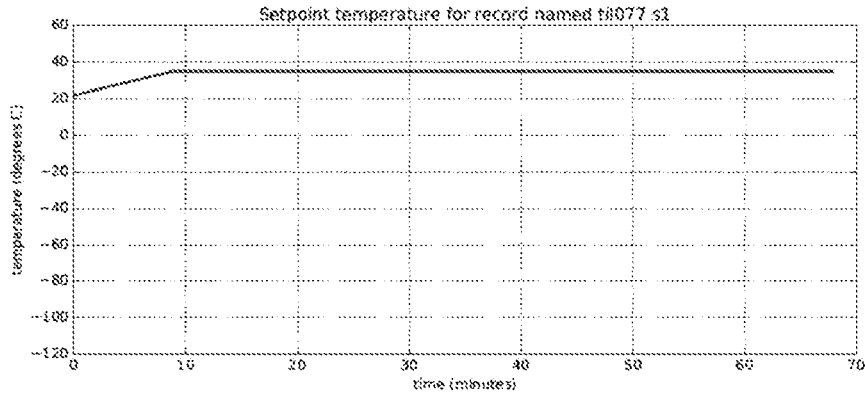
Figure 71D:
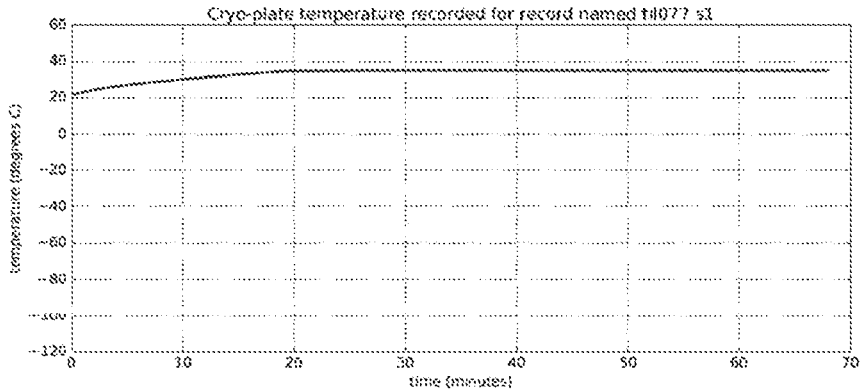
Figure 71E:
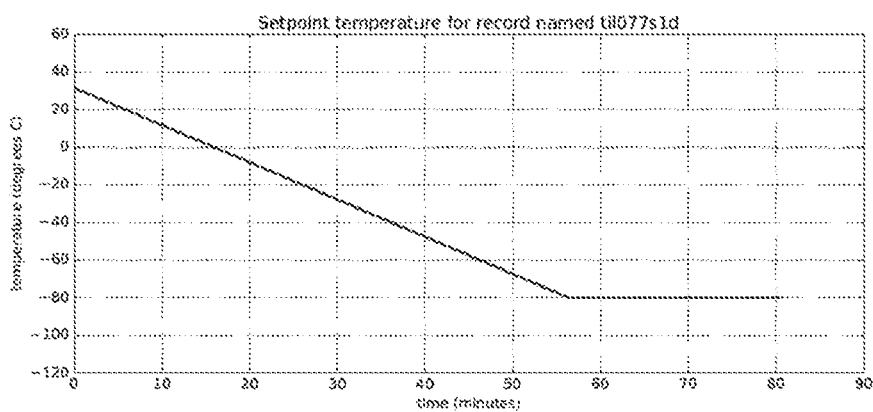
Figure 71F:
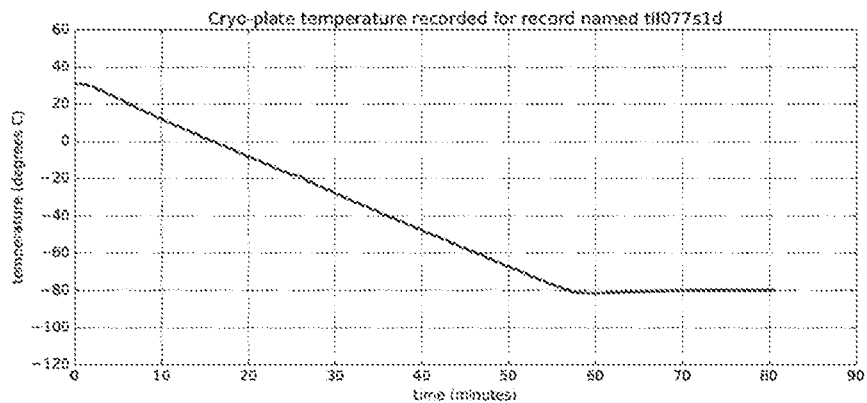
Figure 71G:
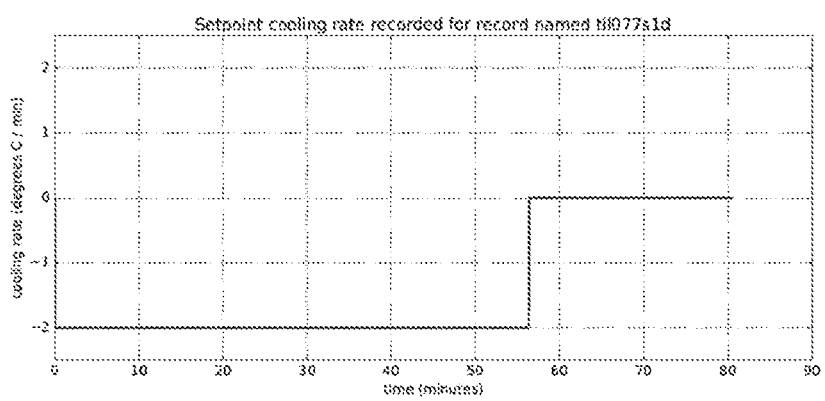
Figure 71H:
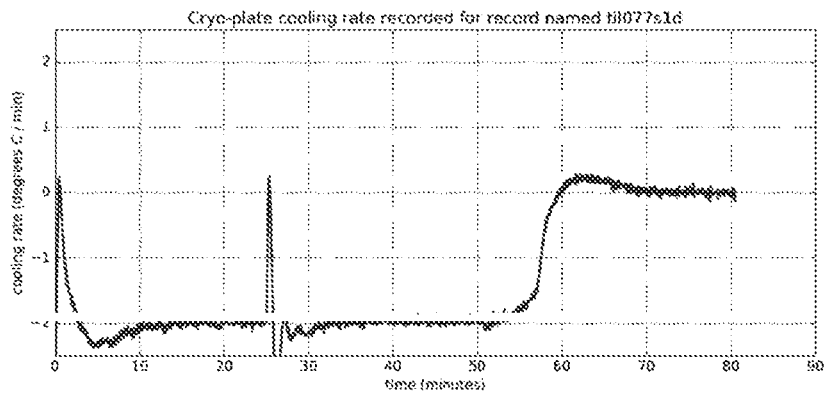
Figure 72A:
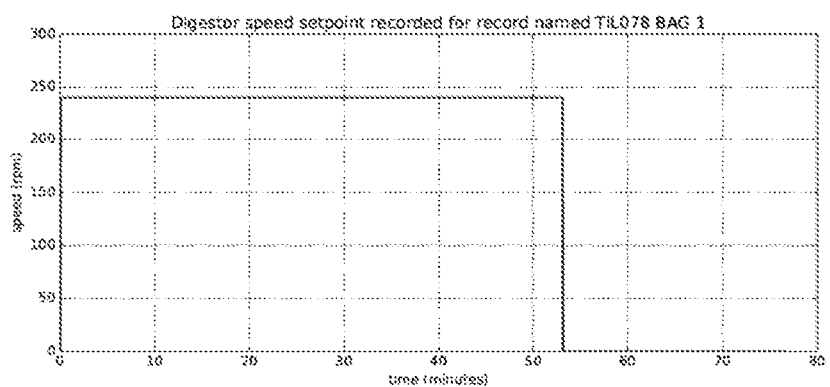
FIG. 72A-72D and FIG. 72E-72H depict Tiss-U-Stor disaggregation and cryopreservation of TIL078 (1 of 2 bags)
Figure 72B:
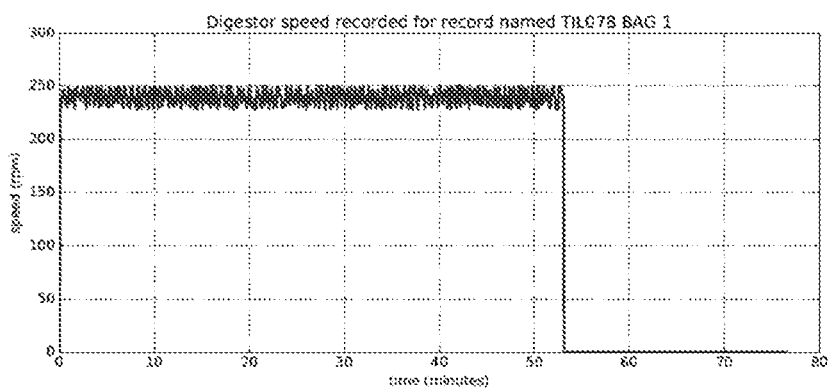
Figure 72C:
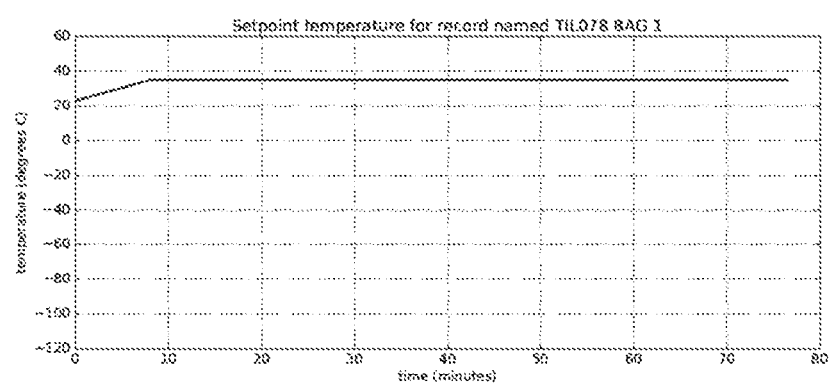
Figure 72D:
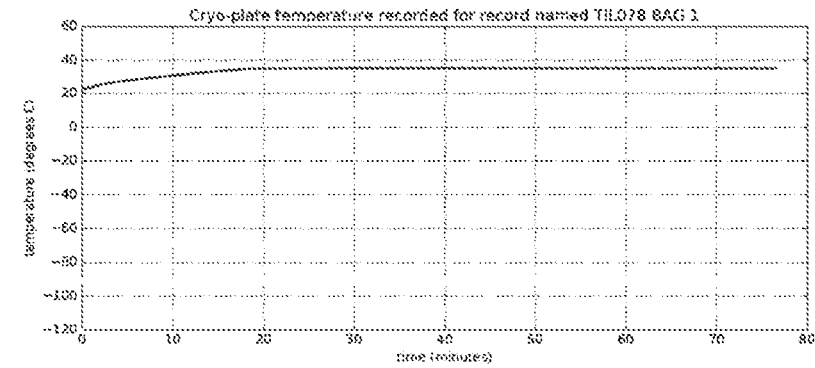
Figures 72E, 72F, 72G, 72H:
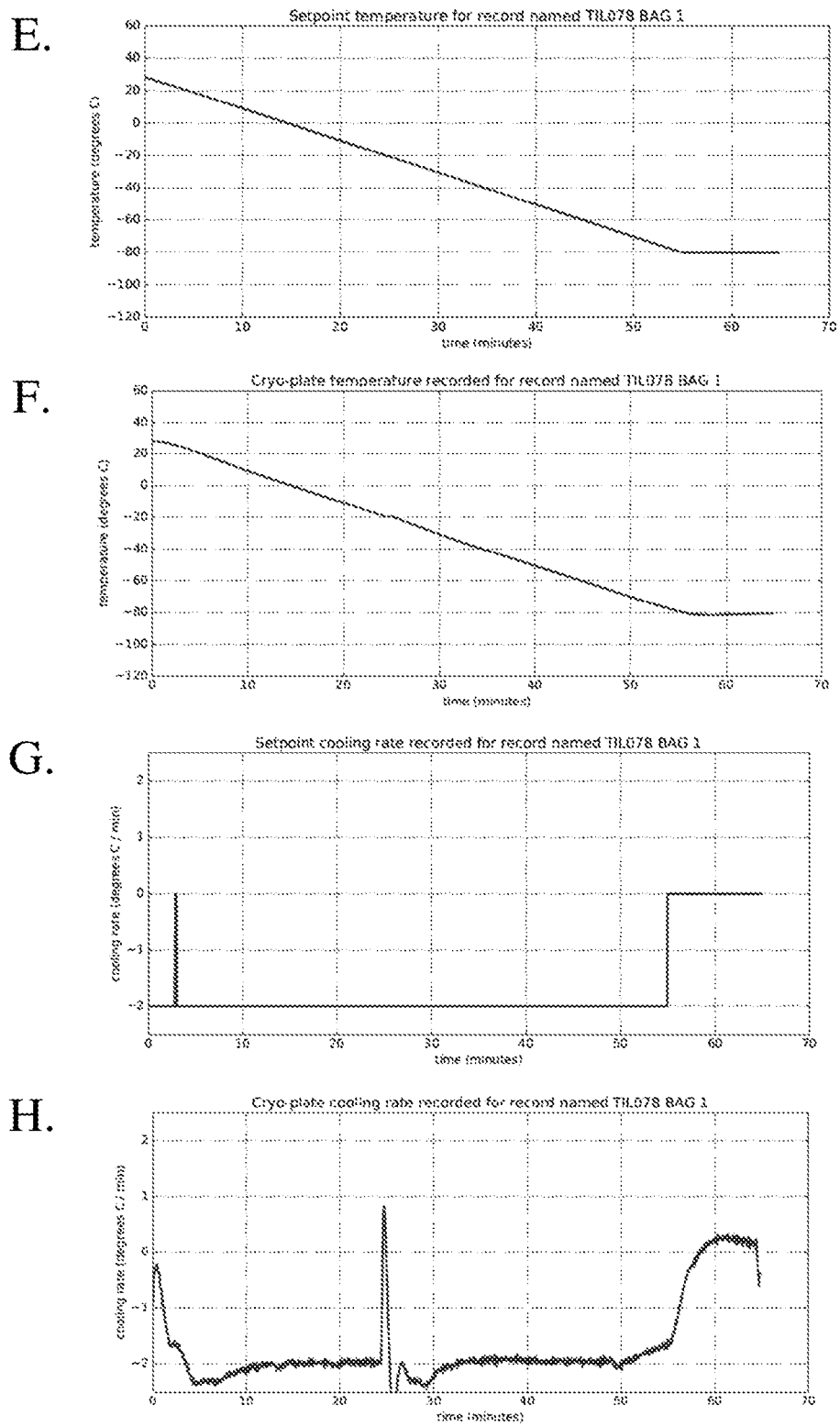

Optimization of Cryopreservation—As a surrogate to tumor material, isolated PBMCs were digested using the Tiss-U-Stor process and materials. Commercial cryopreservation agents (CPAs) were evaluated across a range of conditions to determine which reagent maximized post-thaw viability (FIG. 68). The post-thaw viabilities of two CPAs, Cryostor10 and Stem Cell Banker DMSO free, were similar. CryoStor based DMSO was then compared with Bloodstor 55-5, a DMSO based cryopreservative, and the higher concentration BloodStor product was selected since it was more concentrated thus allowing for a smaller cryobag. Cryopreservation was then compared following a protocol that either held the material at 4° C. for 10 minutes, then decreased the temperature at a rate of −1° C./min or decreased from 35° C. to −80° C. directly at a rate of −2° C./min. Post-thaw viability was similar between the two cryopreservation protocols used (FIG. 69).

During cooling, ice nucleation releases heat. Undercooling, a phenomenon where the released heat appears to warm the solution, is associated with lower post-thaw recoveries. Temperature data was recorded from test articles during cryopreservation using both protocols (FIG. 70). Undercooling was observed in both independent runs using the −1° C./min protocol, whereas the −2° C./min cooling protocol recorded no undercooling event once, and in the second independent run, an undercooling event was observed to release less heat relative to the alternative protocol (FIG. 70).

The cryopreserved DP is transferred to vapor phase LN2 for storage and transport at ≤−130° C.

Sample sterility is tested and retained samples are frozen using a Coolcell® (Biocision, Larkspur, Calif.) at −80° C. then transferred to vapor phase LN2 for storage purposes.

Although the present invention and its advantages have been described in detail, it should be understood that various changes, substitutions and alterations can be made herein without departing from the spirit and scope of the invention as defined in the appended claims.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Figure 39:
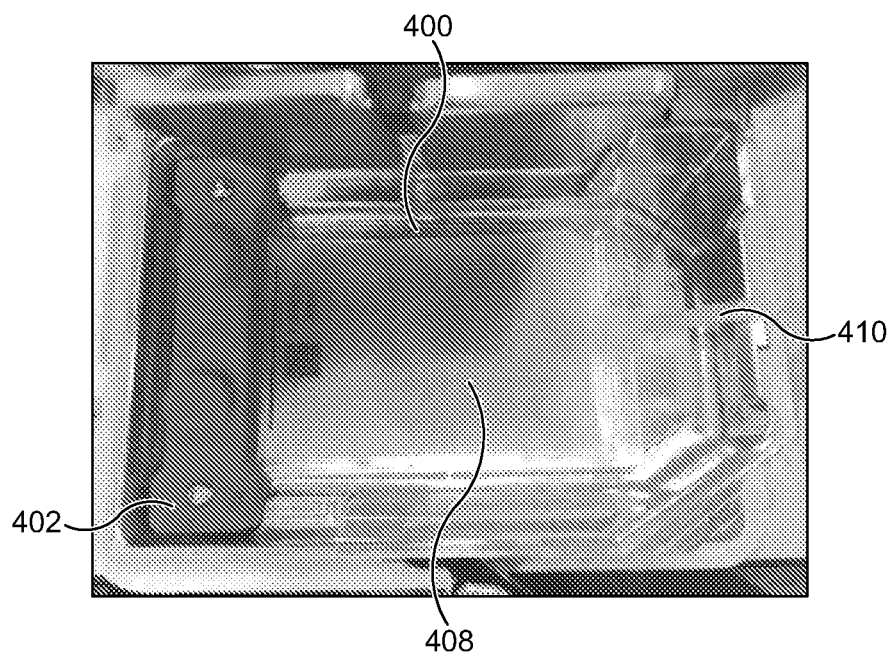
FIG. 39 shows a front view of an embodiment of a collection bag secured by a clamp.

FIG. 39 shows an embodiment of bag 400 during use. As depicted, bag 400 is secured by a securing element such as clamp 402 within device 404 such as tray 406. Tissue 408 is visible through a transparent side of bag 400. Tubing 410 is coupled to bag 400.

Example 2

Figure 40:
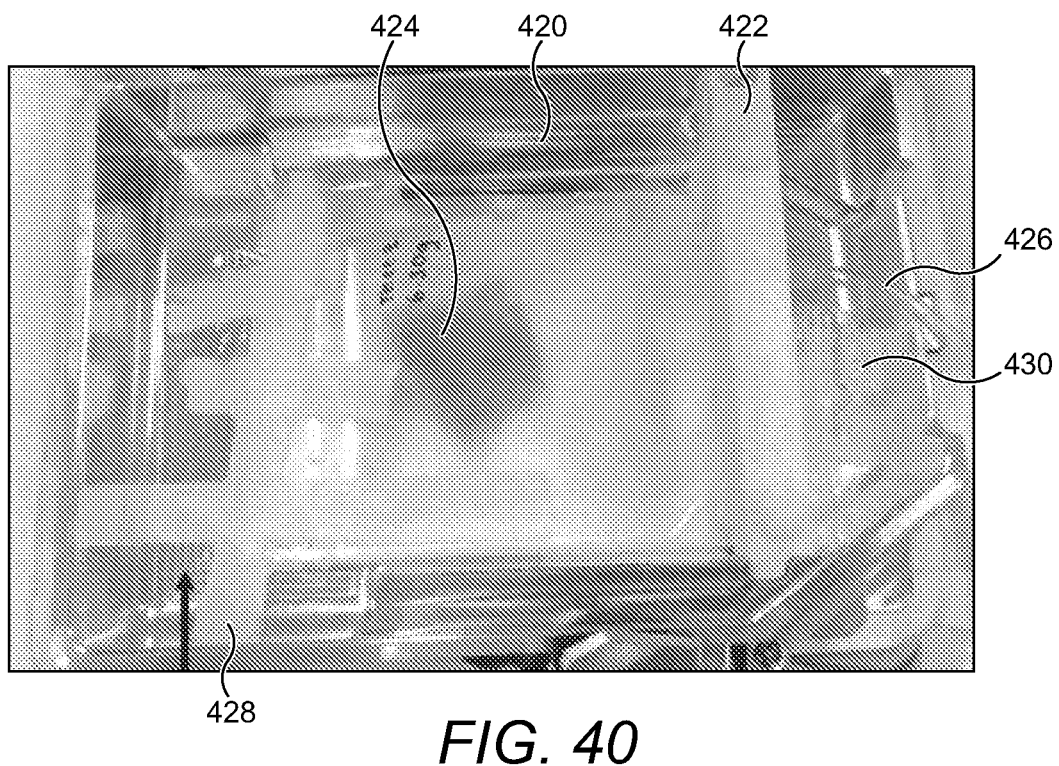
FIG. 40 shows a front view of an embodiment of a collection bag.

FIG. 40 depicts an embodiment of bag 420 for use in the invention as described herein. As depicted, bag 420 is secured by a securing element 422 from device and tray 424. Tissue material 424 is visible through transparent side of bag 420. Tubing 426 is coupled to bag 420. As shown a position of bag 400 within tray 406 is further secured using fixation element 428, in particular tape. Tissue 424 is visible through transparent side of bag 420. As shown in FIG. 40, bag may include ports 430 to access the interior of bag and/or tissue 424.

Example 3—Disaggregation and Cryopreservation

TIL075 was manufactured from metastatic melanoma tumor pieces (samples). The tumor samples were weighed and processed as follows. Si=1.4 g. Si was disaggregated by an automated procedure. S2=19.4 g. S2 was divided, one portion (about 7.7 g) was disaggregated by an automated procedure and the second portion (about 12 g) was disaggregated manually.

Manual disaggregatrion: The tumor sample was cut into smaller 2-4 mm³ pieces and added to a bottle containg 80 ml of digestion media with antibiotics. The bottle was placed on a shaker and disaggregated overnight (about 14 hours) at 37° C. The digest was then filtered through netwells and 100 μM cell strainers into Falcon 50 tubes. 10% of the filtered digest was set aside for sterility testing. The remainder was centrifuged and resuspended in 12 ml of CS10 and divided into 12 cryovials.

Tiss-U-Stor disaggregation: Two CS50N bags were opened with sterile scissors, cutting the end without ports. The Si 1.4 μm sample and the 7.7 μm portion of S2 were placed in the CS50N bags and the bags sealed. 15 ml of disaggregation media and 30 ul of antibiotics are combined and added to each of the sealed bag using a syringe through needleless ports of the bags. The bags were transferred to a Tissue Disaggregator loaded in a ViaFreeze and the disaggregation protocol was initiated. The Disaggregation protocol called for a temperature increase from ambient at a rate of 1.5° C./min to 35° C., and a temperature hold at 35° C. while the disaggregator was active. The disaggregator speed was set to 240 cycles/min. The temperature of the ViaFreeze remained at 35° C. thereafter until the cryopreservation step.

The bag setup includes a direct connection by tubing through an inline filter to a secondary cryobag. The disaggregated material in the CS50 hag was filtered into the cryobag and the tubing connection sealed. 1.5 ml Blood-stor (DMSO) was slowly added through a needleless port of the cryobag, the bag was placed in a casette designed for optimal heat transfer, and the cassette was placed back in the ViaFreeze in place of the disaggregator.

A post-disaggregation cryopreservation protocol was engaged. The freeze cycle ramped the temperature of the ViaFreeze from 35° C. at −2° C./min to −80° C. Frozen bags were transferred to liquid nitrogen storage.

Example 4—Disaggregation and Cryopreservation

TIL077 was manufactured from metastatic melanoma tumor pieces (samples). The tumor samples were weighed and processed as follows. Si=4.6 g. S2=4.6 g.

Tiss-U-Stor disaggregation: Two CS50N bags were opened with sterile scissors, cutting the end without ports. The Si=4.6 μm sample and the S2=4.6 μm sample were placed in the CS50N bags and the bags sealed. 15 ml of disaggregation media and 30 ul of antibiotics are combined and added to each of the sealed bag using a syringe through needleless ports of the bags. The bags were transferred to a Tissue Disaggregator loaded in a ViaFreeze and the disaggregation protocol was initiated. The Disaggregation protocol called for a temperature increase from ambient at a rate of 1.5° C./min to 35° C., and a temperature hold at 35° C. while the disaggregator was active. The disaggregator speed was set to 240 cycles/min. The temperature of the ViaFreeze remained at 35° C. therafter until the cryopreservation step. FIG. 71 shows disaggregation records.

The bag setup includes a direct connection by tubing through an inline filter to a secondary cryobag. The disaggregated material in the CS50 bag was filtered into the cryobag and the tubing connection sealed. 1.5 ml Blood-stor (DMSO) was slowly added through a needleless port of the cryobag, the bag was placed in a casette designed for optimal heat transfer, and the cassette was placed back in the ViaFreeze in place of the disaggregator.

A post-disaggregation cryopreservation protocol was engaged. The freeze cycle ramped the temperature of the ViaFreeze from 35° C. at −2° C./min to −80° C. FIG. 71 shows cryopreservation records. Frozen bags were transferred to liquid nitrogen storage.

Example 5—Disaggregation and Cryopreservation

TIL078 was manufactured from metastatic melanoma tumor pieces (samples). The tumor samples were weighed and processed as follows. Si=11 g. S2=2 g.

Tiss-U-Stor disaggregation: Two CS50N bags were opened with sterile scissors, cutting the end without ports. The tumor material was divided and 6.4 μm of sample was placed in each of two CSSON bags and the bags sealed. 15 ml of disaggregation media and 30 μl of antibiotics are combined and added to each of the sealed bag using a syringe through needleless ports of the bags. The bags were transferred to a Tissue Disaggregator loaded in a ViaFreeze and the disaggregation protocol was initiated. The Disaggregation protocol called for a temperature increase from ambient at a rate of 1.5° C./min to 35° C., and a temperature hold at 35° C. while the disaggregator was active. The disaggregator speed was set to 240 cycles/min. The temperature of the ViaFreeze remained at 35° C. therafter until the cryopreservation step. FIG. 72 shows cryopreservation records The bag setup includes a direct connection by tubing through an inline filter to a secondary cryobag. The disaggregated material in the CS50 bag was filtered into the cryobag and the tubing connection sealed. 1.5 ml Blood-stor (DMSO) was slowly added through a needleless port of the cryobag, the bag was placed in a casette designed for optimal heat transfer, and the cassette was placed back in the ViaFreeze in place of the disaggregator.

A post-disaggregation cryopreservation protocol was engaged. The freeze cycle ramped the temperature of the ViaFreeze from 35° C. at −2° C./min to −80° C. FIG. 72 shows cryopreservation records. Frozen bags were transferred to liquid nitrogen storage.

Example 6—Disaggregation and Cryopreservation

Figure 73A:
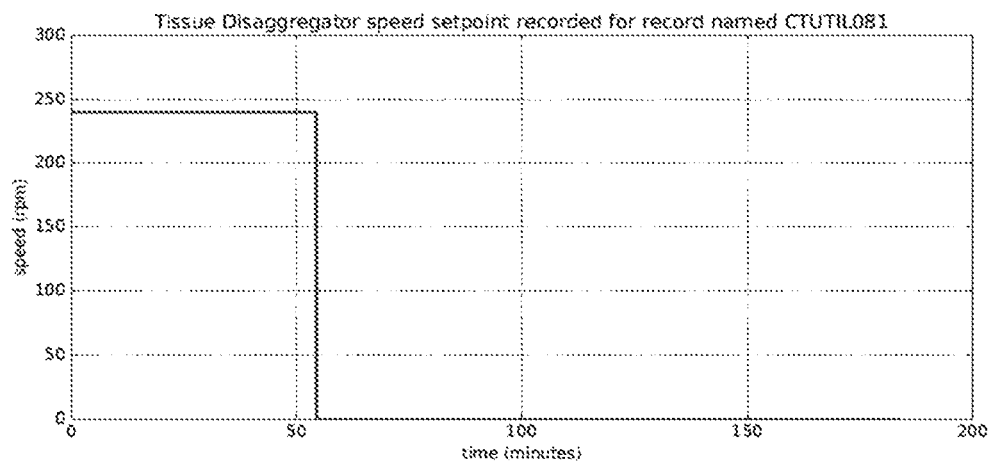
FIG. 73A-73C and FIG. 73D-73F depict Tiss-U-Stor disaggregation and cryopreservation of TIL078 in a continuous process.
Figure 73B:
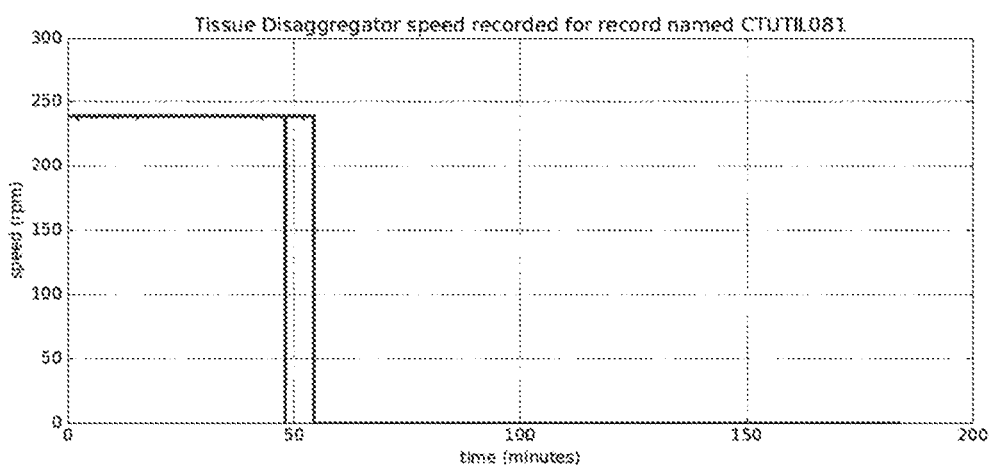
Figure 73C:
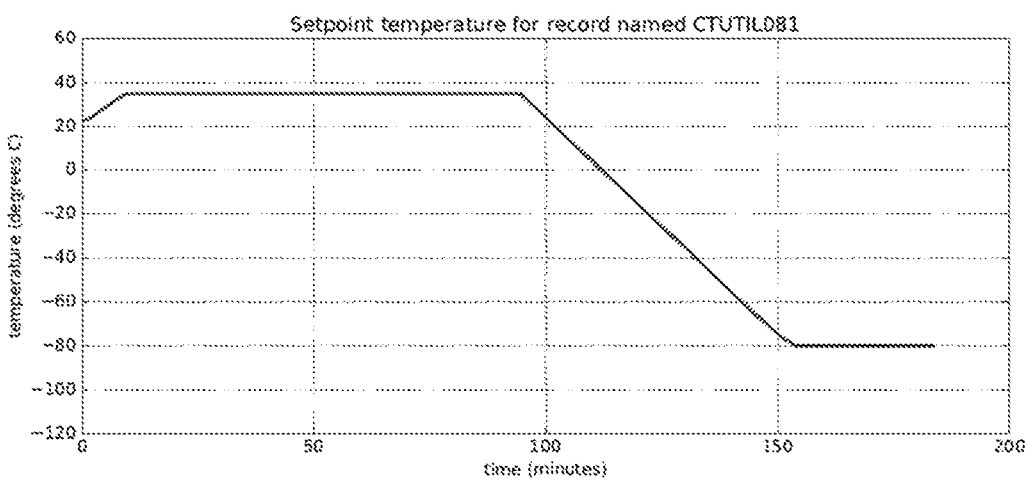
Figure 73D:
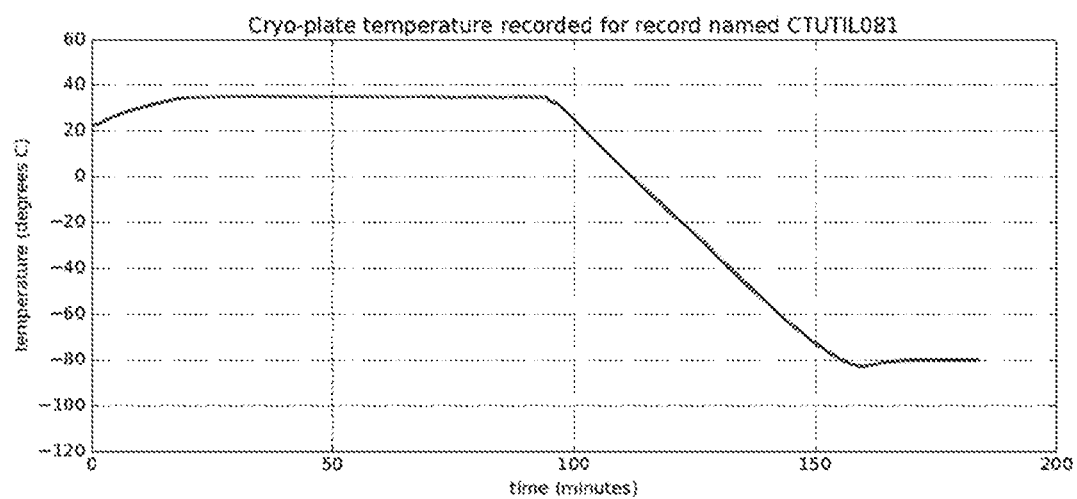
Figure 73E:
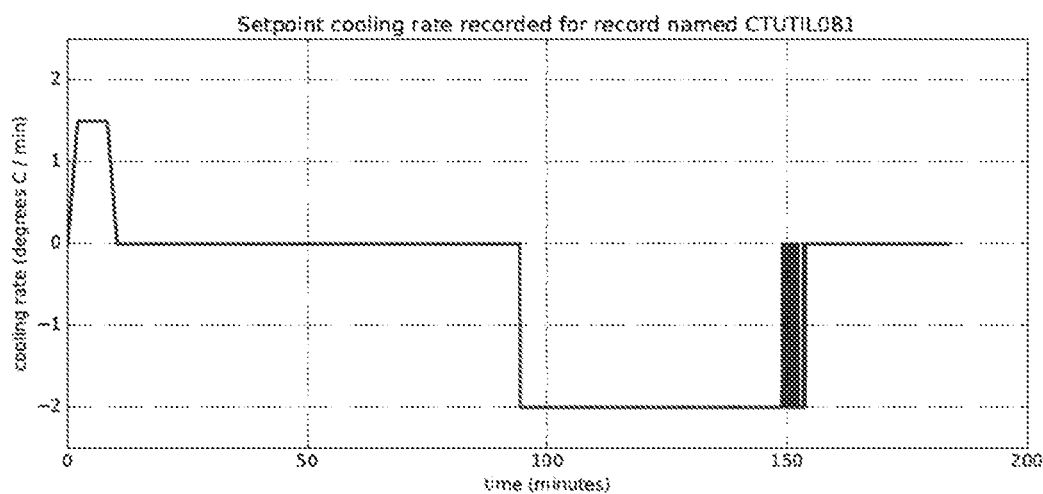
Figure 73F:
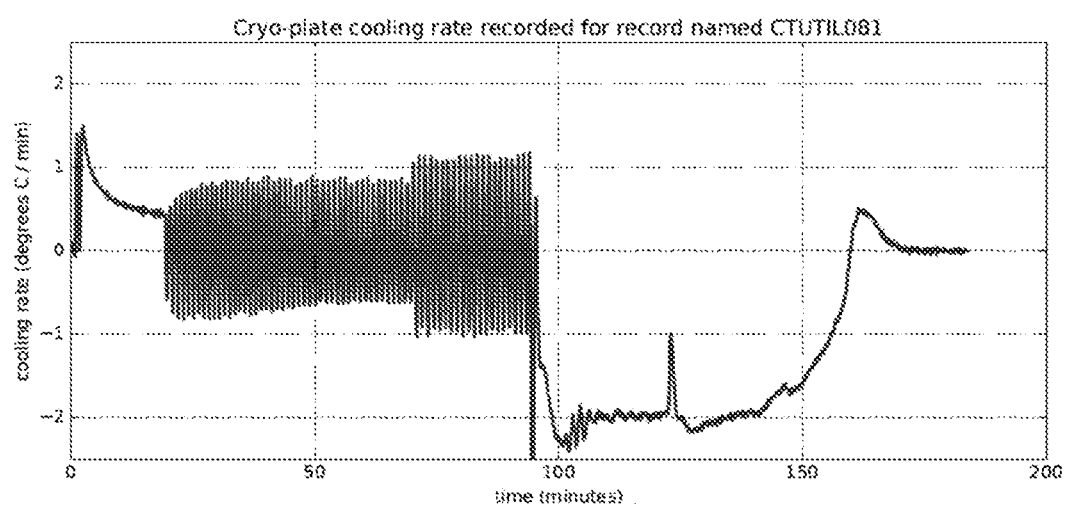

TILOS I was manufactured from metastatic melanoma tumor pieces (samples). The software was updated to include disaggregation and cryopreservation in a single protocol. FIG. 73 shows disaggregation and cryopreservation records. As in the prior examples, the disaggregator was active for about 53 min. (FIGS. 73A, 73B). The disaggregated tissue was transferred from the disaggregation bag through a filter to the cryobag and returned to the ViaFreeze for cryopreservation within about 90 min. from the start of the disaggregation process at which time cryogenic cooling was initiated.

Example 7—Manufacture from Vials

TABLE 9

| Cell cryopreservation and thawing | | |
|---|---|---|
| Reagents/Materials Reagent | Manufacturer | Catalog # |
| Media depending on cell type | NA | NA |
| DPBS | Sigma | D8537-500ML |

TABLE 9-continued

Cell cryopreservation and thawing

| Reagents/Materials Reagent | Manufacturer | Catalog # |
|---|---|---|
| 15 mL Centrifuge Tube | VWR | 339650 |
| Stripette 10 mL | Corning | CLS4101 |
| Stripette 25 mL | Corning | CLS4251 |
| Stripette 5 mL | Corning | CLS4051 |
| Tips 1000 µL filtered | StarLabs | S1182-1730 |
| Trypan Blue | Sigma | T8154-100ML |

TABLE 10

Equipment

| Description | Manufacturer | Part # | Serial #/Asset# |
|---|---|---|---|
| Powerpette pro 1-100 mL | VWR | 452-8344 | NA |
| Pipette ErgoOne 100-1000 µL | Star Labs | S7110-1000 | NA |
| Megafuge 40R Centrifuge | Hereus | 75004518 | 41536283 |
| Hemacytometer | Hawksley | HC002 | NA |
| Water Bath 12 L | VWR | 462-0557 | BP1912001 |
| IncuSafe $CO_2$ Incubator | PHCBI | MC O-170AIC-PE | NA |

Cryovials were removed from liquid nitrogen and placed in a 37° C. water bath until the cell suspension is just melted. Cell suspensions were placed in a 15 mL falcon and topped up with PBS up to 10 mL, and centrifuged at 400 g for 10 minutes. The supernatant was decanted.

For cell culture, cell pellets were resuspended in pre warmed media, initially in a small volume i.e. 2 to 3 mL. Adherent cell lines (i.e. tumor lines, HEK 293s) were added to tissue flasks with media in accordance with the following table. Non adherent cell lines (i.e. T cells, TILs, Jurkat cells) were plated at a density of 0.5 to $1\times10^6$ cells per mL. Flasks were placed in a humidified 37° C. incubator and media replaced every 2-3 days.

TABLE 11

Cell seeding densities for adherent cells in different vessels

| Vessel/flask type | Seeding density | Media volume mL |
|---|---|---|
| 24 well | $0.1 \times 10^6$ | 0.5 to 1 |
| 6 well | $0.5 \times 10^6$ | 2 to 4 |
| T25 | $0.7 \times 10^6$ | 4 to 6 |
| T75 | $2.1 \times 10^6$ | 12 to 15 |
| T 150 | $4.4 \times 10^6$ | 25 to 30 |

Example 8—Manufacture from Cryopreserved Disaggregated Tumors

Manufacturing Process
Thawing Starting Materials

The VIAThaw CB1000 Thawing system was used to control heating of cryopreserved samples stored in cryobags. Cryopreserved cell suspension was thawed, then diluted in T-cell media (TCM) manufactured by Life Technologies (Paisley, United Kingdom). TCM contains 80% Rosewll Park Memorial Institute (RPMI) 1640 medium and 20% AIM V. The cell suspension was filtered through a 70- to 100-µm filter and centrifuged, and the supernatant removed. The cell pellet was resuspended in TCM supplemented with 10% irradiated Fetal bovine serum (FBS) (Life Technologies, Auckland, New Zealand).

A disaggregated, cryopreserved tumor (about 16.5 ml) in an Origin CS50 bag was placed in the thawing tray of a VIAThaw CB1000 Thawing System and warmed to about 0° C.

Example 9—Potency

A co-culture-based potency method quantitates the percentage of T cells activated by an OKT3-expressing target cell line. The TIL product mechanism of action in vivo involves TIL peptide presentation through pMHC-HLA, which binds to the TCR in vivo. The potency assay quantifies the percentage of potent T cells, defined as viable T cells positive for either CD137, IFN-γ, TNFα, or CD107a divided by the total viable T cells when specifically activated by co-culture with a K562 cell line expressing the OCT3 antigen-binding domain. Markers used to quantitate T cell potency include DRAQ7, CD45, CD2, CD107a, CD137, TNF-α, and IFN-γ.

To measure the potency, ITIL-168 DS cells are co-cultured for approximately 5 hours using 1 of 3 cell lines: Condition 1—No stimulation—background cell activity; Condition 2—K562 cell line—background TCR-independent reactivity; Condition 3—K562 cell line expressing an ScFv against OKT-3—TCR-induced T-cell stimulation.

The cultured cells are analysed by flow cytometry and gated on viable white blood cells to quantitate the T cells that express at least 1 of 4 activation markers. For stability tests, cryopreserved DP cells are thawed, washed, and rested overnight.

ITIL-168 TCR potency is calculated as follows: Step 1) the % potency due to non-specific stimulation is obtained from Condition 2; Step 2) the % potency due to CD3 specific and non-specific stimulation is obtained from Condition 3; Step 3) the % potency due to CD3 specific stimulation is calculated as Condition 3 Condition 2.

For both Condition 2 and Condition 3, the % potent result is 100% minus the percentage of all T cells that are CD137−/IFN-γ−/TNFα−/CD107a− (i.e. background). This population does not produce at least one marker.

Example 10—TIL Outgrowth and Rapid Expansion

The TIL manufacturing process begins after the tumour resection, disaggregation, cryopreservation, and optional packaging and shipment. shipment packaging, and shipment from the Tumour Processing Huh to Instil's manufacturing facility in a qualified shipper under controlled conditions. Th cryopreserved tumor and T cells are thawed using controlled conditions, and diluted in T cell media (TCM) composed of 80% Roswell Park Memorial Institute (RPMI) 1640 medium and 20% AIM V, supplemented with 10% FBS, Amphotericin B, Gentamicin, Vancomycin, and IL-2 (herein referred to as ICMT).

The cells are washed by centrifugation in closed bags, resuspended in ICMT and samples are taken for cell counts. Cell suspension is seeded into culture bags with ICMT targeting $0.25\times10^6$ viable cells/mL and incubated under controlled conditions up to Day 8 of the process. On Day 8, samples for cell counts are taken and an equal volume of ICMT is added to the culture bag and incubated under controlled conditions. On Day 11, cell counts are taken and an equal volume of ICMT is added to the culture bag and incubated under controlled conditions. On Day 13, cell counts are taken, and TILs are concentrated by centrifugation in a bag to provide between $1\times10^6$ to $20\times10^6$ viable T cells.

Also on Day 13, the 1×10⁶ to 20×10⁶ viable outgrown TILs are activated using anti-CD3 and irradiated feeder cells (allogenic PBMCs) with TCM containing 8% Human AB serum and IL-2 (herein referred to as WTCM). The TIL activation culture is incubated for up to 6 days under controlled conditions in static culture bags. On Day 19 of incubation, cell counts are performed and activated TILs are seeded into a bioreactor containing WTCM. Cells are incubated for up to 6 days under controlled conditions. On Day 20, TIL expansion is provided a continuous feed of TCM supplemented with IL-2 until harvest target dose is achieved before or by Day 27 of the process.

Once harvest dose is achieved, the cells are counted, washed and concentrated by centrifugation in phosphate buffered saline (PBS) supplemented with 1% human serum albumin (HSA). The TILs in the drug product (DP) bag are then cooled to 2-8° C. and formulated 1:1 with cryoprotectant containing 16% HSA and 20% DMSO to provide a final formulation of DP in PBS containing 8.5% HSA and 10% DMSO. Sample volumes are removed for lot release testing, reference and back-up samples.

Formulated DP is cryopreserved in a CRF using a predefined program until the product reaches a specified temperature. The cryopreserved DP is then transferred to liquid nitrogen storage before transportation at ≤−130° C. to clinics for administration.

TABLE 12

| Equipment | | |
|---|---|---|
| Equipment/Supply | Manufacturer | Model or Catalog# |
| Leukosep ficoll tubes | Greiner Bio-One Lrd | 227288 |
| PermaLife Cell Culture Bag, 325 ml | Origen Biomeical Inc | PL325-2G |
| Cell culture expansion hag | Charter Medical Ltd. | EXP-1L |
| WAVE 10 L bag | Cytiva | 29-108-1-7173 |
| CT800.1 Sefia kit | Cytiva | 2000 I |

TABLE 13

| Reagents | | | | |
|---|---|---|---|---|
| Reagent | Manufacturer | Catalog# | Lot # | Expiry # |
| T-cell media | Life Technologies | 04196658P | 2021537 | 31 Aug. 2020 |
| Gamma-irradiated FBS | Life Technologies | 01190005H-RESERVE 2-2YBT2DS | 2225231RP | 31 May 2024 |
| Proleukin manufacturer vial (IL-2) | Clinigen Group PLC | Proleukin | 801313T | 31 Dec. 2020 |
| Aliquoted Il-2 stock | N/A | N/A | CTU-IL2/02/09/2019 | 31 Aug. 2020 |
| Gentamicin/Amphotericin solution (500x) | Life Technologies | RO1510 | 2217613 | 30 Mar. 2021 |
| Vancomycin manufacturers vial | Bowmed Ibisqus | N/A | 90260 | 28 Feb. 2021 |
| Vancomycin aliquot (50 mg/ml) | N/A | N/A | CTU-12-06-2020 | 28 Feb. 2021 |
| Gamma-irradiated human AB serum | Gemini Bio-Products LLC | 100-812G | H12Y00K | 30 Sep. 2020 |
| OKT-3 manufacturers vial (1 g/ml) | Miltenyi Biotec Ltd | 170-076-116 | 6200108211 | 17 Oct. 2020 |
| Aliquoted OKT-3 | N/A | N/A | CYU-OKT3/05/05/2020 | 17 Oct. 2020 |
| 20% Human serum albumin | Nova Biologics Inc | 68982-0633-02 | M848B6661 | 27 Nov. 2021 |
| CryoSure DMSO | WAK-Chemie Medical GmbH | WAK-DMSO-50 | USP8C1S | 28 Feb. 2022 |

Example 11

Full-scale runs were performed under GMP conditions. The ITIL-168 process used in these runs included the use of cryopreserved tumor digest, a target of 0.25×10⁶ viable cells/mL seeding for the TIL outgrowth stage (stage 1), continuous processing from the TIL outgrowth to TIL rapid expansion phase (REP), and automated formulation of the final product and cryopreservation of the final drug product.

ITIL-168 is a tumor-infiltrating lymphocyte (TIL) therapy for the treatment of adult patients with advanced melanoma who have relapsed from or are refractory to at least one prior line of therapy. ITIL-168 consists of a single infusion of autologous T cells isolated and expanded ex-vivo from a patient's cancer tissue and administered intravenously. Process improvements have been identified and implemented over time, the improved process referred to as ITIL-168. Table summarizes process variations. me and implements been identified and implemented over time, the improved process referred to as ITIL-168. Table summarizes process variations. Me and implements.

TABLE 14

Summary of Manufacturing Process Developments

| Process Step | Unit Operation/ Change | MS v1.0 | MS v1.1 | UTIL-01 | ITIL-168 Process |
|---|---|---|---|---|---|
| Tumour Digest Preparation | Tumour Disaggregation | Manual disaggregation in bottles | Manual disaggregation in bottles | Automated disaggregation in bags (using the Tiss-u-stor device) | Automated disaggregation in bags (using the Tiss-u-stor device) |
| | Tumour Digest Formulation | Non-cryopreserved | Non-cryopreserved | Cryopreserved | Cryopreserved |
| TIL Outgrowth | Culture Vessels for Tumour Digest | Open process in plates | Open process in plates | Open process in plates | Closed process in bags |
| | Seeding Density | Target of 1 × 10⁶ viable cells/mL | Target of 1 × 10⁶ viable cells/mL | Target of 0.5 × 10⁶ viable cells/mL | Target of 0.25 × 10⁶ viable cells/mL |
| | Cell Count Test Method | Hemocytometer | Flow cytometry | Flow cytometry | Flow cytometry |
| | Material | Gentamycin & Amphotericin B | Gentamycin & Amphotericin B | Gentamycin & Amphotericin B | Gentamycin, Amphotericin B, & Vancomycin |
| | Material | Heat inactived and 0.1 μm filtered FBS | Heat inactivated and 0.1 μm filtered FBS | Heat inactivated and 0.1 μm filtered FBS | Heat inactivated and 0.1 μm filtered Irradiated FBS |
| TIL REP | Material | Heat inactivated and 0.1 μm filtered Human AB donors | Heat inactivated and 0.1 μm filtered Human AB donors | Heat inactivated and 0.1 μm filtered Human AB donors | Heat inactivated and 0.1 μm filtered Irradiated Human AB donors |
| TIL Outgrowth to REP | Post TIL Outgrowth, Cryptopreservation, Thaw/wash and Recovery | Hold step with Cryptopreservation and 1-3 days post thaw recovery | Hold step with Cryopreservation and 1-3 days post thaw recovery | Continuous processing without cryopreservation | Continuous processing without cryopreservation |
| Harvest to Drug Product Formulation | Drug Product | Haemonetics Cell Saver 5 (Manual formulation to 270 mL) | Haemonetics Cell Saver 5 (Manual formulation to 270 mL) | Haemonetics Cell Saver 5 (Manual formulation to 270 mL) | Cytiva Sefia S-2000 (Automated formulation to 110 mL) |
| Drug Product Formulation | Drug Product | Non-cryopreserved | Non-cryopreserved | Cryopreserved | Cryopreserved |

An overview of the ITEL-168 manufacturing process used in the two process development runs is shown in Table 15. The two process development runs, labelled as Run 1 (TTL065) and Run 2 (Biopartners 9251), were performed at full scale under GMP conditions and used excess tumor gathered from a patient and tumor sourced from the vendor—Biopartners, respectively.

During these two process development runs, in-process testing for bioburden and final product sterility, endotoxin, mycoplasma and appearance tests were not performed, as these runs were primarily intended to evaluate manufacturing process performance and product quality following the process improvements, as well as serve as training runs for the manufacturing operators, under GMP conditions prior to the process verification runs.

TIL outgrowth and REP were performed as in Example 10 using the materials shown in Table 12 and Table 13.

Figure 76A:
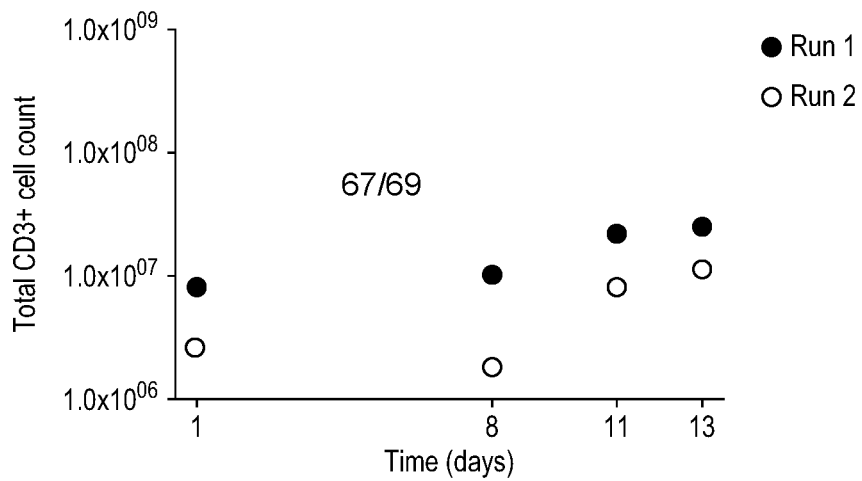
FIG. 76A, FIG. 76B and FIG. 76C depict characteristics of manufactured TILs. (A) Cell count during TIL outgrowth stage (stage 1) of the full-scale ITIL-168 GMP runs. (B) Cell count during TIL REP stage (stage 2) of the full-scale ITIL-168 GMP runs. (C) Percent viability (% viable CD3+ cells) during the full-scale ITIL-168 GMP runs.
Figure 76B:
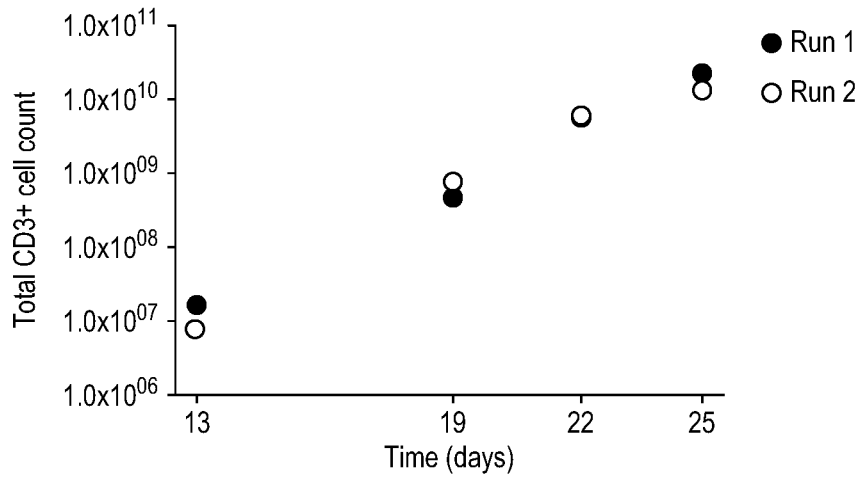

For both runs (Run 1 and Run 2), total CD3+ cell counts were measured on days 1, 8, 11 and 13 for the TIL outgrowth stage or stage 1, and on days 13, 19, 22 and 25 for the TIL Rapid Expansion Phase (REP) or stage 2, per the batch manufacturing record (BMR). FIGS. 76A and 76B show the total CD3+ cell count for the two runs throughout the TIL outgrowth stage (stage 1) and TIL REP stage (stage 2), respectively. Data shown in FIG. 76B demonstrates that for both runs, >1×10¹⁰ CD3+ cells were achieved by the end of the REP stage resulting in both lots meeting the dose acceptance criteria of 5×10⁹ to 5×10¹⁰ CD3+ cells.

Figure 76C:
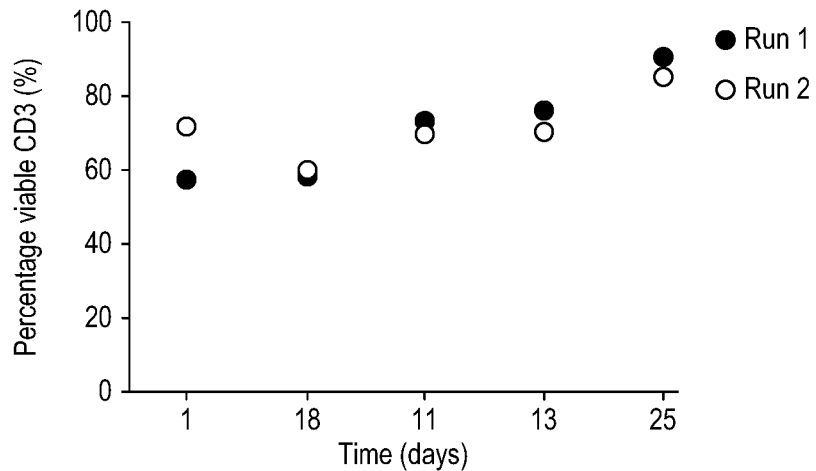

Viability (percentage of viable CD3+ cells) was also measured for both runs on days 1, 8, 11, 13 and 25. FIG. 76C shows that the viability increased during the manufacturing process and towards the end of REP stage and both runs met the final product criteria of >70%.

Fold expansion for the rapid expansion phase (REP) was calculated from the cell count data, for the two runs. Additionally, final product quality attributes such as dose, viability, potency, T cell phenotype and T cell subsets were also evaluated for the two process development runs.

Data presented in Table 16 demonstrates that following the process improvements, the ITIL-168 manufacturing process performs similarly to the historical process and results in final product quality attributes that meet the specification requirements.

TABLE 16

ITIL-168 manufacturing process performance and product quality attributes

| Run | Fold Expansion during REP (Absolute) | Dose (Total viable CD3+ cells) | Viability (%) | Potency[1] (%) |
|---|---|---|---|---|
| Acceptance Criteria/ Specification Requirements | NA | $5 \times 10^9$ to $5 \times 10^{10}$ | ≥70 | ≥40 |
| Historical Range Observed | 395-7526 (n = 22) | $7.90 \times 10^9$ to $6.25 \times 10^{10}$ (n = 23) | 80-99 (n = 23) | Historical retains in the process of being tested |
| Run 1 | 1350 | $3 \times 10^{10}$ | 90 | 63.2 |
| Run 2 | 1700 | $2 \times 10^{10}$ | 88 | 65.2 |

[1]Potency is calculated as the frequency of all viable CD2+ cells that are positive for one or more of CD137, CD107a, TNF-α and IFN-γ

Example 12—Administration

Therapy

Subjects received a lymphodepleting chemotherapy regimen of cyclophosphamide and fludarabine. The therapy is designed to reduce the influence of suppressive cells such as regulatory T cells and to increase the expression of lymphocyte growth-promoting cytokines (e.g., IL-7 and IL-15). A hydration regimen was initiated prior to and during lymphodepleting chemotherapy. Antimicrobial and antifungal prophylaxis was initiated prior to starting lymphodepleting chemotherapy. Fever and neutropenia were assessed and managed. Non-steroidal anti-emetic therapy was commenced prior to lymphodepleting chemotherapy and continued as necessary.

Lymphodepleting chemotherapy was administered as follows. The doses of cyclophosphamide and fludarabine administered was calculated based assessment of body weight taken at baseline visit. In obese subjects (body mass index >35), the practical body weight was used. The dose of cyclophosphamide is based on weight, and the dose of fludarabine is based on body surface area. Doses may be rounded up or down in accordance with practices on dose banding. The following table shows recommended doses, routes of administration, infusion volumes, and duration:

TABLE 15

Lymphodepleting Chemotherapy Regimen

| Day | Drug | Dose | Route | Administration |
|---|---|---|---|---|
| −7 | Fludarabine | 25 mg/m² | IV | In 10-100 ml 0.9% NaCl over approx. 30 mins. |
|  | Cyclophosphamide | 60 mg/kg | IV | In 500 ml 0.9% NaCl over approx. 1 hr. |
| −6 | Fludarabine | 25 mg/m² | IV | In 10-100 ml 0.9% NaCl over approx. 30 mins |
|  | Cyclophosphamide | 60 mg/kg | IV | In 500 ml 0.9% NaCl over approx. 1 hr. |
| −5 | Fludarabine | 25 mg/m² | IV | In 10-100 ml 0.9% NaCl over approx. 30 mins |
| −4 | Fludarabine | 25 mg/m² | IV | In 10-100 ml 0.9% NaCl over approx. 30 mins |
| −3 | Fludarabine | 25 mg/m² | IV | In 10-100 ml 0.9% NaCl over approx. 30 mins |
| −2 |  | Rest Day |  |  |
| −1 |  | Rest Day |  |  |

TABLE 16

Fludarabine Dose Adjustment

| Creatinine clearance (measured by Cockcroft-Gault formula) | Fludarabine dose |
|---|---|
| >/=70 mL/min | 25 mg/m² |
| 51-69 mL/min | 20 mg/m² |

Subjects were premedicated with antihistamine and acetaminophen prior to TIL infusion. The contents of an infusion bag were infused using a non-leukodepleting filter (e.g. in-line/tubing filter of >/=170 microns). Subjects received up to 8 doses of intravenous IL-2 for post-infusion support. IL-2 was administered after the completion of TIL infusion beginning on day 0 and continuing through day 4.

Example 13—Treatment Results

A total of 44 patients with metastatic cutaneous melanoma underwent tumour resection and initiation of TIL Outgrowth manufacturing (stage 1). Of these 44 patients, 42 individual patient lots completed stage 1, with 2 failed attempts. Thirty-one patient lots were taken forward to REP manufacturing (stage 2). One lot failed the TIL outgrowth stage 1 manufacturing and a revised stage 1 manufacturing process was implemented which enabled successful stage 2 manufacturing. The patient was subsequently treated. The remaining 12 lots were not selected for initiation of REP for the following reasons: 8 were due to intercurrent clinical deterioration of patient status rendering them unfit for TIL therapy, 2 patients no longer required TIL due to clinical improvement on other therapies, 1 patient was unable to secure funding for the treatment, and 1 lot failed manufacturing due to lack of tumour tissue on the excised specimen. Four patient lots were manufactured successfully, however, the patients were deemed clinically unfit for the TIL therapy and hence were not treated.

Of the 44 tumours that were resected, 2 failed manufacturing, yielding a 95% manufacturing success rate. Twenty-seven patients were treated with TIL products made utilizing the standard manufacturing process. At the time of completion of TIL manufacturing, 6 of these patients were deemed clinically unfit for the full treatment regimen and received markedly lower doses of conditioning chemotherapy and post-infusion IL-2 and were therefore excluded from the analysis. One patient had a tumour resection which did not meet the criteria to initiate the standard TIL outgrowth manufacturing step (stage 1). Therefore, a modified stage 1 was initiated which did enable a rapid expansion protocol (stage 2) and final product formulation, albeit at a very low final cell dose ($1.7 \times 10^9$). Because this product was produced using a modified manufacturing process and yielded a low dose of cells, it was not considered representative of the MS license process and therefore the clinical data was excluded from the analysis.

The demographics, baseline patient characteristics, treatment details and disposition, and clinical efficacy and safety outcomes of the remaining 21 patients were collected and analysed. By the analysis cutoff date, these patients had a median potential follow-up time of 52.2 months (range: 4.6, 98.8 months) from the TIL infusion date.

Among these 21 patients, the majority (71%) were male, and the median age at the time of TIL treatment was 45 years (range: 16, 68). At baseline, all patients had stage IV metastatic cutaneous melanoma with a median of 39 months since original diagnosis of melanoma (range: 8, 177). A majority (67%) of patients had lesions reported in more than 3 disease sites, including 7 (33%) with brain metastasis documented at the time of the TIL treatment. The median number of prior systemic therapies was 2 (range: 1, 9). Fifty-two percent (52%) of the patients had a BRAF mutation, all of whom had received and progressed on a BRAF inhibitor with or without a MEK inhibitor. All but two patients (90%) had at least one prior checkpoint inhibitor with 12 (57%) having received a PD-1 inhibitor (either nivolumab or pembrolizumab). Additionally, 8 (38%) received ipilimumab and either nivolumab or pembrolizumab given in sequence and 4 (19%) received ipilimumab and nivolumab concurrently. Prior to the tumour resection for TIL production, 20 (95%) had relapsed or refractory progressive melanoma, and 1 (5%) ceased treatment prior to TIL therapy due to intolerability.

Immediately prior to receiving TIL, 10 (48%) of the patients had elevated serum lactose dehydrogenase (LDH) levels with 7 (33%) between 1 and 2 times of the upper limit of the normal range (ULN) and 3 (14%) higher than 2 times of ULN. Baseline tumour burden as measured in the sum of lesion dimensions (SLD) of the target lesions was available for 20 patients; the median baseline SLD was 100 mm (range: 13, 281).

TIL Treatment

All 21 patients received 2 doses of cyclophosphamide and 5 doses of fludarabine as conditioning chemotherapy prior to the TIL infusion. The median total number of TIL cells infused was $31.9 \times 10^9$ (range: $7.9 \times 10^9$, $62.5 \times 10^9$). The median total number of IL-2 doses was 8 (range: 4, 11). Patients remained in the hospital for a median of 10 days (range: 7, 15). Three (14%) patients were admitted for ICU during the treatment period.

Clinically significant AEs during the TIL treatment period were reported. Common AEs (≥10%) reported during the conditioning chemotherapy period included neutropenia (43%) and nausea (19%) and are broadly consistent with the side effect profile of these chemotherapy agents.

Common AEs with onset post TIL infusion included thrombocytopenia (62%), pyrexia (57%), rigors (43%), tachycardia (29%), neutropenia (29%), pulmonary oedema (24%), vascular leak (24%), rash (19%), atrial fibrillation (14%), cardiovascular instability (14%), chest infection (14%), and oedema (14%) (Table 19). These AEs are consistent with those reported in other TIL trials (Dafni et al, 2019; Rohaan et al, 2018).

The patient whose manufacturing process failed stage 1 but was treated with a product generated from a modified manufacturing process died on day 6 following TIL therapy due to extensive tumour burden exacerbated by renal failure, fluid overload and possible sepsis.

TABLE 17

AEs With Onset Post TIL Infusion (All Treated Subjects)

| AE Term - n (%) | All Treated Subjects (N = 21) |
|---|---|
| Thrombocytopenia | 13 (61.9) |
| Pyrexia | 12 (57.1) |
| Rigors | 9 (42.9) |
| Neutropenia | 6 (28.6) |
| Tachycardia | 6 (28.6) |
| Pulmonary oedema | 5 (23.8) |
| Vascular leak | 5 (23.8) |
| Rash | 4 (19.0) |
| Atrial Fibrillation | 3 (14.3) |
| Cardiovascular instability | 3 (14.3) |
| Chest infection | 3 (14.3) |
| Oedema | 3 (14.3) |
| Confusion | 2 (9.5) |
| Hypokalaemia | 2 (9.5) |
| Hypotension | 2 (9.5) |
| Neurological deficit | 2 (9.5) |
| Renal impairment | 2 (9.5) |
| Respiratory sepsis | 2 (9.5) |
| Seizure | 2 (9.5) |
| Weight gain | 2 (9.5) |
| Wheezing | 2 (9.5) |
| Cough | 1 (4.8) |
| Diarrhoea | 1 (4.8) |
| Dysphasia | 1 (4.8) |
| Engraftment syndrome | 1 (4.8) |
| Hallucinations | 1 (4.8) |
| Lethargy | 1 (4.8) |
| PICC line infection | 1 (4.8) |
| Pleural effusion | 1 (4.8) |
| Pneumonia | 1 (4.8) |
| Pneumonitis | 1 (4.8) |
| Respiratory problems | 1 (4.8) |
| Tachypnoea | 1 (4.8) |

Peripheral blood counts were measure during the treatment period. A trend of decrease in neutrophils, platelets, lymphocytes, white cell count, and haemoglobin was observed at the time of initiation of conditioning chemotherapy. Blood cell counts and haemoglobin levels generally reached their nadirs 1-4 days after the TIL infusion. The blood count recovery to baseline levels was generally observed approximately 7 days after the TIL infusion date.

A recent change in the manufacturing process was implemented to improve robustness and enable multicentre clinical trials with centralized manufacturing. In this update, digested tumour material is cryopreserved to prolong stability. Importantly, in the four patients treated with products made with up-front cryopreservation, the AE profile observed was broadly consistent with the other patients treated in the series (Table 20) and with that reported in clinical trials of other TIL products.

TABLE 18

AEs With Onset Post TIL Infusion (Subjects Treated with Cryo-in Products)

| AE Term - n (%) | All Treated Subjects (N = 4) |
|---|---|
| Thrombocytopenia | 4 (100) |
| Pyrexia | 2 (50.0) |
| Rash | 2 (50.0) |
| Rigors | 2 (50.0) |
| Hypotension | 1 (25.0) |
| Renal impairment | 1 (25.0) |
| Vascular leak | 1 (25.0) |
| Vitiligo | 1 (25.0) |

Fifteen of the 21 patients underwent disease assessments by serial CT and/or MRI scans that included radiological measurements of target lesions. Among these patients, the quantitative response rate (confirmation of response not required) was 53%, including 2 (13%) patients who achieved a CR and 6 (40%) who achieved a PR (Table 21).

TABLE 19

Summary of Best Overall Response
(Efficacy Evaluable Analysis Set)

|  | Efficacy Evaluable Analysis Set (N = 15) |
| --- | --- |
| Best Overall Response |  |
| Complete Response (CR) | 2 (13.3) |
| 95% CI (Clopper-Pearson method) | 1.7, 40.5 |
| Partial Response (PR) | 6 (40.0) |
| 95% CI (Clopper-Pearson method) | 16.3, 67.7 |
| Stable Disease (SD) | 3 (20.0) |
| 95% CI (Clopper-Pearson method) | 4.3, 48.1 |
| Progressive Disease (PD) | 4 (26.7) |
| 95% CI (Clopper-Pearson method) | 7.8, 55.1 |
| Response Rate (CR + PR) | 8 (53.3) |
| 95% CI (Clopper-Pearson method) | 26.6, 78.7 |
| Disease Control Rate (CR + PR + SD) | 11 (73.3) |
| 95% CI (Clopper-Pearson method) | 44.9, 92.2 |

The response rate inclusive of all patients based on both quantitative and qualitative response was 57%, including 3 (14%) who achieved a CR and 9 (43%) who achieved a PR. Two additional patients had developed resistance to the BRAF inhibitor dabrafenib and were experiencing disease progression on therapy before being referred for TIL treatment. Dabrafenib was stopped just prior to TIL therapy and was restarted approximately 1-2 weeks following TIL to prevent rapid tumour growth that often accompanies dabrafenib discontinuation. Each of these 2 patients achieved a qualitative response following TIL (1 durable CR and 1 PR). Both patients subsequently discontinued dabrafenib once in response following TIL. Because both of these patients had disease that had become refractory to dabrafenib, it is reasonable to conclude that the clinical benefit they experienced following TIL was due to TIL and not the transient resumption of dabrafenib. Therefore, a sensitivity analysis of response was performed including these patients as responders. In this sensitivity analysis, the response rate was 14/21 (67%) with 4 (19%) complete responders and 10 (48%) partial responders (Table 22).

TABLE 20

Summary of Best Overall Response. Sensitivity
Analysis (All Treated Subjects)

|  | All Treated Subjects (N = 21) |
| --- | --- |
| Best Overall Response |  |
| Complete Response (CR) | 4 (19.0) |
| 95% CI (Clopper-Pearson method) | 5.4, 41.9 |
| Partial Response (PR) | 10 (47.6) |
| 95% CI (Clopper-Pearson method) | 25.7, 70.2 |
| Stable Disease (SD) | 4 (19.0) |
| 95% CI (Clopper-Pearson method) | 5.4, 41.9 |
| Progressive Disease (PD) | 3 (14.3) |
| 95% CI (Clopper-Pearson method) | 3.0, 36.3 |
| Response Rate (CR + PR) | 14 (66.7) |
| 95% CI (Clopper-Pearson method) | 43.0, 85.4 |
| Disease Control Rate (CR + PR + SD) | 18 (85.7) |
| 95% CI (Clopper-Pearson method) | 63.7, 97.0 |

Figure 74:
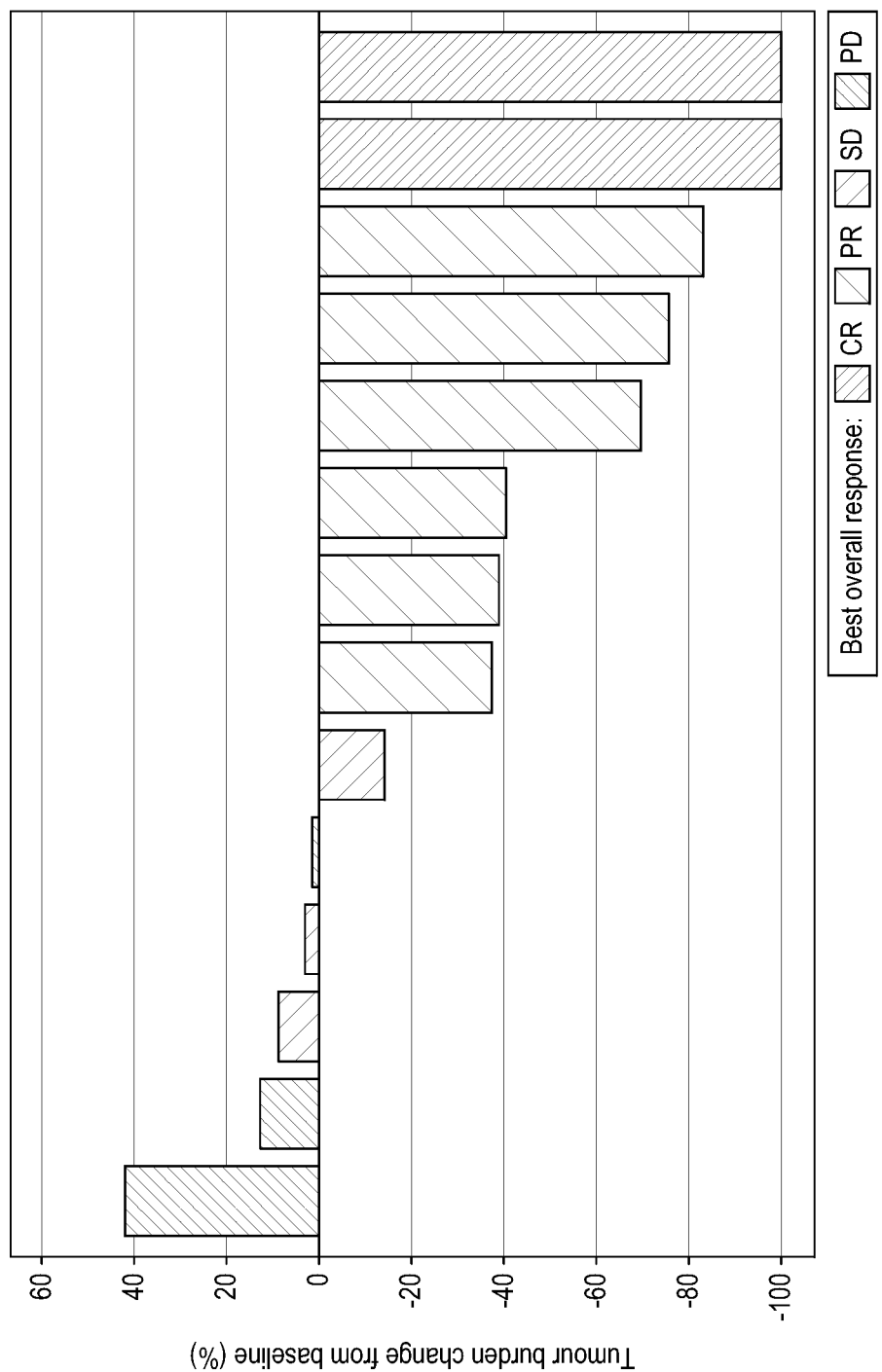
FIG. 74 depicts a waterfall plot showing best overall response and percent change in tumor burden. CR, complete response; PD, progressive disease; PR, partial response; SD, stable disease. The tumor burden is defined as the sum of the diameters of the target lesions; The change in tumor burden is defined as the change from baseline to post-baseline nadir. A minimum post-baseline SLD of 0 was used in both CR patients, who did not have target lesion measures reported at the visits when CR was assessed (no disease or metastasis was observed through CT/MRI scans). One subject with a best overall response of PD did not have any post-treatment target lesion measures reported (progression determined by observation of new lesions) and hence was not presented in the plot.

Responses were generally consistent across subgroups by important baseline and disease characteristics including age, number of disease sites, number of prior lines of therapies, prior BRAF inhibitor, prior PD-1 inhibitor, baseline brain metastasis, and baseline tumour burden. Notably, in the 4 patients treated with the manufacturing process most similar to that of ITIL-168, the overall response rate (75%) and the CR rate (25%) were consistent with the broader population. Of the 15 patients with quantitative response based on CT and/or MRI scans, 14 had detailed tumour measurements and the maximum percentages of tumour reduction from baseline were presented in a waterfall plot (FIG. 74). One patient had a best overall response of PD but did not have any post-treatment target lesion measures reported (progression determined by observation of new lesions) and hence was not presented in the plot.

Figure 75A:
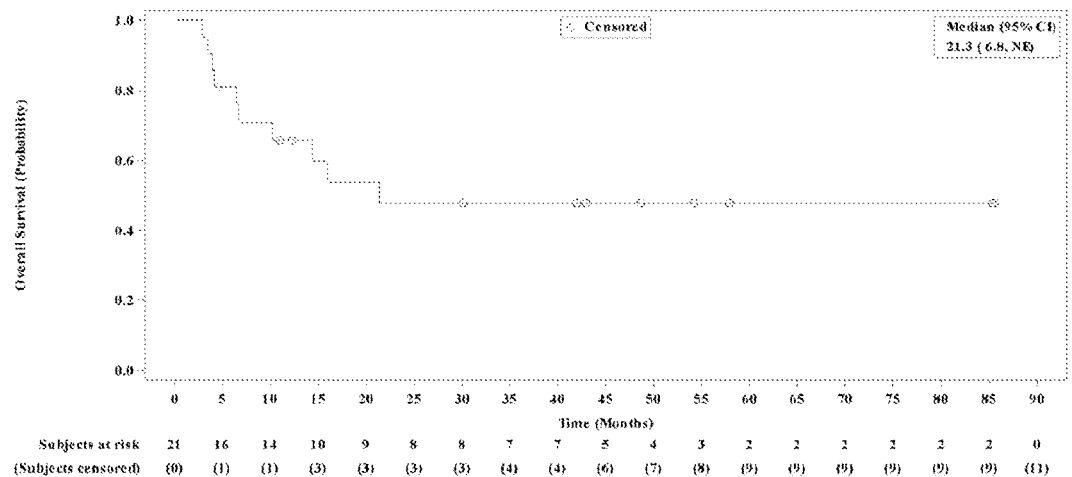
FIG. 75A-75C depict overall survival time.
Figure 75B:
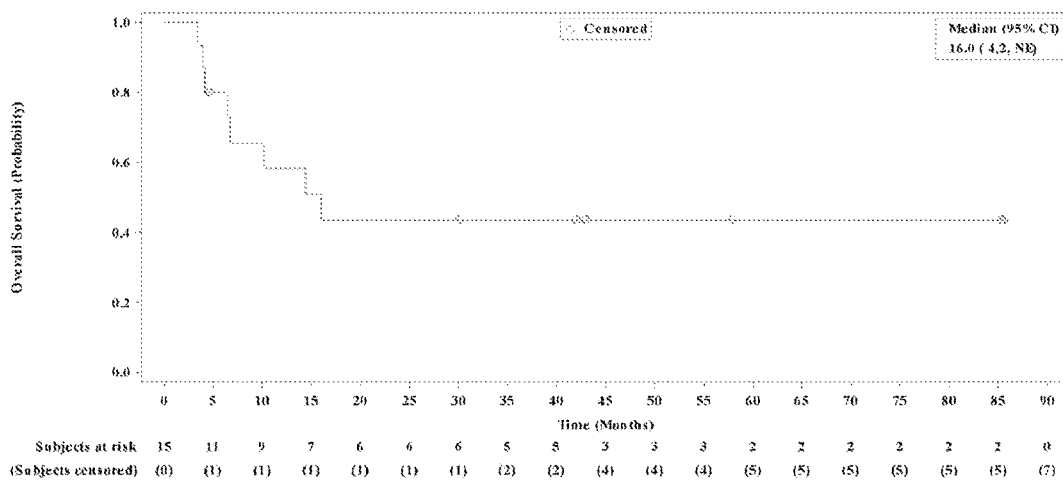
Figure 75C:
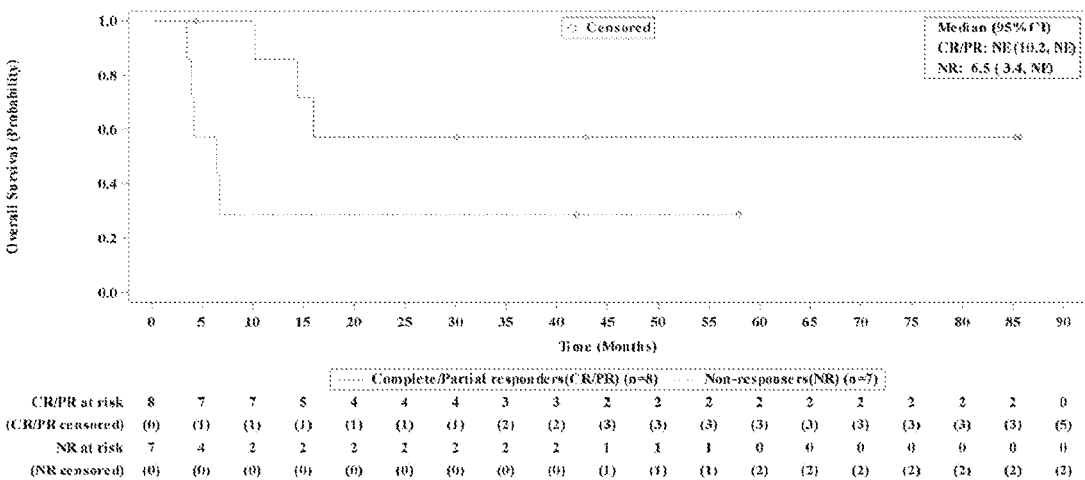

The median progression-free survival (PFS) time per quantitative responses data (N=15) was 6.7 months, with 4 patients having an ongoing response (2 CRs and 2 PRs) without any subsequent therapies at the time of the analysis cutoff. The median PFS time based on both quantitative and qualitative responses data (N=21) was 6.7 months, with 5 subjects having an ongoing response (3 CRs and 2 PRs) without any subsequent therapies. The median overall survival (OS) time with all 21 treated patients was 21.3 months (FIG. 75A). The median OS time of the 15 patients with quantitative response data was 16 months (FIG. 75B). However, the median OS time for responders (per quantitative response only, N=8) was not reached, whereas the median OS time for nonresponders (N=7) was 6.5 months (FIG. 75C).

Example 14—Genetically Modified TIL

TABLE 21

| Reagents and Equipment | | |
| --- | --- | --- |
| Reagent | Manufacturer | Catalog # |
| 15 mL Polypropylene Centrifuge Tubes | Appleton Woods | AB031 |
| 50 mL Polypropylene Centrifuge Tubes | Appleton Woods | AB028 |
| Dulbecco's Phosphate Buffered Saline | Sigma-Aldrich | D8537-24X500ML |
| Fetal Bovine Serum (Heat inactivated) | Sigma-Aldrich | F9665-500ML |
| TCM- CT4834/GIBCO CUSTOM P158718 | Gibco |  |
| Penicillin-Streptomycin | Sigma-Aldrich | P0781-100ML |
| TC 6-well plate | StarLab | CC7682-7506 |
| Sterile 1.5 mL Eppendorf | StarLab | S1615-5510 |
| Non-TC flat-bottom 96-well plate | Falcon | 353072 |

TABLE 21-continued

Reagents and Equipment

| Reagent | Manufacturer | Catalog # |
|---|---|---|
| 96 well U bottom plate | Falcon | 351177 |
| FACS tube | SLS | 352063 |
| TC 24-well plate | StarLab | CC7682-7524 |
| Microplate For Suspension Culture, 96 Well, F-Bottom | Grenier, Bio-One | 655185 |
| T cell TransACT (TM), human | Miltenyi | 130-111-160 |
| Gentamycin amphotericin | Invitrogen (ThermoFisher Scientific) | 10184583 |
| Proleukin (Aldesleukin) IL-2 | Novartis | PL-00101/0936 |
| Heraeus Megafuge 40R, Refrigerated Centrifuge | Thermo Scientific | 75004518 |
| IncuSafe CO2 Incubator | PHCBI | MCO-170AIC-PE |
| NovoCyte 3005 Flow Cytometer System (CE-IVD) | Agilent Technologies | 2010064D |
| NovoExpress Software | Agilent Technologies | |

Tumor digest cryovials are removed from liquid nitrogen storage and thawed in a 37° C. water bath until the cell suspension is just melted (D1). The cell suspension is removed to a 15 mL falcon, topped up with PBS up to 10 mL, centrifuged at 400 g for 5 min and the supernatant decanted.

The cell pellet is resuspended in pre warmed appropriate T-cell media, and cell counts are performed to determine viability using Trypan blue. Cells are resuspended at a density of $1 \times 10^6$ cells per mL.

Cells to be cultured without activation are resuspended at $0.5 \times 10^6$ cells per ml and 2 ml ($1 \times 10^6$ cells) are placed in a well of a 24 well tissue culture plate with IL-2 (3000 IU/mL). The cells are cultured in a humidified 37° C. incubator until transduction with IL-2 (3000 IU/mL) addition every 2-3 days.

For the cells to be transduced on D3 and D4 activation of the cells occurs on D1. For the cells to be transduced on D7 and D8 activation of the cells occurs on D5.

For TIL activation, $0.5 \times 10^6$ cells/mL are place in a 24 well tissue culture plate with 3000 IU/mL IL-2. 10 µL of T cell TransACT™ is added per $1 \times 10^6$ cells of TIL suspension (1:1 ratio) and the cells are incubated for 48 h in a 37° C. incubator Transduction First Day (D3 or D7)

Collect the cells from the 24 well plate into a 15 mL falcon tube, top up with 10 mL TCM and spin at 400 g for 5 min. Count the cells using Trypan blue and resuspend at $1 \times 10^6$ cells per mL.

Use $1 \times 10^5$ cells (100 µL) per well in 96 well flat bottom plate are used for each transduction method. If transducing in 24 well plate, place $1 \times 10^6$ cells per well (500 µL). If transducing in 6 well plate, place $5 \times 10^6$ cells per well (2 mL).

Prepare a master mix of lentivirus (MOI5) and IL-2 (3000 IU/mL) by resuspending in TCM to a final of 100 µl per 105 cells per condition (or the appropriate density and volume for 24 well and 6 well plates). Prepare a mastermix volume for number of wells +1 to account for pipetting losses.

For the NT cells (MOCK) prepare a master mix of TCM and IL-2 (3000 IU/mL) per 100 µL in 96 well flat bottom plate. For the 24 well and 6 well plates, resuspend the MOCK T cells in 500 µL and 2 mL, respectively, with IL-2 (3000 IU/mL).

Remove the supernatant from the cells in Eppendorf or 15 mL falcon tubes and resuspend cells in the appropriate 100 µL of master mix per $1 \times 10^5$ cells (or the appropriate density and volume for 24 well and 6 well plates) depending on the condition.

Resuspend properly each condition and transfer the cells onto a non-TC flat-bottom 96-well, 24 well or 6 well plates, accordingly.

In the 96 well plate transduction add 200 µL PBS to surrounding wells to prevent evaporation.

Incubate cells overnight in a humidified 37° C. incubator.

Transduction second day (D4 or D8)

Collect the cells by resuspending up and down from the 96 well flat bottom plates and transfer to a 96 well U bottom plate. (Collection from a 24 well or a 6 well plates is performed in a 15 mL falcon.) Spin the plate at 400 g for 5 min and wash the cells with TCM.

Use $1 \times 10^5$ cells (100 µL) per well in 96 well flat bottom plate for each transduction method. if transducing in 24 well plate, place $1 \times 10^6$ cells per well (500 µL). if transducing in 6 well plate, place $5 \times 10^6$ cells per well (2 mL).

Prepare a master mix of lentivirus (MOI5) and IL-2 (3000 IU/mL) by resuspending in TCM to a final of 100 µl per $10^5$ cells per condition (or the appropriate density and volume for 24 well and 6 well plates). Prepare a mastermix volume for number of wells+1 to account for pipetting losses.

For the NT cells (MOCK) prepare a master mix of TCM and IL-2 (3000 IU/mL) per 100 µL for the 96 well flat bottom plate. For the 24 well and 6 well plates, resuspend the MOCK T cells in 500 µL and 2 mL, respectively, with IL-2 (3000 IU/mL).

Remove the supernatant from the cells in Eppendorf or falcon tubes and resuspend cells in the appropriate 100 µL of master mix per $1 \times 10^5$ cells (or the appropriate density and volume for 24 well and 6 well plates) depending on the condition.

Resuspend properly each condition and transfer the cells onto a non-TC flat-bottom 96-well, 24 well or 6 well plates, accordingly. In the 96 well plate transduction add 200 µl, PBS to surrounding wells to prevent evaporation. Incubate cells overnight a humidified 37° C. incubator.

The next day transfer the cells into new 96 well round bottom plates, 24 well or 6 well plates, in fresh media with IL-2 (3000 IU/mL) and incubate for 72 hrs in a humidified 37° C. incubator.

The final volume for 96 well plate is 200 µL per well; the final volume for 24 well plate is 2 mL per well; the final volume for 6 well plate is 5 mL per well. IL-2 (3000 IU/mL) is added every 2-3 days.

The cells are stained for transduction efficiency on D8 for D3+D4 transductions and D12 for D7+D8 transductions.

Outgrowth of TILS

Mock and transduced cells are maintained in 96 well U-bottom plates until they are placed into a REP.

For the cell maintenance, every 2-3 days half of the media is removed and replaced with fresh TCM and IL-2 (3000 IU/mL). For a 96 well plate remove and replace 100 µl of media to a final volume of 200 µL. For a 24 well plate remove and replace 1 mL of media to a final volume of 2 mL. For a 6 well plate remove and replace 1 mL of media to a final volume of 2 mL.

The REP begins on D13 (12 days of outgrowth).

The invention is further described by the following numbered paragraphs:

1. A method for isolating a therapeutic population of cryopreserved unmodified tumor infiltrating lymphocytes (UTIL) comprising: (a) aseptically disaggregating a tumor resected from a subject thereby producing a disaggregated tumor, wherein the tumor is sufficiently disaggregated so that the cell suspension can be cryopreserved; (b) cryopreserving the disaggregated tumor the same day as step (a) by cooling or maintaining at a low temperature; (c) optionally storing the cryopreserved disaggregated tumor; (d) performing a first expansion by culturing the disaggregated tumor in a cell culture medium comprising IL-2 to produce a first population of UTILs; (e) performing a second expansion by culturing the first population of UTILs with additional IL-2, OKT-3, and antigen presenting cells (APCs), to produce a second population of TILs; and (f) harvesting and/or cryopreserving the second population of UTILs.

2. The method of paragarph 1, wherein the disaggregation comprises physical disaggregation, enzymatic disaggregation, or physical and enzymatic disaggregation.

3. The method of paragraph 1 or 2, wherein the cooling is at a controlled rate.

4. The method of paragraph 3, wherein controlled rate freezing is about −2° C./minute to about −60° C.

5. The method of any one of paragraphs 1-5, wherein the disaggregated tumor is cellularized.

6. The method of any one of paragraphs 1-5, wherein the disaggregated tumor is purified.

7. The method of any one of paragraphs 1-6, wherein a single cell suspension is provided after step (a).

8. The method of any one of paragraphs 1-7, wherein the first population of UTILs is about 1-20 million UTILs.

9. The method of any one of paragraphs 1-8, wherein step (d) further comprises growth of the UTIL out of the tumor starting material followed by a rapid expansion in step (e).

10. The method of paragraphs 9 wherein step (d) is performed for about two weeks and step (e) is performed for about two weeks.

11. The method of any one of paragraphs 1-10 wherein step (d) and/or step (e) further comprises adding IL-7, IL-12, IL-15, IL-18, IL-21 or a combination thereof.

12. The method of any one of paragraphs 1-11, further comprising step (g) suspending the second population of UTILs.

13. The method of paragraphs 12, wherein the suspending is in buffered saline, human serum albumin and dimethylsulfoxide (DMSO).

14. The method of any one of paragraphs 1-13, wherein step (f) is cryopreserving and further comprising a final step of thawing the UTILs.

15. The method of paragraphs 14, wherein the thawed UTILs are ready for infusion as a single dose with no further modification.

16. A therapeutic population of cryopreserved unmodified tumor infiltrating lymphocytes (UTIL) obtained by the method of any one of paragraphs 1-15.

17. The therapeutic population of paragraphs 16 wherein the population comprises about $5 \times 10^9$ to $5 \times 10^{10}$ of T cells.

18. A cryopreserved bag of the therapeutic population of paragraphs 16 or 17.

19. The cryopreserved bag of paragraphs 18 for use in intravenous infusion.

20. A method for treating cancer comprising administering the therapeutic population of paragraphs 14 or 15 or the cryopreserved bag of paragraphs 18 or 19.

21. The method of paragraphs 20, wherein the cancer is bladder cancer, breast cancer, cancer caused by human papilloma virus, cervical cancer, head and neck cancer (including head and neck squamous cell carcinoma (HN-SCC), lung cancer, melanoma, ovarian cancer, non-small-cell lung cancer (NSCLC), renal cancer or renal cell carcinoma.

The invention is further described by the following numbered paragraphs:

1. A method for isolating a therapeutic population of cryopreserved unmodified tumor infiltrating lymphocytes (UTIL) comprising: (a) resecting a tumor from a subject; (b) storing the resected tumor in a single use aseptic kit, wherein the aseptic kit comprises: a disaggregation module for receipt and processing of material comprising solid mammalian tissue; an optional enrichment module for filtration of disaggregated solid tissue material and segregation of non-disaggregated tissue and filtrate; and a stabilization module for optionally further processing and/or storing disaggregated product material, wherein each of the modules comprises one or more flexible containers connected by one or more conduits adapted to enable flow of the tissue material there between; and wherein each of the modules comprises one or more ports to permit aseptic input of media and/or reagents into the one or more flexible containers; (c) aseptically disaggregating the resected tumor in the disaggregation module thereby producing a disaggregated tumor, wherein the resected tumor is sufficiently disaggregated if it can be cryopreserved without cell damage; (d) cryopreserving the disaggregated tumor in the stabilization module; (e) performing a first expansion by culturing the disaggregated tumor in a cell culture medium comprising IL-2 to produce a first population of UTILs; (f) performing a second expansion by culturing the first population of UTILs with additional IL-2, OKT-3, and antigen presenting cells (APCs), to produce a second population of TILs; (g) harvesting and/or cryopreserving the second population of UTILs. In some embodiments, step a) is optional.

2. The method of paragraph 1, wherein the disaggregation comprises physical disaggregation, enzymatic disaggregation, or physical and enzymatic disaggregation.

3. The method of paragraph 1 or 2, wherein the disaggregated tumor is cellularized.

4. The method of any one of paragraphs 1-3, wherein a single cell suspension is provided after step (c).

5. The method of any one of paragraphs 1-4, wherein the first population of UTILs is about 1-20 million UTILs.

6. The method of any one of paragraphs 1-5, wherein step (e) further comprises growth of the UTILs out of the resected tumor starting material followed by the rapid expansion of step (f).

7. The method of paragraph 6, wherein step (e) is performed for about two weeks and step (f) is performed for about two weeks.

8. The method of any one of paragraphs 1-7, wherein step (e) and/or step (f) further comprises adding IL-7, IL-12, IOL-15, IL-18, IL-21, or a combination thereof.

9. The method of any one of paragraphs 1-7, further comprising step (h) suspending the second population of UTILs.

10. The method of paragraph 9, wherein the suspending is in buffered saline, human serum albumin, and dimethylsulfoxide (DMSO).

11. The method of any one of paragraphs 1-9, wherein step (g) is cryopreserving and further comprising a final step of thawing the UTILs.

12. The method of paragraph 10, wherein the thawed UTILs are ready for infusion as a single dose with no further modification.

13. A therapeutic population of cryopreserved UTILs obtained by the method of any one of paragraphs 1-11.

14. The therapeutic population of paragraph 13, wherein the population comprises about $5\times10^9$ to $5\times10^{10}$ of T cells.

15. A cryopreserved bag of the therapeutic population of paragraph 13 or 14.

16. The cryopreserved bag of paragraph 15 for use in intravenous infusion.

17. A method for treating cancer comprising administering the therapeutic population of paragraph 13 or 14 or the cryopreserved bag of paragraph 15 or 16.

18. The method of paragraph 17, wherein the cancer is bladder cancer, breast cancer, cancer caused by human papilloma virus, cervical cancer, head and neck cancer (including head and neck squamous cell carcinoma [HNSCC]), lung cancer, melanoma, ovarian cancer, non-small-cell lung cancer (NSCLC), renal cancer or renal cell carcinoma.

19. The method of paragraph 1, wherein the one or more flexible containers of the aseptic kit comprises a resilient deformable material.

20. The method of paragraph 1, wherein the one or more flexible containers of the disaggregation module of the aseptic kit comprises one or more sealable openings.

21. The method of paragraph 20, wherein the flexible container of the disaggregation module of the aseptic kit comprises a heat sealable weld.

22. The method of paragraph 1, wherein the one or more flexible containers of the aseptic kit comprises internally rounded edges.

23. The method of paragraph 1, wherein the one or more flexible containers of the disaggregation module of the aseptic kit comprises disaggregation surfaces adapted to mechanically crush and shear the solid tissue therein.

24. The method of paragraph 1, wherein the one or more flexible containers of the enrichment module of the aseptic kit comprises a filter that retains a retentate of cellularized disaggregated solid tissue.

25. The method of paragraph 1, wherein the one or more flexible containers of the stabilization module of the aseptic kit comprises media formulation for storage of viable cells in solution or in a cryopreserved state.

26. The method of paragraph 1, wherein the aseptic kit further comprises a digital, electronic, or electromagnetic tag identifier.

27. The method of paragraph 26, wherein the tag identifier of the aseptic kit relates to a specific program that defines: a type of disaggregation and/or enrichment and/or stabilization process; one or more types of media used in said processes; including and optional freezing solution suitable for controlled rate freezing.

28. The method of paragraph 1, wherein the same flexible container can form part of one or more of the disaggregation module, the stabilization module, and the optional enrichment modules.

29. The method of paragraph 1, wherein the disaggregation module of the aseptic kit comprises a first flexible container for receipt of the tissue to be processed.

30. The method of paragraph 1, wherein the disaggregation module of the aseptic kit comprises a second flexible container comprising the media for disaggregation.

31. The method of paragraph 1, wherein the optional enrichment module of the aseptic kit comprises the first flexible container and a third flexible container for receiving the enriched filtrate.

32. The method of paragraph 1, wherein both the disaggregation module and the stabilization module of the aseptic kit comprise the second flexible container and wherein the second container comprises digestion media and stabilization media.

33. The method of paragraph 1, wherein the stabilization module of the aseptic kit comprises a fourth flexible container comprising stabilization media.

34. The method of paragraph 1, wherein the stabilization module of the aseptic kit also comprises the first flexible container and/or third flexible container for storing and/or undergoing cryopreservation.

35. A method for isolating a therapeutic population of cryopreserved unmodified tumor infiltrating lymphocytes (UTIL) comprising: (a) resecting a tumor from a subject; (b) storing the resected tumor in an automated device for semi-automated aseptic disaggregation and/or enrichment and/or stabilization of cells or cell aggregates from mammalian solid tissue comprising a programmable processor and a single use aseptic kit, wherein the aseptic kit comprises: a disaggregation module for receipt and processing of material comprising solid mammalian tissue; an optional enrichment module for filtration of disaggregated solid tissue material and segregation of non-disaggregated tissue and filtrate; and a stabilization module for optionally further processing and/or storing disaggregated product material, wherein each of the modules comprises one or more flexible containers connected by one or more conduits adapted to enable flow of the tissue material there between; and wherein each of the modules comprises one or more ports to permit aseptic input of media and/or reagents into the one or more flexible containers; (c) aseptically disaggregating the resected tumor thereby producing a disaggregated tumor, wherein the resected tumor is sufficiently disaggregated if it can be cryopreserved without cell damage; (d) cryopreserving the disaggregated tumor in the stabilization module; (e) performing a first expansion by culturing the disaggregated tumor in a cell culture medium comprising IL-2 to produce a first population of UTILs; (f) performing a second expansion by culturing the first population of UTILs with additional IL-2, OKT-3, and antigen presenting cells (APCs), to produce a second population of TILs; (g) harvesting and/or cryopreserving the second population of UTILs. In some embodiments, step a) is optional.

36. The method of paragraph 35, wherein the automated device further comprises a radio frequency identification tag reader for recognition of the aseptic kit.

37. The method of paragraph 36, wherein the programmable processor of the automated device is capable of recognizing the aseptic kit via the tag and subsequently executes the kit program defining the type of disaggregation, enrichment, and stabilization processes, and the respective media types required for said processes.

38. The method of paragraph 35, wherein the programmable processor of the automated device is adapted to communicate with and control one or more of: the disaggregation module; the enrichment module; and the stabilization module.

39. The method of paragraph 38, wherein the programmable processor of the automated device controls the disaggregation module to enable a physical and/or biological breakdown of the solid tissue material.

40. The method of paragraph 39, wherein the programmable processor controls the disaggregation module to enable a physical and enzymatic breakdown of the solid tissue material.

41. The method of paragraph 40, wherein the enzymatic breakdown of the solid tissue material is by one or more media enzyme solutions selected from the group consisting of collagenase, trypsin, lipase, hyaluronidase, deoxyribonuclease, Liberase HI, pepsin, and mixtures thereof.

42. The method of paragraph 35, wherein the programmable processor controls disaggregation surfaces within the disaggregation flexible containers that mechanically crush and shear the solid tissue, optionally wherein the disaggregation surfaces are mechanical pistons.

43. The method of paragraph 35, wherein the programmable processor controls the stabilization module to cryopreserve the enriched disaggregated solid tissue in the container, optionally using a programmable temperature.

44. The method of paragraph 35, wherein the automated device further comprises one or more of, in any combination: sensors capable of recognizing whether a disaggregation process has been completed in the disaggregation module prior to transfer of the disaggregated solid tissue to the optional enrichment module; weight sensors to determine an amount of media required in the containers of one or more of the disaggregation module; the enrichment module; and/or the stabilization module and control the transfer of material between respective containers; sensors to control temperature within the containers of the one or more of the disaggregation module; the enrichment module; and/or the stabilization module; at least one bubble sensor to control transfer of media between the input and output ports of each container in the module; at least one pump, optionally a peristaltic pump, to control transfer of media between the input and output ports; pressure sensors to assess the pressure within the enrichment module; one or more valves to control a tangential flow filtration process within the enrichment module; and/or one or more clamps to control the transfer of media between the input and output ports of each module.

45. The method of paragraph 35, wherein the programmable processor of the automated device is adapted to maintain an optimal storage temperature range in the stabilization module until the container is removed; or executes a controlled freezing step.

46. The method of paragraph 35, wherein the automated device further comprises a user interface.

47. The method of paragraph 46, wherein the interface comprises a display screen to display instructions that guide a user to input parameters, confirm pre-programmed steps, warn of errors, or combinations thereof.

48. The method of paragraph 35, wherein the automated device is adapted to be transportable.

49. A semi-automatic aseptic tissue processing method for isolating a therapeutic population of UTILs comprising the steps of: (a) automatically determining aseptic disaggregation tissue processing steps and their associated conditions from a digital, electronic, or electromagnetic tag identifier associated with an aseptic processing kit, wherein the aseptic kit comprises: a disaggregation module for receipt and processing of material comprising solid mammalian tissue; an optional enrichment module for filtration of disaggregated solid tissue material and segregation of non-disaggregated tissue and filtrate; and a stabilization module for optionally further processing and/or storing disaggregated product material, wherein each of the modules comprises one or more flexible containers connected by one or more conduits adapted to enable flow of the tissue material there between; and wherein each of the modules comprises one or more ports to permit aseptic input of media and/or reagents into the one or more flexible containers; (b) resecting a tumor from a subject; (c) placing the tumor into the flexible plastic container of the disaggregation module of the aseptic kit; (d) processing the tumor by automatically executing the one or more tissue processing steps by communicating with and controlling: the disaggregation module; wherein the resected tumor is aseptically disaggregated thereby producing a disaggregated tumor, wherein the resected tumor is sufficiently disaggregated if it can be cryopreserved without cell damage; the optional enrichment module wherein the disaggregated tumor is filtered to remove disaggregated solid tissue material and to segregate non-disaggregated tissue and filtrate; the stabilization module wherein the disaggregated tumor is cryopreserved; (e) performing a first expansion by culturing the disaggregated tumor in a cell culture medium comprising IL-2 to produce a first population of UTILs; (f) performing a second expansion by culturing the first population of UTILs with additional IL-2, OKT-3, and antigen presenting cells (APCs), to produce a second population of TILs; and (g) harvesting and/or cryopreserving the second population of UTILs.

The invention is further described by the following numbered paragraphs:

1. A flexible container for processing tissue comprising: one or more layers made of a sealable polymer, wherein at least three edges of the flexible container are sealed during manufacturing; an open edge on the flexible container through which tissue material is inserted during use; and one or more connectors configured to couple the flexible container to at least one element through tubing; wherein a section proximate the open edge is sealed after tissue material is positioned within the flexible container to form a seal.

2. The flexible container of paragraph 1 wherein the seal comprises at least a three mm wide area parallel to the open edge and spaced away from the open edge of the flexible container.

3. The flexible container of paragraph 1 further comprises a clamp having protrusions and positioned proximate the seal and spaced further from the open edge of the flexible container than the seal.

4. The flexible container of paragraph 3 wherein during use a combination of the seal and the clamp is configured to withstand a 100 N force applied to the flexible container.

5. The flexible container of paragraph 3 wherein during use a combination of the seal and the clamp is configured to withstand a 75 N force applied to the flexible container.

6. The flexible container of paragraph 1 wherein the seal comprises at least a five mm wide area parallel to the open edge and spaced away from the open edge of the flexible container.

7. The flexible container of paragraph 1 wherein the flexible container is used for disaggregation of the tissue material.

8. The flexible container of paragraph 1, wherein the flexible container is used for disaggregation of the tissue material, filtration of disaggregated tissue material, and segregation of non-disaggregated tissue and filtrate.

9. The flexible container of paragraph 1, further comprising a resilient deformable material.

10. The flexible container of paragraph 1, further comprising one or more indicators.

11. The flexible container of paragraph 1, further comprising one or more marks.

12. The flexible container of paragraph 1 wherein the seal is formed using a heat sealer operating at a predetermined pressure, a predetermined temperature, and predetermined time frame.

13. The flexible container of paragraph 1 wherein the flexible container is configured to be used with a device that mechanically crushes tissue material placed in the flexible container.

14. The flexible container of paragraph 1 wherein the flexible container is configured to shear the tissue material.

15. Use of the flexible container according to paragraph 1 in a semi-automated or an automated process for the aseptic disaggregation, stabilization and optional enrichment of mammalian cells or cell aggregates.

16. A system for extraction of a desired material from tissue comprising: a kit comprising: a disaggregation flexible container; a stabilization flexible container; and at least one indicator tag positioned on at least one of the disaggregation flexible container or the stabilization flexible container capable of providing at least one of a source of tissue, a status of the tissue, or an identifier; a disaggregation element capable of treating at least some tissue in a disaggregation flexible container to form a processed fluid; an enrichment element capable of enriching at least some of the processed fluid to form the desired material; a stabilization element capable of storing a portion of the desired material in the stabilization flexible container; and at least one indicator tag reader positioned on at least one of the disaggregation element or the stabilization element capable of providing at least one of a source of tissue, or a status of the tissue at the stabilization element.

17. The system of paragraph 15 wherein the desired material comprises tumor infiltrating lymphocytes (TILs).

18. The system of paragraph 15 wherein one or more types of media are used in the processes by the disaggregation element and the stabilization element.

19. The system of paragraph 15 further comprising a cryopreservation media for use in the stabilization element capable of controlled rate freezing.

20. The system of paragraph 15 wherein the disaggregation flexible container comprises a disaggregation bag having an open edge which is sealed during use and the stabilization flexible container is a stabilization bag.

21. An automated device for semi-automated aseptic disaggregation and/or enrichment and/or stabilization of cells or cell aggregates from mammalian solid tissue comprising: a programmable processor; and a kit comprising at least one of the flexible container of any of paragraphs 1 to 15 as a disaggregation flexible container.

22. The automated device of paragraph 21, further comprising an indicator tag reader.

23. The automated device of paragraph 21, further comprising a radio frequency identification tag reader to recognize a component of the kit.

24. The automated device of paragraph 21, wherein the programmable processor is capable of recognizing the component of the kit via the tag and subsequently executes a program defining the type of disaggregation, enrichment and stabilization processes and the respective media types required for those processes.

25. The automated device of paragraph 21 wherein the programmable processor controls a disaggregation element of the automated device to enable a physical and/or biological breakdown of the solid tissue in the disaggregation flexible container.

26. The automated device of paragraph 25 wherein the programmable processor controls a disaggregation surface proximate the disaggregation flexible container which mechanically crushes and shears the solid tissue positioned in the disaggregation flexible container, optionally wherein the disaggregation surfaces are mechanical pistons.

27. The automated device of paragraph 21 wherein the programmable processor controls a disaggregation element of the automated device to enable a physical and enzymatic breakdown of the solid tissue in the disaggregation flexible container.

28. The automated device of paragraph 27 wherein the enzymatic breakdown of the solid tissue is by one or more media enzyme solutions selected from collagenase, trypsin, lipase, hyaluronidase, deoxyribonuclease, Liberase HI, pepsin, or mixtures thereof.

29. The automated device of paragraph 21 wherein the device comprises at least two of a disaggregation element; an enrichment element; and a stabilization element; and wherein the programmable processor is adapted to communicate with and control one or more of: the disaggregation element; the enrichment element; and the stabilization element.

30. The automated device of any one of paragraphs 29 wherein the programmable processor controls the stabilization element to cryopreserve the enriched disaggregated solid tissue in the cryopreservation container, optionally using a programmable temperature.

31. The automated device of any one of paragraphs 29 wherein the device further comprises one or more of the additional components in any combination: sensors capable of recognizing whether a disaggregation process has been completed in the disaggregation element prior to transfer of the disaggregated solid tissue to the optional enrichment element; weight sensors to determine an amount of media required in the containers of one or more of the disaggregation element; the enrichment element; and/or the stabilization element and control the transfer of material between respective containers; sensors to control temperature within the containers of the one or more of the disaggregation element; the enrichment element; and/or the stabilization element; at least one bubble sensor to control the transfer of media between the input and output ports of each container in the element; at least one pump, optionally a peristaltic pump, to control the transfer of media between the input and output ports; pressure sensors to assess the pressure within the enrichment element; one or more valves to control a tangential flow filtration process within the enrichment element; and/or one or more clamps to control the transfer of media between the input and output ports of each element.

32. The automated device of paragraph 29 wherein the programmable processor is adapted to maintain an optimal storage temperature range in the stabilization element until the container is removed; or executes a controlled freezing step.

33. The automated device of any preceding paragraph, further comprising a user interface.

34. The automated device of paragraph 26, wherein the interface comprises a display screen to display instructions that guide a user to input parameters, confirm pre-programmed steps, warn of errors, or combinations thereof.

35. The automated device of paragraph 21 wherein the automated device is adapted to be transportable.

36. An automatic tissue processing method comprising: automatically determining conditions for processing steps and their associated conditions from a digital, electronic or electromagnetic tag indicator associated with a kit; placing a tissue sample into a flexible container of the kit; and sealing at least one edge of the flexible container; processing the tissue sample by automatically executing one or more tissue processing steps by communicating with the indicator and controlling the flexible container; and filtering at least a portion of the processed tissue sample to generate a filtered fluid; and providing at least some of the filtered fluid to a cyropreservation flexible container.

37. The method of paragraph 31 wherein processing comprises agitation, extraction, and enzymatic digestion of at least a portion of the tissue sample in the flexible container.

38. The method of paragraph 31 wherein processing comprises agitation, extraction, and enzymatic digestion of at least a portion of the tissue sample in the flexible container and resulting in the extraction of a desired material.

39. The method of paragraph 31 wherein processing comprises agitation, extraction, and enzymatic digestion of at least a portion of the tissue sample in the flexible container and resulting in the extraction of tumor infiltrating lymphocytes (TILs).

40. The method of paragraph 31 wherein the flexible container comprises heat-sealable material.

41. The method of paragraph 31 wherein the flexible container comprises at least one of EVA, a vinyl acetate and polyolefin polymer blend, or polyamide.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of identifying potent T-cells in a population of TILs, comprising:
   in an isolated and ex vivo expanded population of TILs from a subject's cancer tissue, identifying the presence of T-cells expressing a combination of markers, the combination comprising each of:
   CD107a;
   CD137;
   TNF-α; and,
   IFN-γ;
   wherein, a T-cell is determined to be potent by the presence of the combination of markers.

2. The method of claim 1, wherein the isolated and ex vivo expanded population of TILs has undergone one or more processes selected from the group consisting of disaggregation, cryopreservation, thawing, incubation, washing, isoform enrichment, activation with an anti-CD3 antibody, co-culturing with an inactivated feeder cell, and co-culturing with an activator cell.

3. The method of claim 1, wherein the isolated and ex vivo expanded population of TILs has undergone ex vivo expansion comprising outgrowth and rapid expansion.

4. The method of claim 1, wherein the identifying comprises intracellular staining and flow cytometry.

5. A method of identifying potent T-cells in a population of TILs, comprising:
   in an isolated and ex vivo expanded population of TILs from a subject's cancer tissue, identifying CD2+ T-cells expressing a combination of markers, the combination comprising each of:
   a T-cell expressing CD107a;
   a T-cell expressing CD 137;
   a T-cell expressing TNF-α; and,
   a T-cell expressing IFN-γ;
   wherein, a T-cell is determined to be potent by the presence of the combination of markers.

6. The method of claim 5, wherein the isolated and ex vivo expanded population of TILs has undergone one or more processes selected from the group consisting of disaggregation, cryopreservation, thawing, incubation, washing, isoform enrichment, activation with an anti-CD3 antibody, co-culturing with an inactivated feeder cell, and co-culturing with an activator cell.

7. The method of claim 5, wherein the isolated and ex vivo expanded population of TILs has undergone ex vivo expansion comprising outgrowth and rapid expansion.

8. The method of claim 5, wherein the identifying comprises intracellular staining and flow cytometry.

9. A method of determining potency of a population of TILs, comprising:
   in an isolated and ex vivo expanded population of TILs from a subject's cancer tissue, quantifying T-cells expressing a combination of markers, the combination comprising each of:
   a T-cell expressing CD 107a;
   a T-cell expressing CD 137;
   a T-cell expressing TNF-α; and,
   a T-cell expressing IFN-γ;
   wherein, a T-cell is determined to be potent by the presence of the combination of markers;
   quantifying the total number of T-cells in the expanded population of TILs; and,
   determining the percent potency of the expanded population of TILs by the ratio of T-cells expressing the combination of markers to the total number of T-cells in the expanded population of TILs.

10. The method of claim 9, wherein the isolated and ex vivo expanded population of TILs has undergone one or more processes selected from the group consisting of disaggregation, cryopreservation, thawing, incubation, washing, isoform enrichment, activation with an anti-CD3 antibody, co-culturing with an inactivated feeder cell, and co-culturing with an activator cell.

11. The method of claim 9, wherein the isolated and ex vivo expanded population of TILs has undergone ex vivo expansion comprising outgrowth and rapid expansion.

12. The method of claim 9, wherein the identifying comprises intracellular staining and flow cytometry.

13. A method for treating cancer in a subject comprising identifying potent T-cells in a population of TILs, comprising:
   in an isolated and ex vivo expanded population of TILs from a subject's cancer tissue, identifying the presence of T-cells expressing a combination of markers, the combination comprising each of:
   CD107a;
   CD137;
   TNF-α; and,
   IFN-γ;
   wherein, a T-cell is determined to be potent by the presence of the combination of markers,
   and administering to the subject the identified potent T-cells.

14. The method of claim 13, wherein the isolated and ex vivo expanded population of TILs has undergone one or more processes selected from the group consisting of disaggregation, cryopreservation, thawing, incubation, washing, isoform enrichment, activation with an anti-CD3 antibody, co-culturing with an inactivated feeder cell, and co-culturing with an activator cell.

* * * * *